United States Patent
Lee et al.

(10) Patent No.: US 12,207,547 B2
(45) Date of Patent: Jan. 21, 2025

(54) ORGANIC ELECTROLUMINESCENT COMPOUND, ORGANIC ELECTROLUMINESCENT MATERIAL COMPRISING THE SAME, AND ORGANIC ELECTROLUMINESCENT DEVICE

(71) Applicant: ROHM AND HAAS ELECTRONIC MATERIALS KOREA LTD., Chungcheongnam-do (KR)

(72) Inventors: Hyo-Jung Lee, Gyeonggi-do (KR); Dominea Rathwell, Gyeonggi-do (KR); Sang-Hee Cho, Gyeonggi-do (KR); Hyun-Ju Kang, Gyeonggi-do (KR)

(73) Assignee: Rohm and Haas Electronic Materials Korea Ltd. (KR)

(*) Notice: Subject to any disclaimer, the term of this patent is extended or adjusted under 35 U.S.C. 154(b) by 178 days.

(21) Appl. No.: 16/757,844

(22) PCT Filed: Nov. 9, 2018

(86) PCT No.: PCT/KR2018/013603
§ 371 (c)(1),
(2) Date: Apr. 21, 2020

(87) PCT Pub. No.: WO2019/093809
PCT Pub. Date: May 16, 2019

(65) Prior Publication Data
US 2021/0193931 A1 Jun. 24, 2021

(30) Foreign Application Priority Data

Nov. 10, 2017 (KR) .................. 10-2017-0149498
Nov. 7, 2018 (KR) .................. 10-2018-0135786

(51) Int. Cl.
*C07D 487/04* (2006.01)
*C09K 11/06* (2006.01)
*H10K 50/11* (2023.01)
*H10K 85/60* (2023.01)
*H10K 101/10* (2023.01)

(52) U.S. Cl.
CPC ......... *H10K 85/654* (2023.02); *C07D 487/04* (2013.01); *C09K 11/06* (2013.01); *H10K 85/6572* (2023.02); *C09K 2211/1007* (2013.01); *C09K 2211/1011* (2013.01); *C09K 2211/1018* (2013.01); *H10K 50/11* (2023.02); *H10K 2101/10* (2023.02)

(58) Field of Classification Search
CPC ............. H01L 51/0067; H01L 51/0072; H01L 51/5016; H01L 51/0085; H01L 51/0052; H01L 51/0071; H01L 51/50; C09K 11/06; C09K 2211/1007; C09K 2211/1011; C09K 2211/1018; C09K 2211/1044; C09K 2211/1059; C07D 487/04
See application file for complete search history.

(56) References Cited

U.S. PATENT DOCUMENTS

| 9,156,843 | B2 | 10/2015 | Kai et al. | |
|---|---|---|---|---|
| 2012/0104940 | A1 | 5/2012 | Shin et al. | |
| 2016/0118590 | A1 | 4/2016 | Ito et al. | |
| 2017/0047527 | A1 | 2/2017 | Lee et al. | |
| 2018/0033975 | A1 | 2/2018 | Kim et al. | |
| 2018/0312514 | A1* | 11/2018 | Ma ...................... | H01L 51/0073 |
| 2019/0157569 | A1 | 5/2019 | Lee et al. | |
| 2020/0343540 | A1* | 10/2020 | Han ...................... | H01G 11/06 |

FOREIGN PATENT DOCUMENTS

| CN | 106565433 | A | 4/2017 | | |
|---|---|---|---|---|---|
| KR | 20140006708 | A | 1/2014 | | |
| KR | 20190006353 | A | 1/2019 | | |
| KR | 101953175 | B1 | 2/2019 | | |
| WO | WO-2015160224 | A1 * | 10/2015 | ........... | C07D 209/86 |
| WO | WO-2016148390 | A1 * | 9/2016 | ........... | C07D 209/80 |
| WO | WO-2017200210 | A1 * | 11/2017 | ........... | C07D 251/24 |

OTHER PUBLICATIONS

Search Report from JPO for Japanese application No. 2020-524842; Application Date: Nov. 9, 2018.
Search Report from Korean Intellectual Property Office for Korean application No. 10-2018-0135786; Application Date: Nov. 7, 2018.

* cited by examiner

*Primary Examiner* — Amanda L. Aguirre
(74) *Attorney, Agent, or Firm* — G. Creston Campbell

(57) ABSTRACT

The present disclosure relates to an organic electroluminescent compound, an organic electroluminescent material, and an organic electroluminescent device comprising the same. The organic electroluminescent compound of the present disclosure can provide an organic electroluminescent device having improved lifespan properties compared to the organic electroluminescent device comprising a conventional organic electroluminescent compound.

6 Claims, No Drawings

ORGANIC ELECTROLUMINESCENT COMPOUND, ORGANIC ELECTROLUMINESCENT MATERIAL COMPRISING THE SAME, AND ORGANIC ELECTROLUMINESCENT DEVICE

TECHNICAL FIELD

The present disclosure relates to an organic electroluminescent compound, an organic electroluminescent material comprising the same and an organic electroluminescent device.

BACKGROUND ART

Among display devices, an electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device is light-emitting materials. Until now, fluorescent materials have been widely used as the light-emitting material. However, in view of electroluminescent mechanisms, since phosphorescent light-emitting materials theoretically enhance luminous efficiency by four (4) times compared to fluorescent light-emitting materials, phosphorescent light-emitting materials have been widely researched. Iridium(III) complexes have been widely known as phosphorescent light-emitting materials, including bis(2-(2'-benzothienyl)-pyridinato-N,C-3') iridium(acetylacetonate) [(acac)Ir(btp)$_2$], tris(2-phenylpyridine)iridium [Ir(ppy)$_3$] and bis(4,6-difluorophenylpyridinato-N,C2)picolinato iridium (Firpic) as red-, green- and blue-emitting materials, respectively.

In conventional technology, 4,4'-N,N'-dicarbazol-biphenyl (CBP) is the most widely known phosphorescent host material. Recently, Pioneer (Japan) et al., developed a high performance organic electroluminescent device using bathocuproine (BCP) and aluminum(III) bis(2-methyl-8-quinolinate)(4-phenylphenolate) (BAlq), etc., as host materials, which were known as hole blocking materials.

Although these materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the organic electroluminescent device is given by [($\pi$/voltage)× current efficiency], and the power efficiency is inversely proportional to the voltage. Although the organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the organic electroluminescent device is short, and it is still necessary to improve luminous efficiency. Accordingly, the materials constituting the organic layer in the device, in particular a host or a dopant constituting the light-emitting material, should be selected appropriately in order to realize the excellent characteristics of the organic EL device.

Korean Patent No. 1477613 discloses an organic electroluminescent device using a substituted indolocarbazole compound as a host material; however, it does not disclose a compound having naphthalene as a linker.

Korean Patent No. 1313730 discloses a host material comprising a compound having a substituted indolocarbazole compound as a core and naphthalene group as a linker; however, it does not disclose a compound having an asymmetric naphthalene linker.

DISCLOSURE OF INVENTION

Technical Problem

The object of the present disclosure is firstly, to provide an organic electroluminescent compound capable of improving lifespan properties of an organic electroluminescent device; secondly, to provide an organic electroluminescent material comprising the organic electroluminescent compound; and thirdly, to provide an organic electroluminescent device having improved lifespan properties, comprising the organic electroluminescent compound.

Solution to Problem

As a result of intensive studies to solve the technical problem above, the present inventors found that an organic electroluminescent device having a low driving voltage and/or a high luminous efficiency and/or long lifespan characteristics by forming a structure in that a hole-transporting group and an electron-transporting group are asymmetrically linked through naphthalene as a linker, can be provided, so that the present invention was completed.

Specifically, an organic electroluminescent compound according to one embodiment, by linking an indolocarbazole moiety being likely to receive a hole to a nitrogen-containing aromatic hexagonal ring group being likely to receive an electron at 1, 3-position or 1, 6-position (meta-type regiochemical position) of the naphthalene linker, has a high HOMO energy level since an electron conjugation breaks between two modules and the donor-acceptor electron bonding of the compound is weakened in the excited state. Due to this energy level, the hole current characteristic is improved, thereby improving the charge balance and enhancing the characteristics of the phosphorescent device. Accordingly, the asymmetric naphthalene-linked compound according to one embodiment can improve the efficiency of the organic electroluminescent device, as compared with the conventional compound.

More specifically, the aforementioned objective can be achieved by the organic electroluminescent compound represented by the following formula 1.

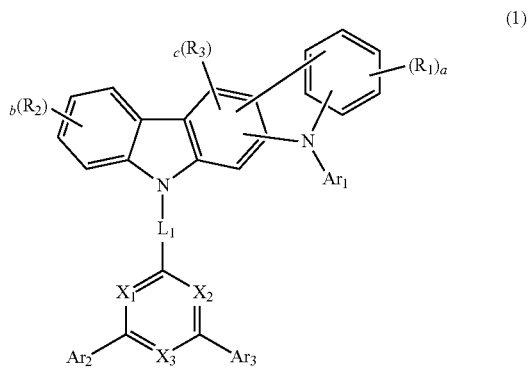

wherein $X_1$ to $X_3$ each independently represent $CR_{12}$ or N;

at least one of $X_1$ to $X_3$ represents N;

$Ar_1$ to $Ar_3$ each independently represent a substituted or unsubstituted (C1-C30)alkyl, a substituted or unsubstituted (C6-C30)aryl or a substituted or unsubstituted (3- to 30-membered)heteroaryl;

$R_1$ to $R_3$, and $R_{12}$ each independently represent hydrogen, deuterium, halogen, cyano, carboxyl, nitro, hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl; or $R_1$ and $R_3$ may be linked to an adjacent substituent to form a substituted or unsubstituted (C3-C30) mono- or polycyclic, alicyclic or aromatic ring or the combination thereof;

a and b each independently represent an integer from 0 to 4, c represents an integer from 0 to 2, when a or b is an integer of 2 or more or c is 2, each of $R_1$, each of $R_2$, or each of $R_3$ may be the same or different;

$L_1$ is represented by any one of the following formulae R-1 to R-3:

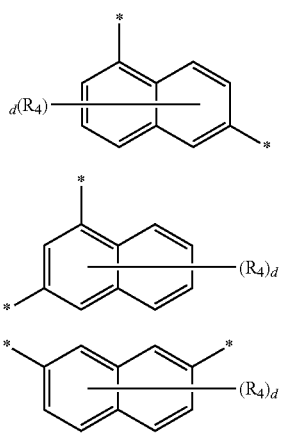

wherein, $R_4$ represents hydrogen, deuterium, halogen, cyano, carboxyl, nitro, hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl;

d represents an integer from 0 to 6, when d is an integer of 2 or more, each of $R_4$ may be the same or different;

* represents a linkage position with an adjacent ring in formula 1.

Advantageous Effects of Invention

By using the organic electroluminescent compound of the present disclosure, it is possible to provide an organic electroluminescent device having long driving lifespan.

MODE FOR THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material, etc.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is a cycloalkyl having 3 to 7, preferably 5 to 7, ring backbone atoms, including at least one heteroatom selected from B, N, O, S, Si, and P, and preferably O, S, and N. The above heterocycloalkyl may include tetrahydrofuran, pyrrolidine, thiolan, tetrahydropyran, etc. "(C6-C30)aryl" is a monocyclic or fused ring radical derived from an aromatic hydrocarbon having 6 to 30 ring backbone carbon atoms, in which the number of the ring backbone carbon atoms is preferably 6 to 20, more preferably 6 to 15, and may comprise a spiro structure. The above aryl may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered)heteroaryl" is an aryl having 3 to 30 ring backbone atoms, including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, etc., and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, benzocarbazolyl, phenoxazinyl, phenothiazinyl, phenanthridinyl, benzodioxolyl, and dihydroacridinyl, etc. "Halogen" includes F, Cl, Br, and I.

Herein, "ring formed in linked to an adjacent substituent" means a substituted or unsubstituted (C3-C30) mono- or polycyclic, alicyclic, aromatic ring, or a combination thereof, formed by linking or fusing two or more adjacent substituents; preferably, may be a substituted or unsubstituted (C3-C26) mono- or polycyclic, alicyclic, aromatic ring, or a combination thereof. In addition, at least one of the carbon atoms in the formed ring may be replaced with at least one heteroatom selected from the group consisting of B, N, O, S, Si, and P, preferably, N, O, and S.

In addition, "substituted" in the expression "substituted or unsubstituted" means that a hydrogen atom in a certain functional group is replaced with another atom or functional group, i.e., a substituent. The substituents of the substituted (C1-C30)alkyl, the substituted (C3-C30)cycloalkyl, the substituted (C3-C30)cycloalkenyl, the substituted (3- to 7-membered)heterocycloalkyl, the substituted (C6-C30)aryl, the substituted (3- to 30-membered)heteroaryl, and the substituted (C3-C30) mono- or polycyclic, alicyclic, aromatic ring, or the combination thereof, in $Ar_1$, $Ar_2$, $Ar_3$, $R_1$ to $R_4$, and $R_{12}$ each independently, are at least one selected from the group consisting of deuterium, halogen, cyano, carboxyl, nitro, hydroxyl, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (C6-C30)aryl-substituted or unsubstituted (5- to 30-membered)heteroaryl, (5- to 30-membered)heteroaryl-substituted or unsubstituted (C6-C30)aryl, tri(C1-C30)alkylsilyl, tri(C6-C30)arylsilyl, di(C1-C30)alkyl(C6-C30)arylsilyl, (C1-C30)alkyldi(C6-C30)arylsilyl, amino, mono- or di-(C1-C30)alkylamino, (C1-C30)alkyl-substituted or unsubstituted mono- or di-(C6-C30)arylamino, (C1-C30)alkyl(C6-C30)arylamino, (C1-C30)alkylcarbonyl, (C1-C30)alkoxycarbonyl, (C6-C30)arylcarbonyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl (C6-C30)aryl.

Hereinafter, the organic electroluminescent compound according to one embodiment will be described in more detail.

The organic electroluminescent compound according to one embodiment is represented by the following formula 1.

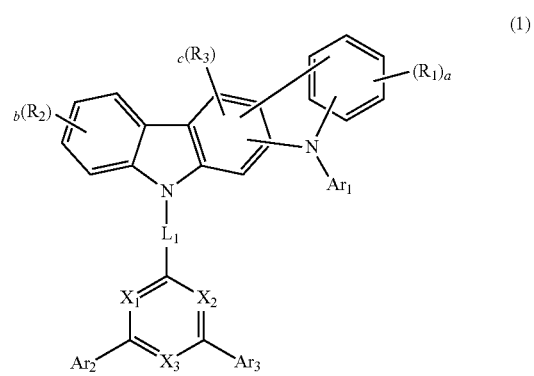

(1)

In formula 1,
$X_1$ to $X_3$ each independently represent $CR_{12}$ or N;
at least one of $X_1$ to $X_3$ represents N;
$Ar_1$ to $Ar_3$ each independently represent a substituted or unsubstituted (C1-C30)alkyl, a substituted or unsubstituted (C6-C30)aryl, or a substituted or unsubstituted (3- to 30-membered)heteroaryl;
$R_1$ to $R_3$, and $R_{12}$ each independently represent hydrogen, deuterium, halogen, cyano, carboxyl, nitro, hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl or a substituted or unsubstituted (3- to 30-membered)heteroaryl; or $R_1$ and $R_3$ may be linked to an adjacent substituent to form a substituted or unsubstituted (C3-C30) mono- or polycyclic, alicyclic or aromatic ring or the combination thereof;
a and b each independently represent an integer from 0 to 4, c represents an integer from 0 to 2, when a or b is an integer of 2 or more or c is 2, each of $R_1$, each of $R_2$, or each of $R_3$ may be the same or different;
$L_1$ is represented by any one of the following formulae R-1 to R-3:

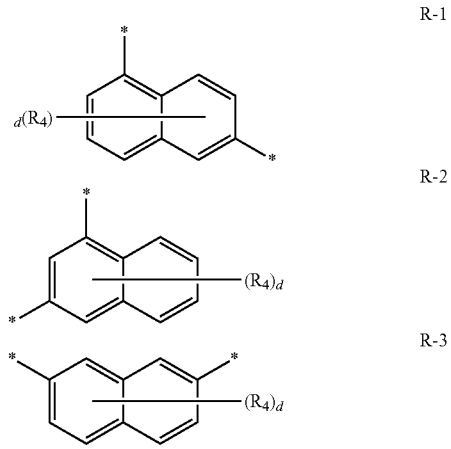

In formulae R-1 to R-3,
$R_4$ represents hydrogen, deuterium, halogen, cyano, carboxyl, nitro, hydroxyl, a substituted or unsubstituted (C1-C30)alkyl, a substituted or unsubstituted (C3-C30) cycloalkyl, a substituted or unsubstituted (C3-C30)

cycloalkenyl, a substituted or unsubstituted (3- to 7-membered)heterocycloalkyl, a substituted or unsubstituted (C6-C30)aryl, or a substituted or unsubstituted (3- to 30-membered)heteroaryl;

d represents an integer from 0 to 6, when d is an integer of 2 or more, each of $R_4$ may be the same or different;

* represents a linkage position with an adjacent ring in formula 1.

In one embodiment, in formula 1, $L_1$ represents a substituted or unsubstituted naphthylene, which may be represented by the following formula a, e.g., 1- and 3-position carbons, 1- and 6-position carbons, 3- and 6-position carbons, 3- and 8-position carbons, or 6- and 8-position carbons, of naphthylene may be linked to the adjacent rings, respectively; or 2- and 4-position carbons, 2- and 5-position carbons, 2- and 7-position carbons, 4- and 7-position carbons, or 2- and 7-position carbons, of naphthylene may be linked to the adjacent rings, respectively.

(a)

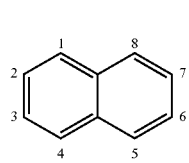

Specifically, $L_1$ may be represented by any one of the following formulae R-1 to R-3, i.e., $L_1$ is asymmetrically linked to an indolocarbazole and a nitrogen-containing aromatic hexagonal ring group, which are adjacent substituents.

An organic luminescent device according to one embodiment has a low driving voltage and/or a high luminous efficiency and/or a long lifespan by comprising the organic electroluminescent compound represented by formula 1. By linking an indolecarbazole moiety as a hole-transporting group and a nitrogen-containing aromatic hexagonal ring group as an electron-transporting group at the above specific positions of the naphthylene, the electron conjugation between the hole-transporting group and the electron-transporting group is broken, thereby the above effects are obtained.

Formula 1 according to one embodiment may be represented by any one of the following formulae 1-1 to 1-5.

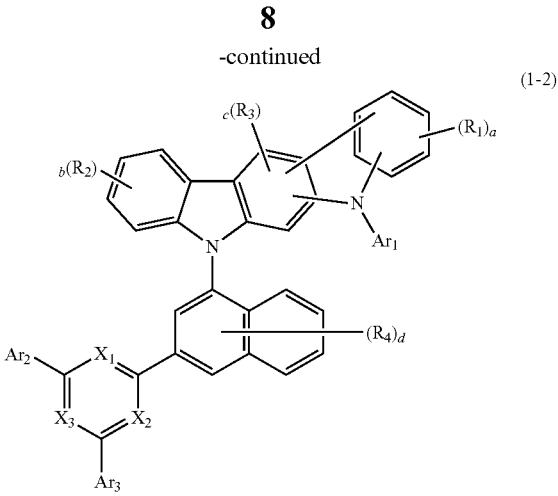

(1-2)

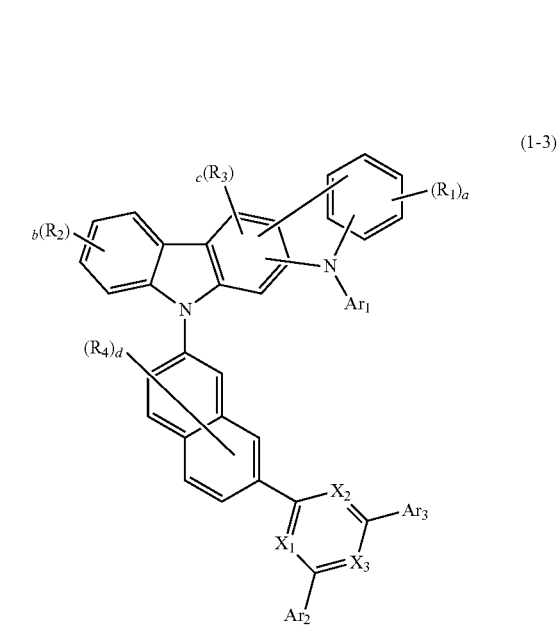

(1-3)

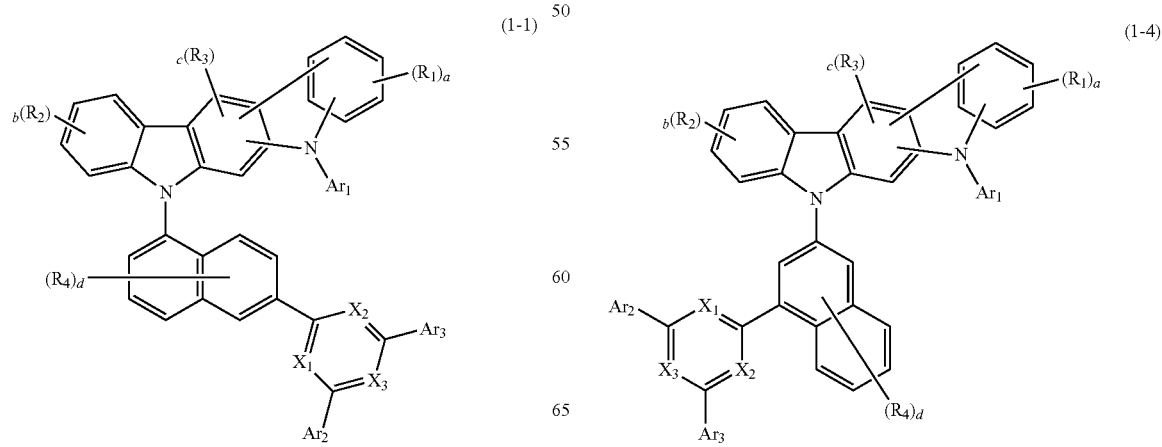

(1-1)

(1-4)

-continued (1-5)
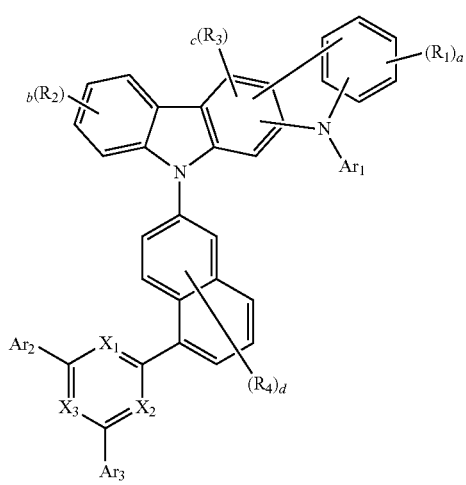

(2)
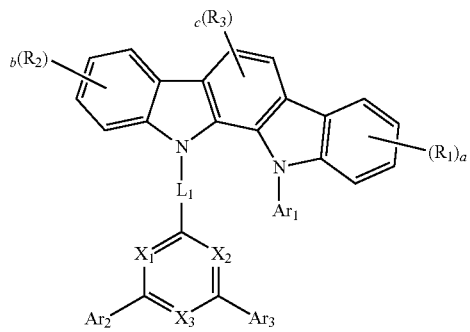

(3)
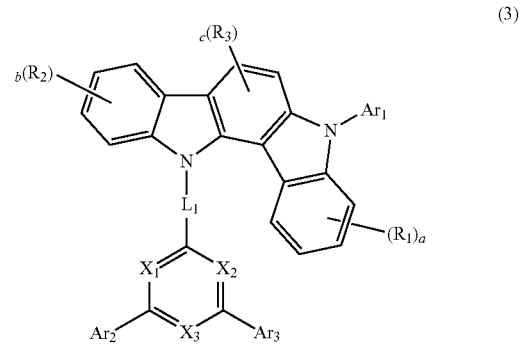

In formulae 1-1 to 1-5, $X_1$ to $X_3$, $Ar_1$ to $Ar_3$, $R_1$ to $R_4$, and a to d are as defined in formula 1.

In one embodiment, $Ar_1$ to $Ar_3$ each independently represent a substituted or unsubstituted (C6-C25)aryl, preferably may be a substituted or unsubstituted (C6-C18)aryl. For example, $Ar_1$ to $Ar_3$ each independently represent a substituted or unsubstituted phenyl, a substituted or unsubstituted biphenyl, or a substituted or unsubstituted naphthyl.

In one embodiment, $R_1$ to $R_4$, and $R_{12}$ each independently represent hydrogen, deuterium, halogen, cyano, carboxyl, nitro, hydroxyl, or a substituted or unsubstituted (C1-C20) alkyl, preferably each independently may be hydrogen, deuterium, halogen, cyano, carboxyl, nitro, hydroxyl, or a substituted or unsubstituted (C1-C10)alkyl. For example, $R_1$ to $R_4$, and $R_{12}$ may all be hydrogen.

In one embodiment, at least two of $X_1$ to $X_3$ may be N. For example, $X_1$ and $X_2$ may be N, and $X_3$ may be $CR_{12}$, e.g., $X_1$ and $X_3$ may be N, and $X_2$ may be $CR_{12}$, e.g., $X_2$ and $X_3$ may be N, and $X_3$ may be $CR_{12}$.

In one embodiment, $X_1$ to $X_3$ may all be N.

In formula 1, the heteroaryl contains at least one heteroatom selected from B, N, O, S, Si, and P, preferably may contain at least one heteroatom selected from N, O, and S, more preferably may contain at least one N.

In formula 1, a, b, c, and d, preferably, each independently represent an integer of 0 or 1. For example, a, b, c, and d may all be 0.

According to one embodiment of the present disclosure, the organic electroluminescent compound may be represented by any one of the following formulae 2 to 7.

(4)
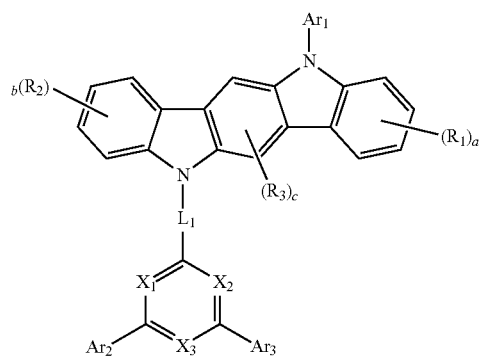

(5)
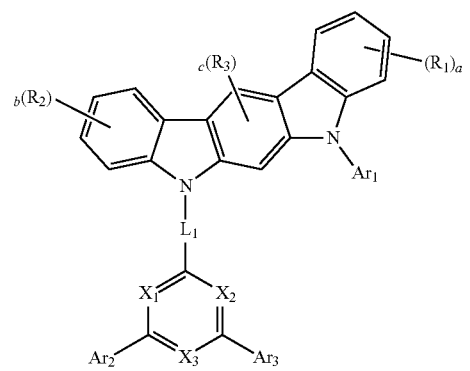

-continued (6)

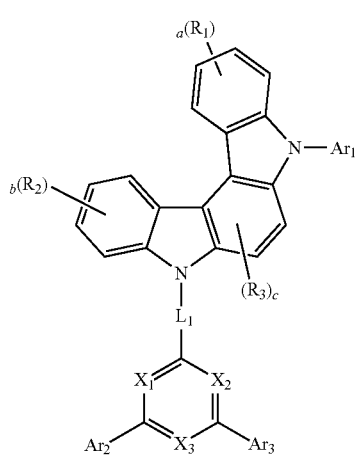

C-1

(7)

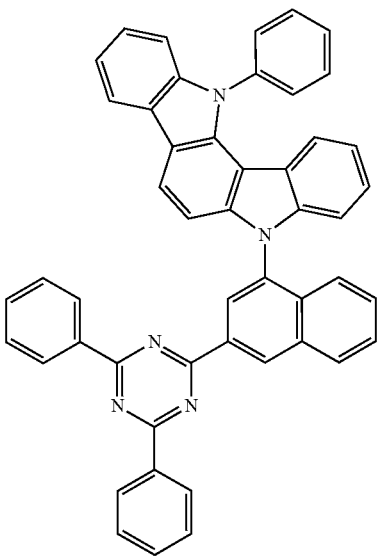
C-2

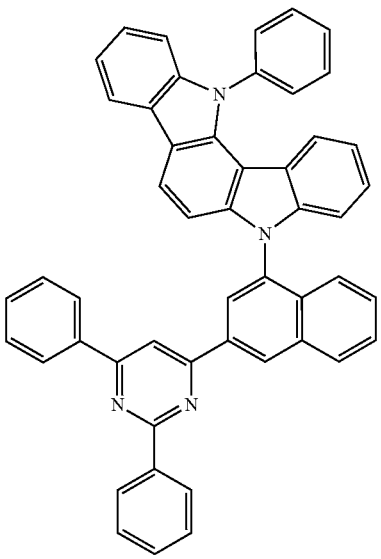
C-3

In formulae 2 to 7, $L_1$, $X_1$ to $X_3$, $Ar_1$ to $Ar_3$, $R_1$ to $R_3$, and a to c are as defined in formula 1.

According to one embodiment of the present disclosure, in formula 1, at least two of $X_1$ to $X_3$ represent N, $Ar_1$ to $Ar_3$ each independently represent a substituted or unsubstituted (C6-C25)aryl, $R_1$ to $R_4$, and $R_{12}$ each independently represent hydrogen or deuterium, and a, b, c, and d each independently represent an integer of 0 or 1.

According to another embodiment of the present disclosure, in formula 1, $X_1$ to $X_3$ all represent N, $Ar_1$ to $Ar_3$ each independently represent a substituted or unsubstituted (C6-C18)aryl, $R_1$ to $R_4$, and $R_{12}$ all represent hydrogen, and a, b, c, and d all represent 0.

The compound represented by formula 1 may be more specifically illustrated by the following compounds, but is not limited thereto:

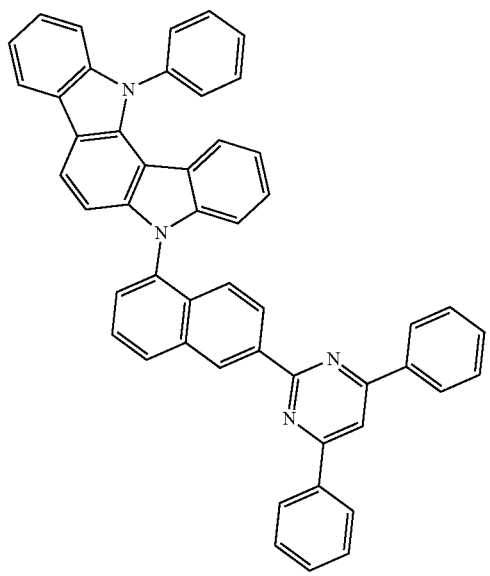
C-4
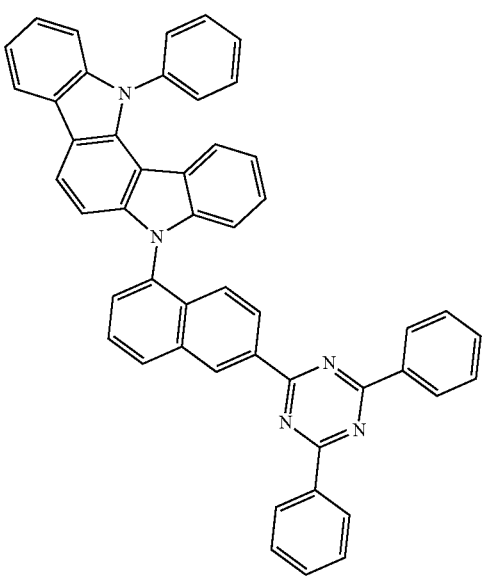
C-6
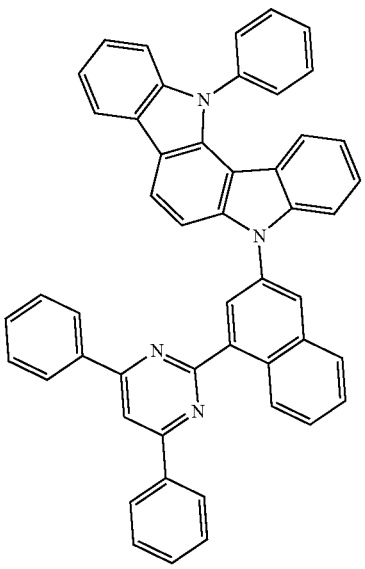
C-7

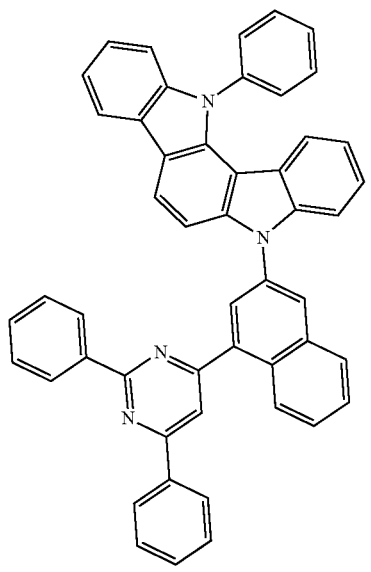
C-8
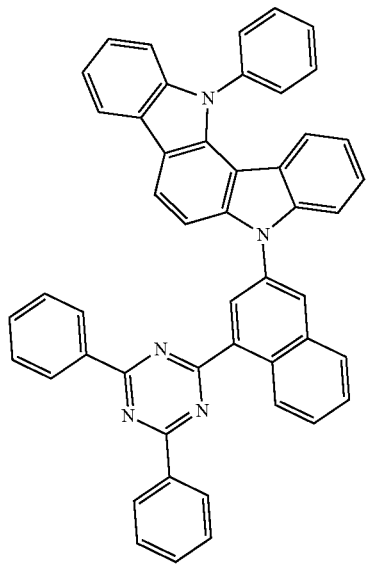
C-9
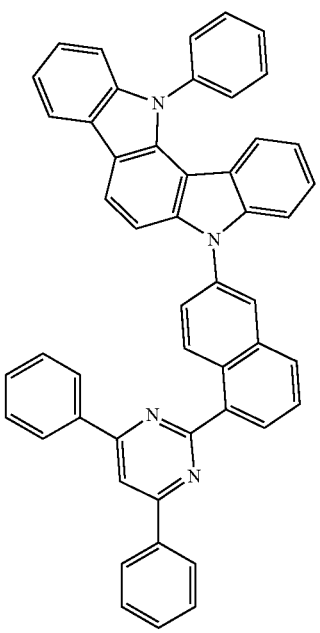
C-10
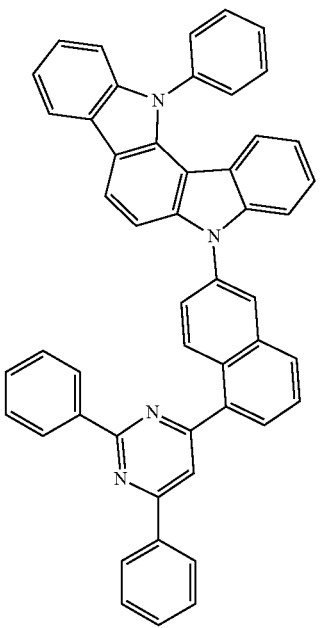
C-11

C-12
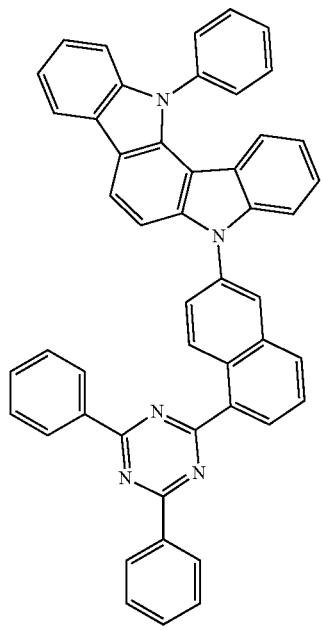
C-14
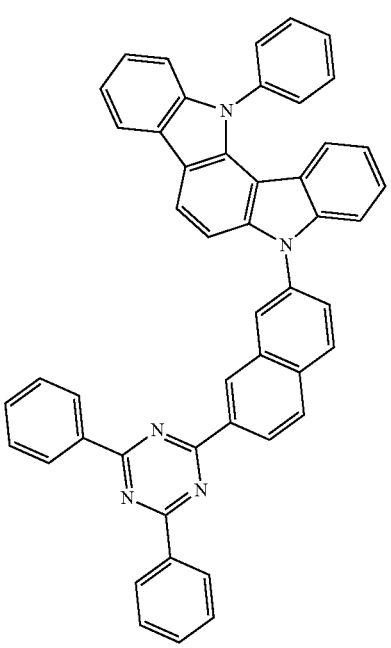
C-13
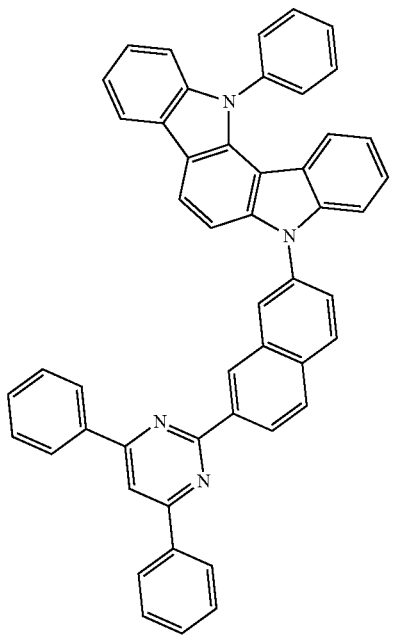
C-15
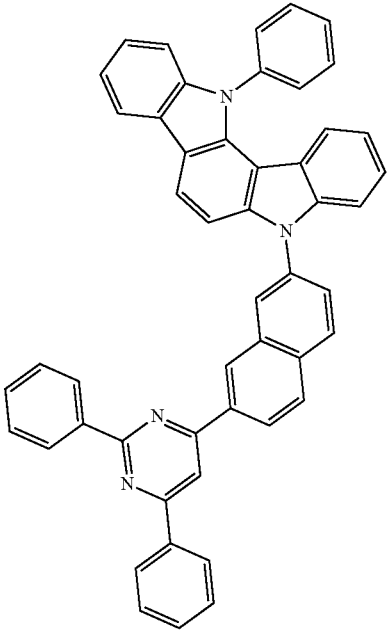

C-16
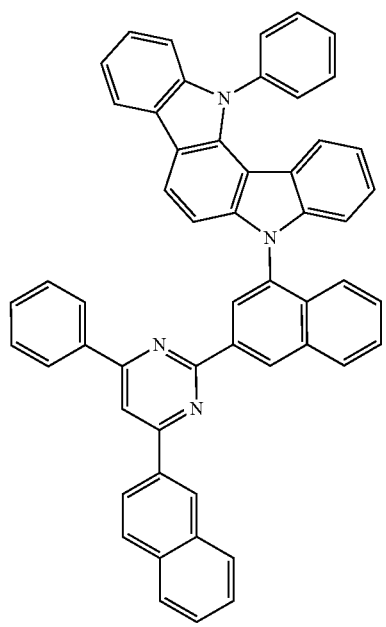
C-17
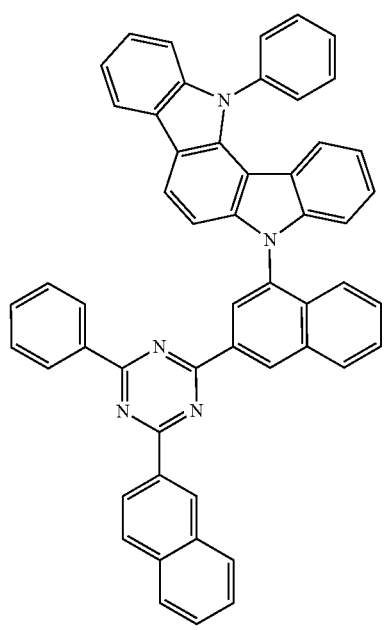
C-18
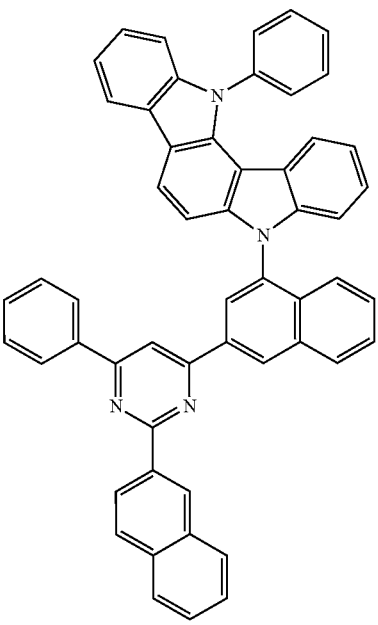
C-19
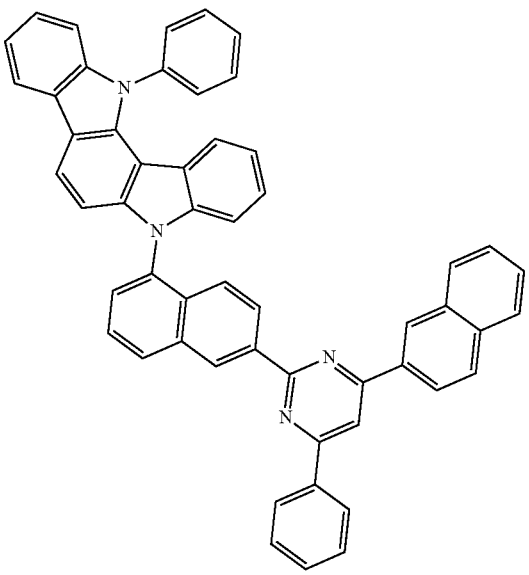

C-20
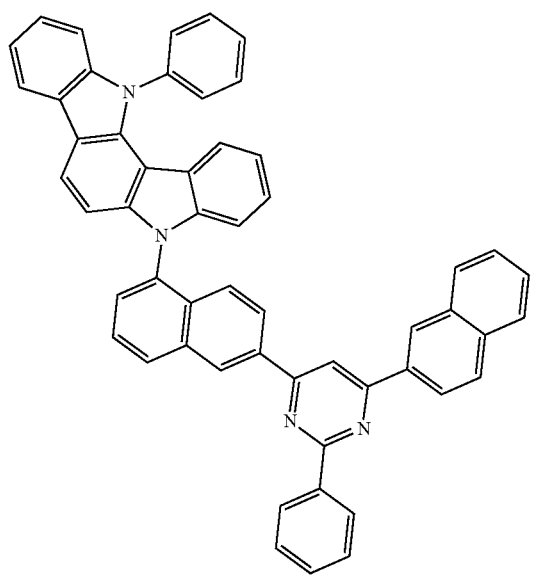
C-22
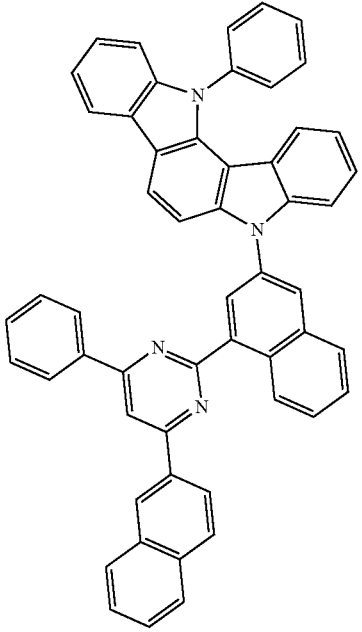
C-21
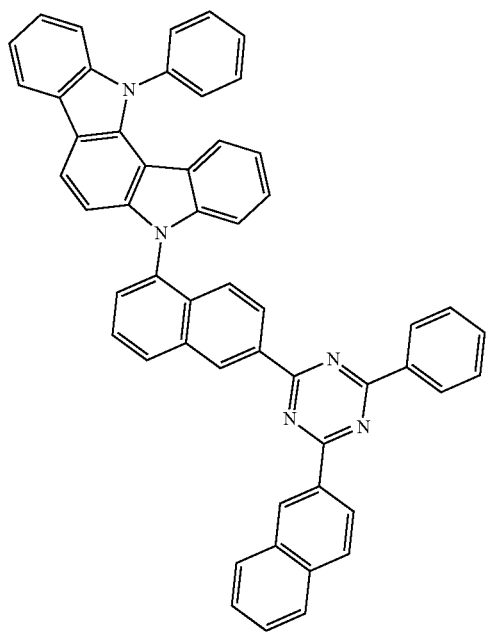
C-23
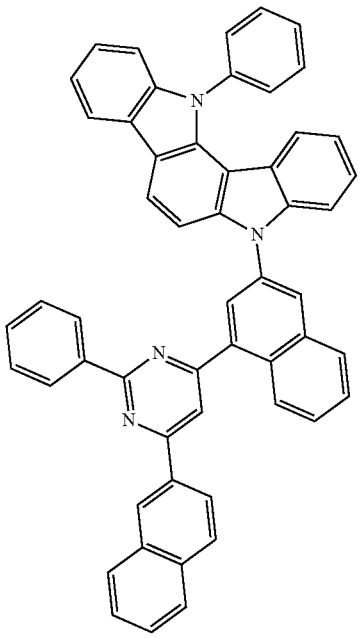

C-24
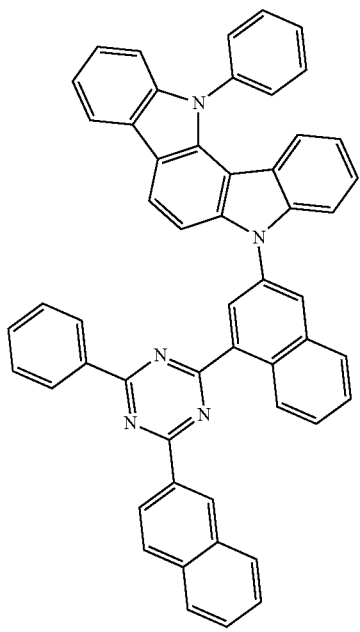
C-25
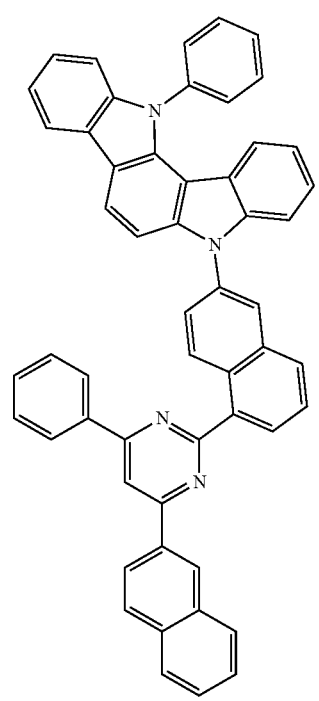
C-26
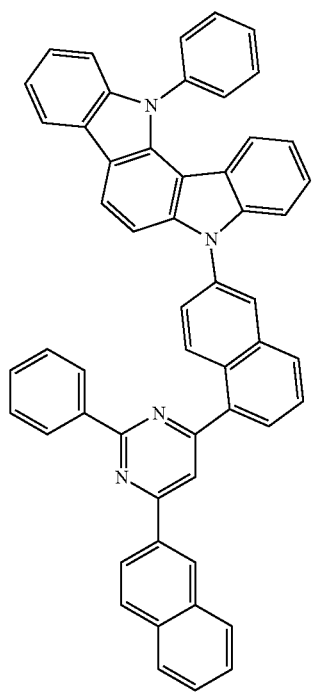
C-27
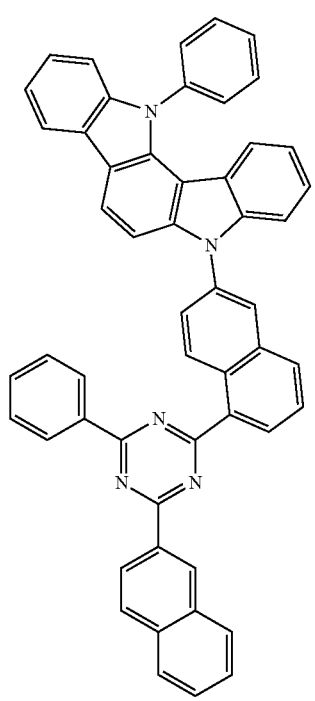

C-28
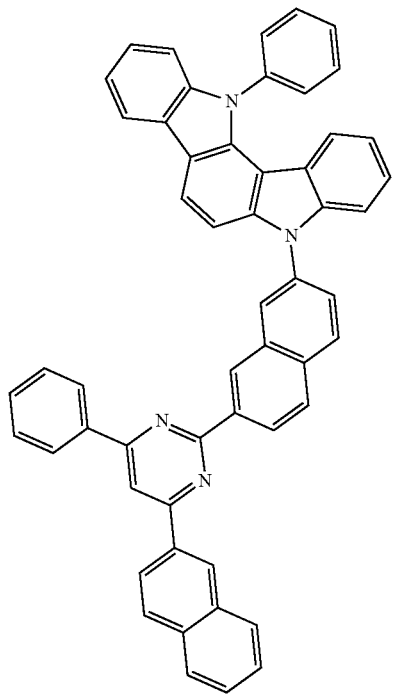
C-29
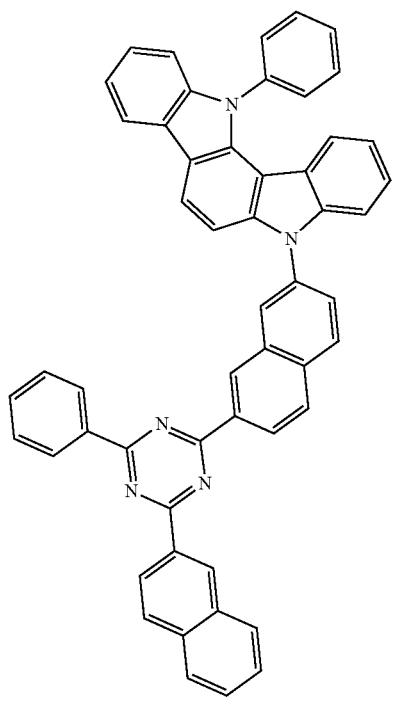
C-30
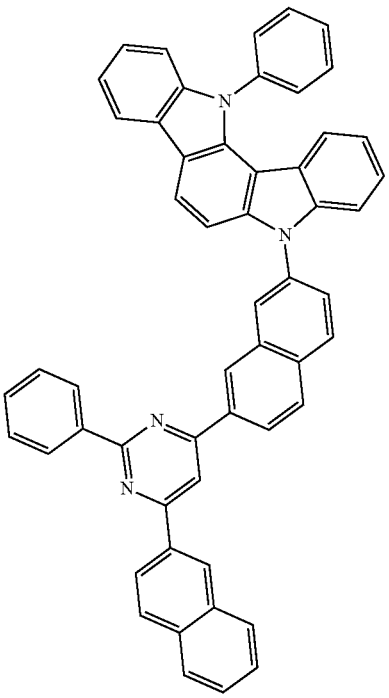
C-31
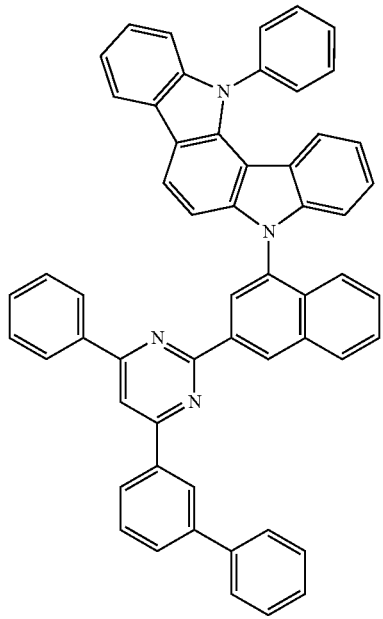

-continued
C-32
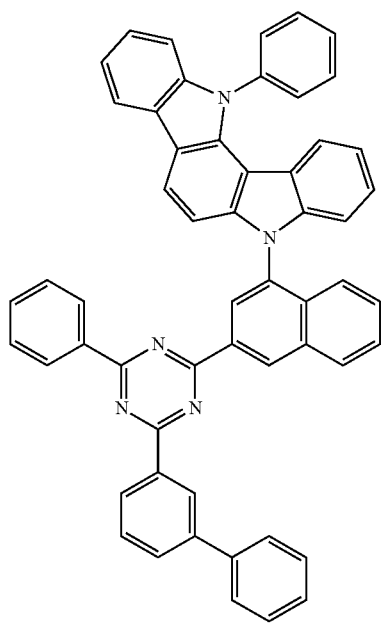
C-34
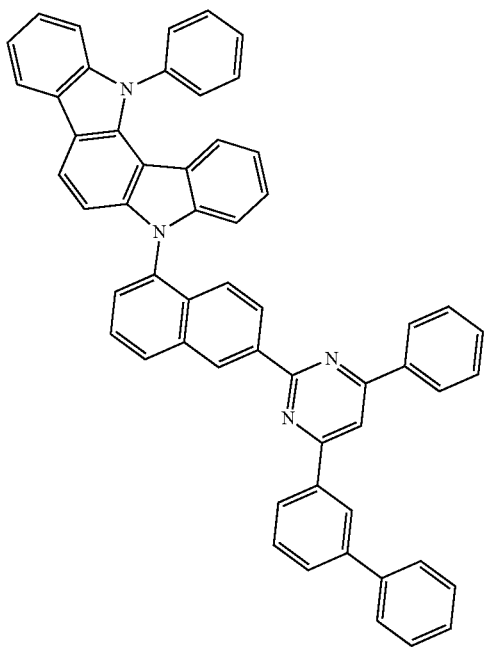
C-33
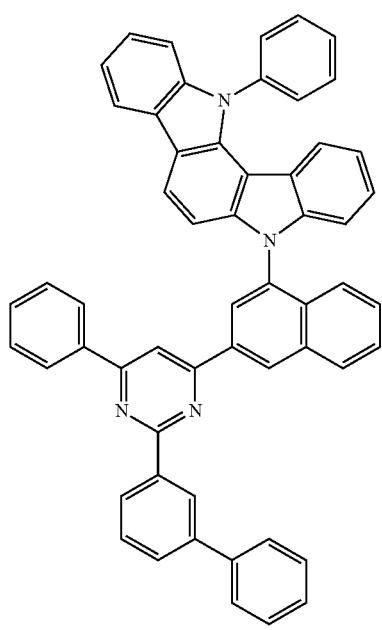
C-35
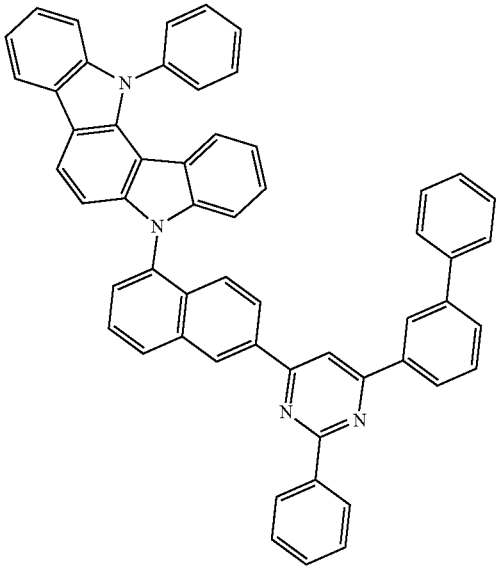

C-36
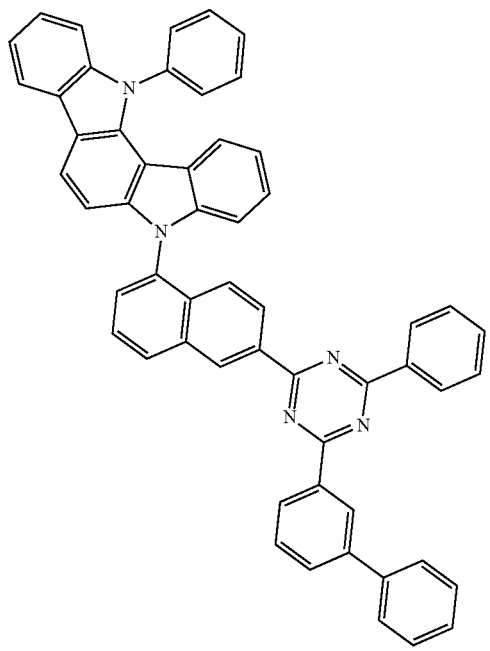
C-38
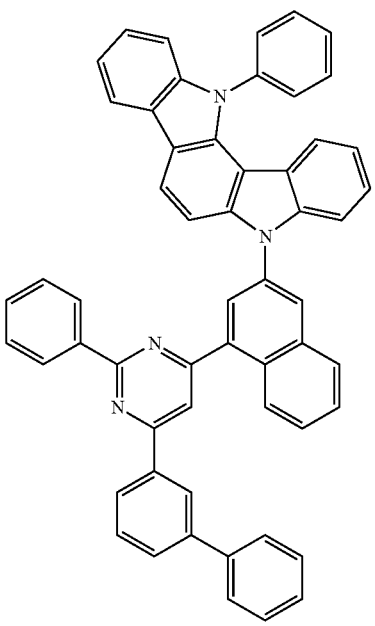
C-37
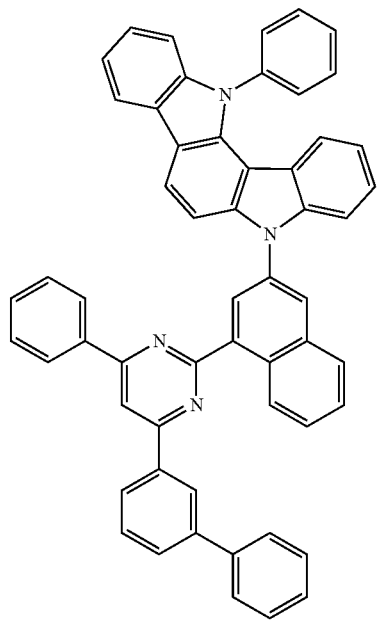
C-39
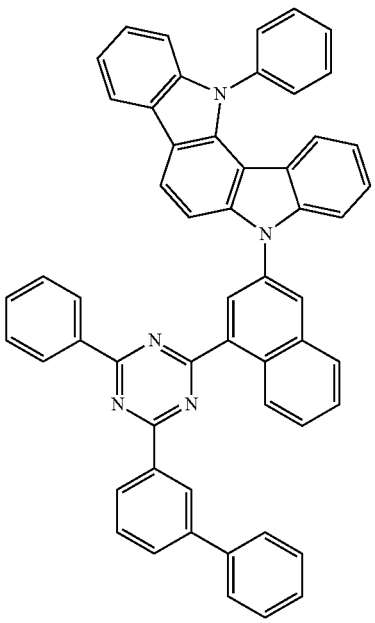

C-40
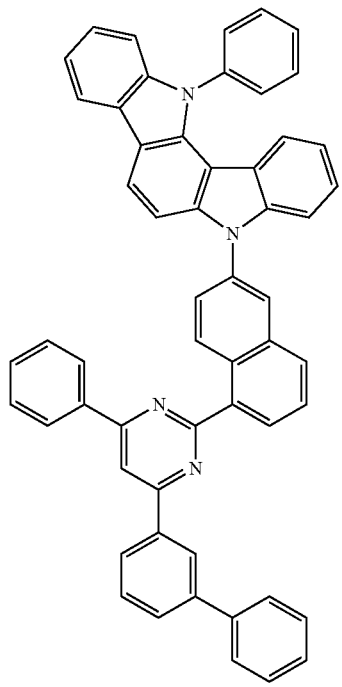
C-42
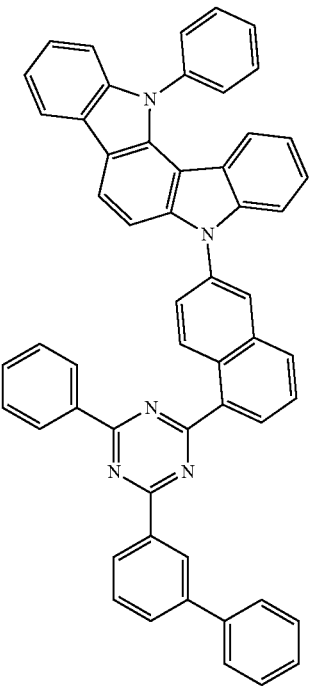
C-41
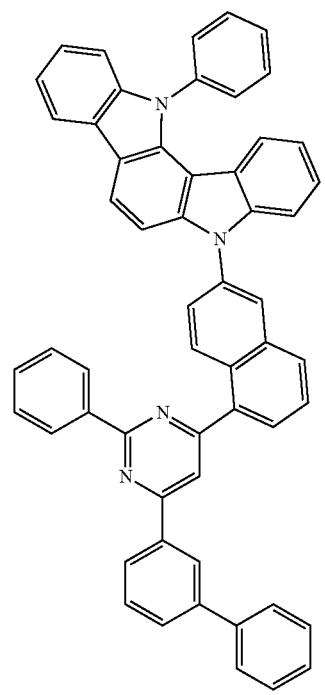
C-43
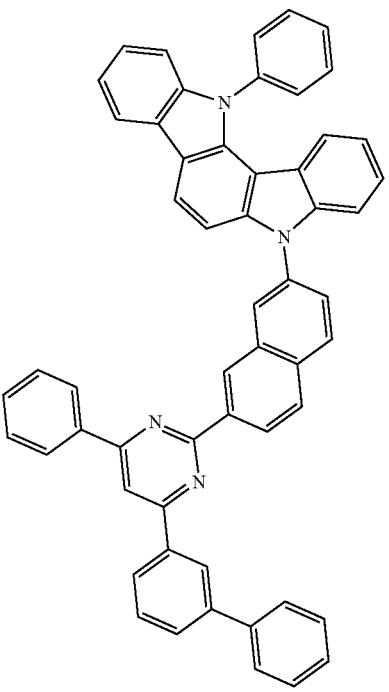

C-44
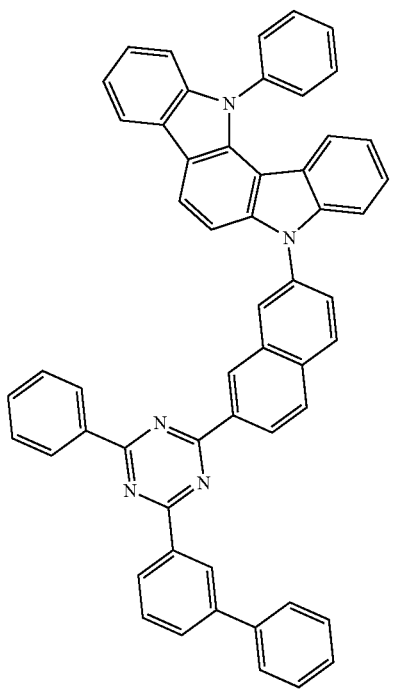
C-46
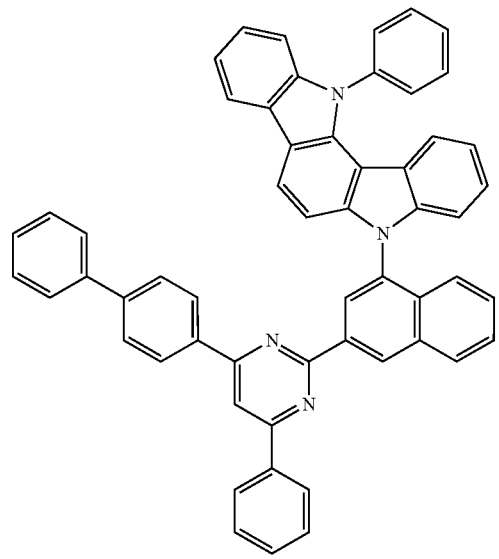
C-45
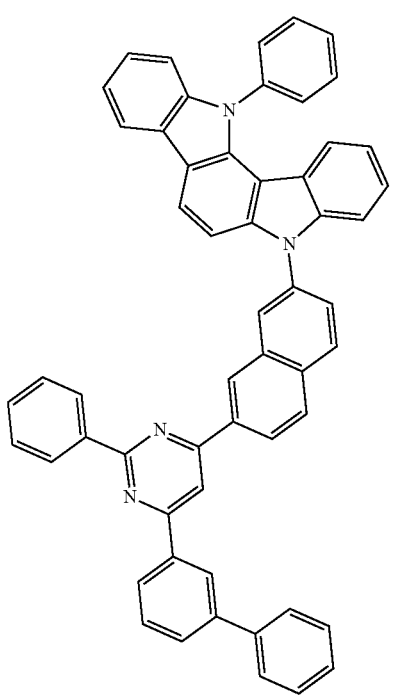
C-47
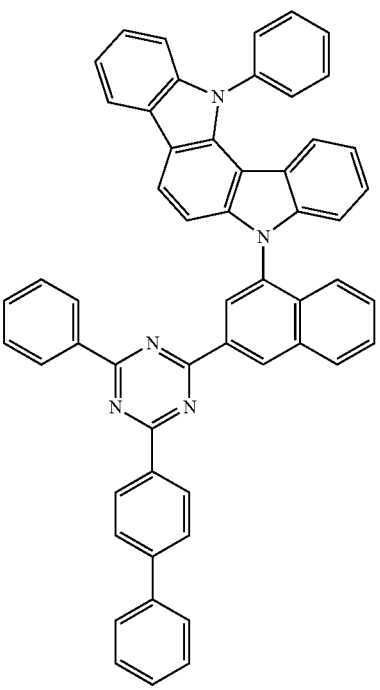

C-48
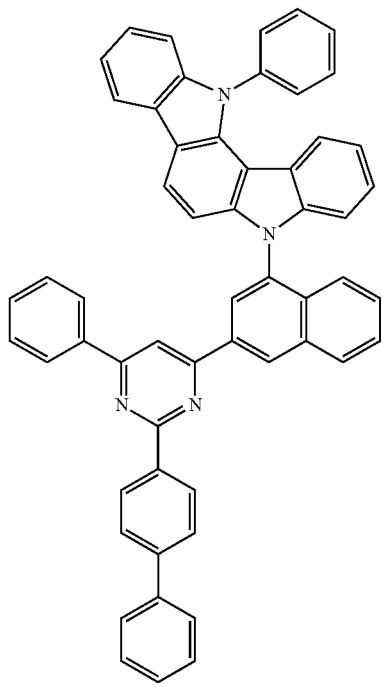
C-50
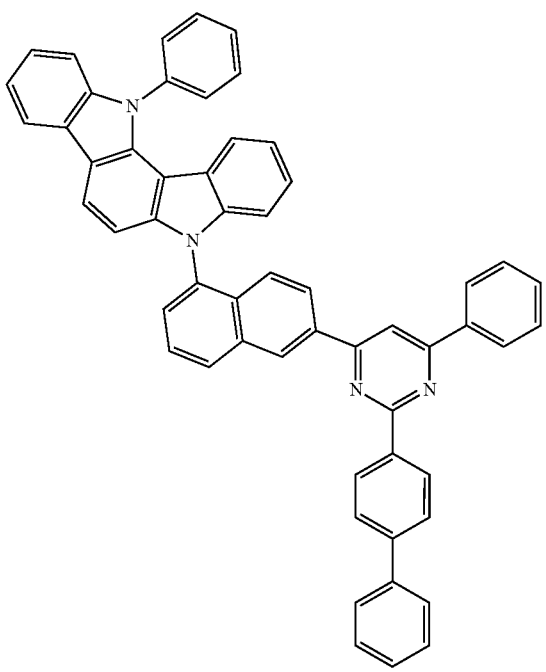
C-49
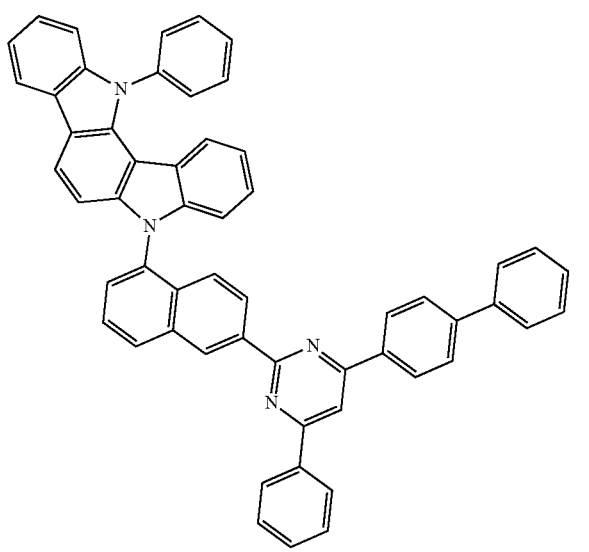
C-51
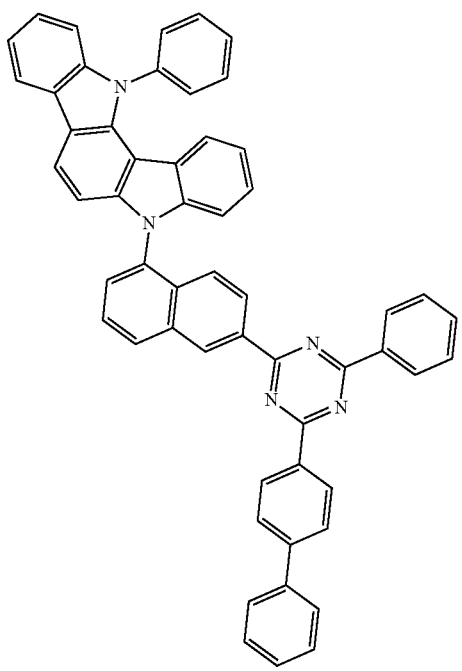

-continued
C-52
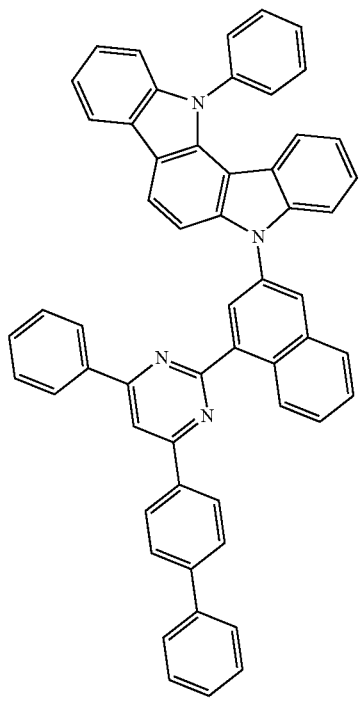
C-53
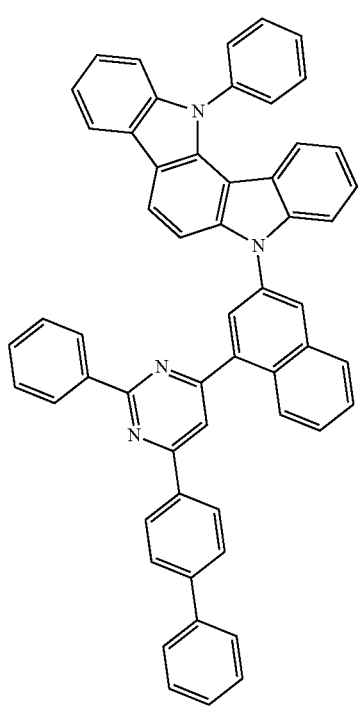
-continued
C-54
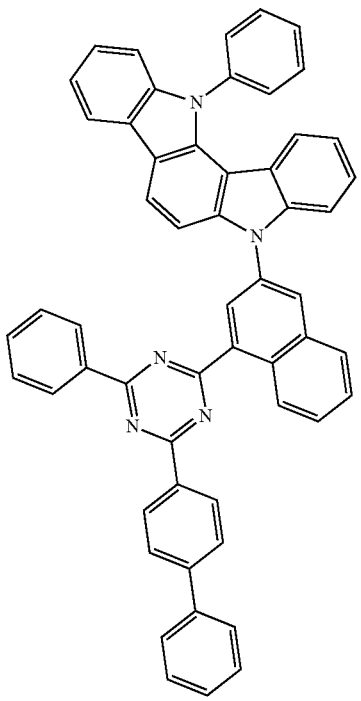
C-55
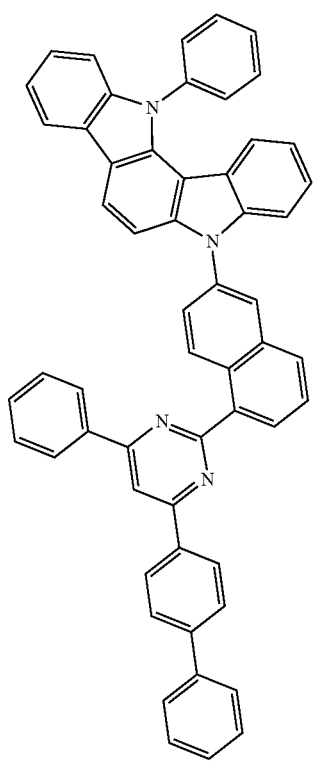

C-56
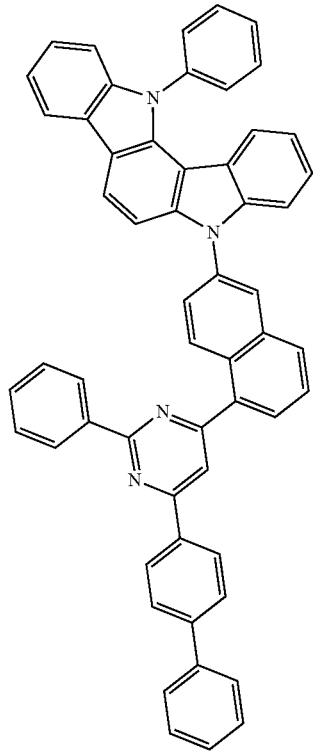
C-57
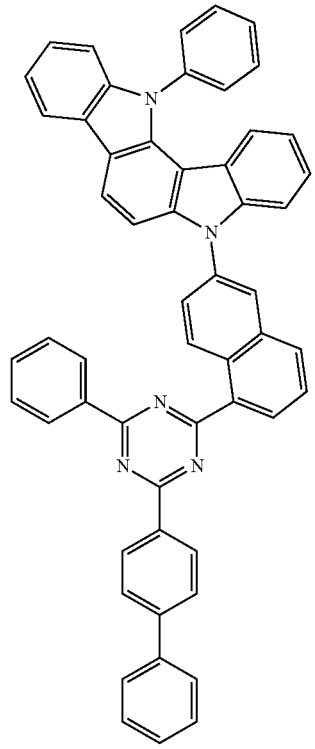
C-58
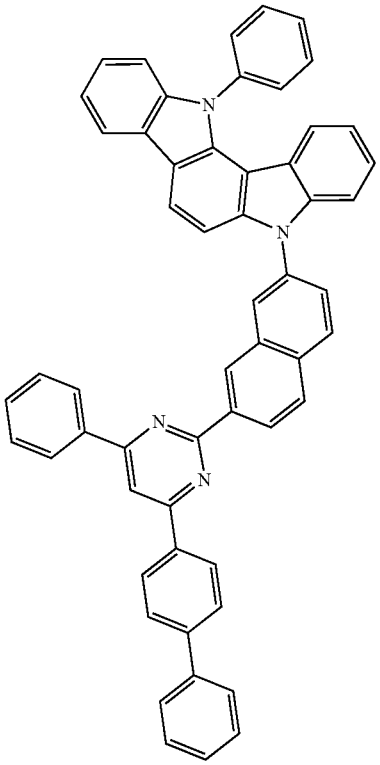
C-59
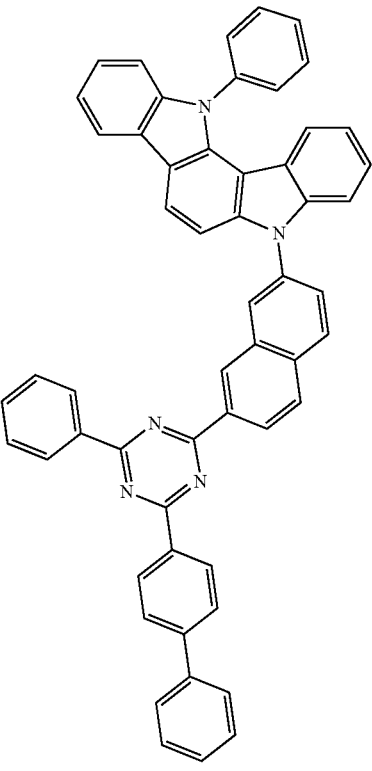

-continued
C-60
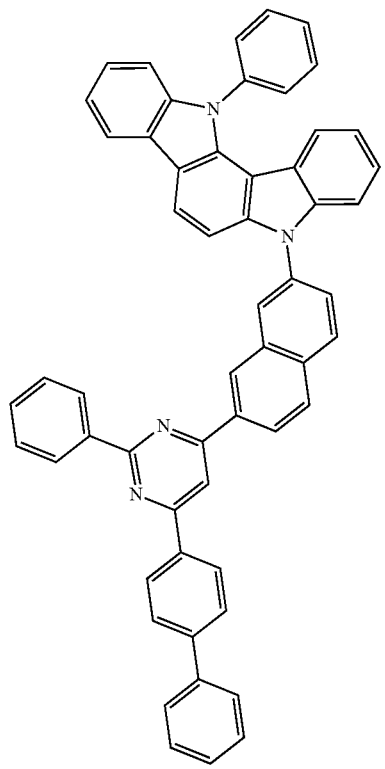
C-62
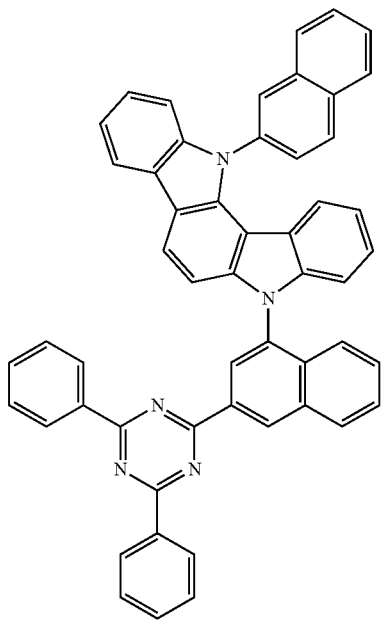
C-61
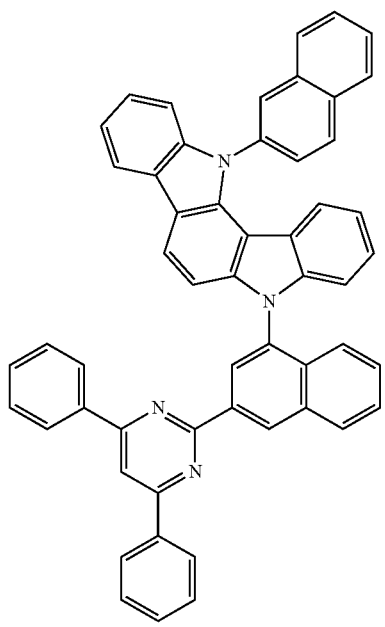
C-63
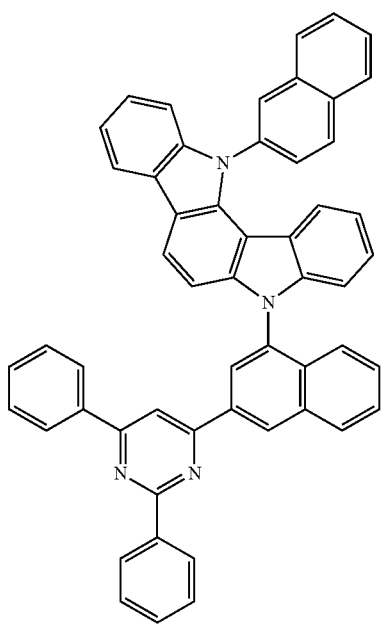

C-64
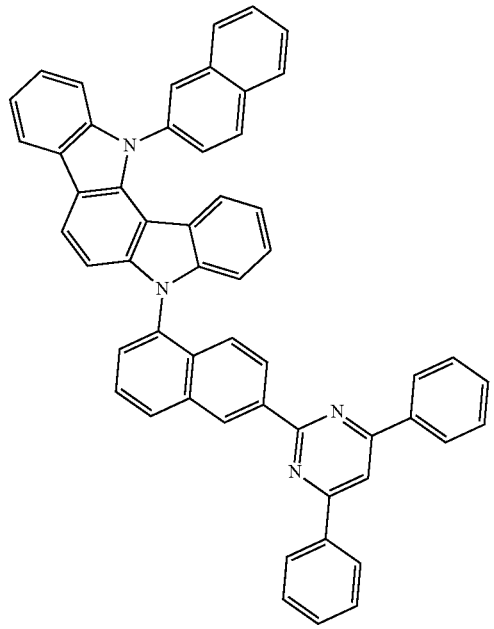
C-66
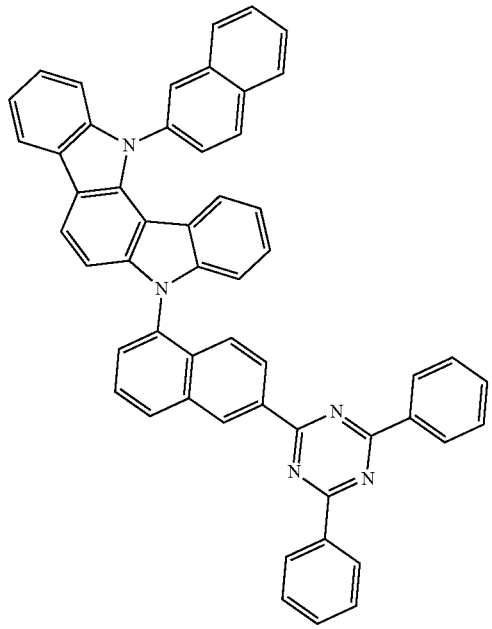
C-65
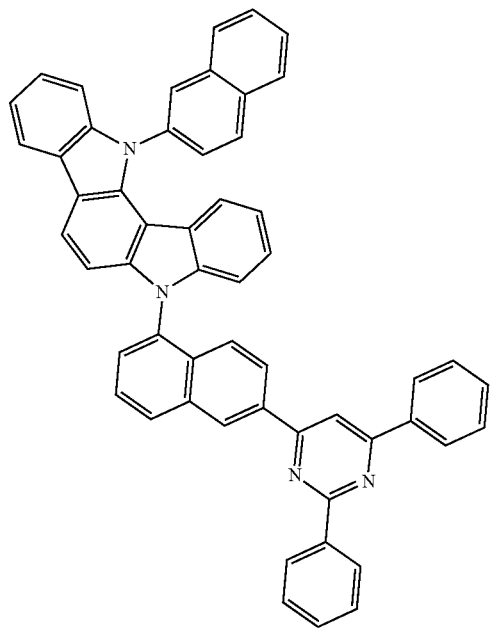
C-67
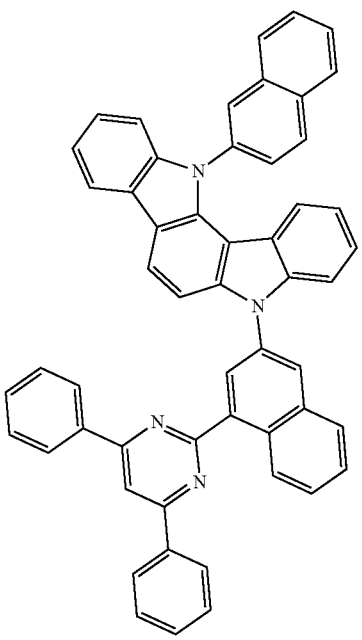

C-68
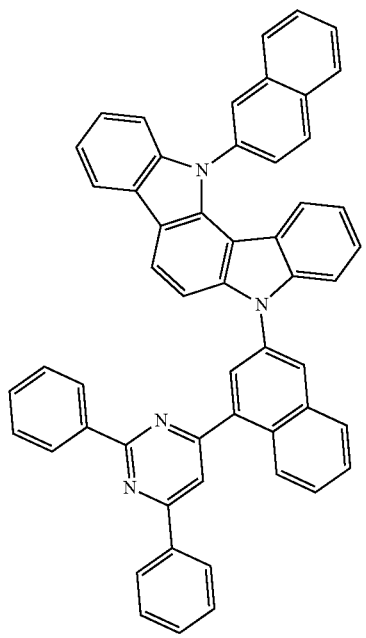
C-70
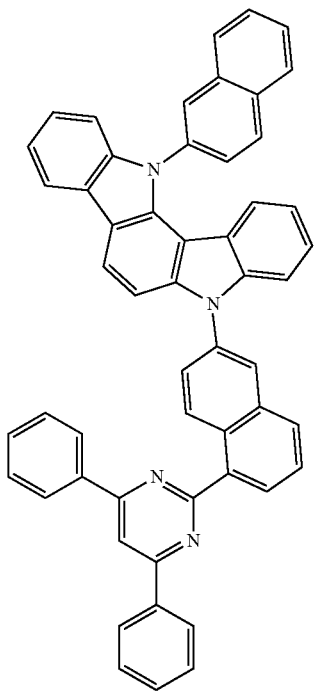
C-69
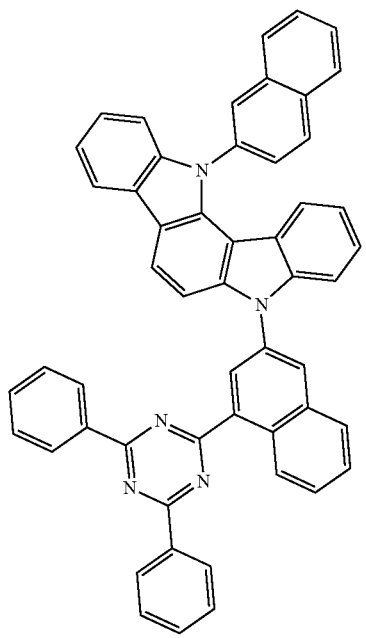
C-71
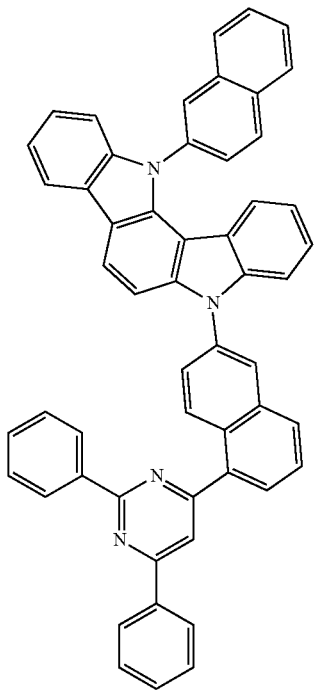

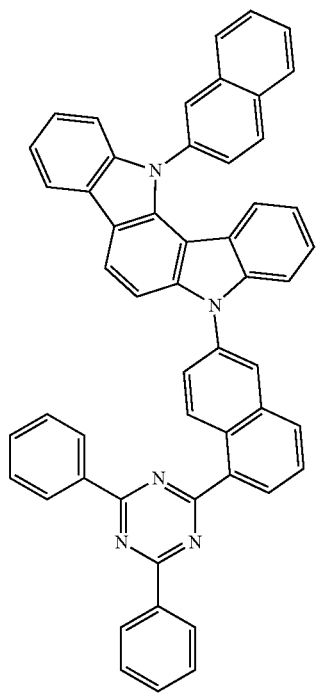
C-72
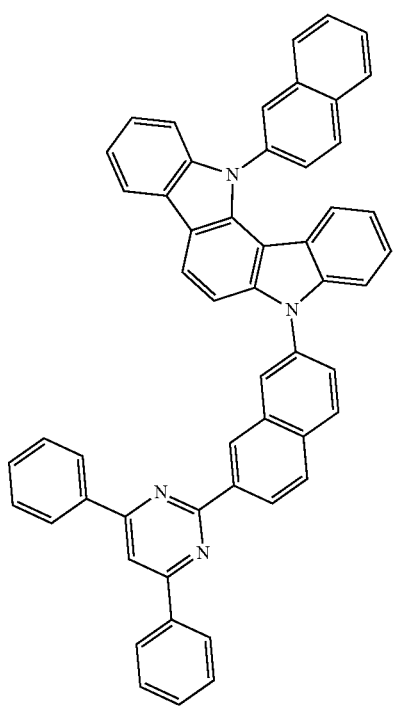
C-73
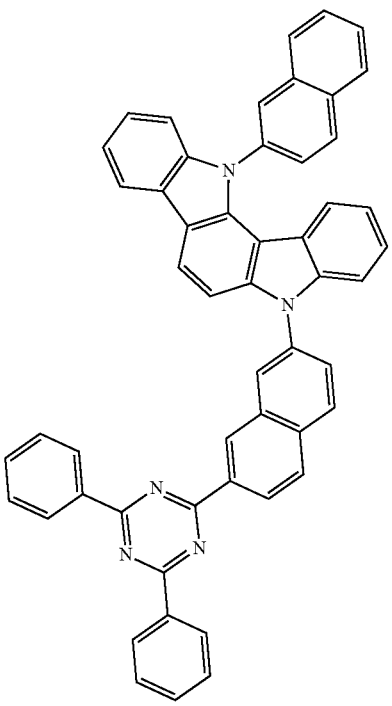
C-74
C-75

C-76
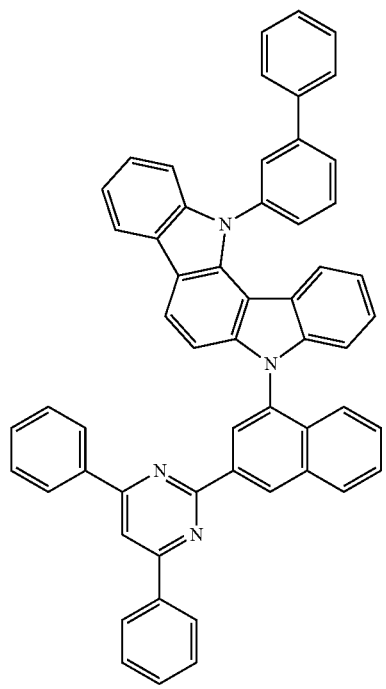
C-78
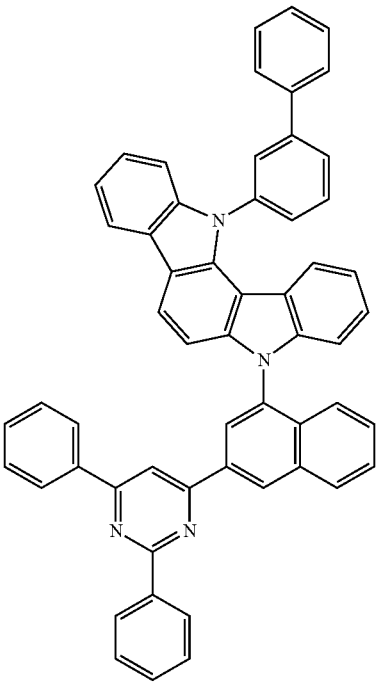
C-77
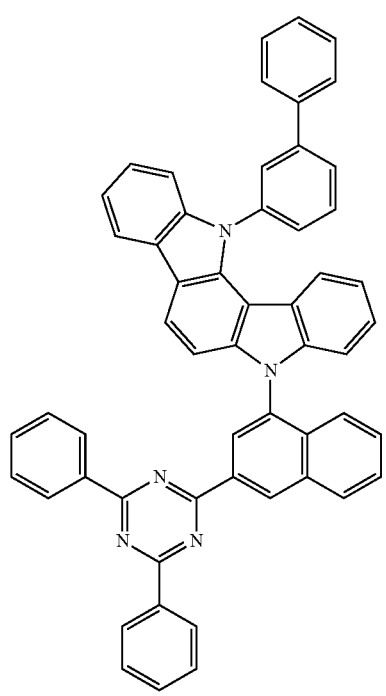
C-79
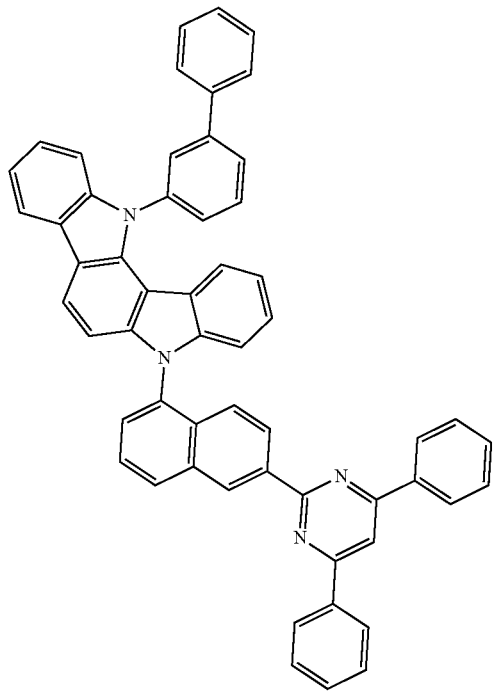

C-80
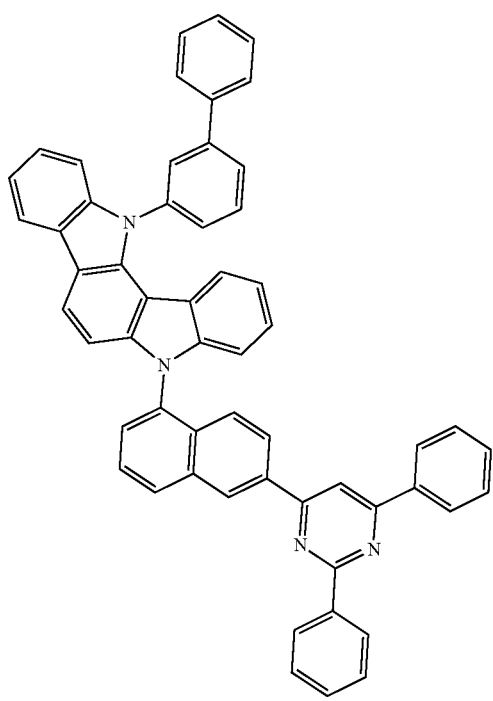
C-82
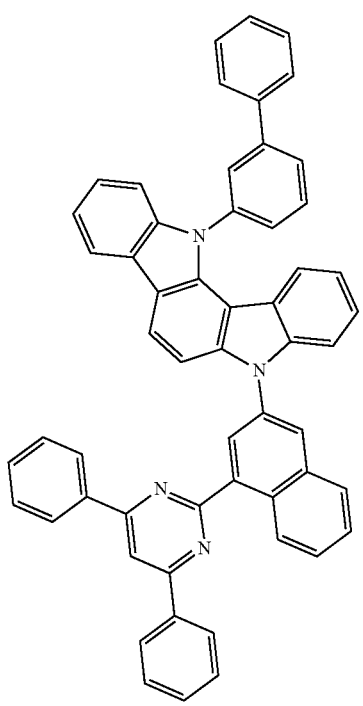
C-81
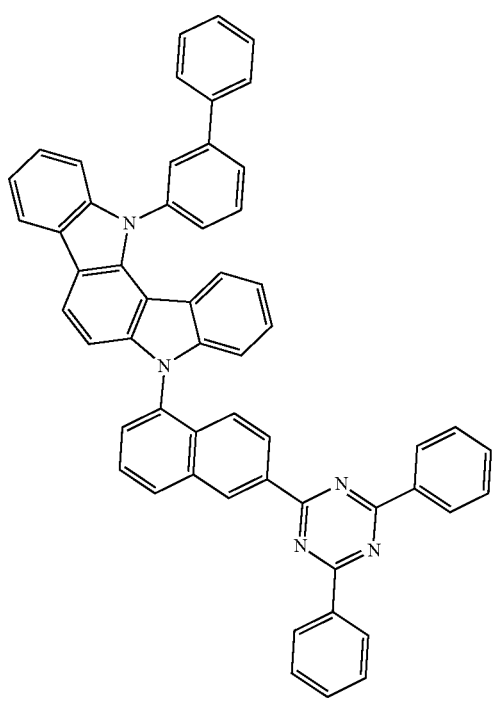
C-83
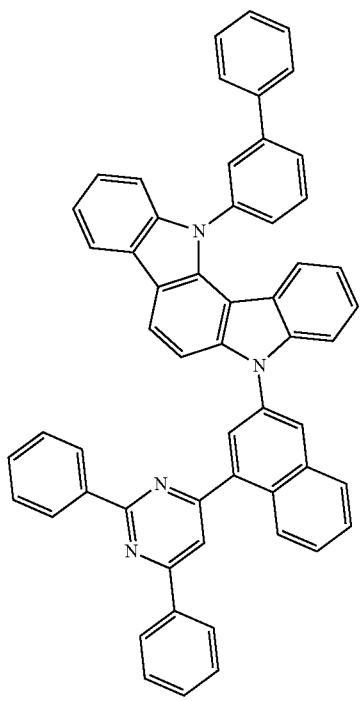

C-84
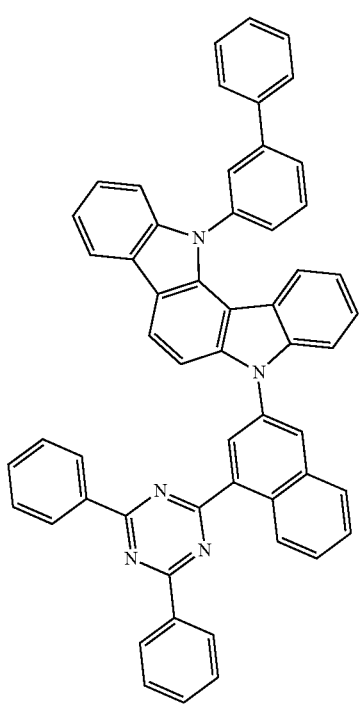
C-85
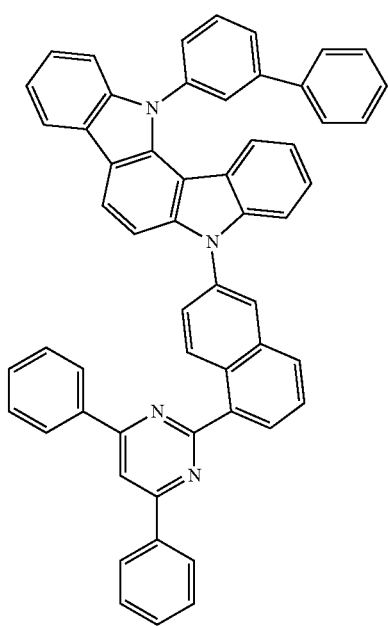
C-86
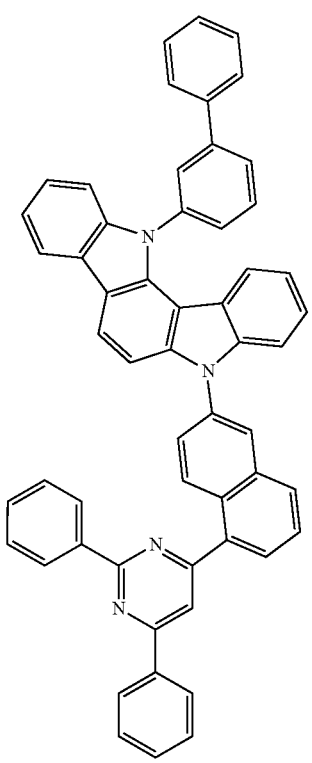
C-87
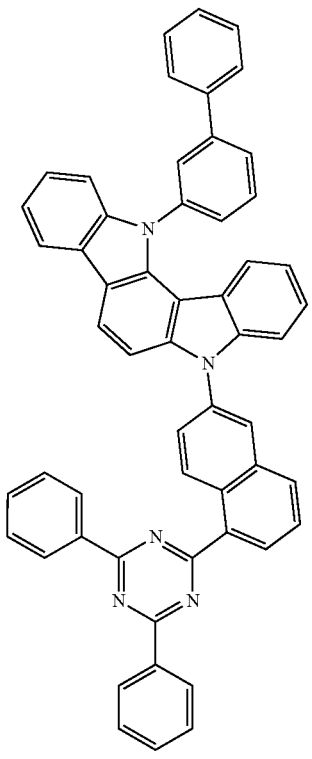

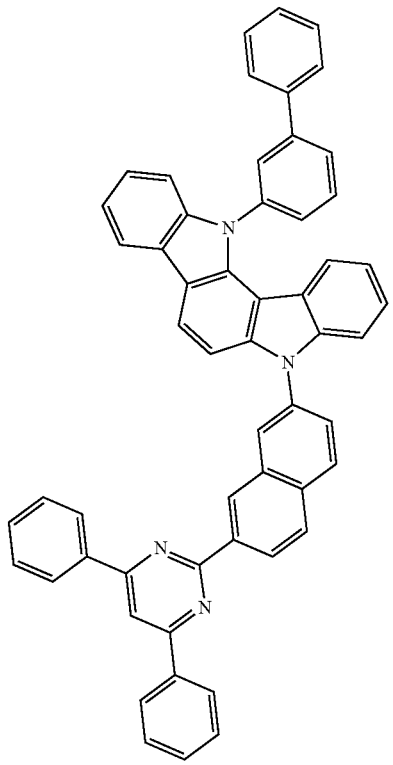
C-88
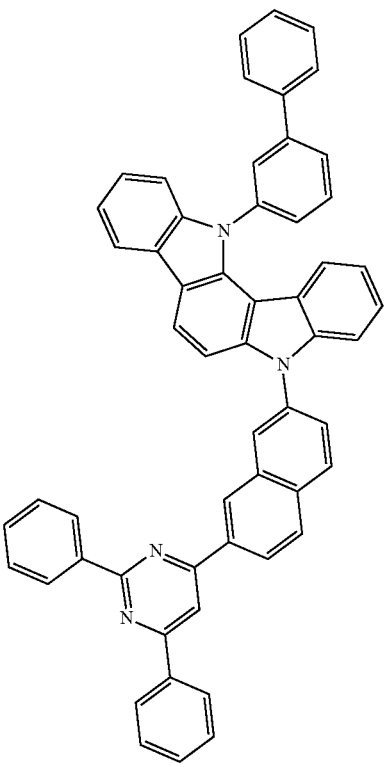
C-90
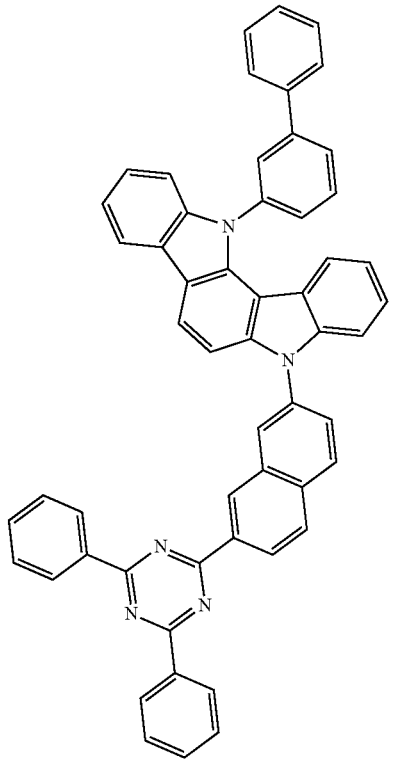
C-89
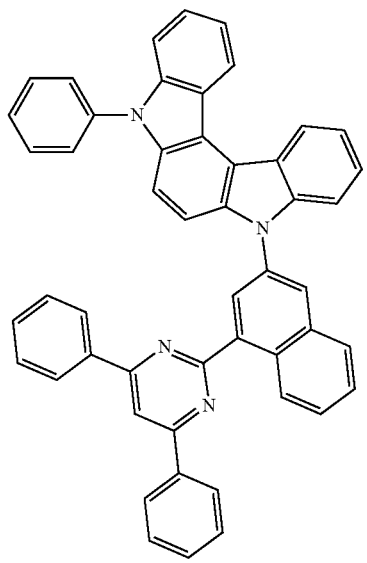
C-91

C-92
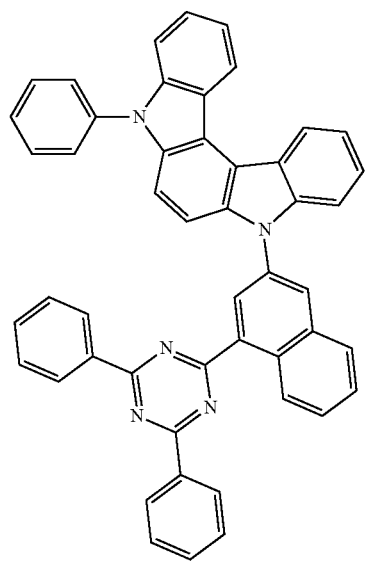
C-94
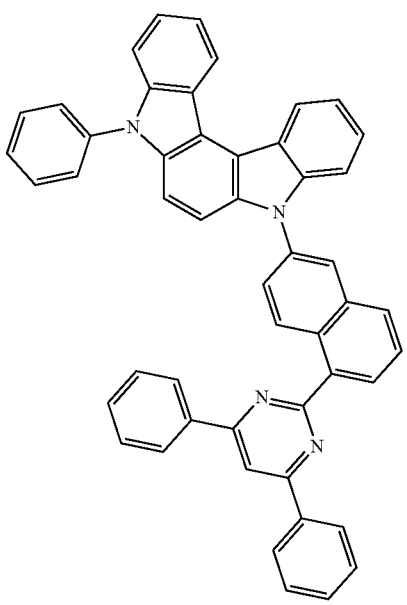
C-93
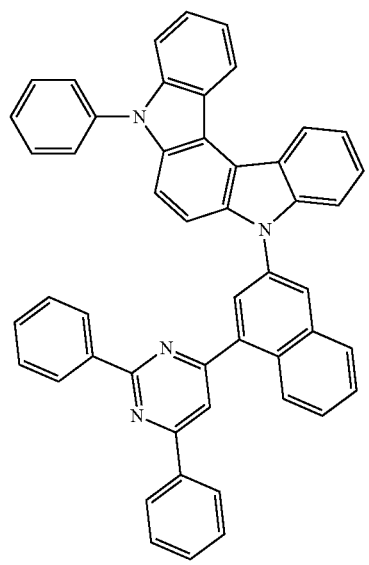
C-95
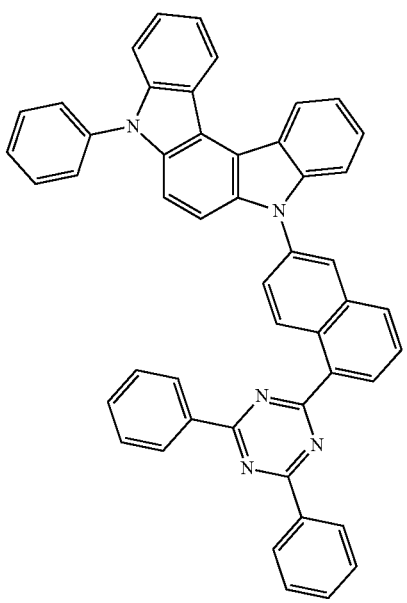

C-96
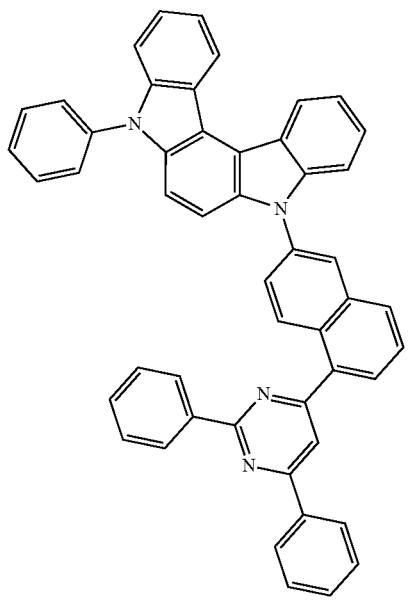
C-97
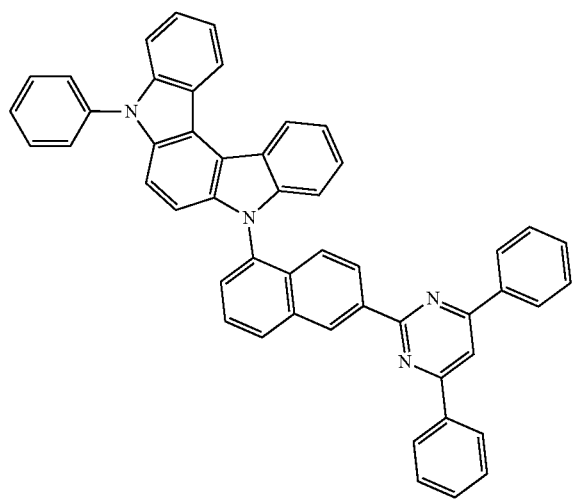
C-98
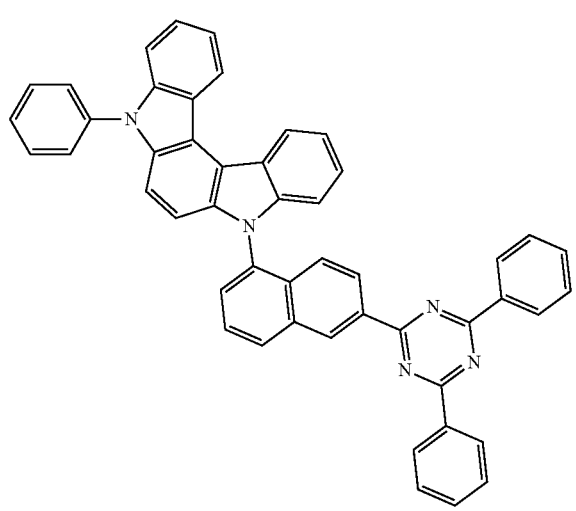
C-99
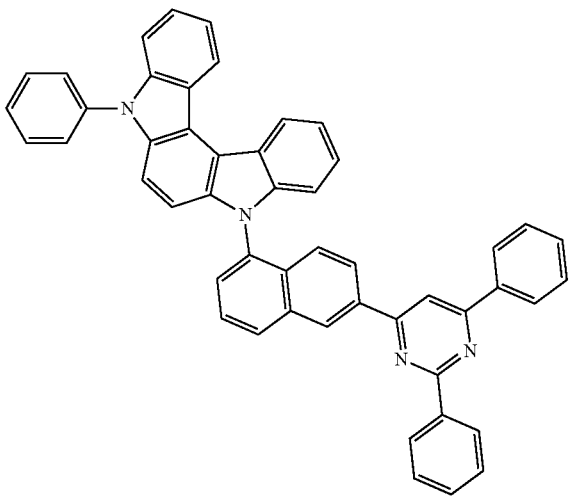
C-100
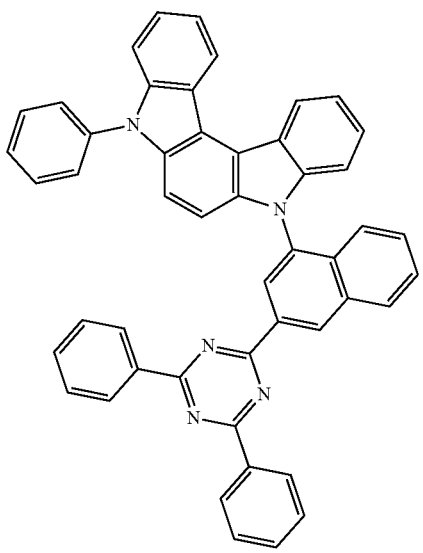
C-101
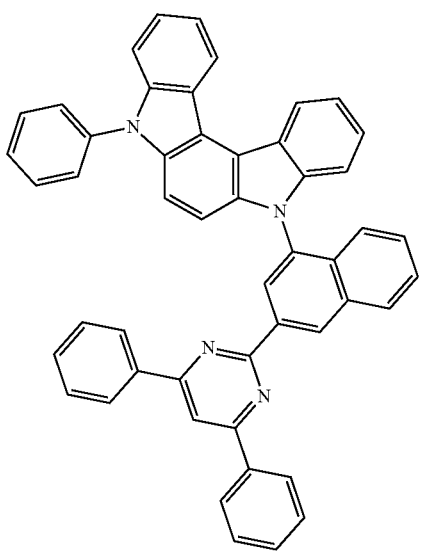

C-102
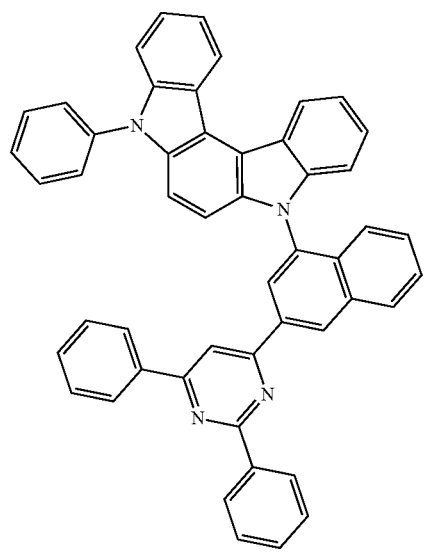
C-103
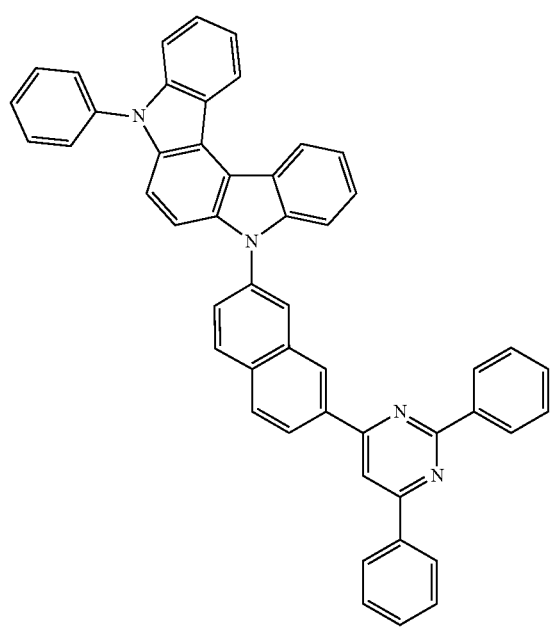
C-104
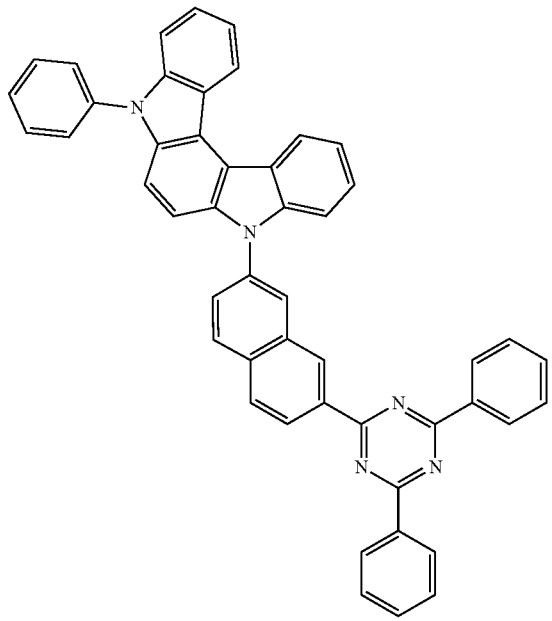
C-105
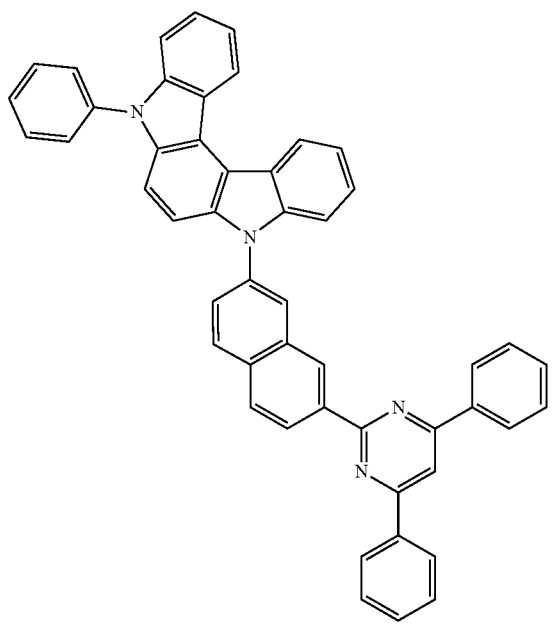

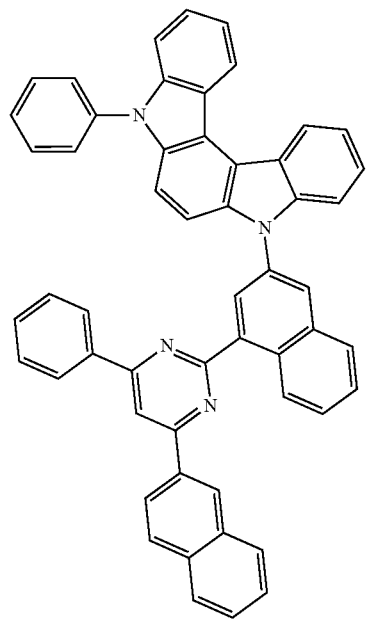
C-106
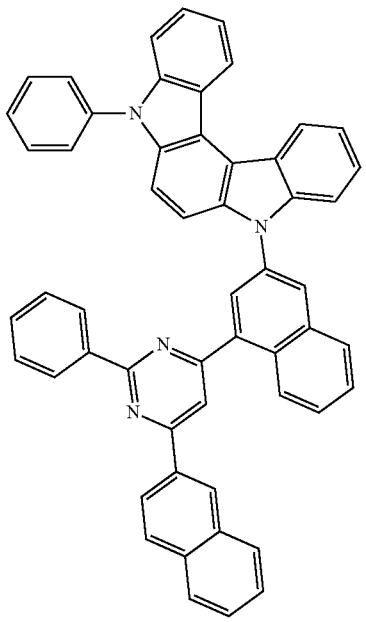
C-108
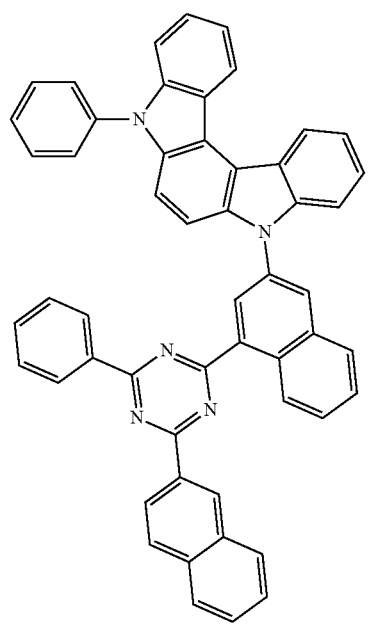
C-107
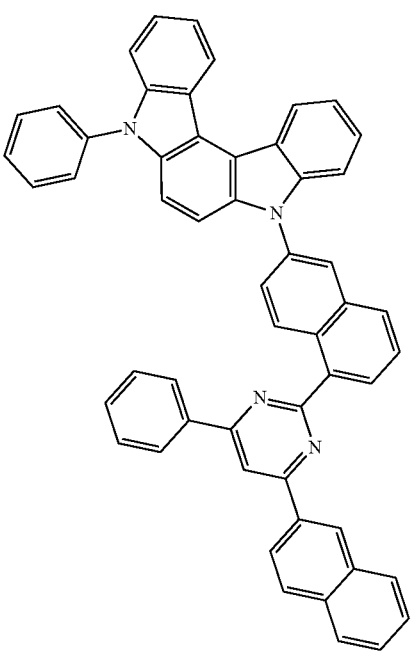
C-109

C-110
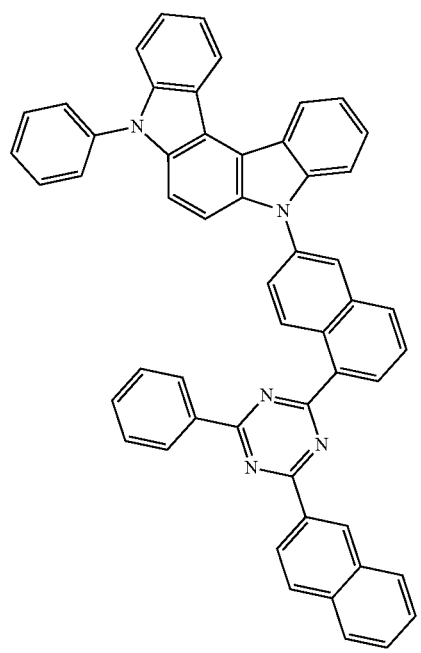
C-111
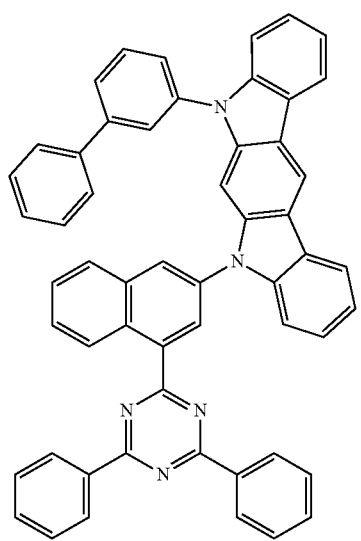
C-112
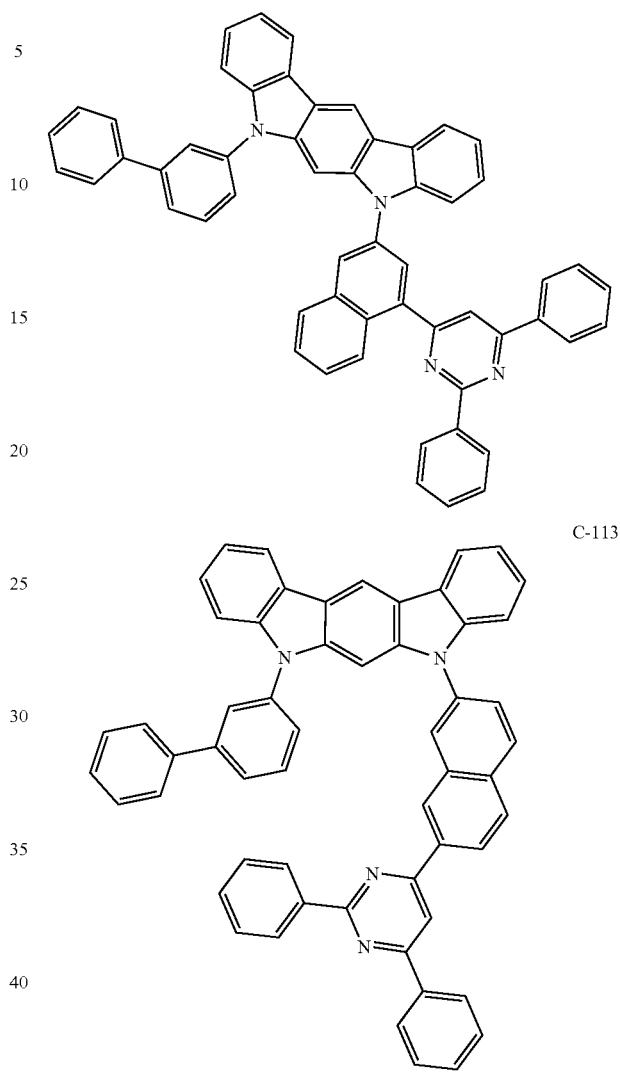
C-113
C-114
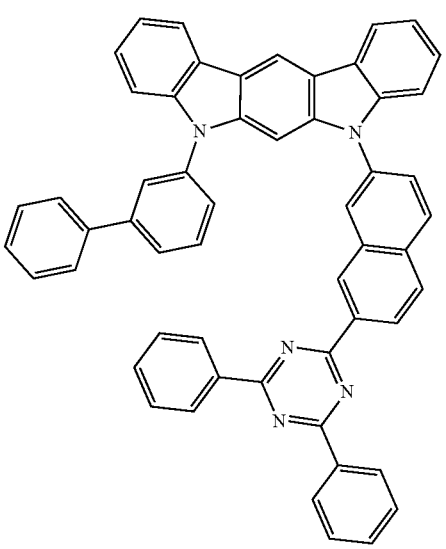

C-115
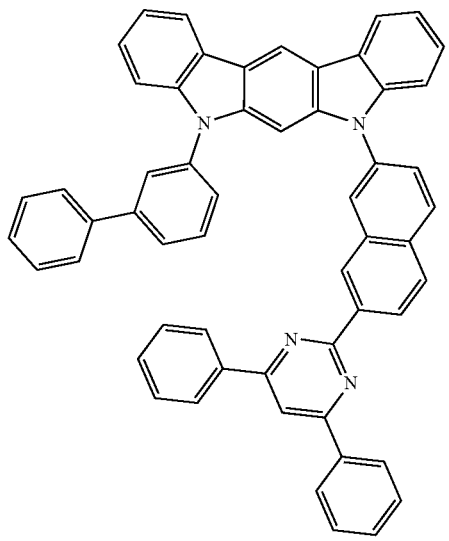
C-116
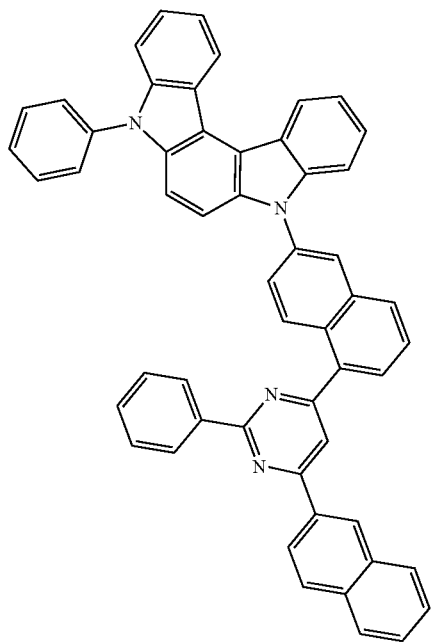
C-117
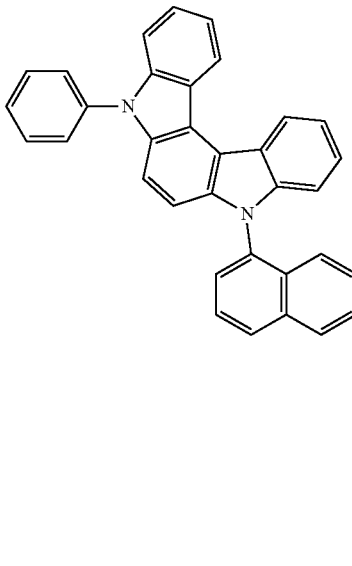
C-118
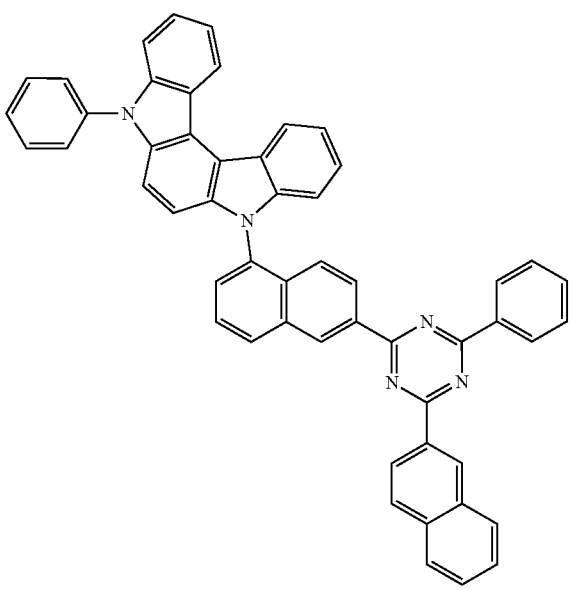

C-119
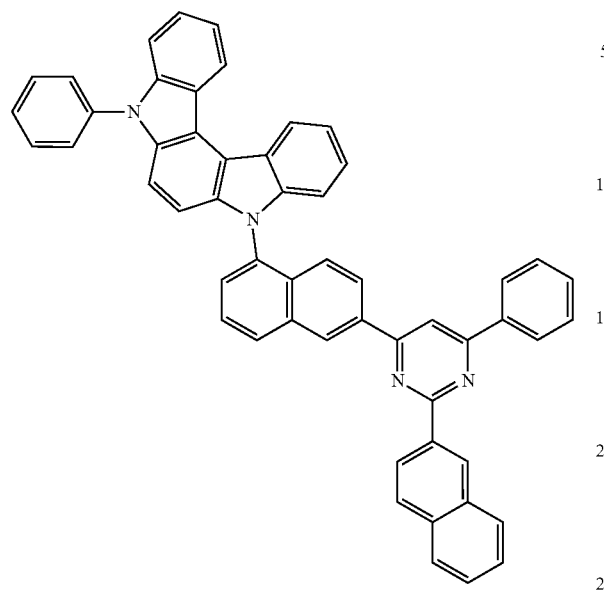
C-120
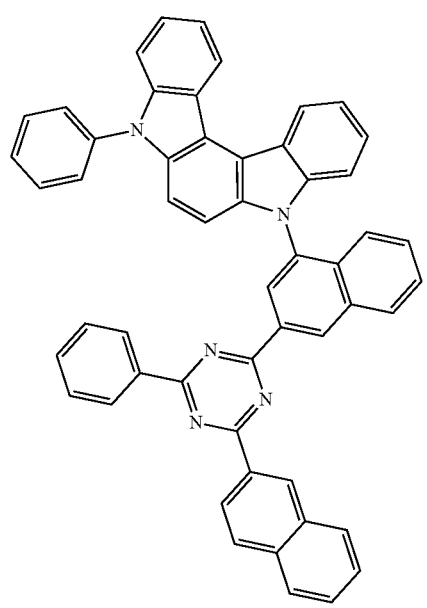
C-121
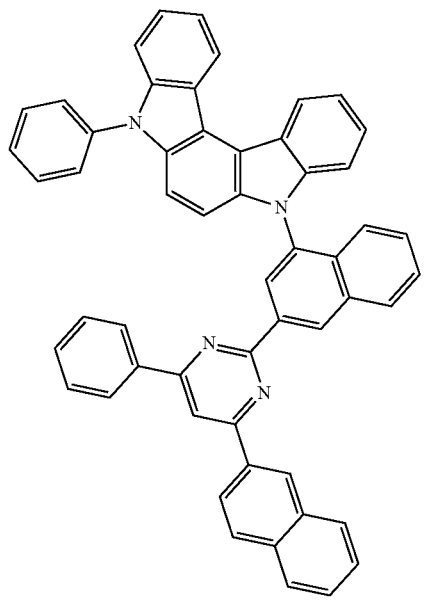
C-122
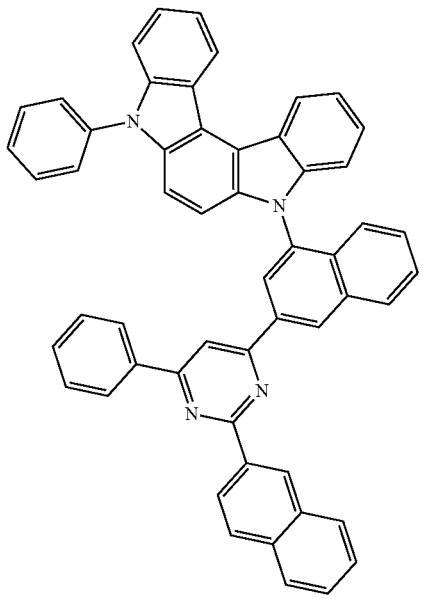

C-123
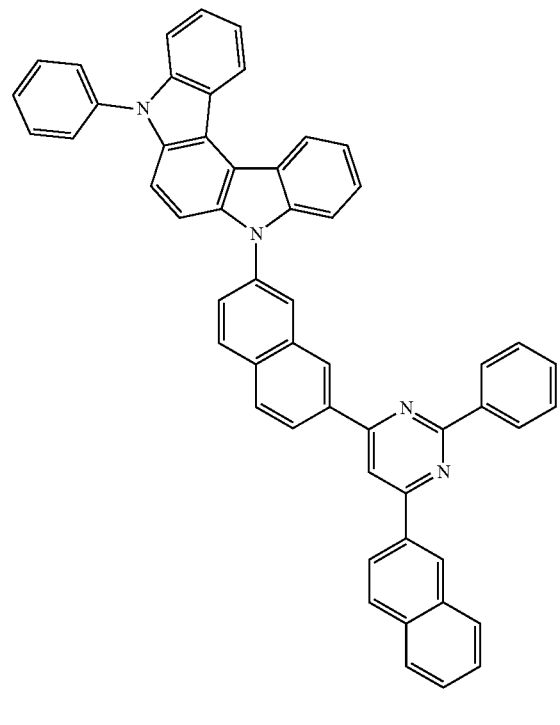
C-124
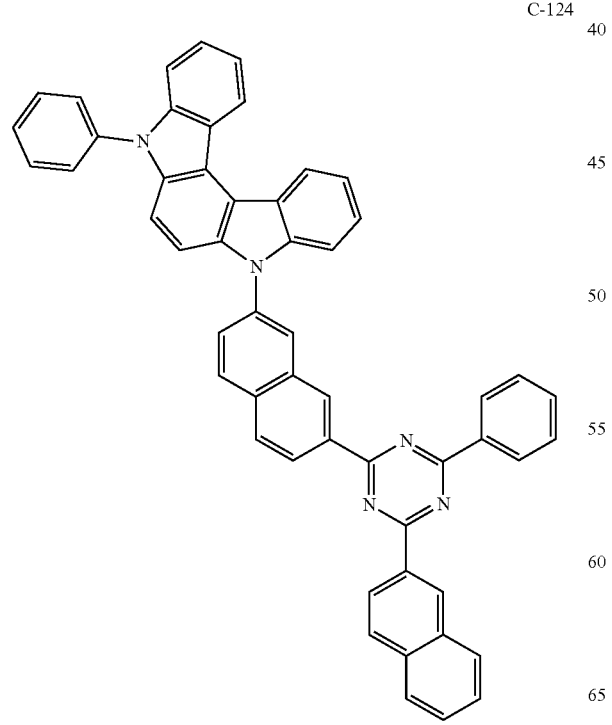
C-125
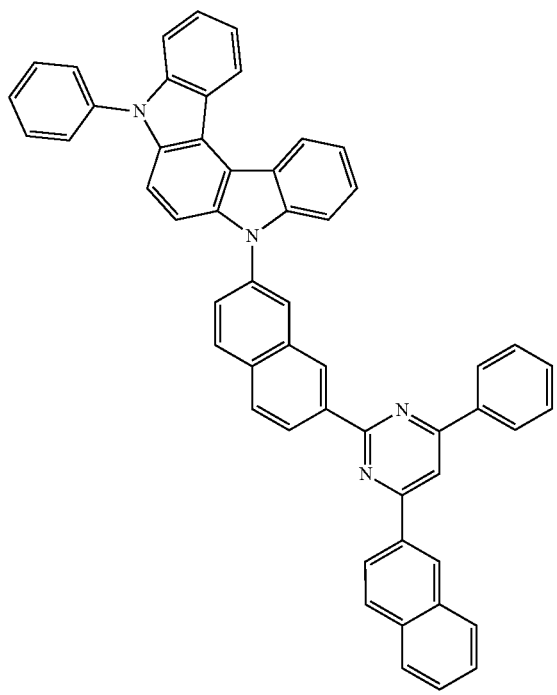
C-126
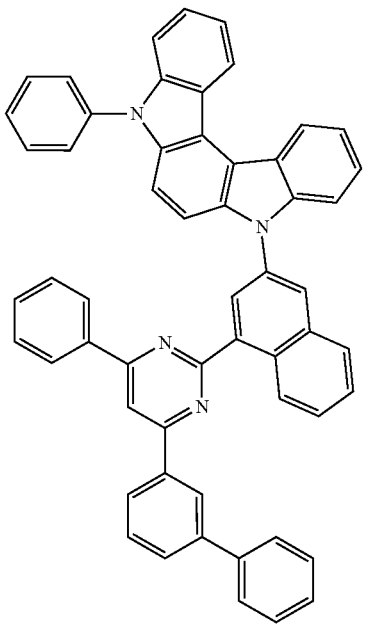

C-127
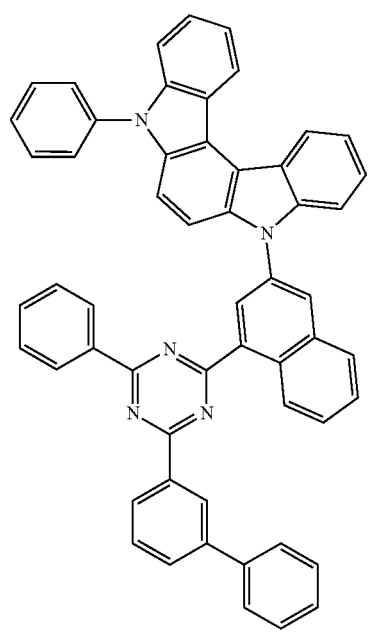
C-128
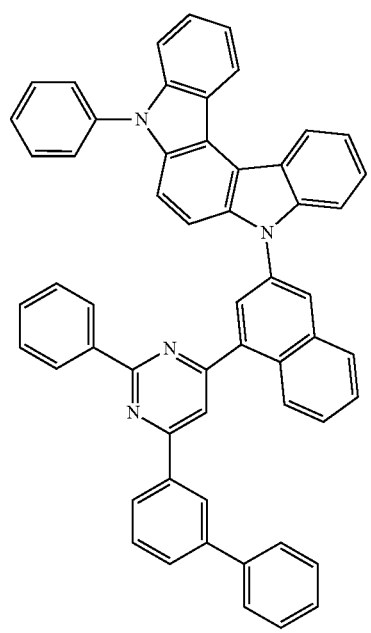
C-129
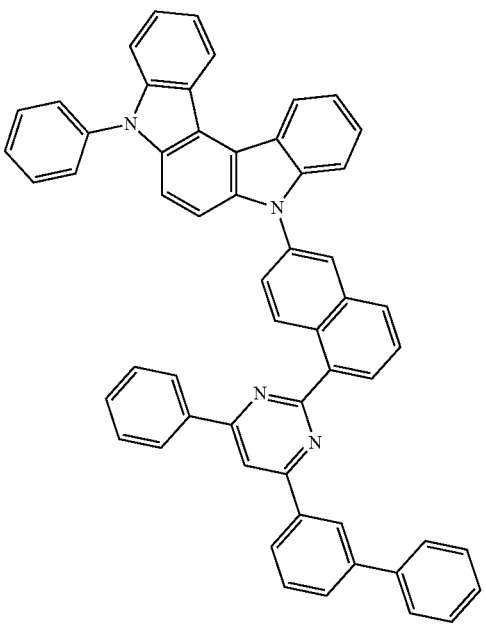
C-130

C-131
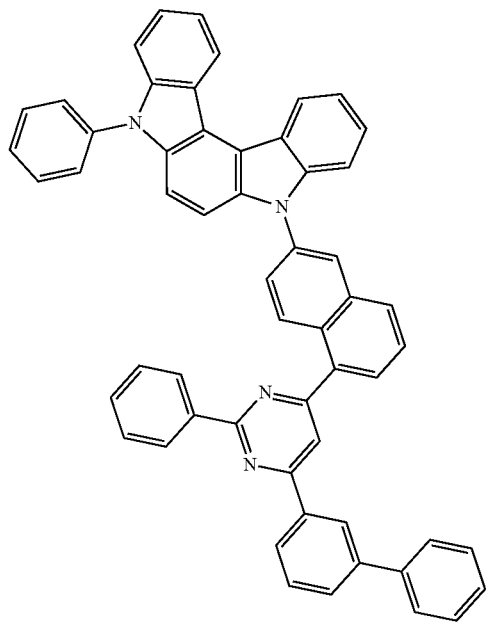
C-133
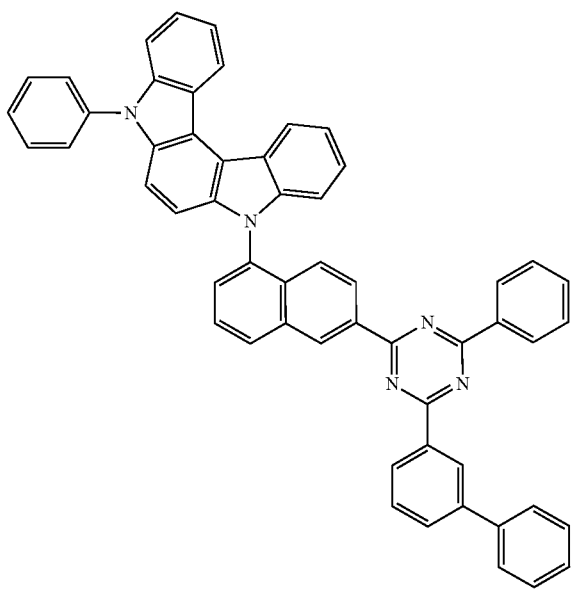
C-132
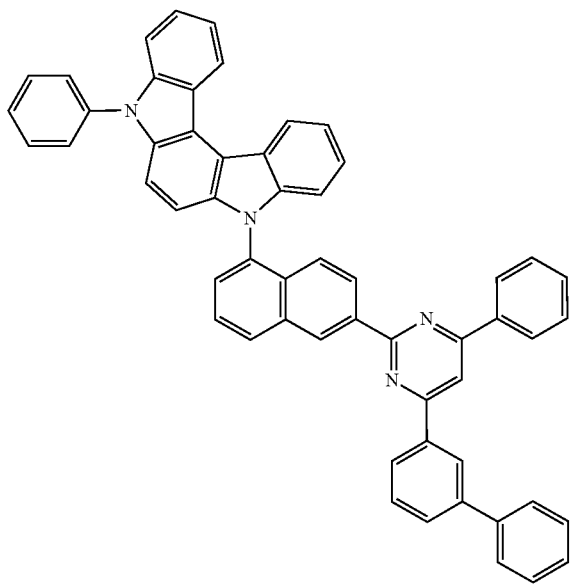
C-134
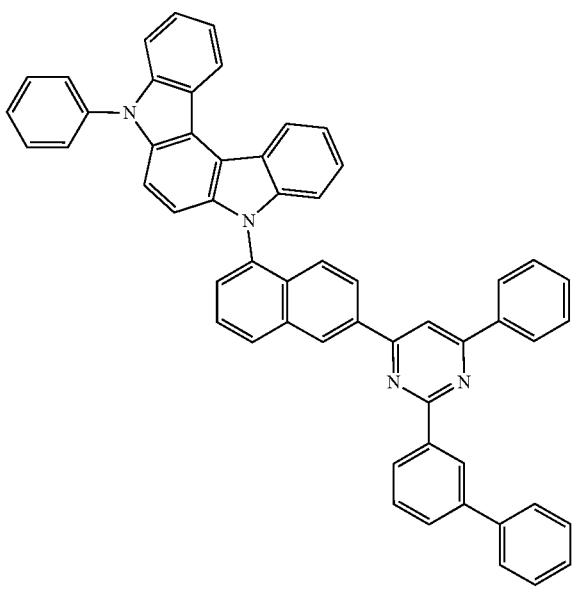

C-135
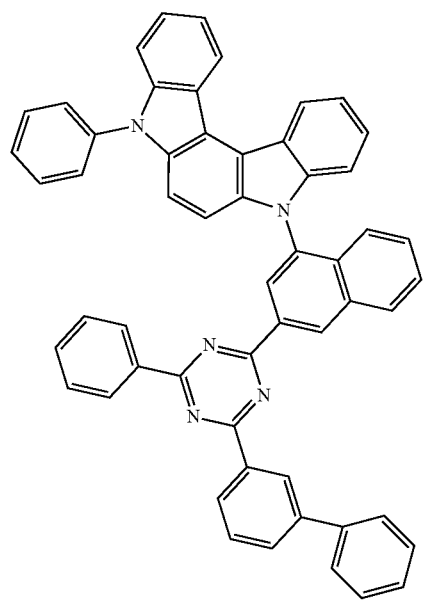
C-137
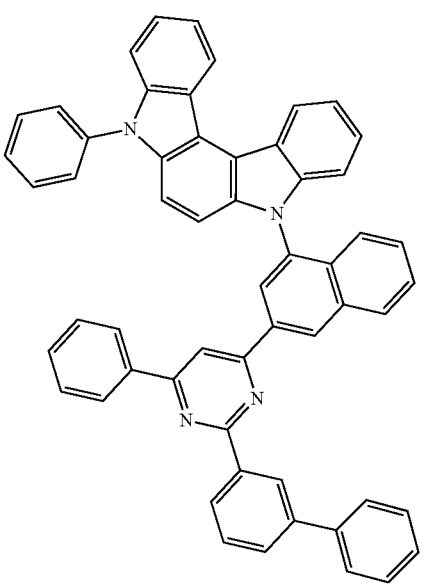
C-136
C-138
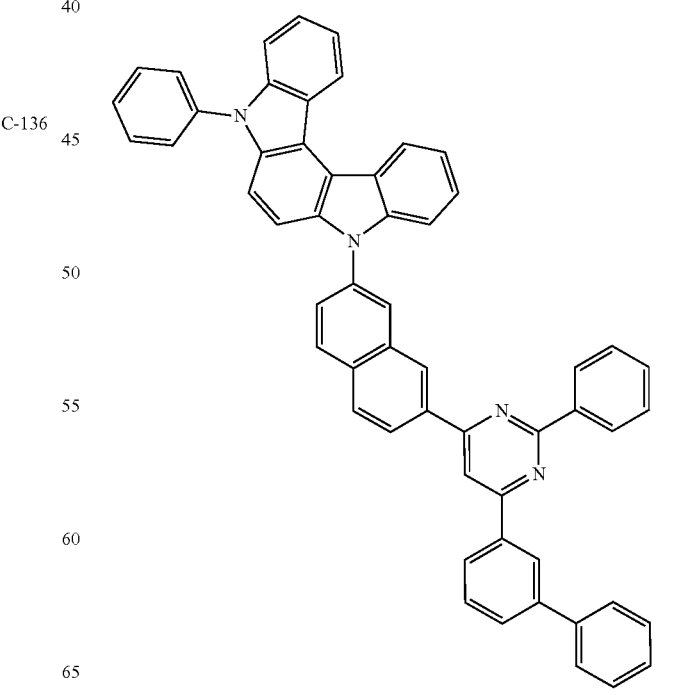

C-139
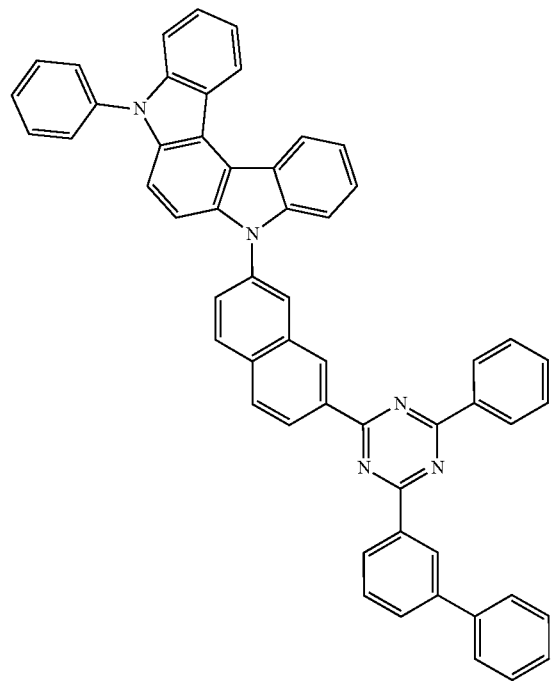
C-140
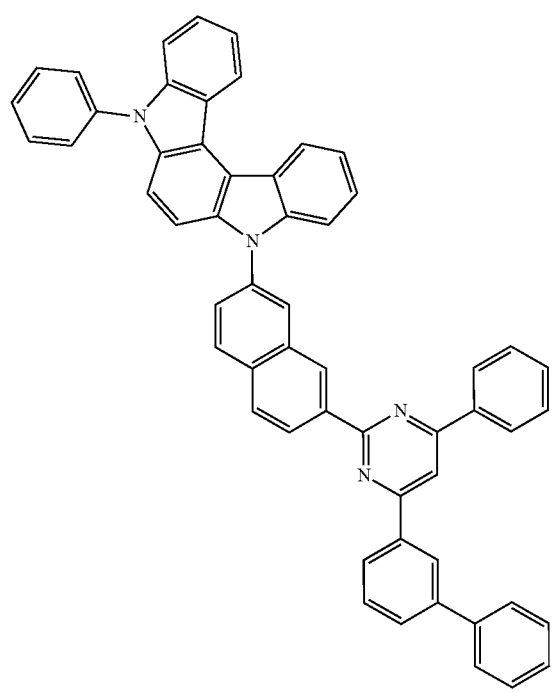
C-141
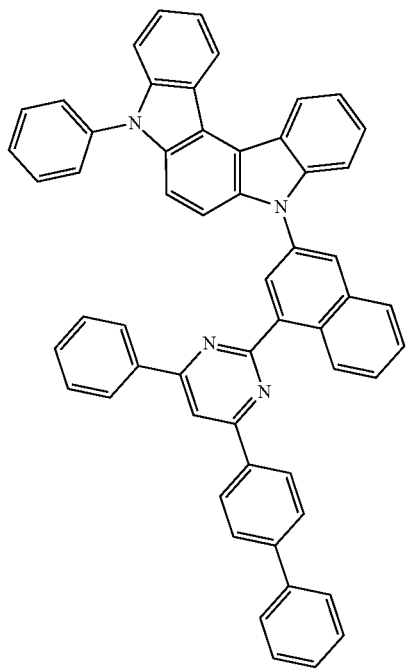
C-142
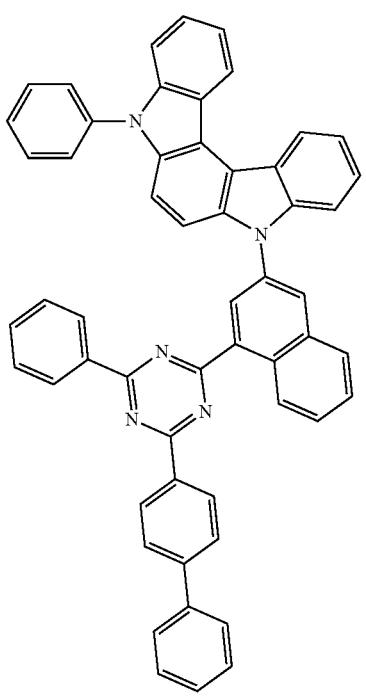

C-143
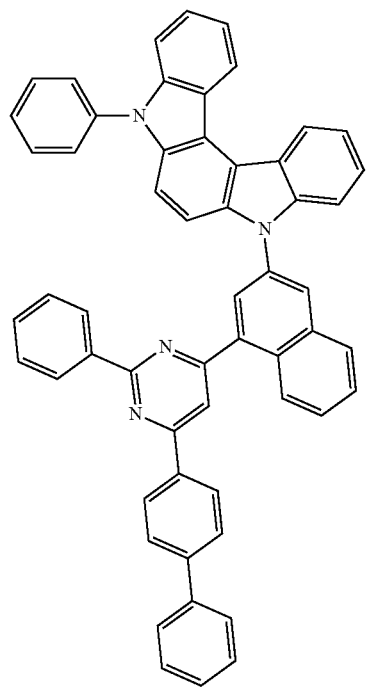
C-145
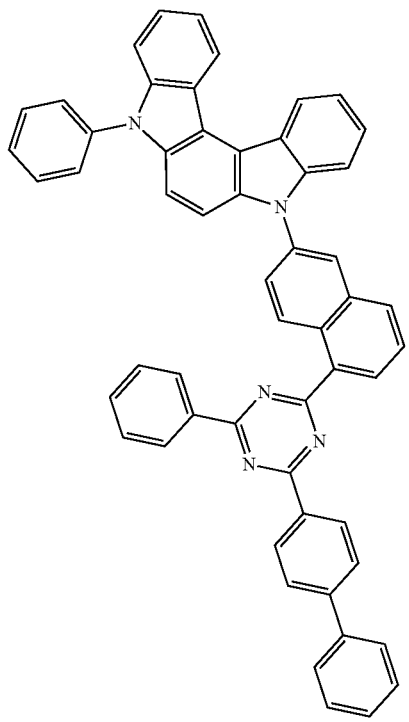
C-144
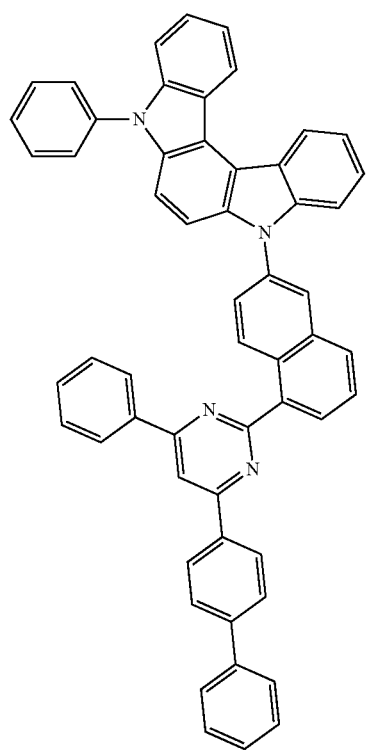
C-146
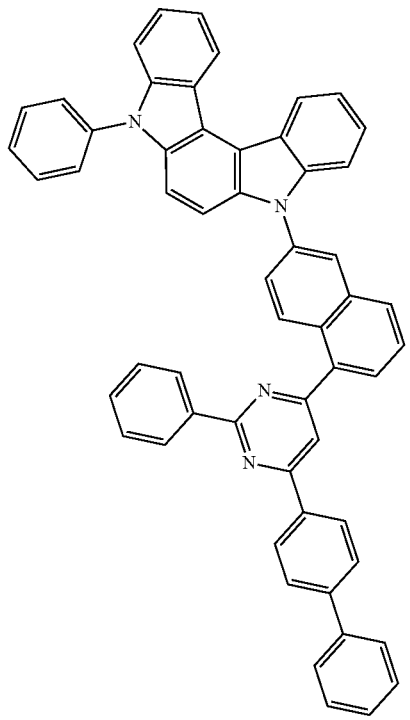

C-147
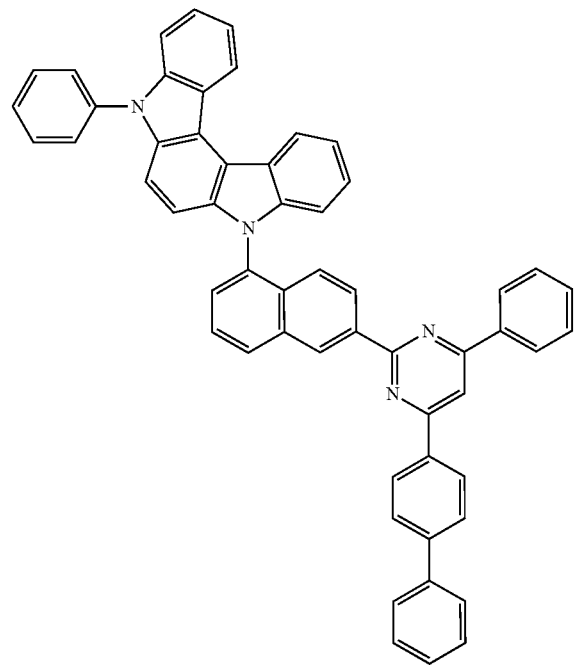
C-149
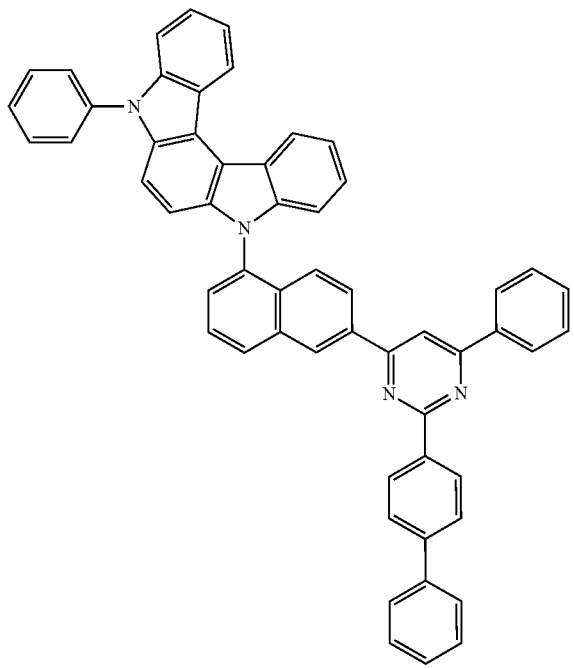
C-148
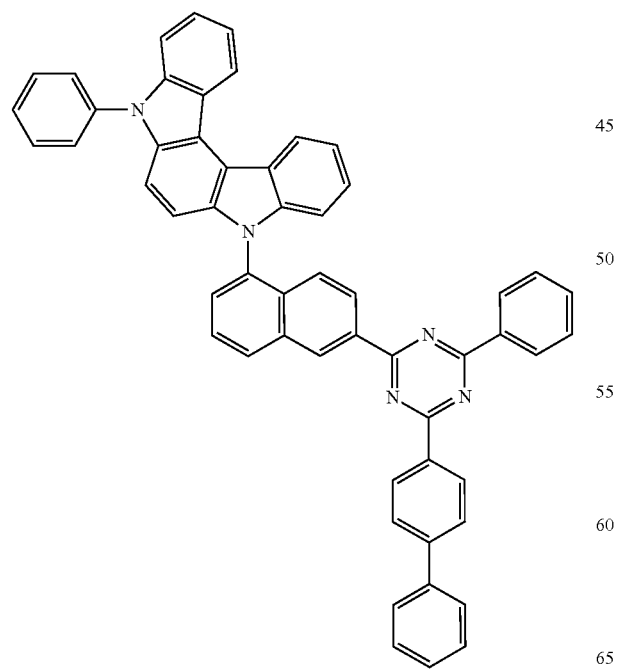
C-150
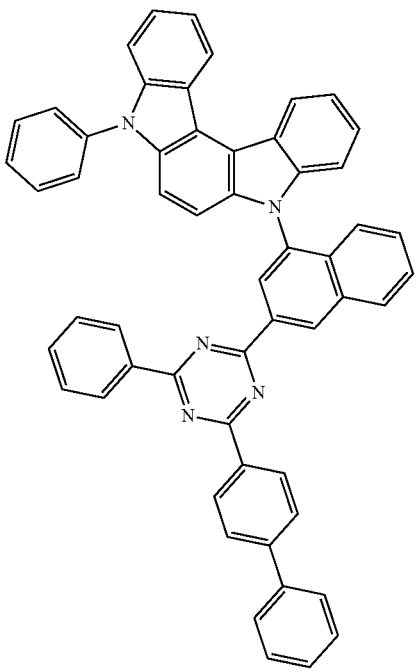

C-151
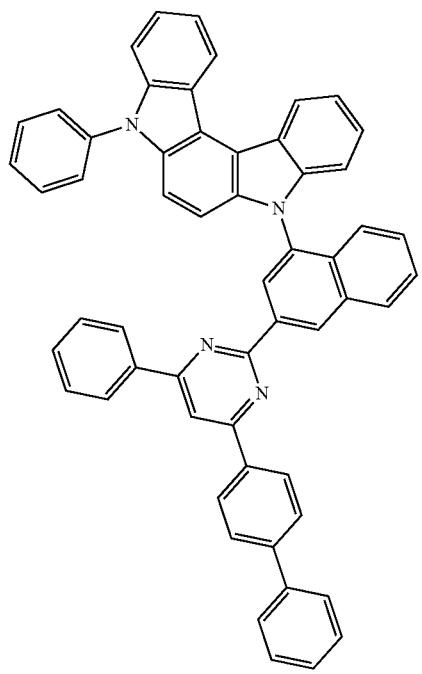
C-152
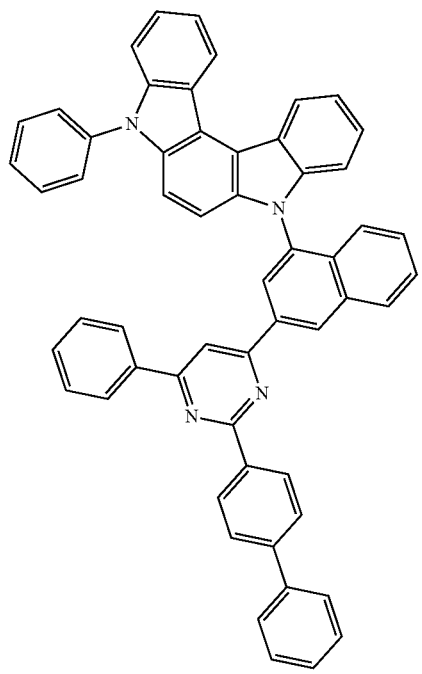
C-153
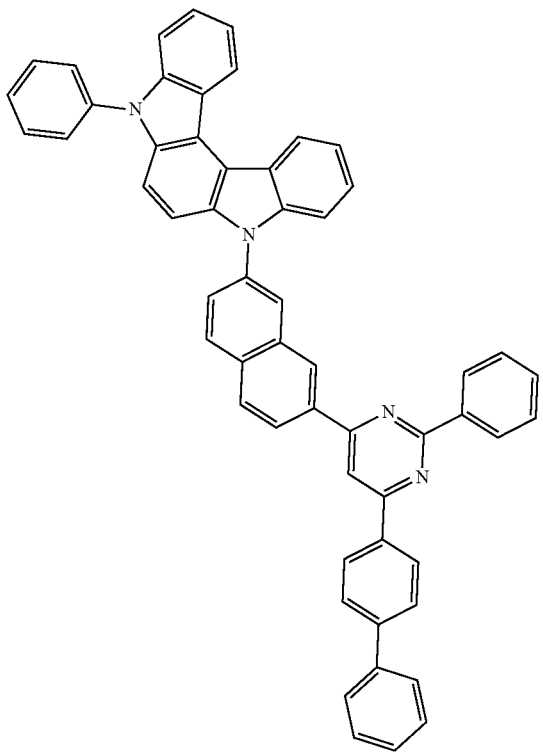
C-154
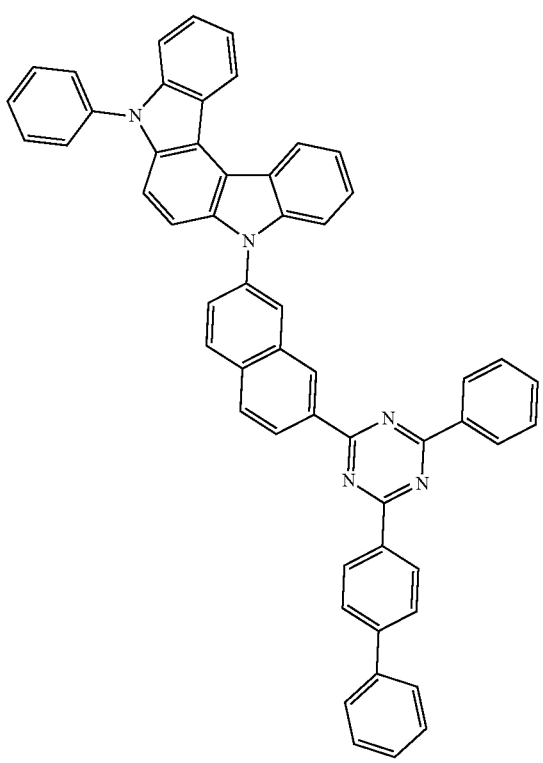

C-155
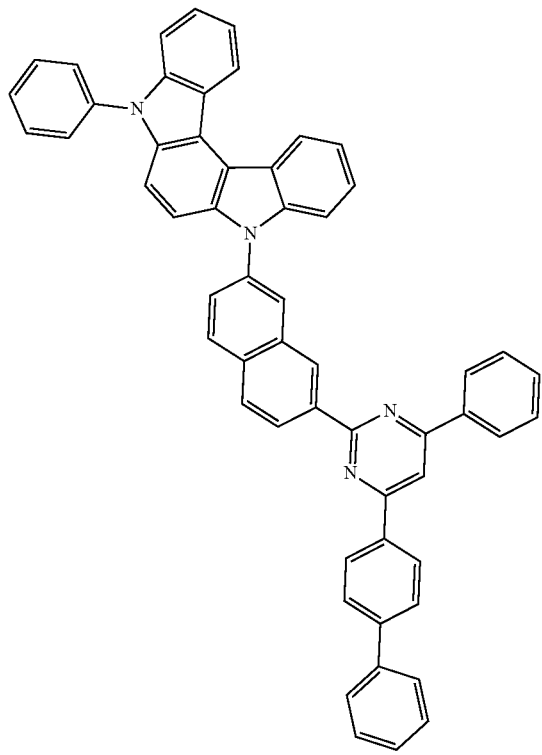
C-157
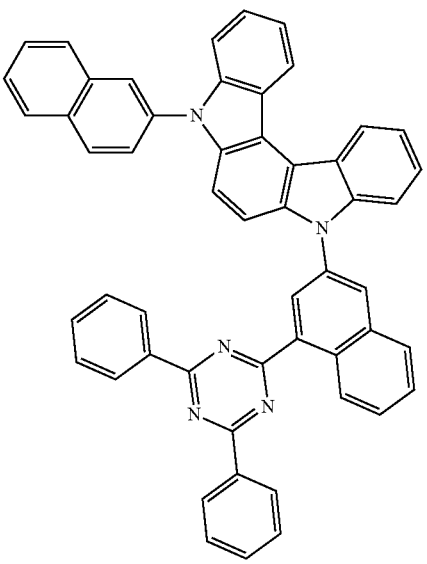
C-156
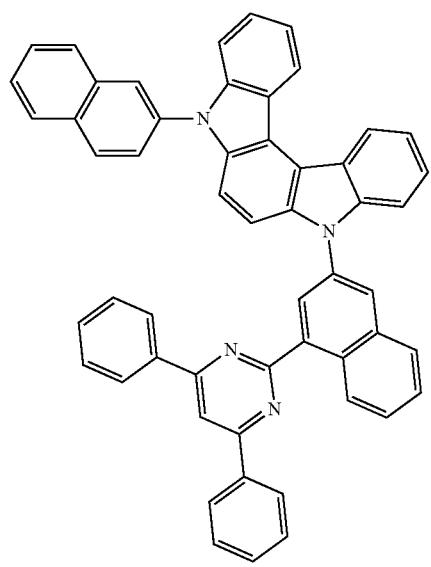
C-158
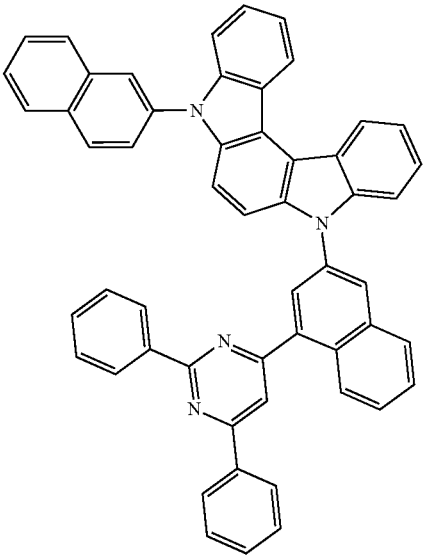

C-159
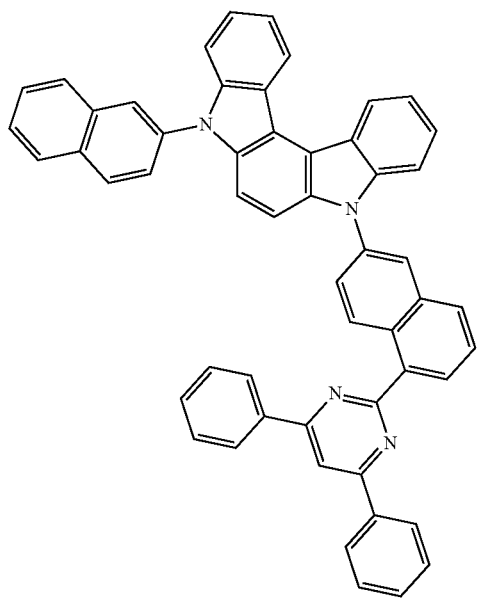
C-160
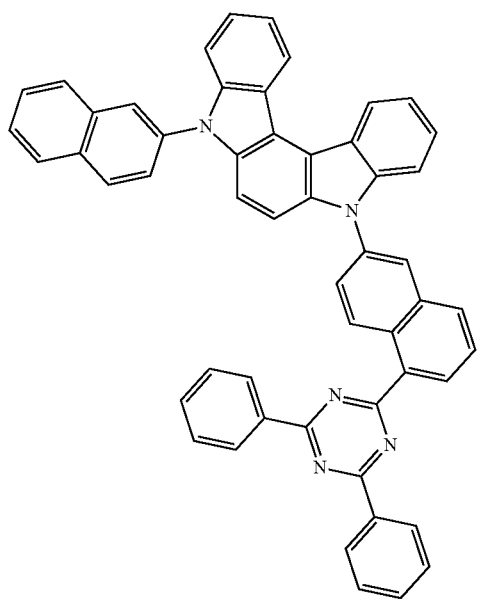
C-161
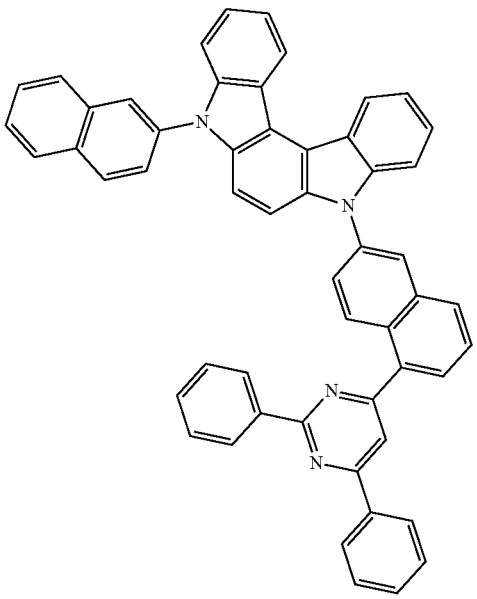
C-162
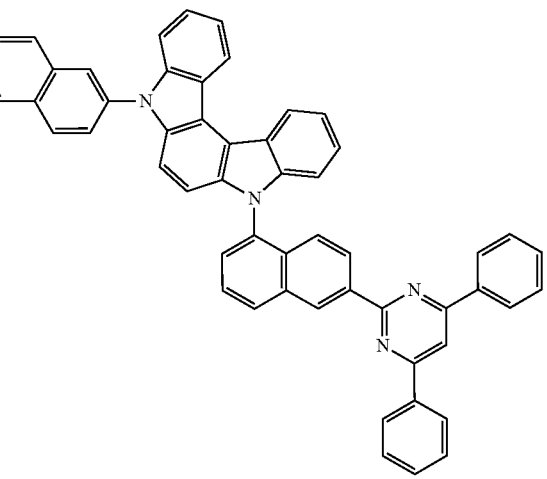
C-163
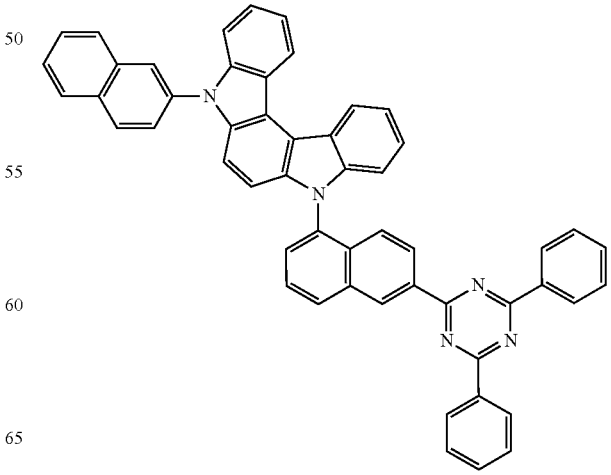

-continued
C-164
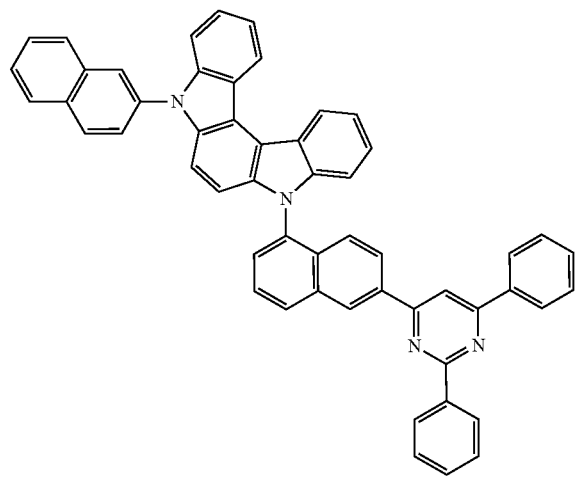
C-165
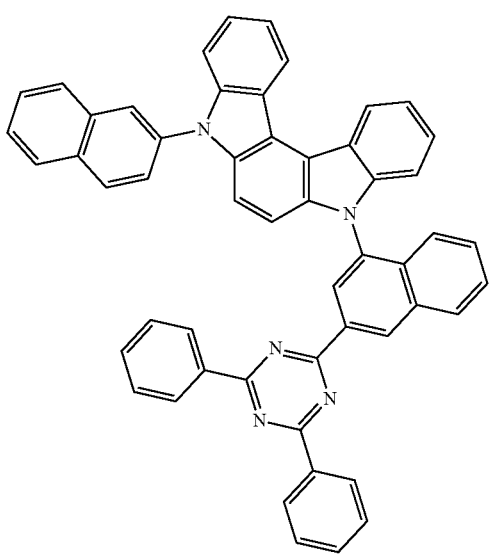
C-166
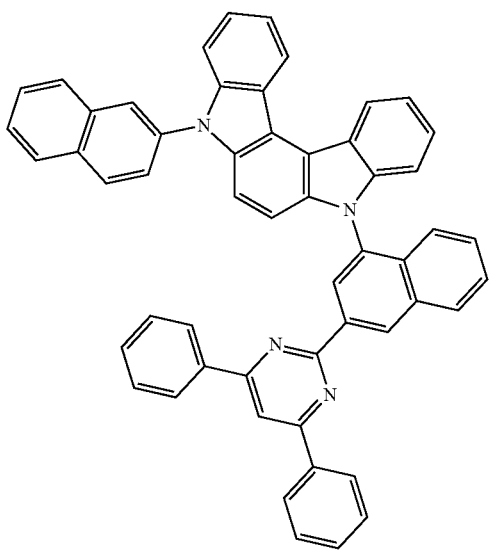
-continued
C-167
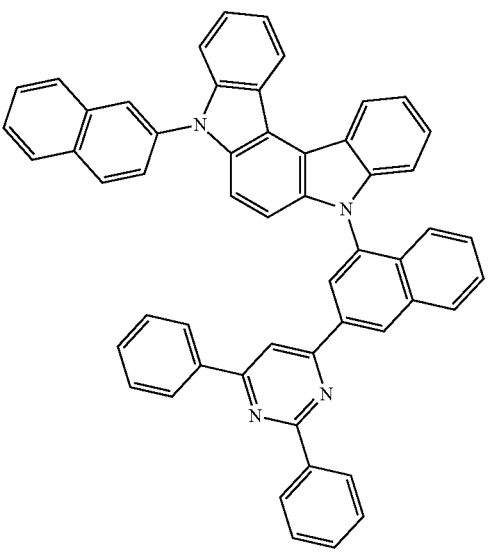
C-168
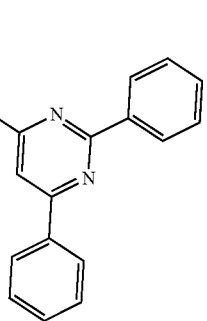

C-169
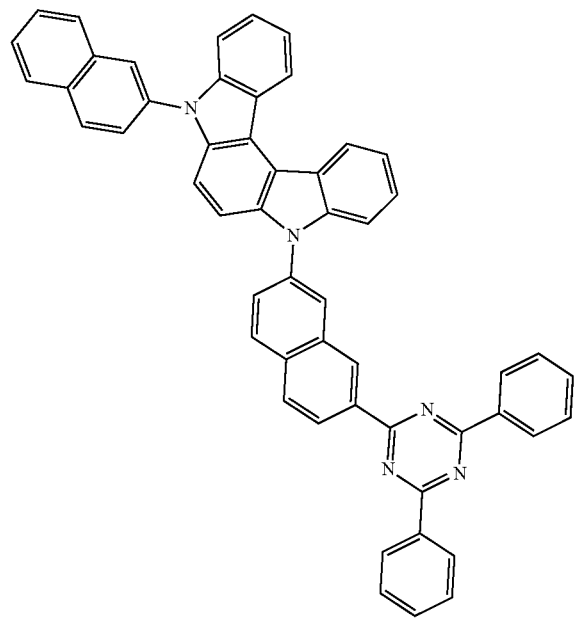
C-170
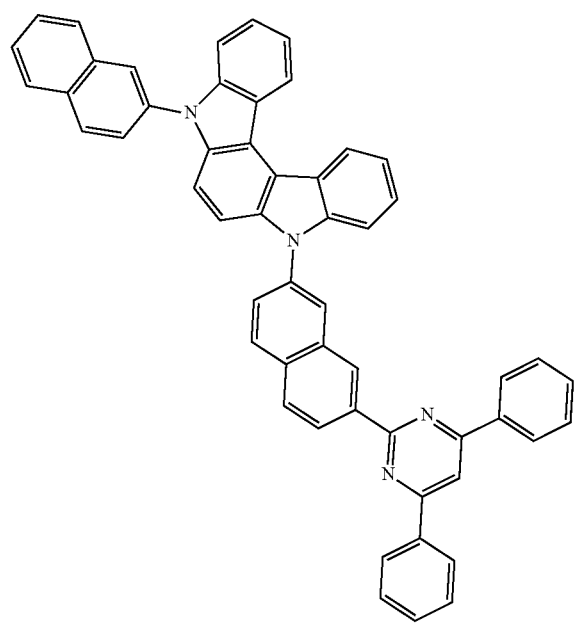
C-171
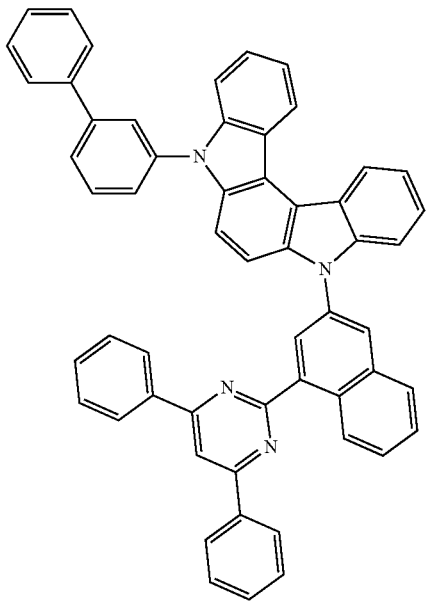
C-172

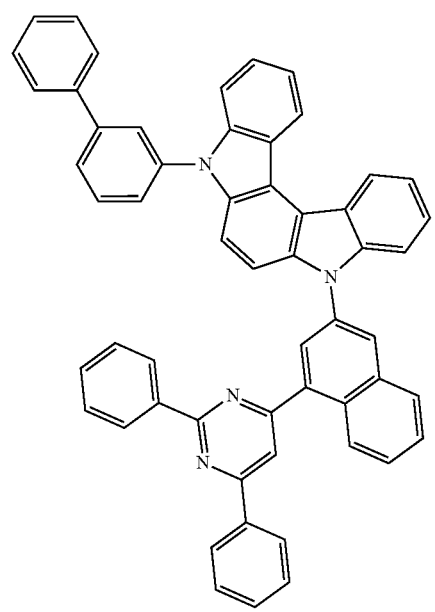
C-173
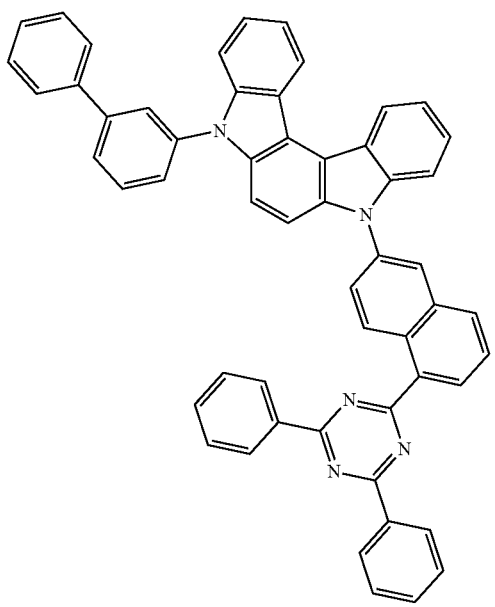
C-175
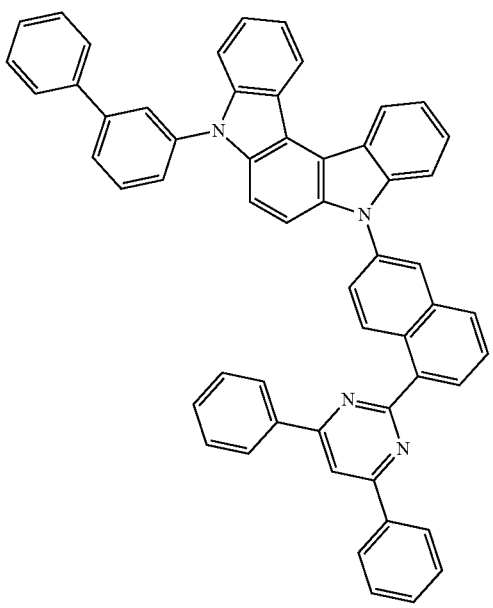
C-174
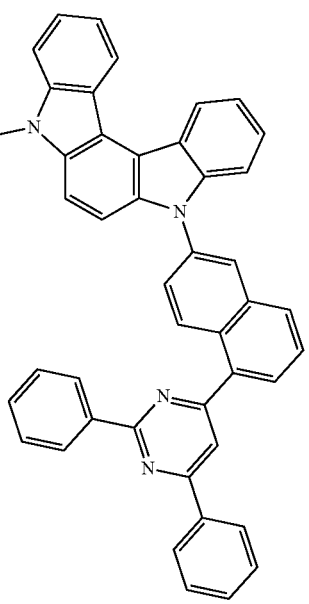
C-176

C-177
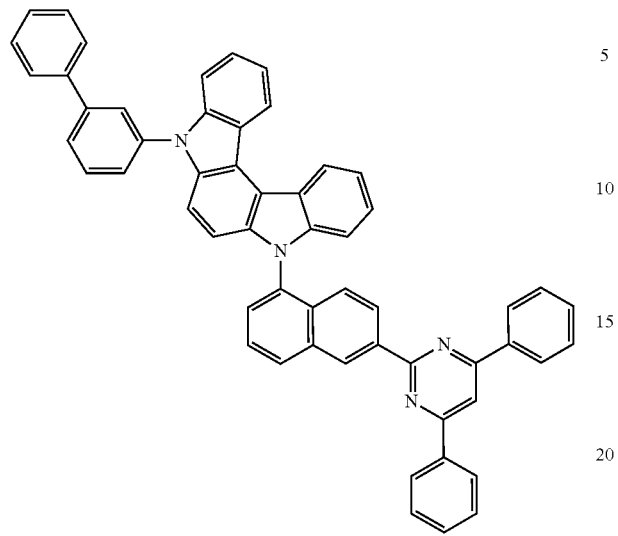
C-178
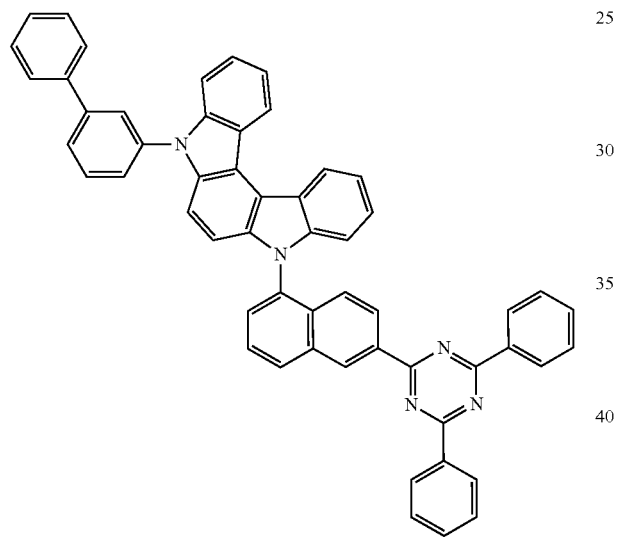
C-179
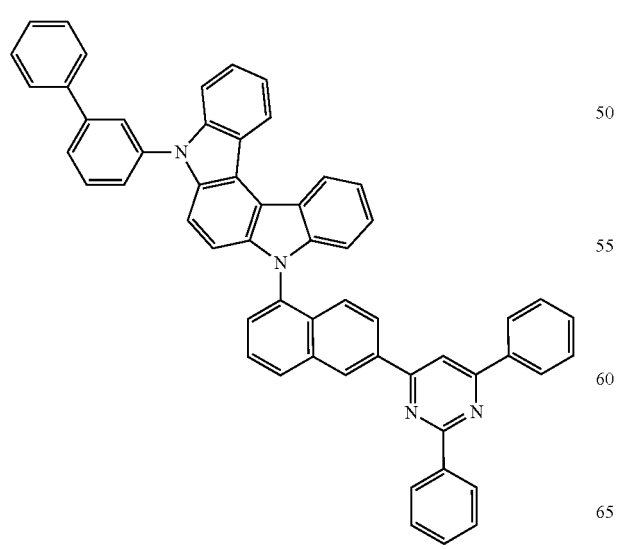
C-180
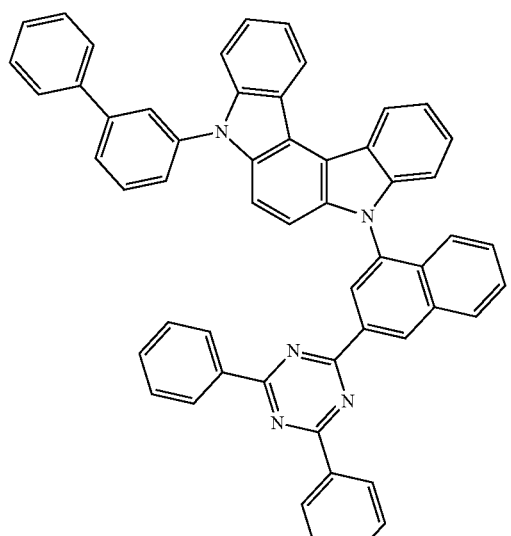
C-181
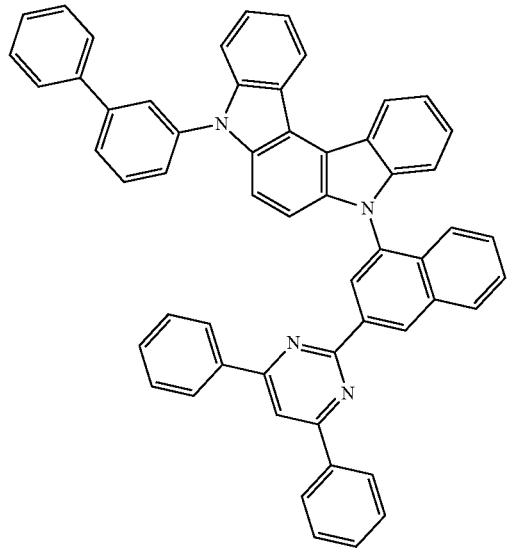

C-182
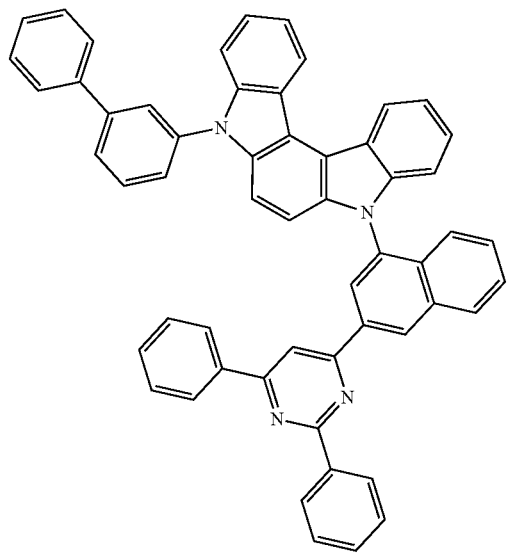
C-183
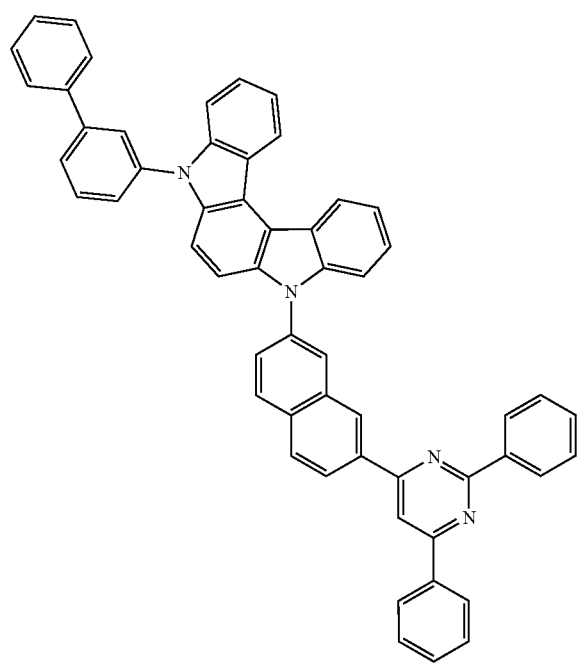
C-184
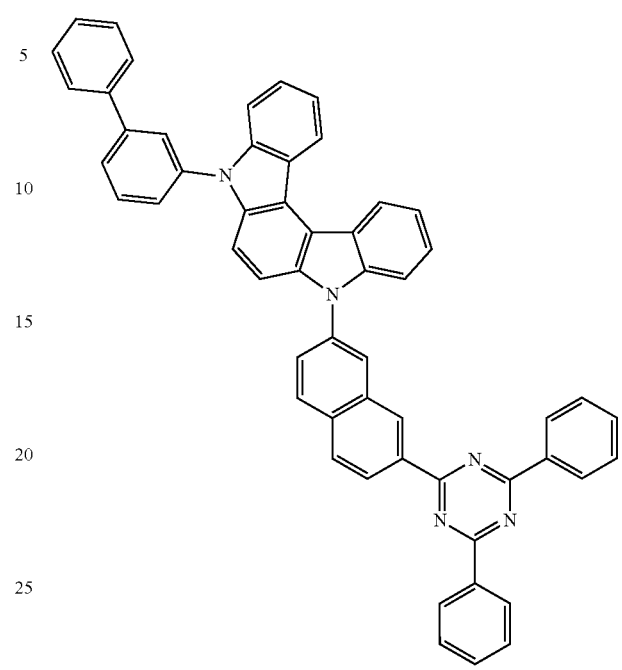
C-185
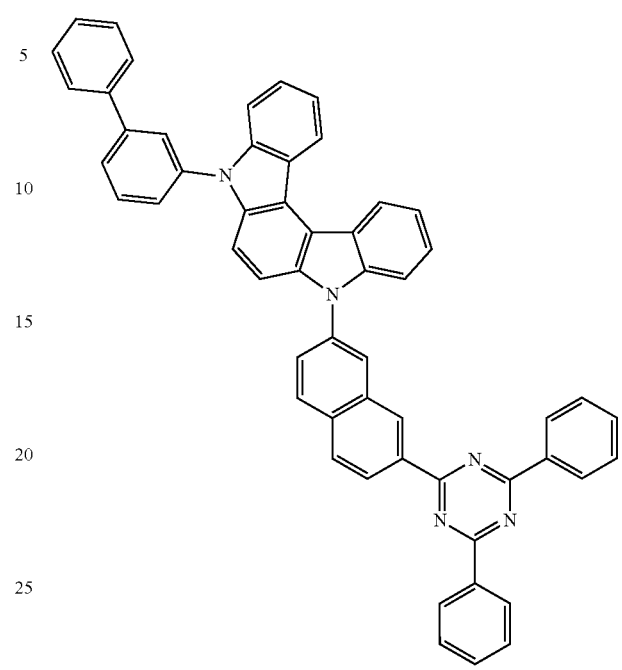

-continued
C-186
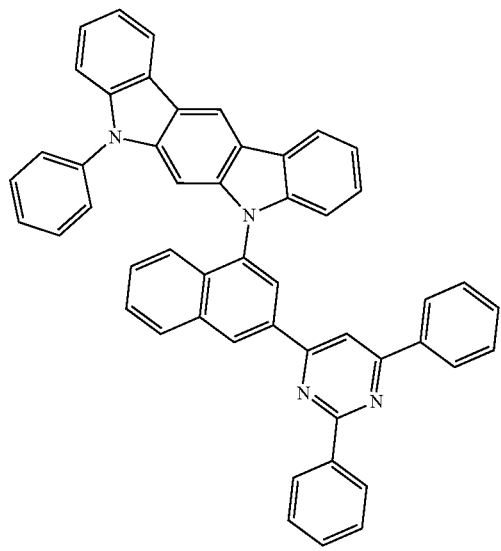
C-187
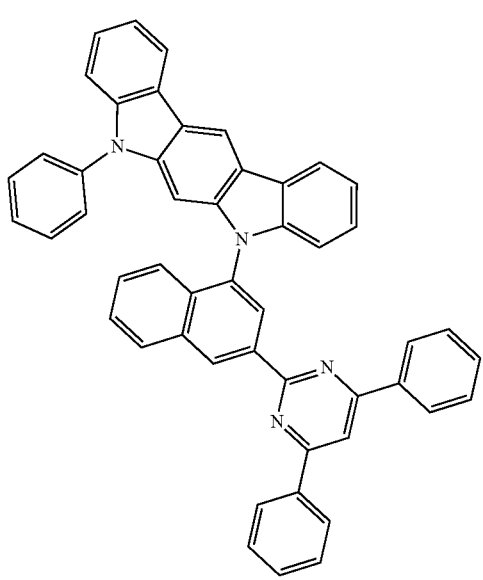
-continued
C-188
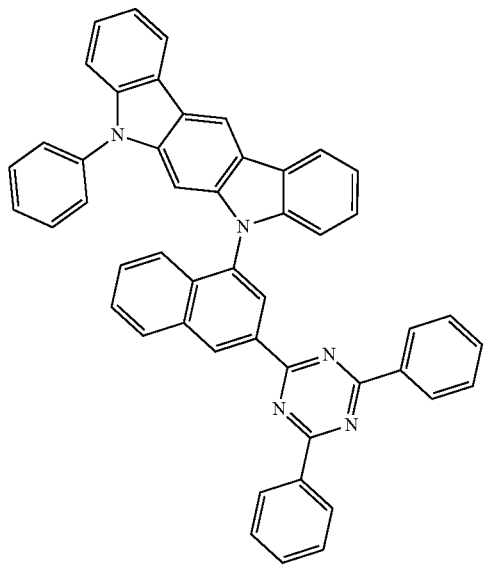
C-189
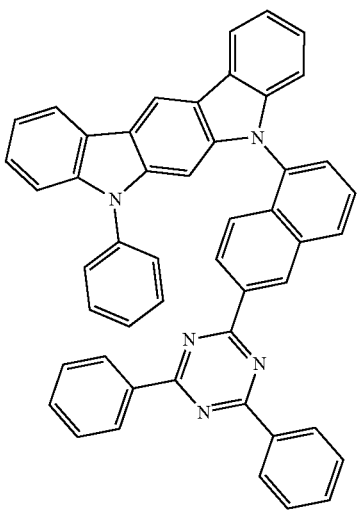
C-190
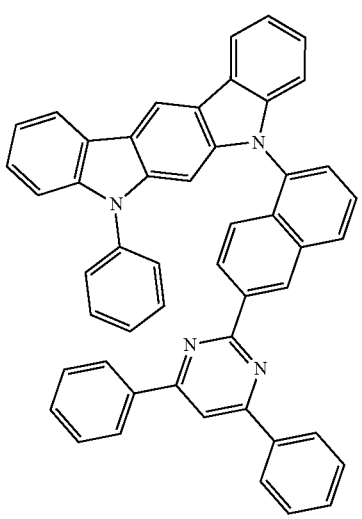

C-191
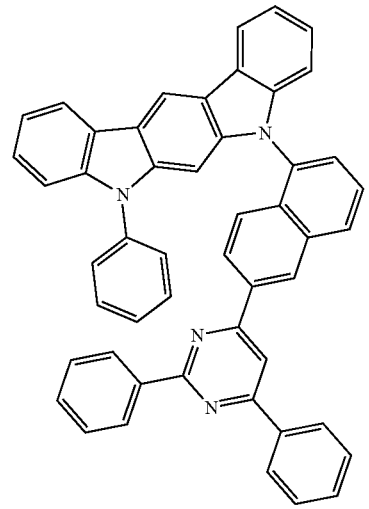
C-192
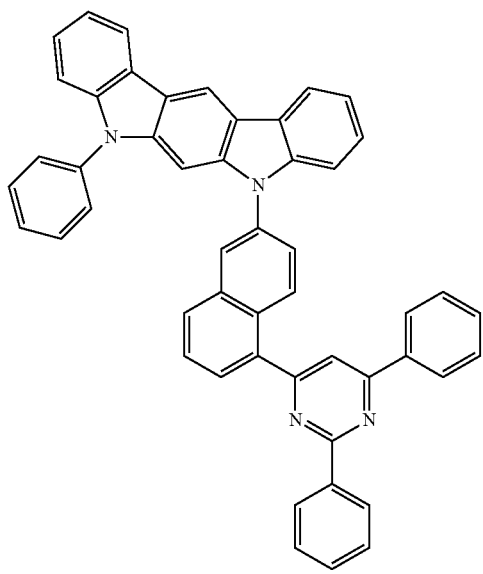
C-193
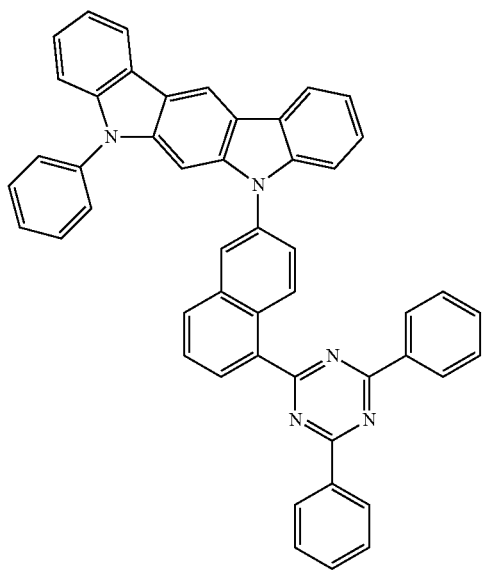
C-194
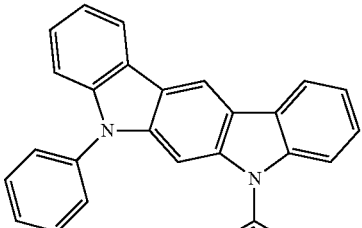
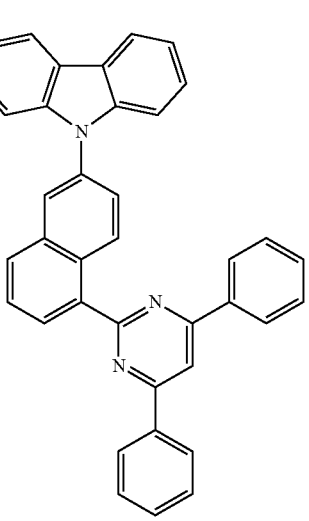
C-195
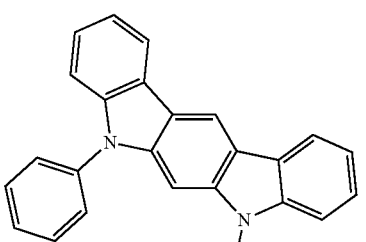
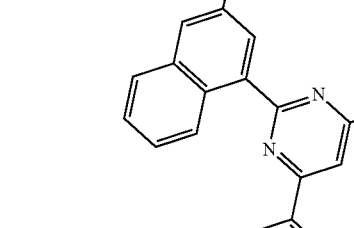

C-196
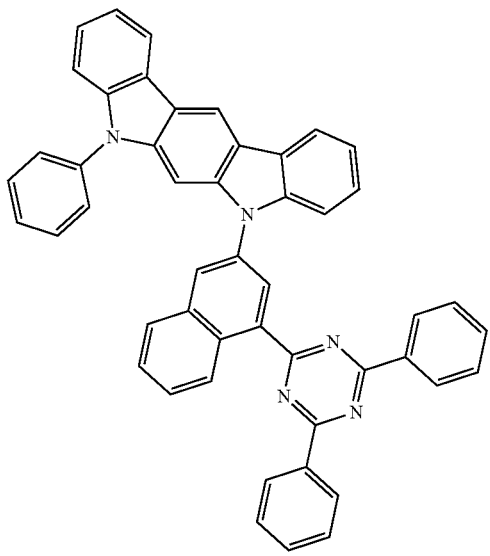
C-197
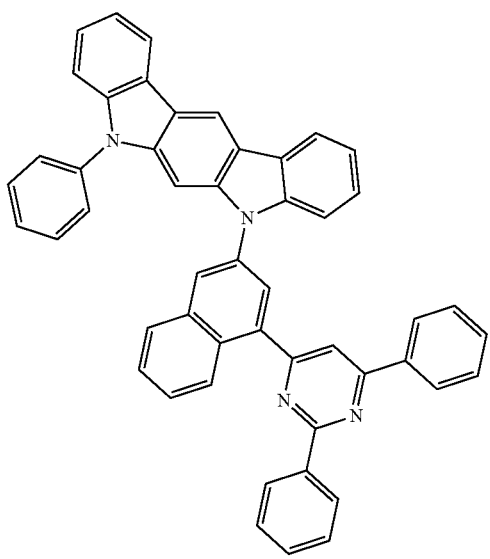
C-199
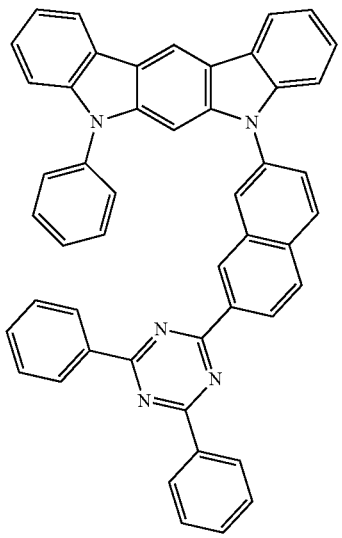
C-198
C-200
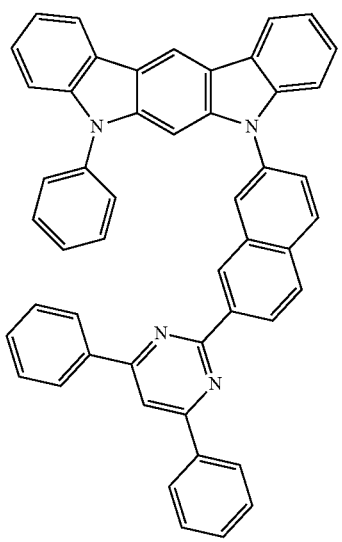

C-201
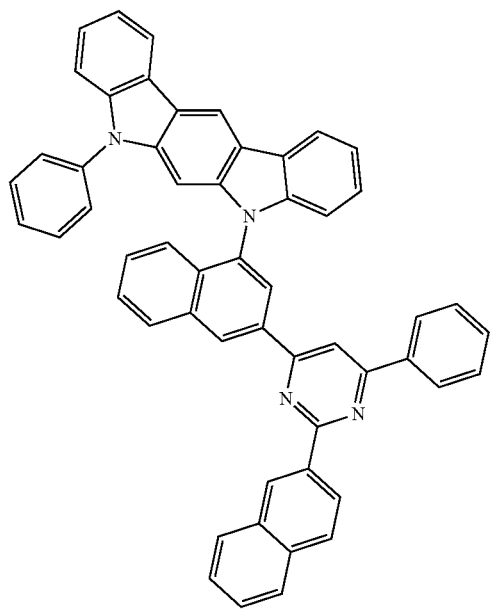
C-203
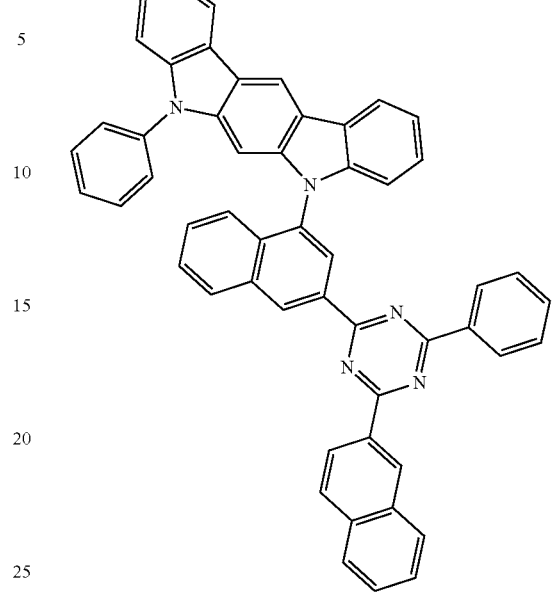
C-202
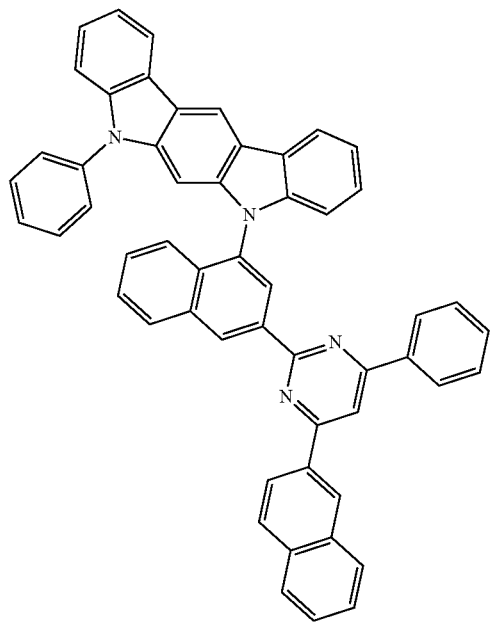
C-204
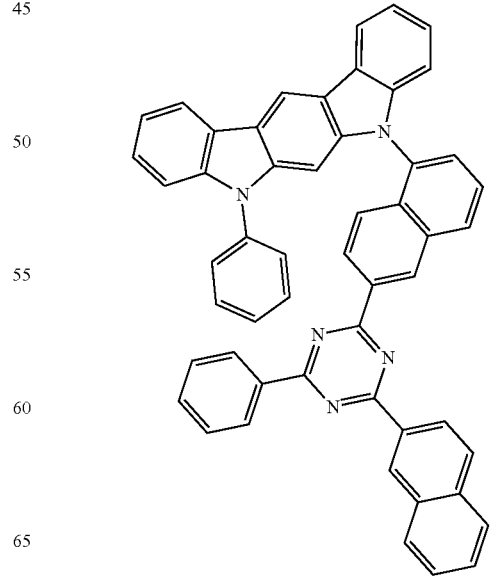

C-205
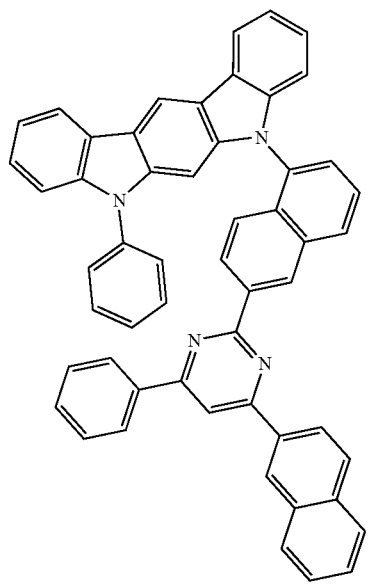
C-207
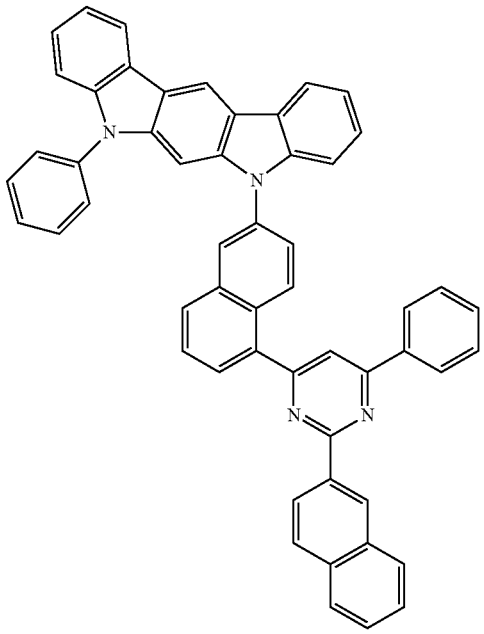
C-206
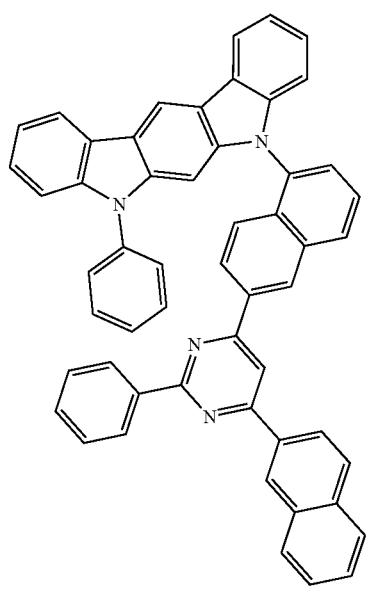
C-208
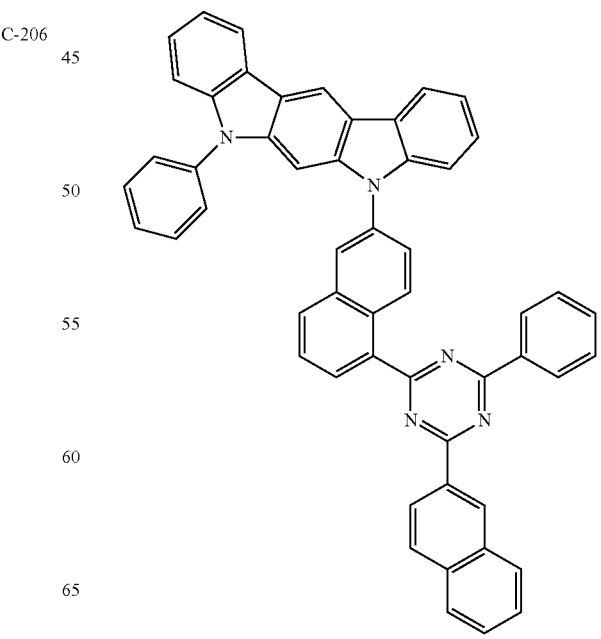

C-209
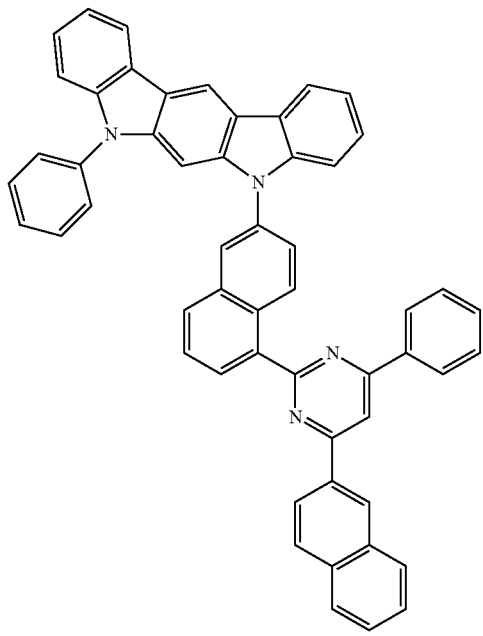
C-210
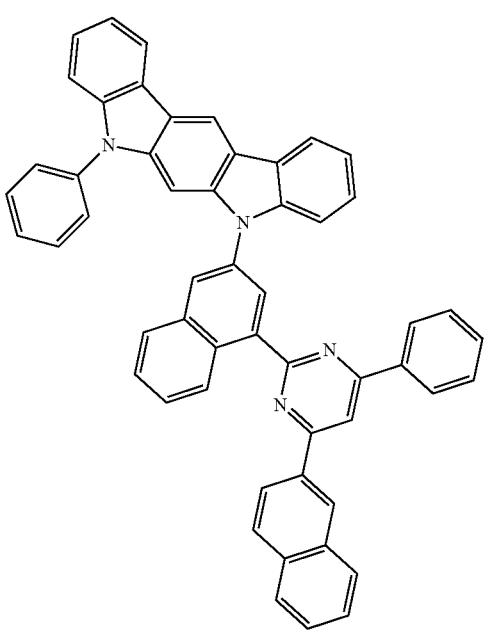
C-211
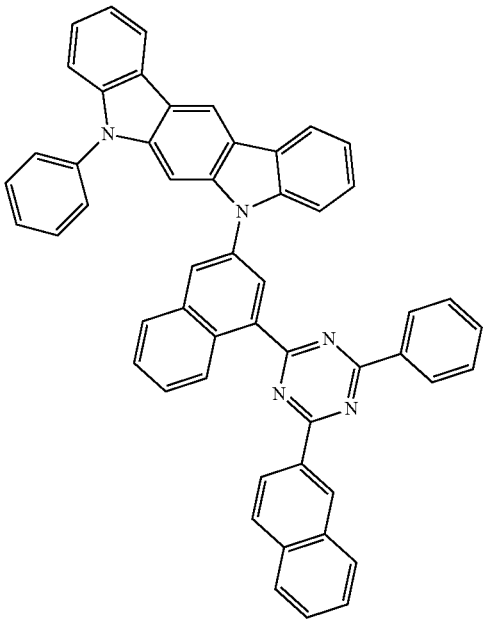
C-212
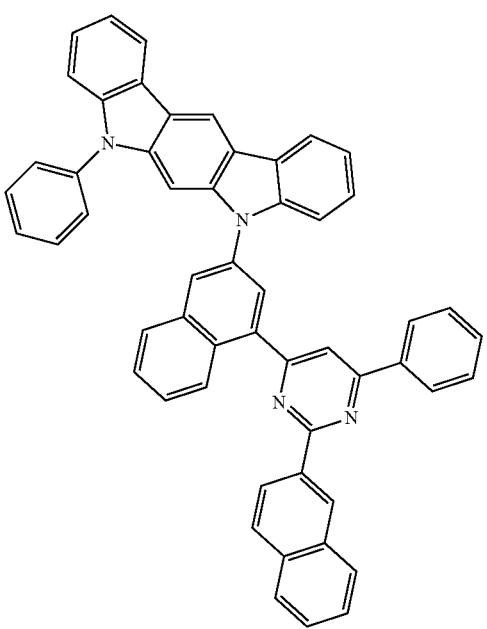

C-213
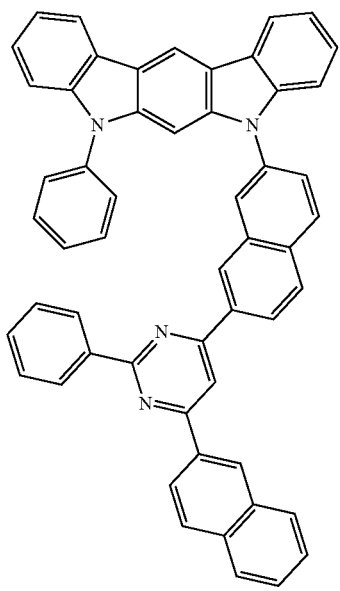
C-214
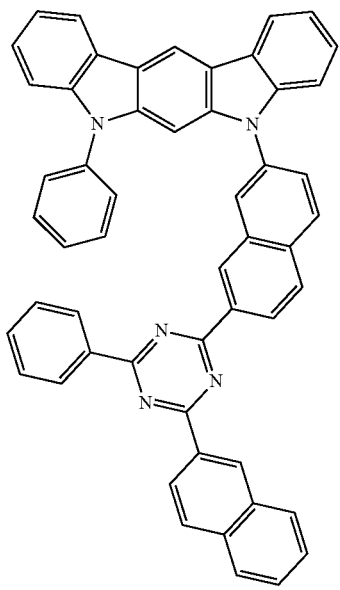
C-215
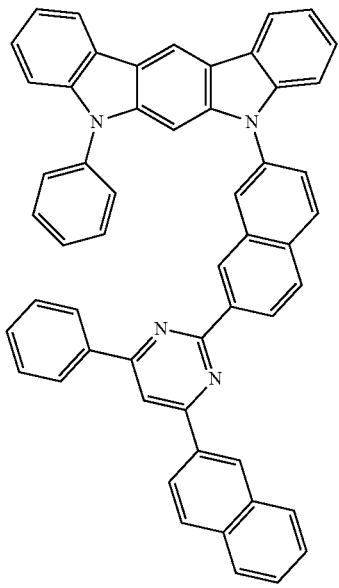
C-216

C-217
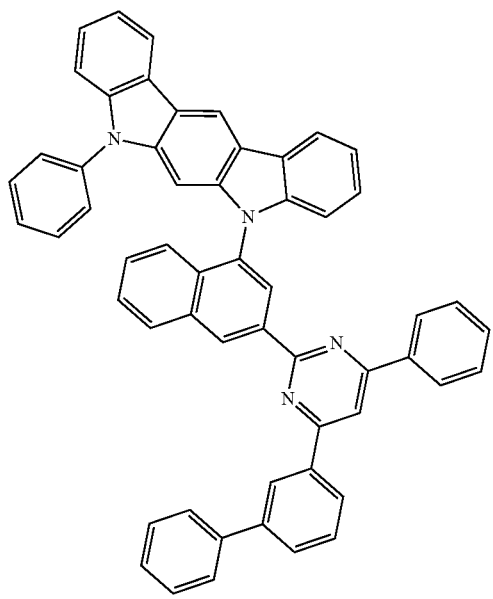
C-218
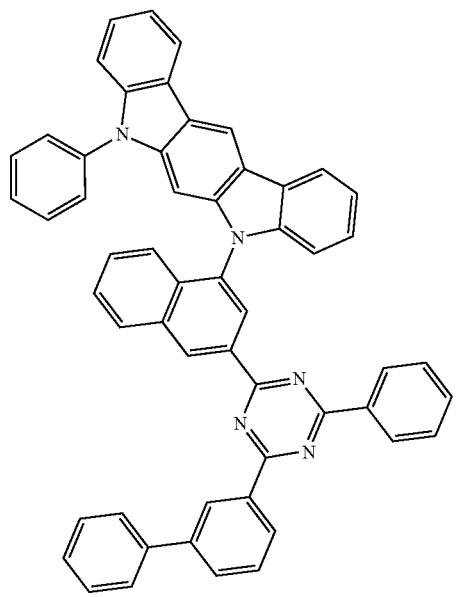
C-219
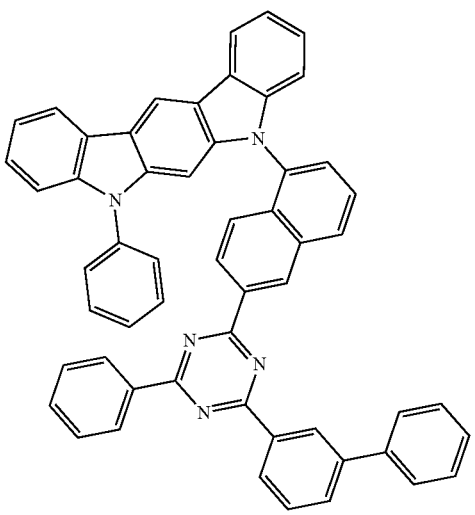
C-220
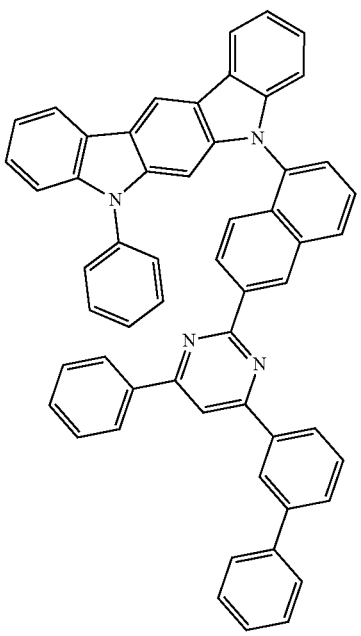
C-221
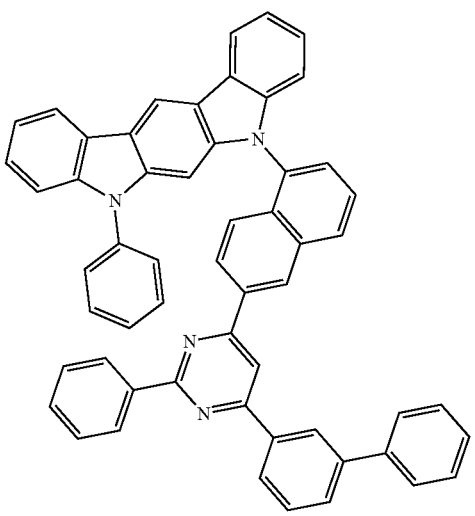

C-222
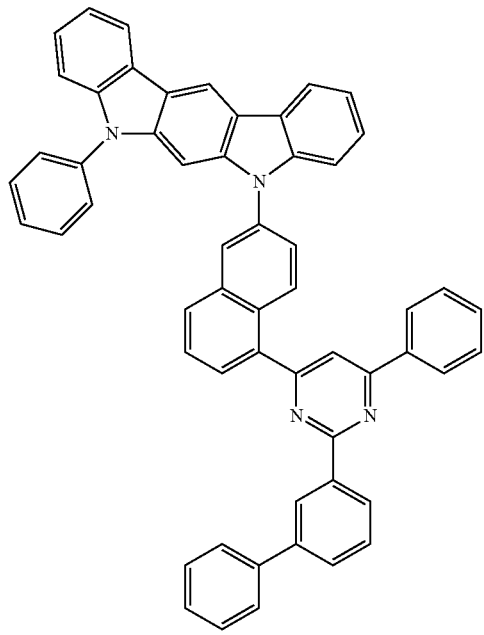
C-224
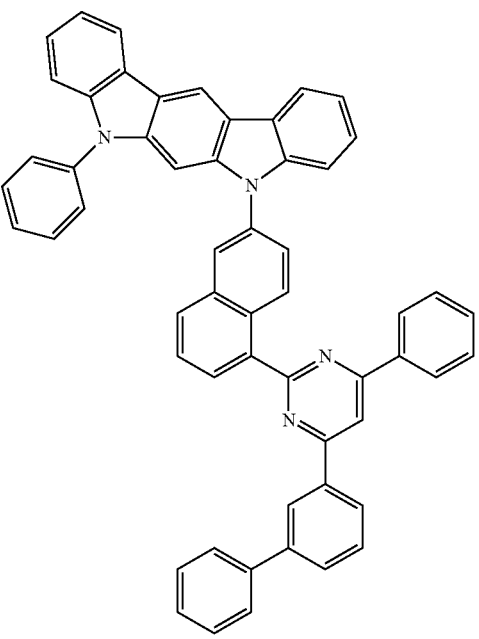
C-223
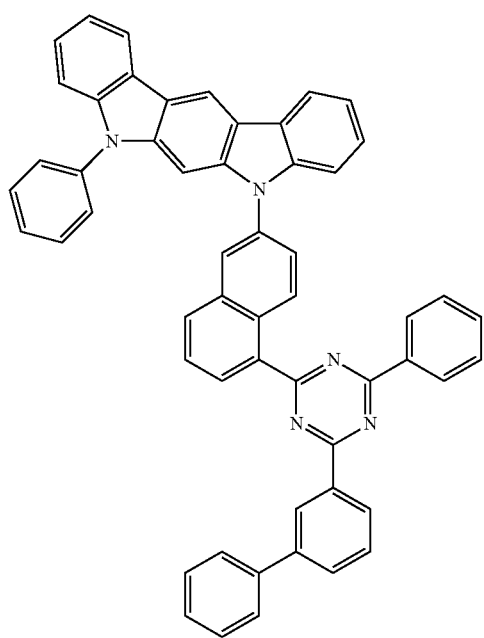
C-225
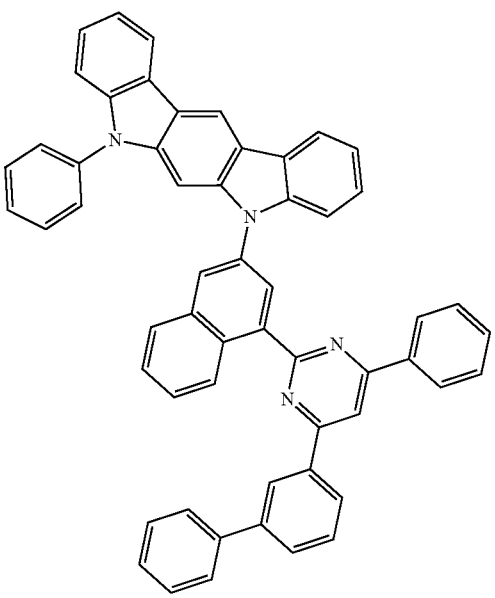

C-226
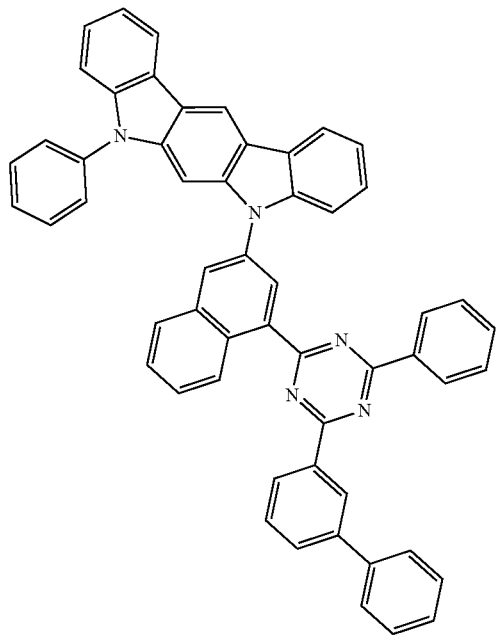
C-227
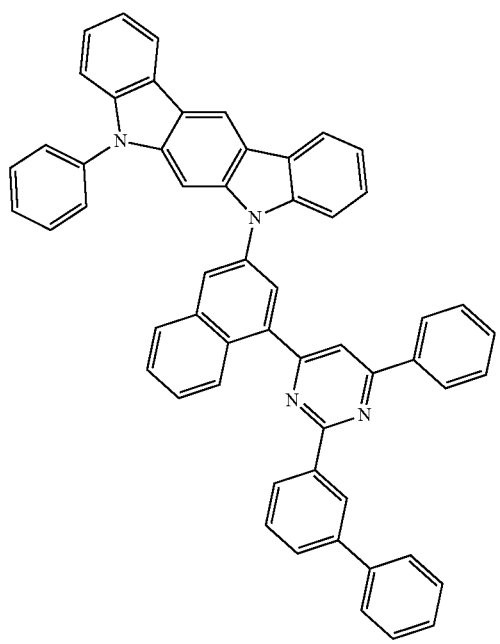
C-228
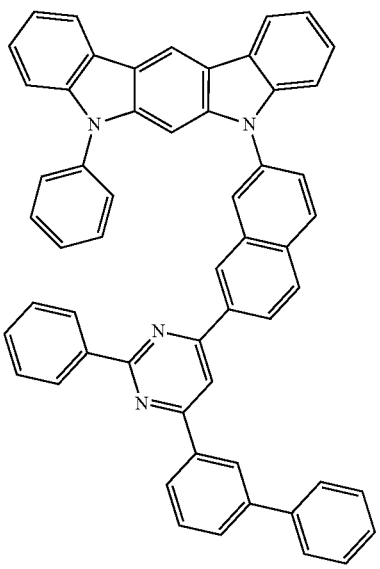
C-229
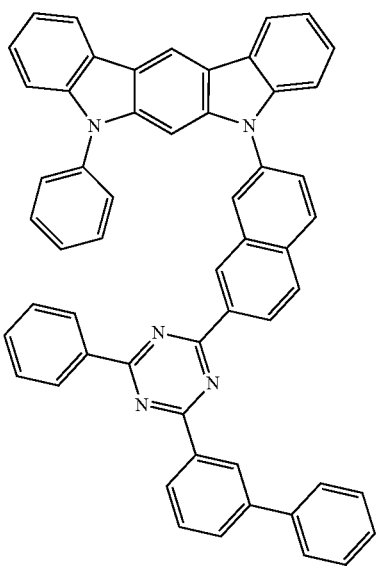

-continued
C-230
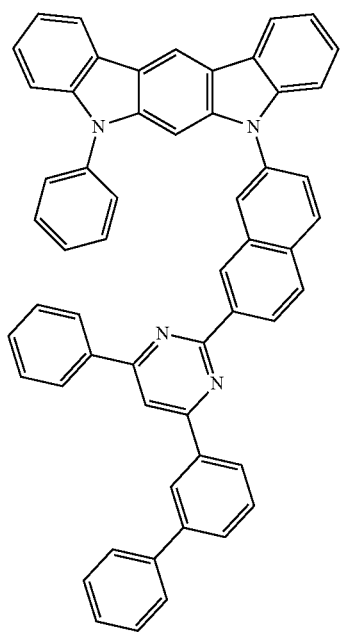
C-231
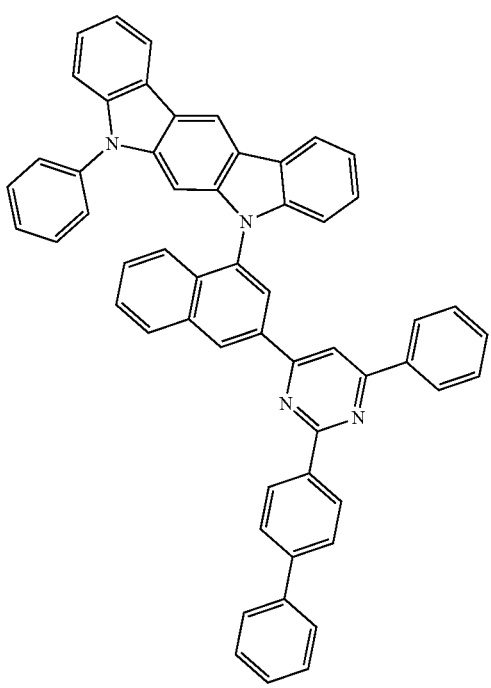
-continued
C-232
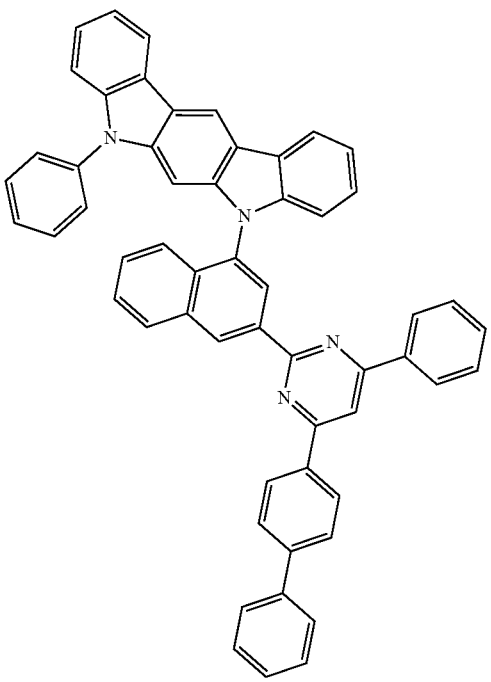
C-233
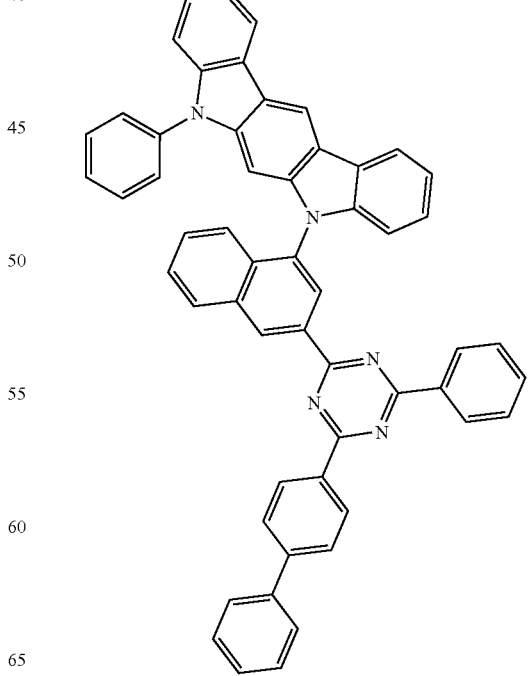

C-234
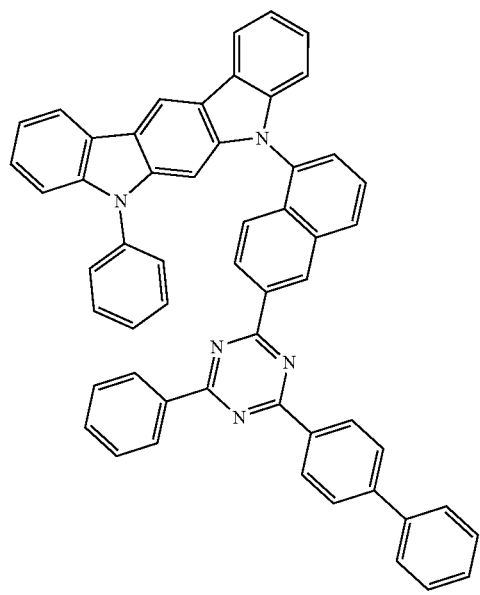
C-236
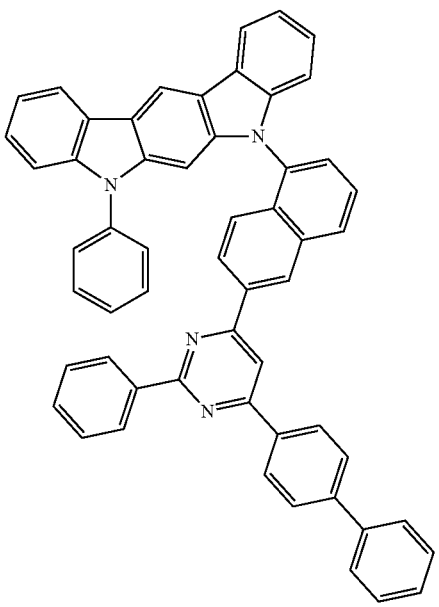
C-235
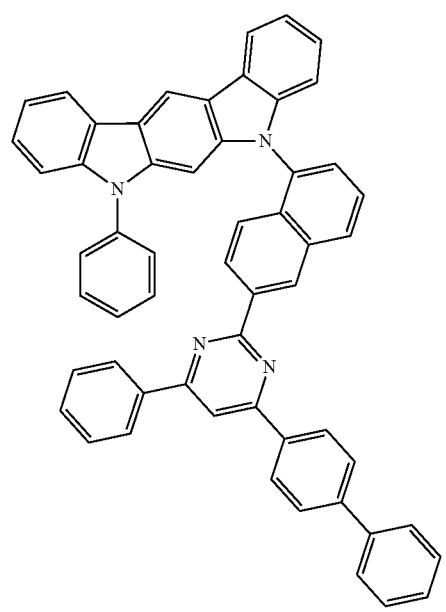
C-237
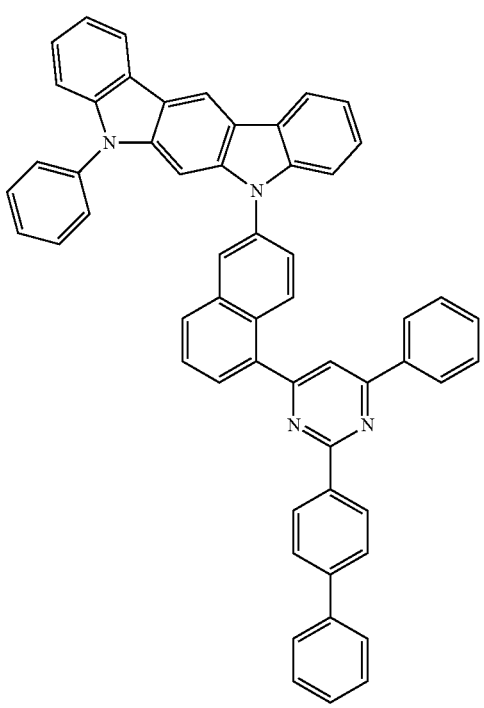

C-238
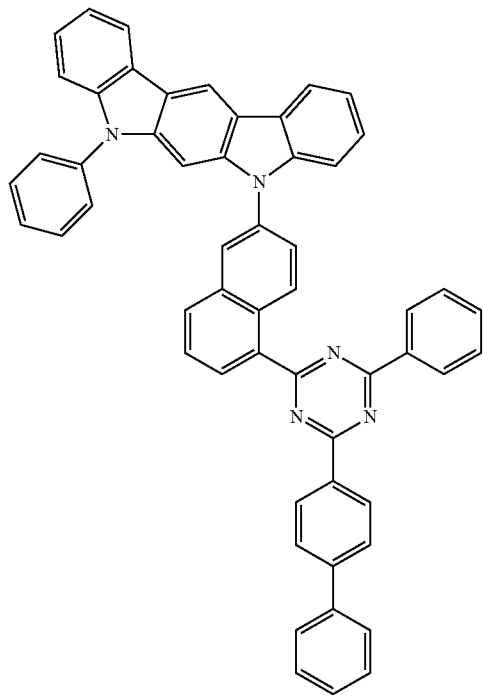
C-240
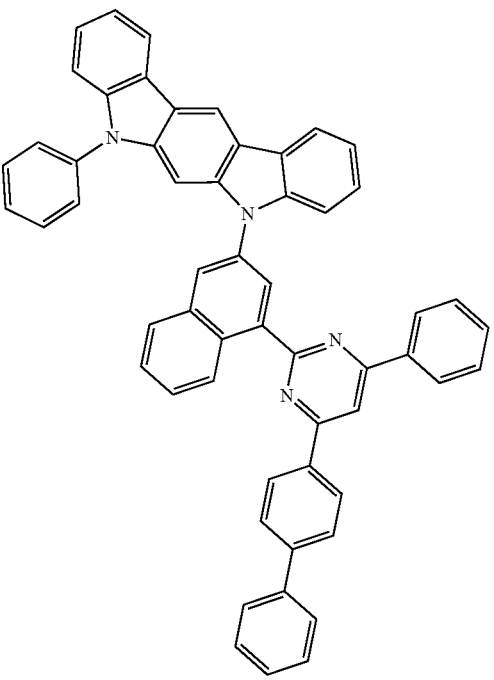
C-239
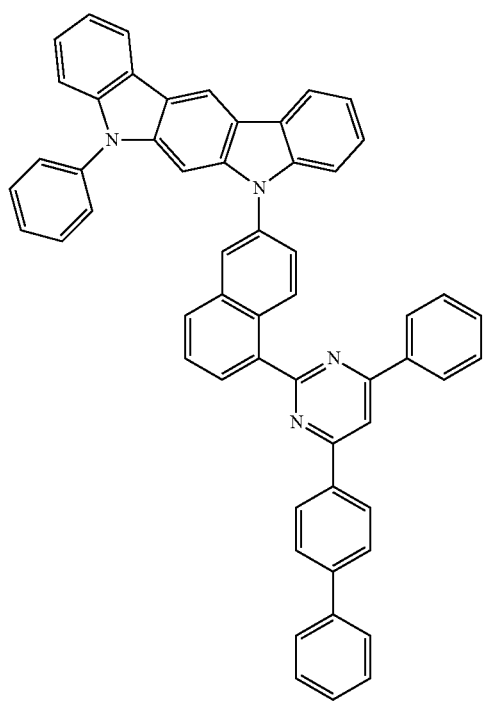
C-241
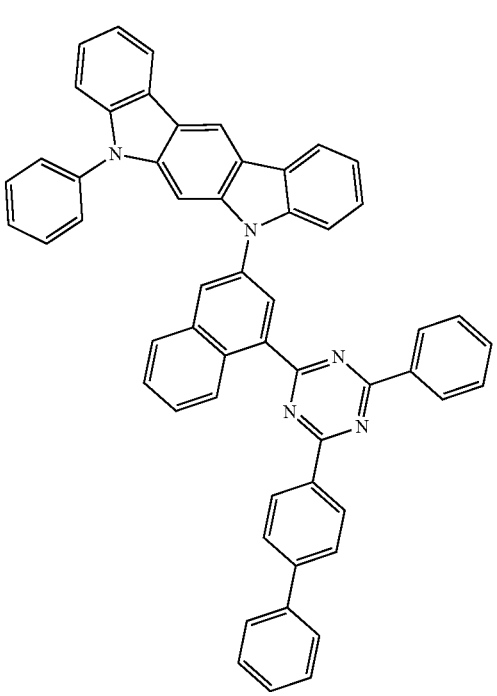

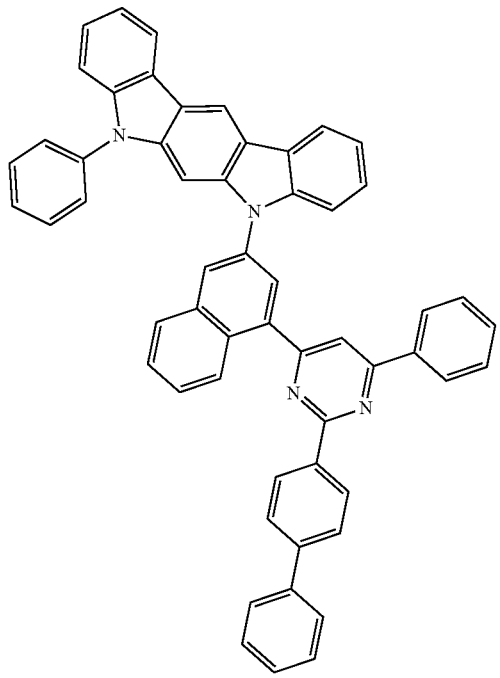
C-242
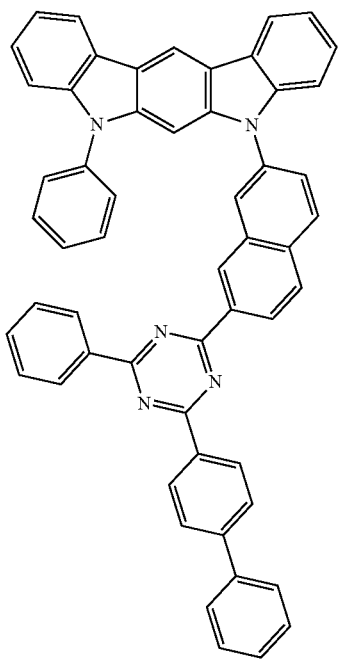
C-244
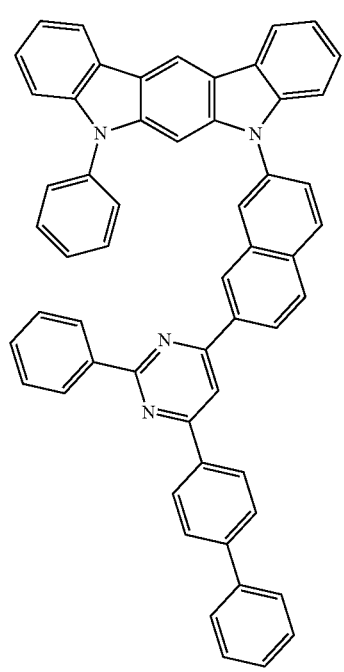
C-243
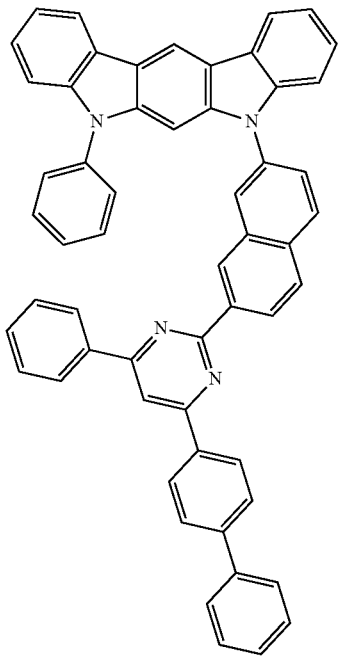
C-245

C-246
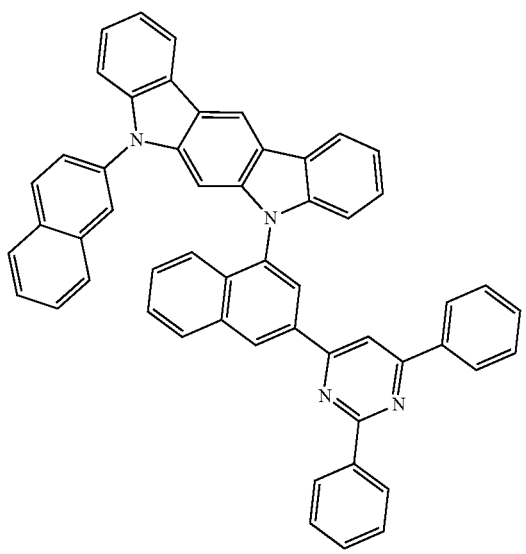
C-248
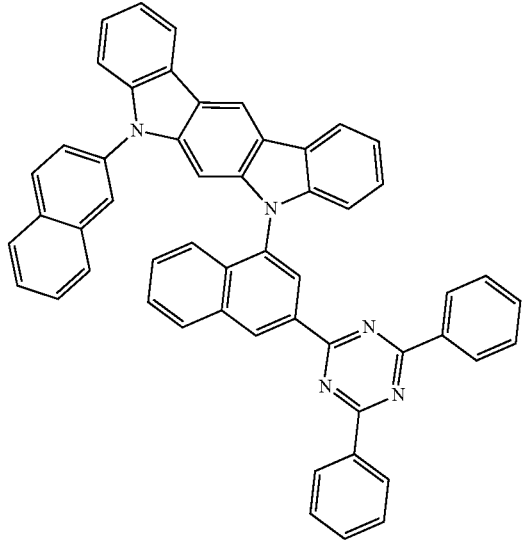
C-247
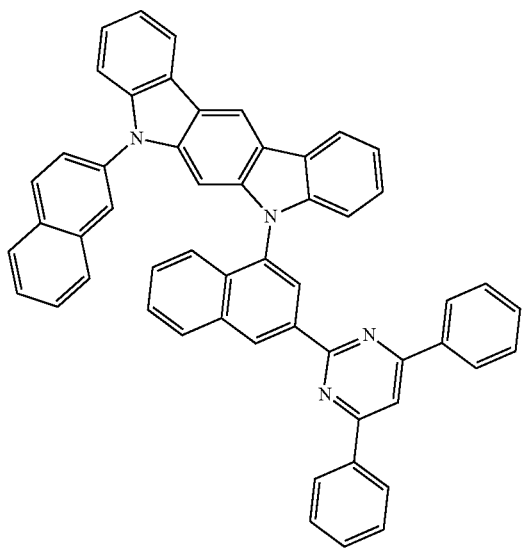
C-249
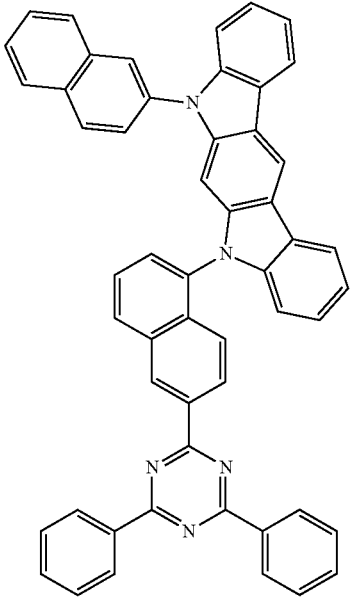

C-250
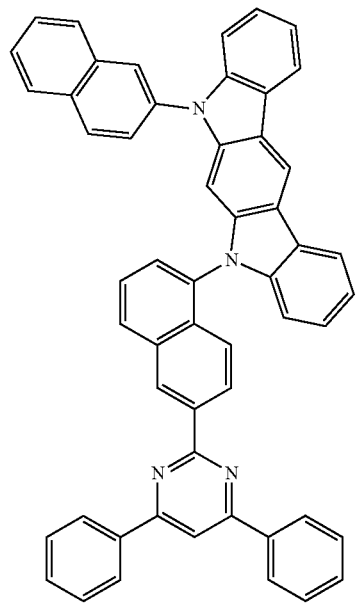
C-252
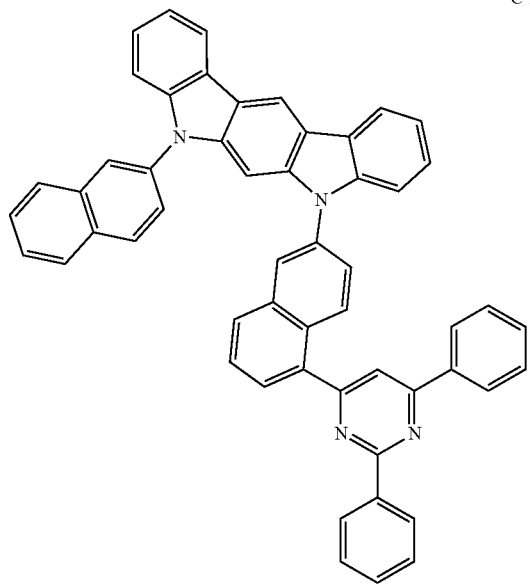
C-251
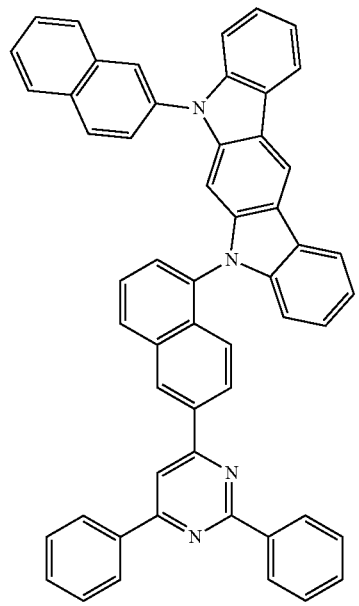
C-253
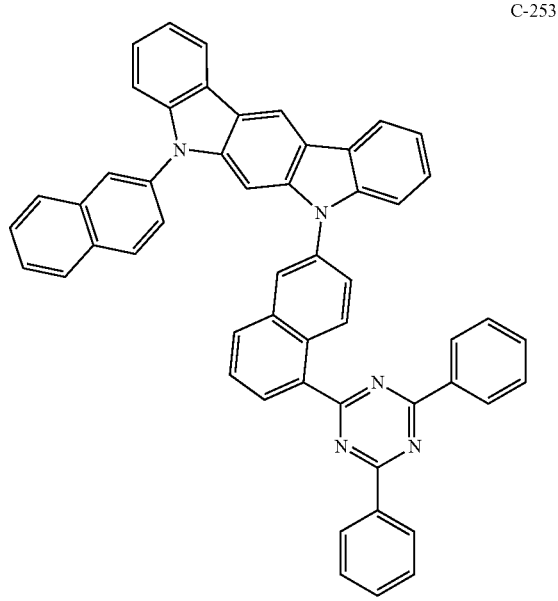

C-254
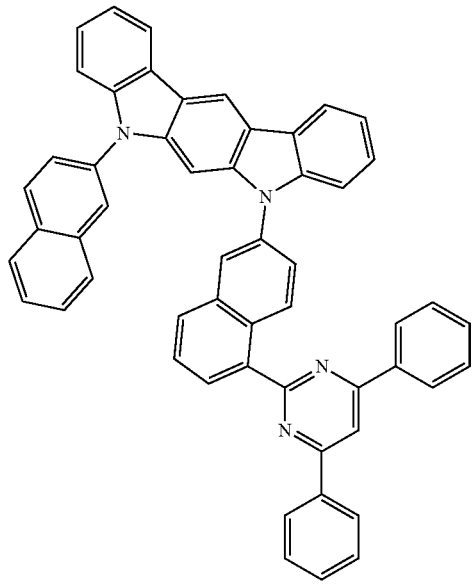
C-255
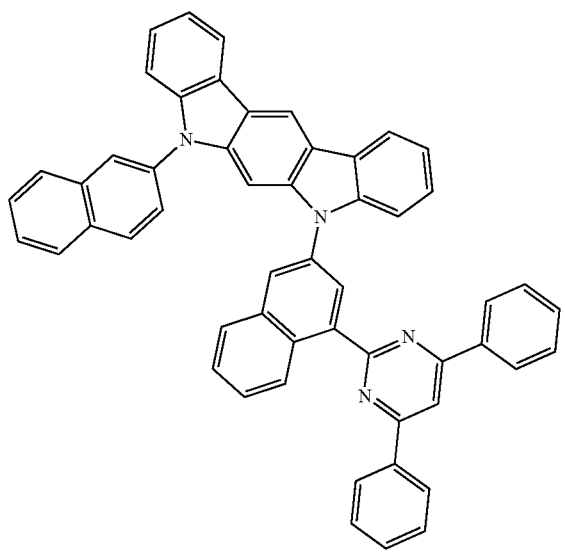
C-256
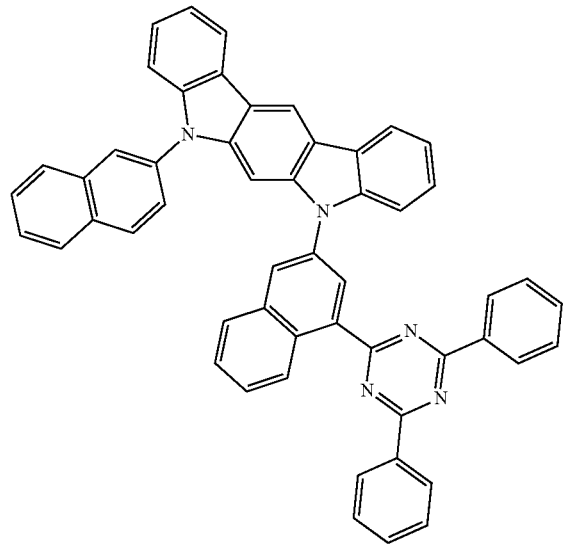
C-257
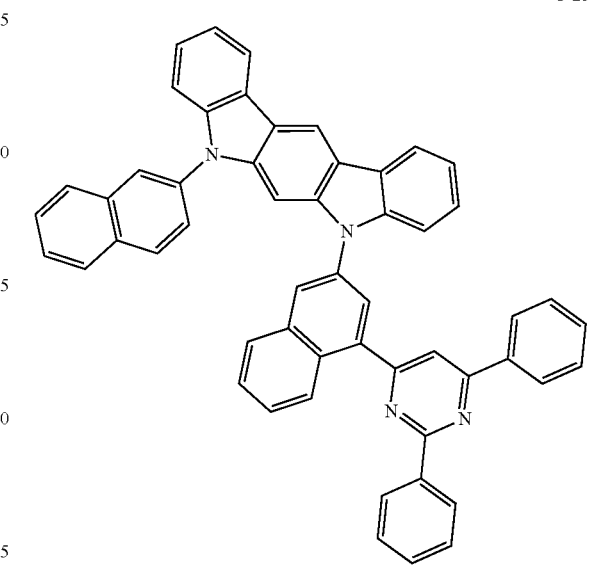
C-258
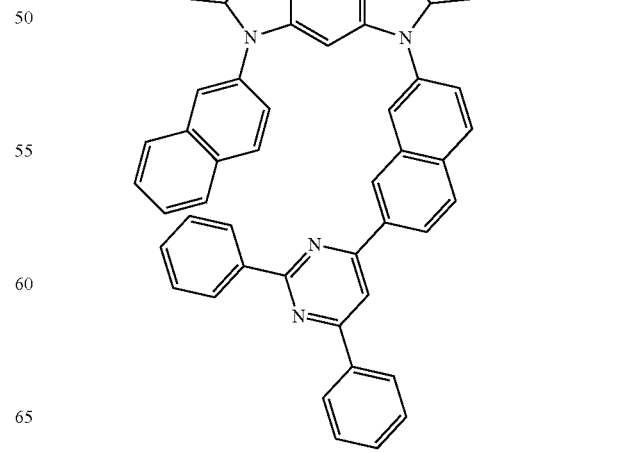

C-259
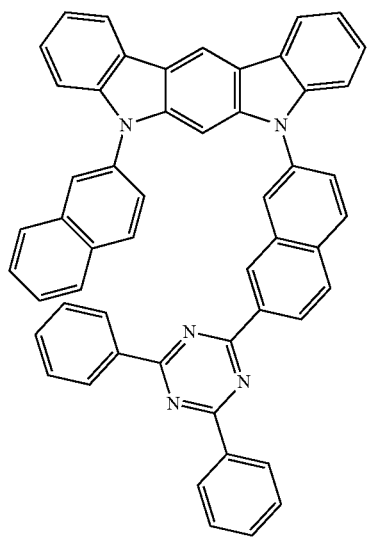
C-260
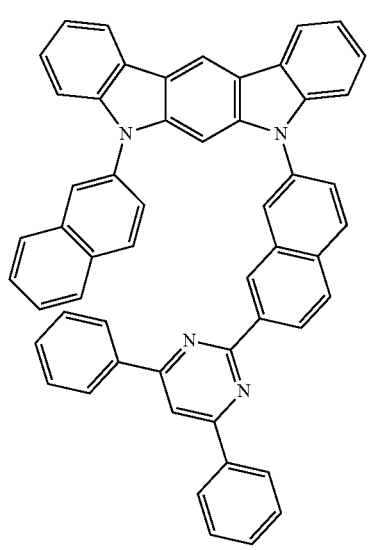
C-261
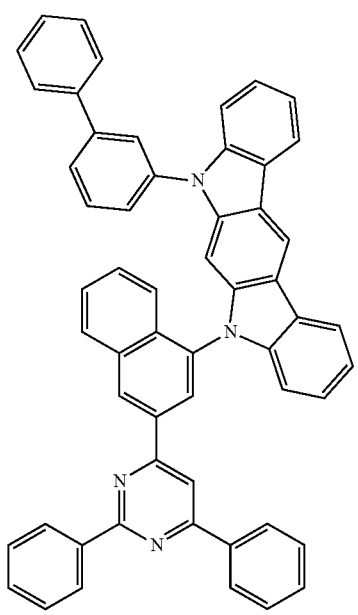
C-262
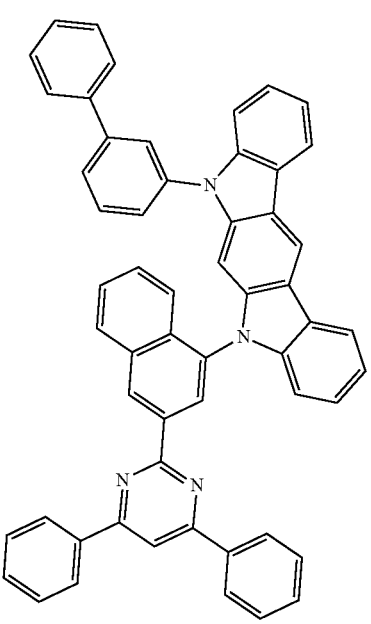

-continued
C-263
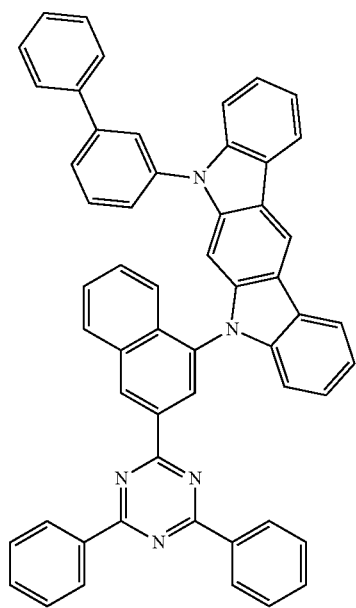
C-265
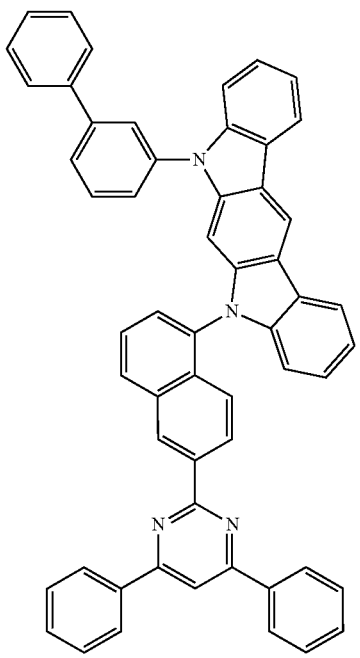
C-264
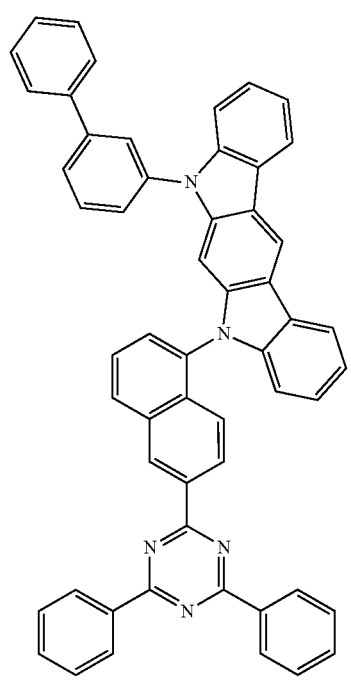
C-266
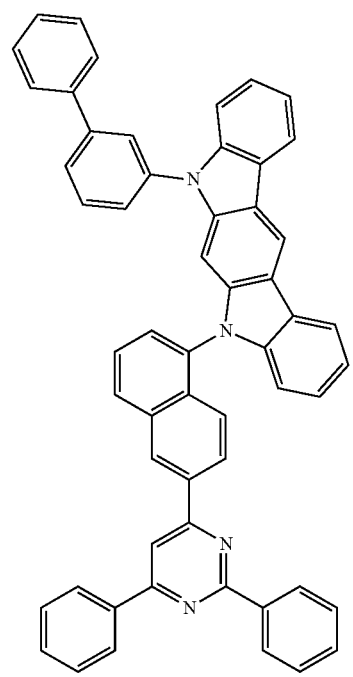

C-267

C-268

C-269

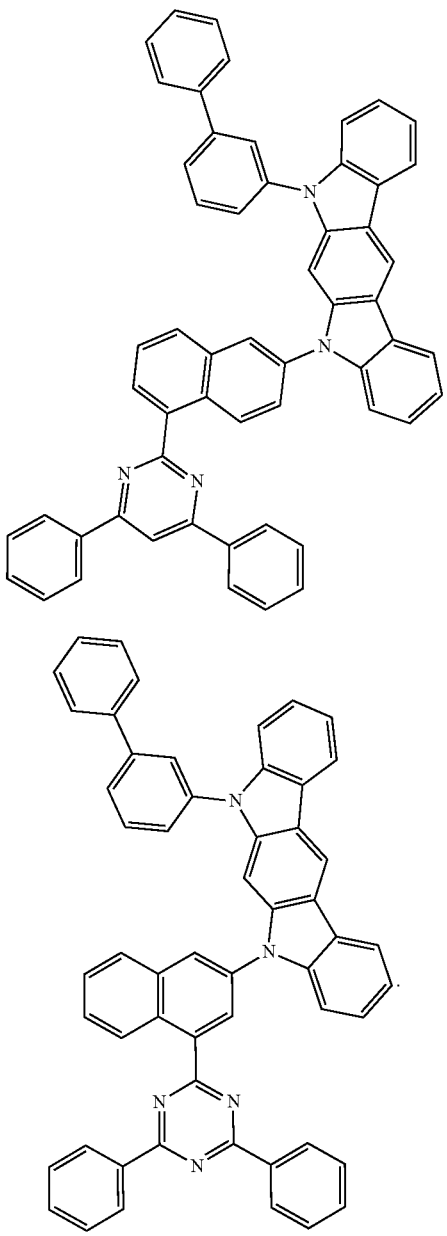

C-270

The present disclosure may provide an organic electroluminescent material comprising the organic electroluminescent compound of formula 1, and an organic electroluminescent device comprising the material.

The organic electroluminescent material according to one embodiment may consist of the organic electroluminescent compound of the present disclosure as a sole compound, or may further comprise conventional materials generally used in organic electroluminescent materials.

Meanwhile, the organic electroluminescent device of the present disclosure may comprise a first electrode, a second electrode, and at least one organic layer between the first and second electrodes. The organic layer may comprise at least one organic electroluminescent compound of formula 1. The organic layer may further comprise at least one compound selected from the group consisting of arylamine-based compounds and styrylarylamine-based compounds. Also, the organic layer may further comprise at least one metal selected from the group consisting of metals of Group 1, metals of Group 2, transition metals of the 4$^{th}$ period, transition metals of the 5$^{th}$ period, lanthanides, and organic metals of the d-transition elements of the Periodic Table, or at least one complex compound comprising the metal.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The electron blocking layer may be placed between the hole transport layer (or the hole injection layer) and the light-emitting layer, and can confine the excitons within the light-emitting layer by blocking the overflow of electrons from the light-emitting layer to prevent a light-emitting leakage. The hole transport layer or the electron blocking layer may also be multi-layers, wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. Also, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as a hole auxiliary layer or an electron blocking layer. The light-emitting auxiliary layer, the hole auxiliary layer or the electron blocking layer may have an effect of improving the efficiency and/or the lifespan of the organic electroluminescent device.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The operation stability for the organic electroluminescent device may be obtained by the surface layer. Preferably, the chalcogenide includes SiO$_x$ (1≤X≤2), AlO$_x$ (1≤X≤1.5), SiON, SiAlON, etc.; the metal halide includes LiF, MgF$_2$, CaF$_2$, a rare earth metal fluoride, etc.; and the metal oxide includes Cs$_2$O, Li$_2$O, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent compound represented by formula 1 may be comprised in the light-emitting layer. When used in the light-emitting layer, the organic electroluminescent compound of formula 1 may be comprised as a host material. Preferably, the light-emitting layer may further comprise at least one dopant. If necessary, another compound besides the organic electroluminescent compound of formula 1 may be further comprised as a second host material. Herein, the weight ratio of the first host material to the second host material is in the range of 1:99 to 99:1.

The second host material can use any of the known phosphorescent hosts. In terms of luminous efficiency, the second host material may be particularly preferable selected from the group consisting of the compounds represented by the following formula 11 to 16.

  (11)

  (12)

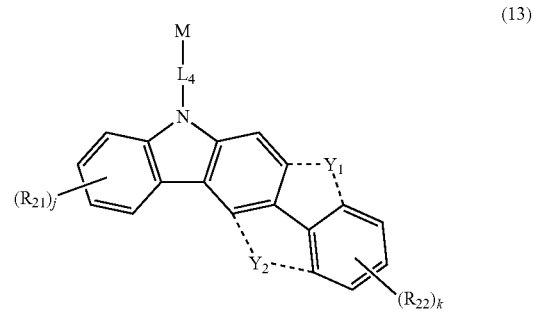  (13)

(14)

(15)

In formulae 11 to 15,

Cz represents the following structure:

A represents —O— or —S—;

$R_{21}$ to $R_{24}$ each independently, represent hydrogen, deuterium, halogen, a substituted or unsubstituted (C1-C30)alkyl, a substituted or unsubstituted (C6-C30)aryl, a substituted or unsubstituted (5- to 30-membered) heteroaryl, or —$SiR_{25}R_{26}R_{27}$, in which $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered) heteroaryl; $Y_1$ and $Y_2$, each independently, represent —O—, —S—, —N($R_{31}$)— or —C($R_{32}$)($R_{33}$)—, provided that $Y_1$ and $Y_2$ are not present simultaneously; $R_{31}$ to $R_{33}$ each independently, represent a substituted or unsubstituted (C1-C30)alkyl, a substituted or unsubstituted (C6-C30)aryl, or a substituted or unsubstituted (5- to 30-membered)heteroaryl, $R_{32}$ and $R_{33}$ may be the same or different; h and i each independently, represent an integer of 1 to 3; j, k, l and v each independently, represent an integer of 0 to 4; u represents an integer of 0 to 3; when h, i, j, k, l, u or v represents an integer of 2 or more, each (Cz-$L_4$), each (Cz), each $R_{21}$, each $R_{22}$, each $R_{23}$ or each $R_{24}$ may be the same or different;

(16)

In formula 16, $Y_3$ to $Y_5$ each independently, represent $CR_{34}$ or N;

$R_{34}$ represents hydrogen, a substituted or unsubstituted (C1-C30)alkyl, a substituted or unsubstituted (C6-C30) aryl, or a substituted or unsubstituted (5- to 30-membered)heteroaryl;

$B_1$ and $B_2$ each independently, represent hydrogen, a substituted or unsubstituted (C6-C30)aryl, or a substituted or unsubstituted (5- to 30-membered)heteroaryl;

$B_3$ represents a substituted or unsubstituted (C6-C30)aryl or a substituted or unsubstituted (5- to 30-membered) heteroaryl;

$L_5$ represents a single bond, a substituted or unsubstituted (C6-C30)arylene, or a substituted or unsubstituted (5- to 30-membered)heteroarylene.

Specifically, the preferred examples of the second host material are as follows:

B-1

B-2

B-3
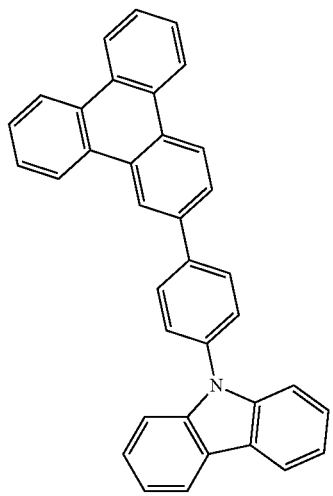
B-4
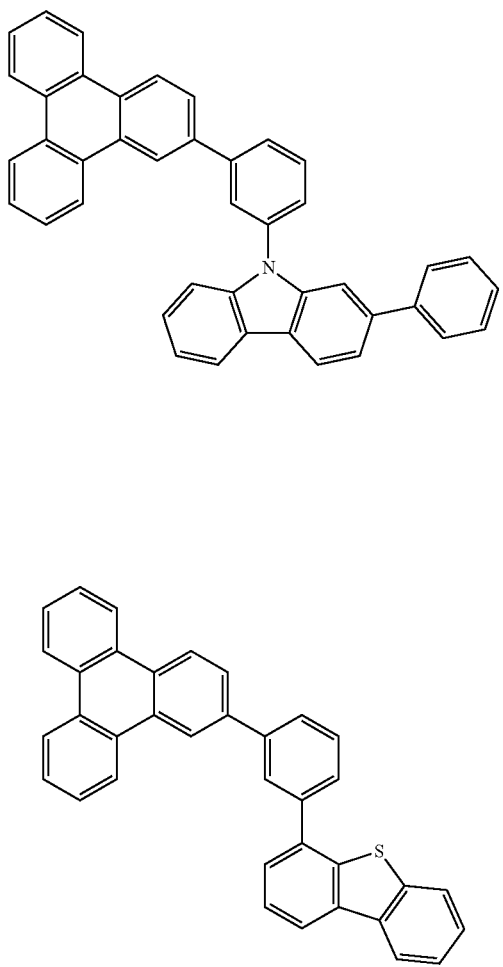
B-5
B-6
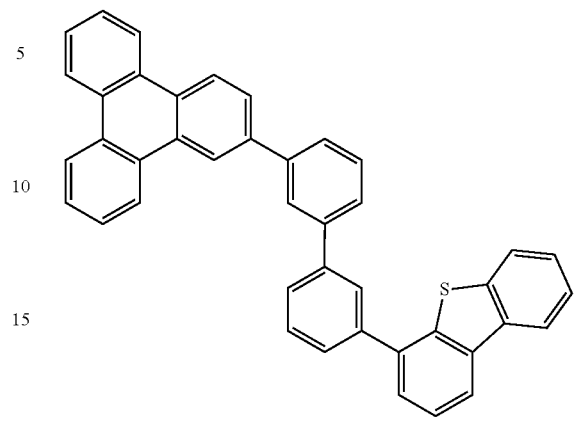
B-7
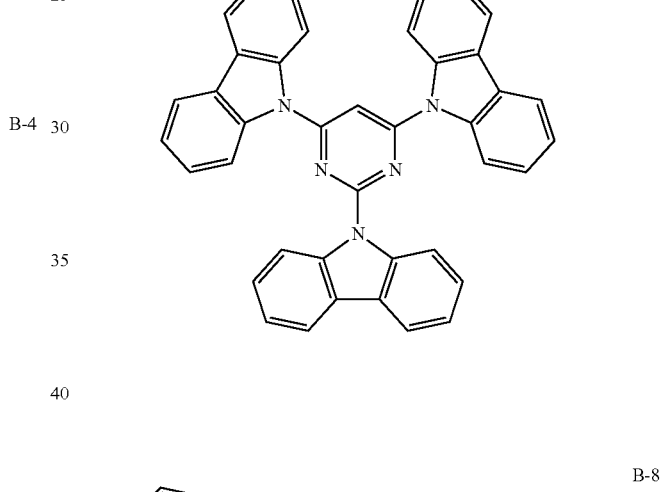
B-8
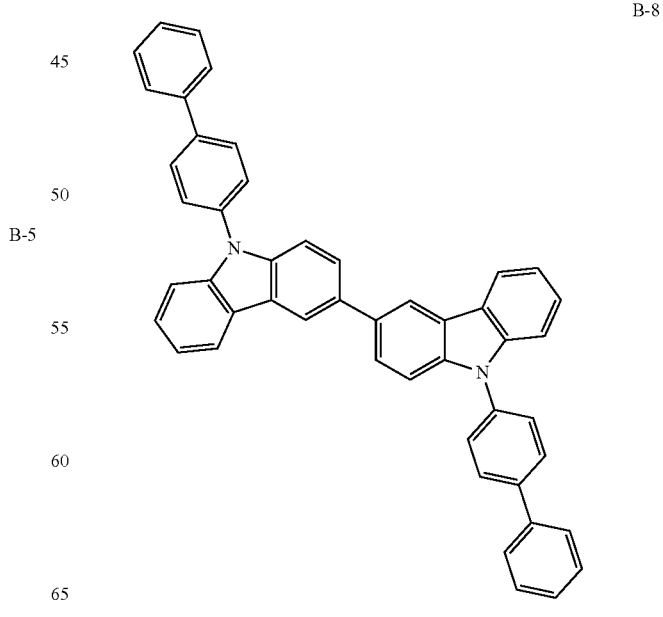

B-9
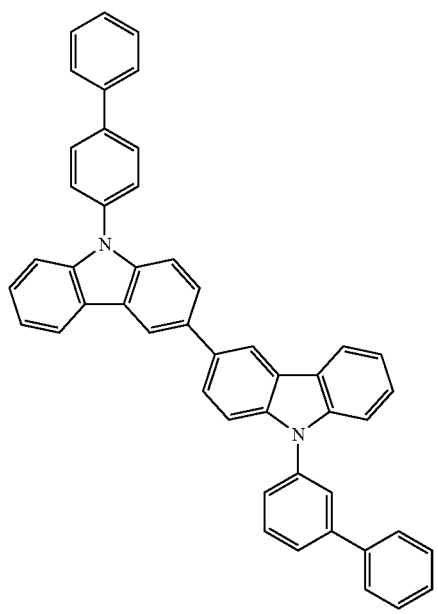
B-11
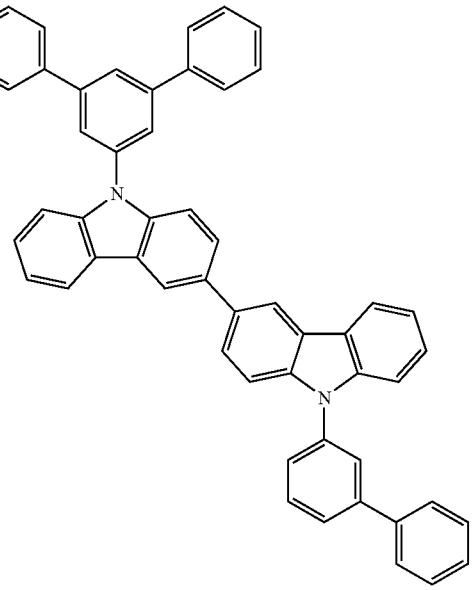
B-10
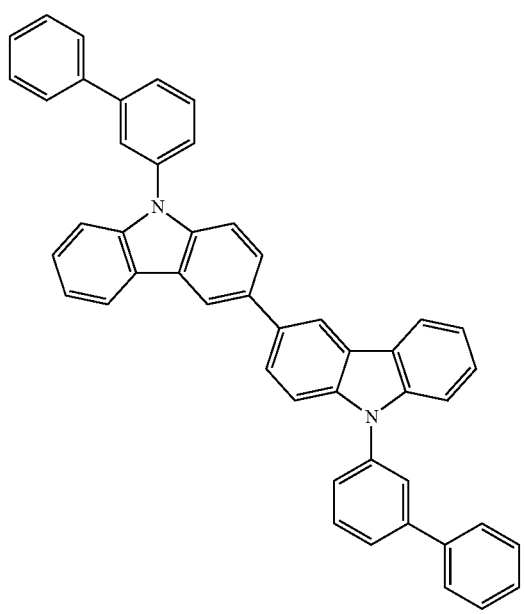
B-12
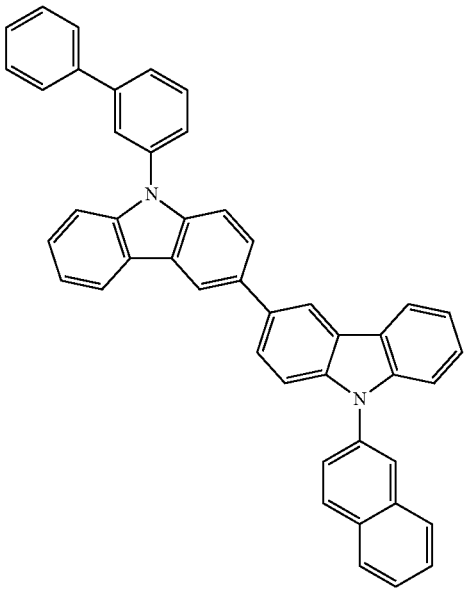

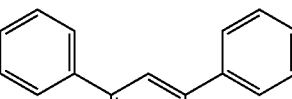
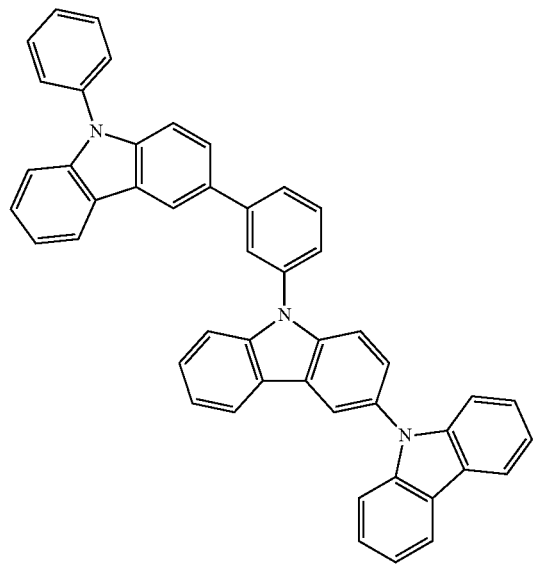
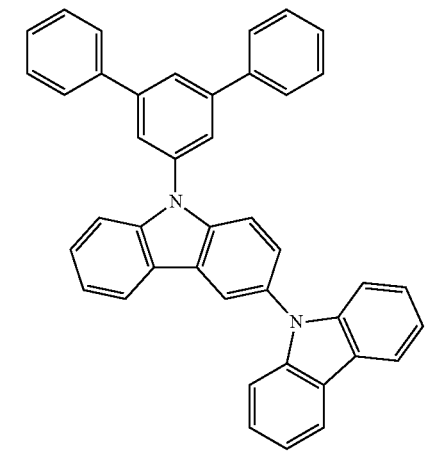
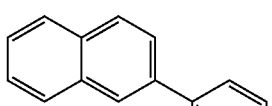
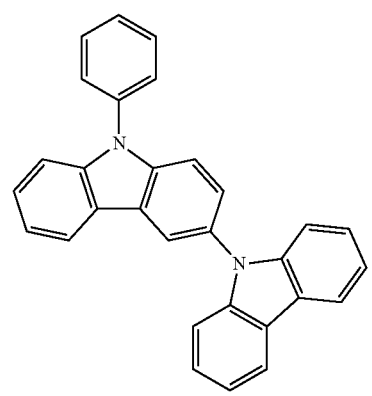
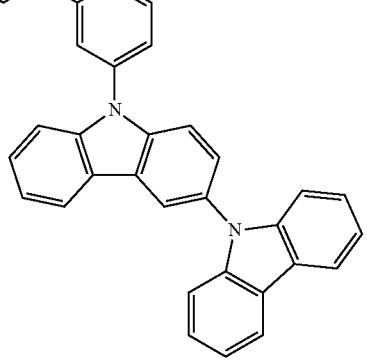
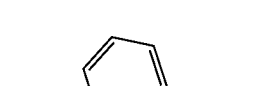
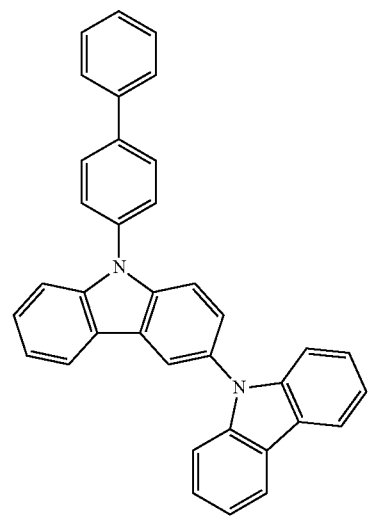
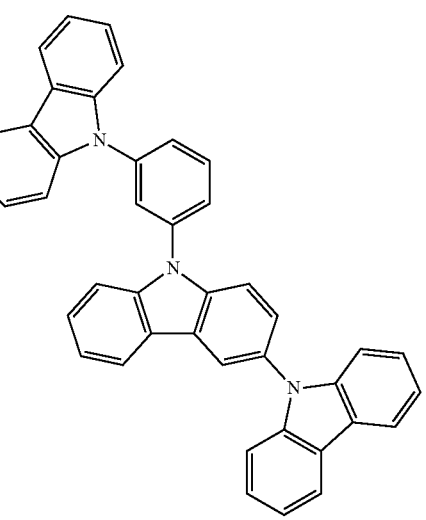

B-19
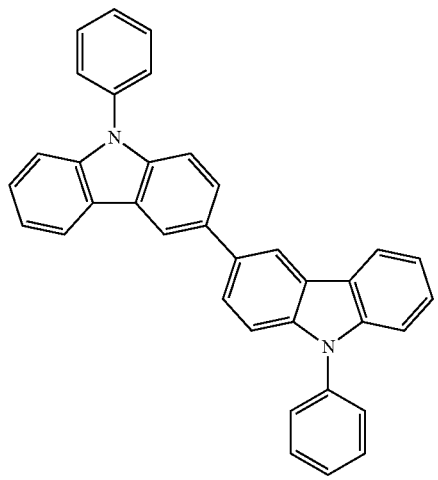
B-20
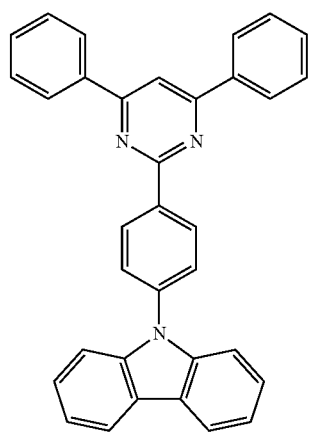
B-21
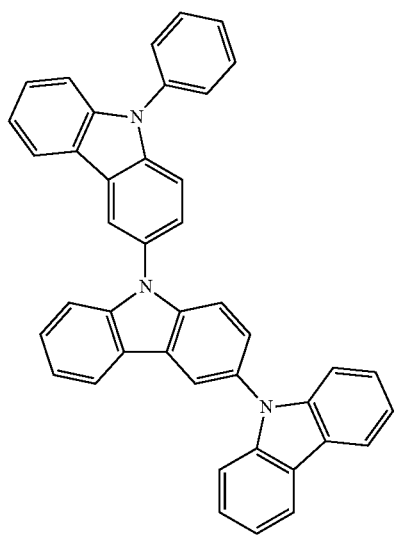
B-22
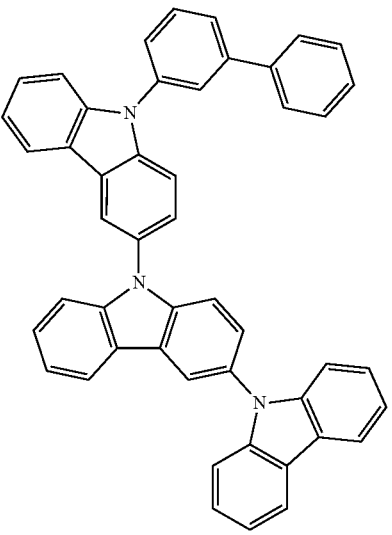
B-23
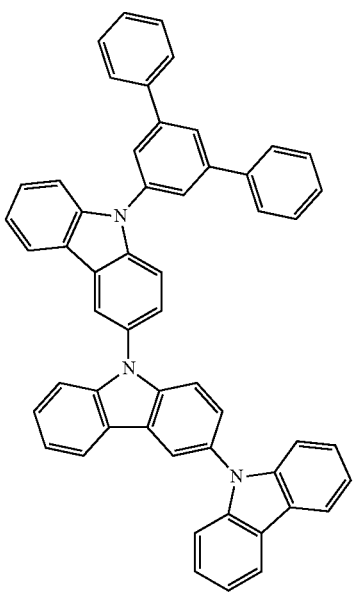

B-24
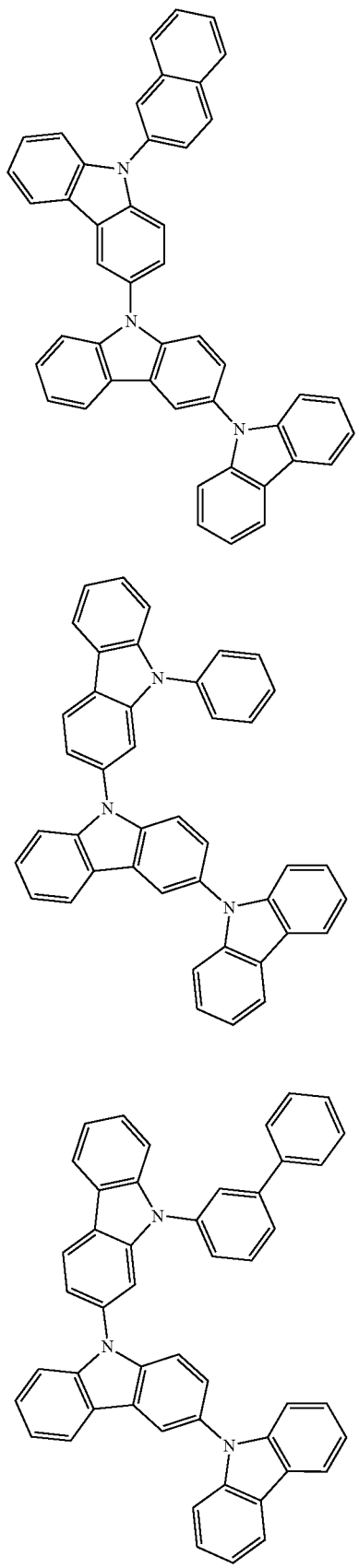
B-25
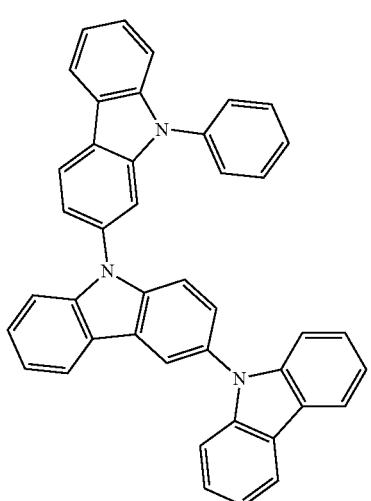
B-26
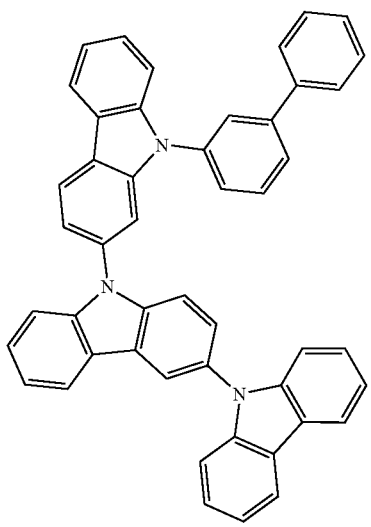
B-27
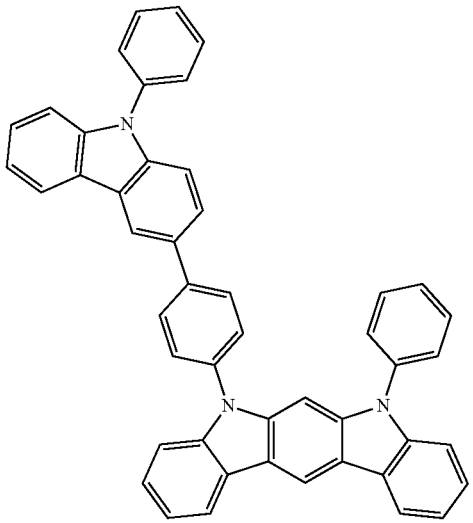
B-28
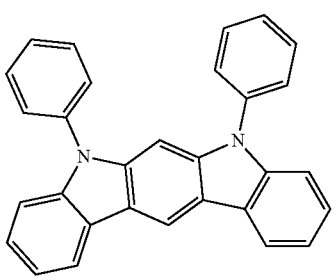
B-29
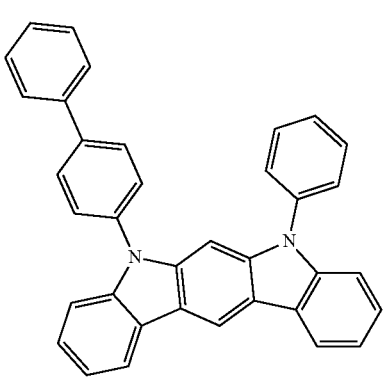
B-30
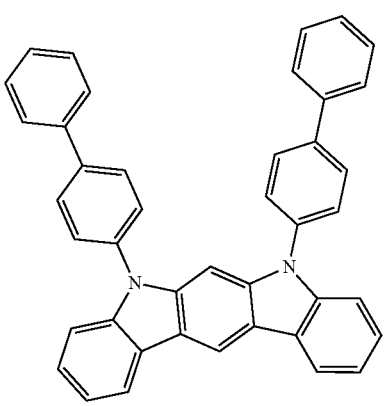

B-31
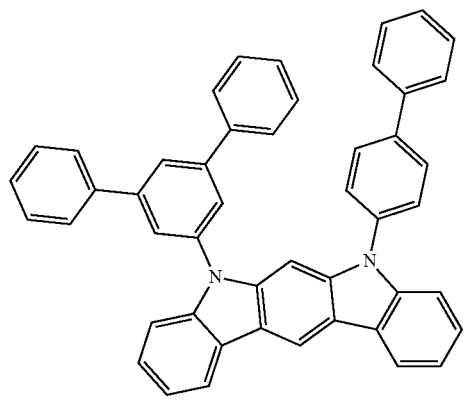
B-32
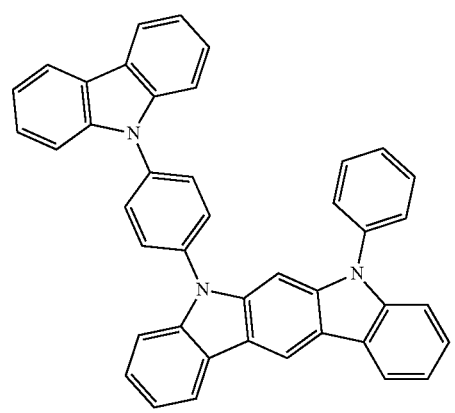
B-33
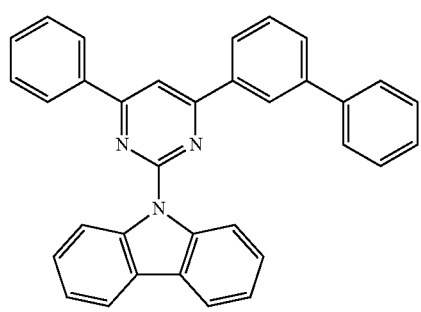
B-34
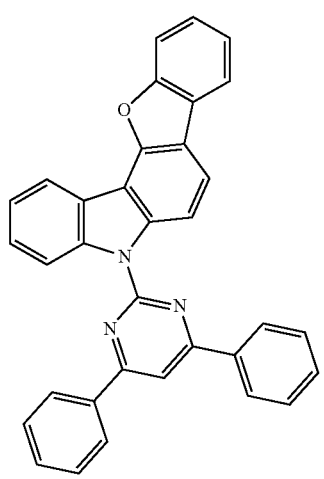
B-35
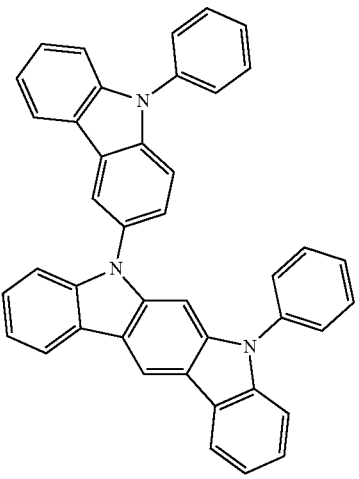
B-36
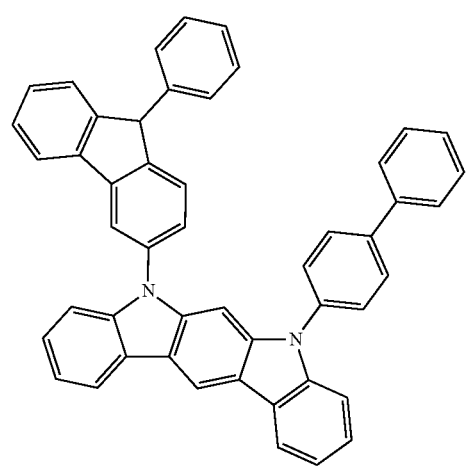
B-37
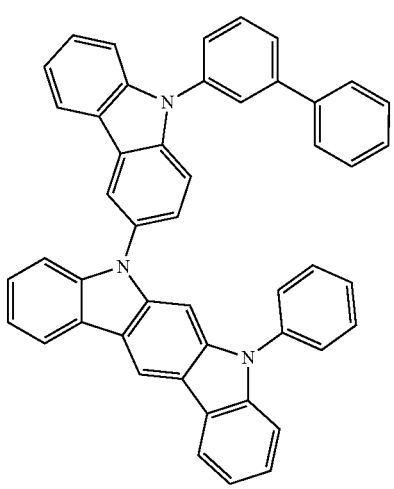

-continued
B-38
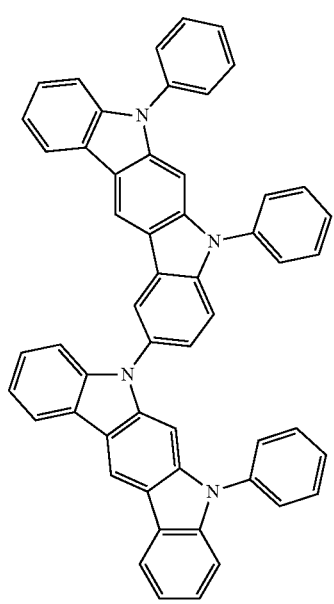
B-39
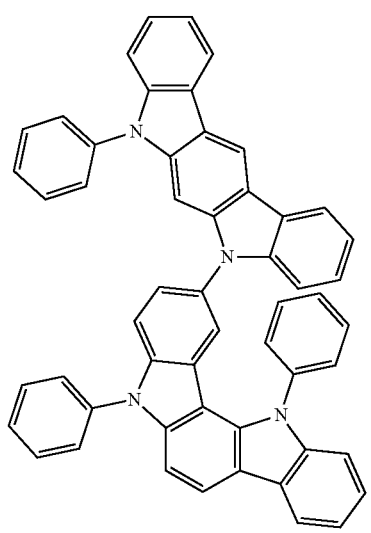
B-40
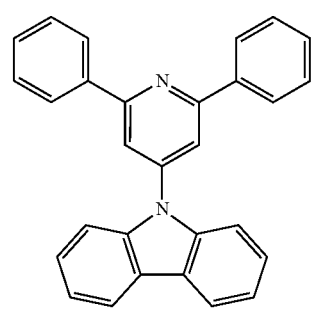
-continued
B-41
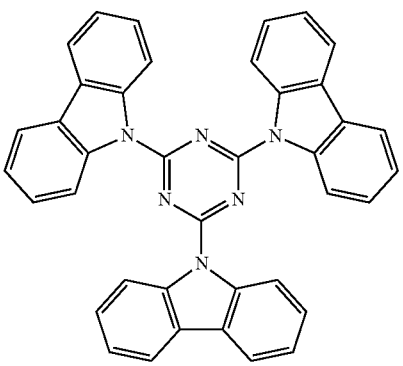
B-42
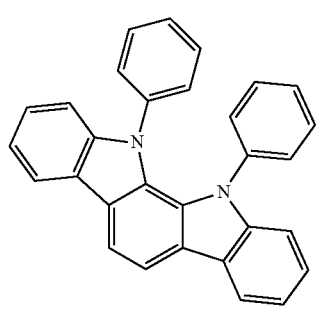
B-43
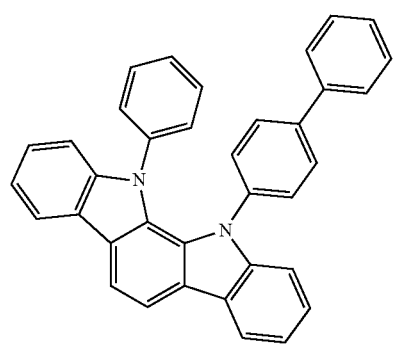
B-44
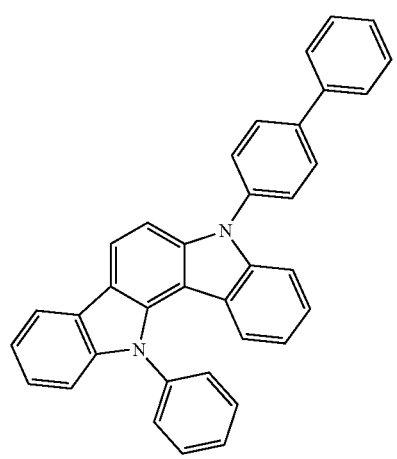

-continued
B-45
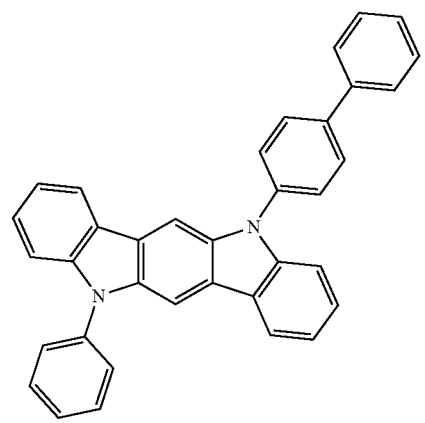
B-46
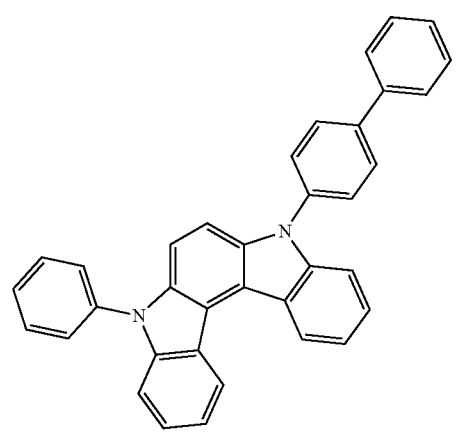
B-47
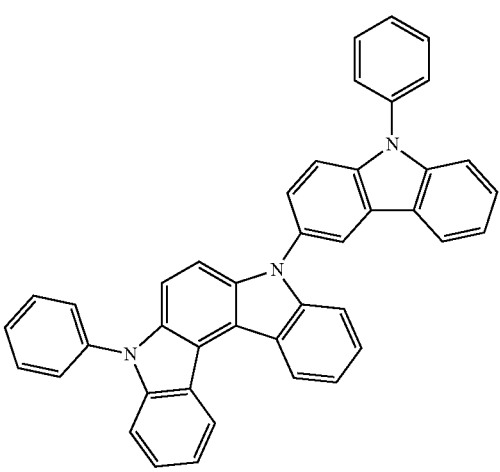
-continued
B-48
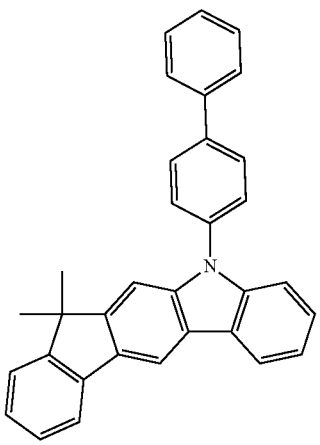
B-49
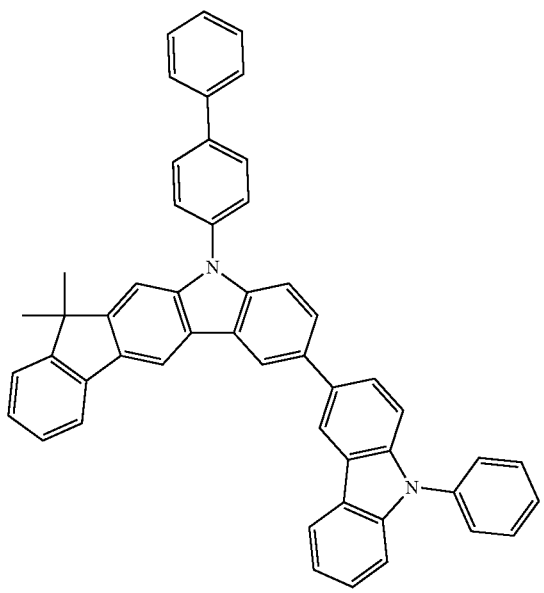
B-50
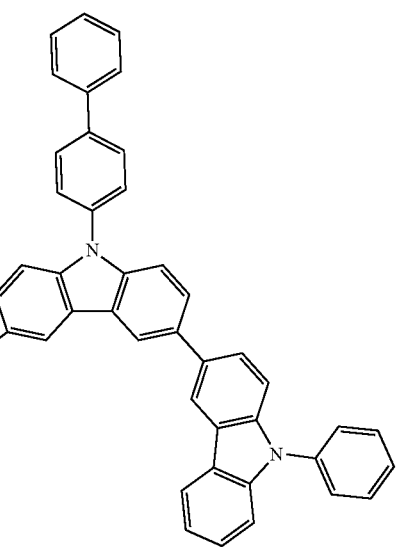

B-51
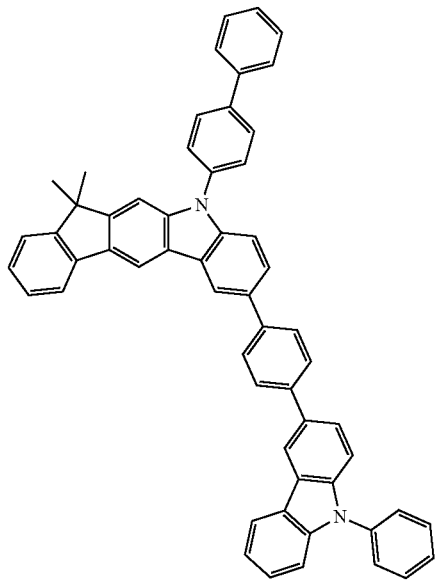
B-52
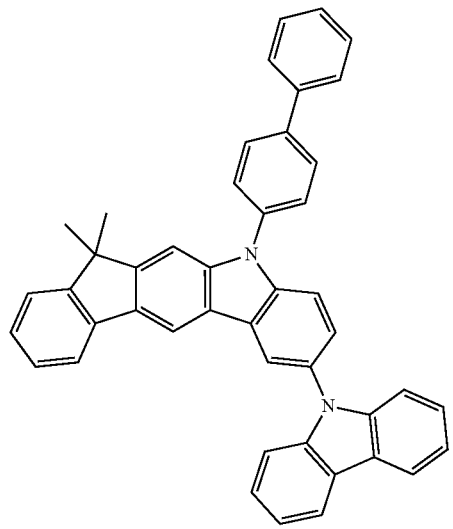
B-53
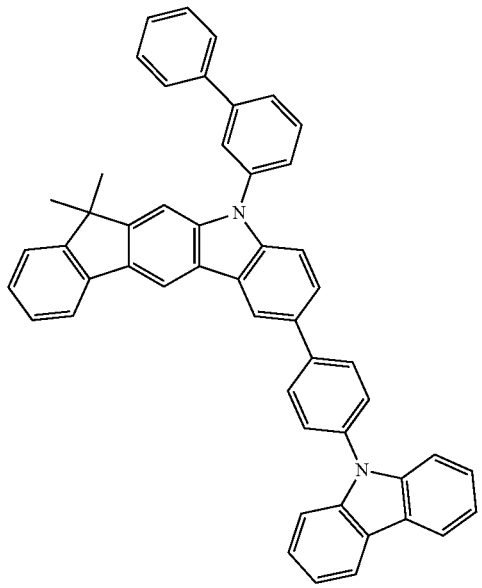
B-54
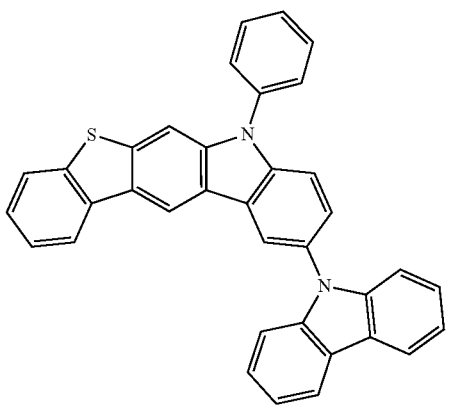
B-55
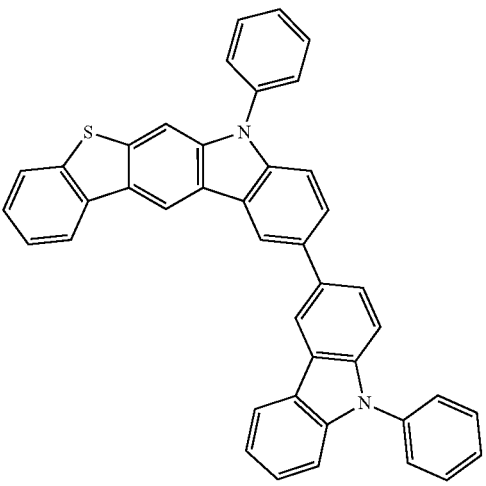

B-56
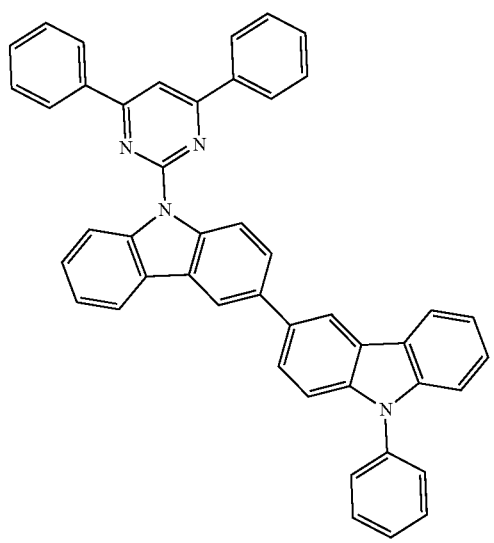
B-57
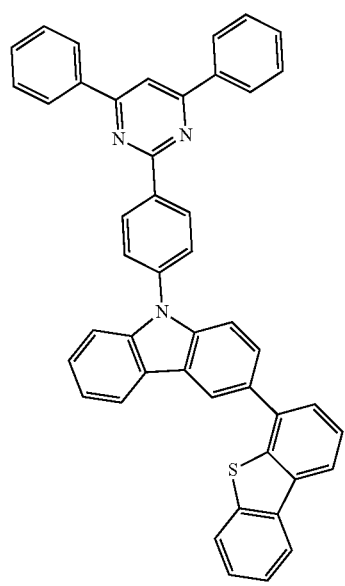
B-58
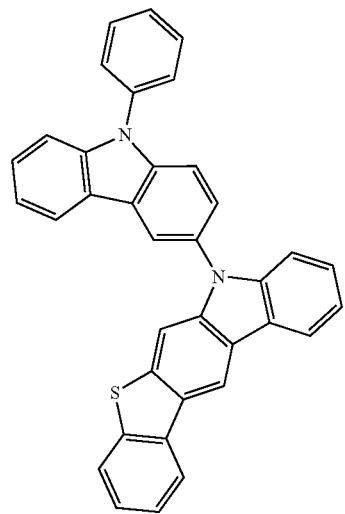
B-59
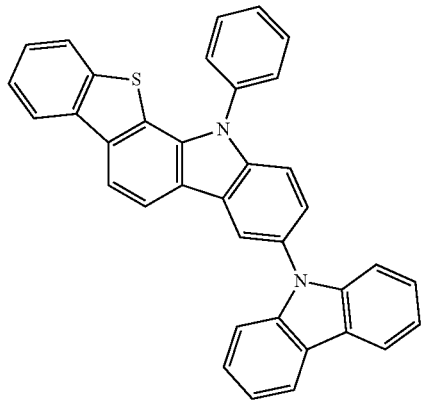
B-60
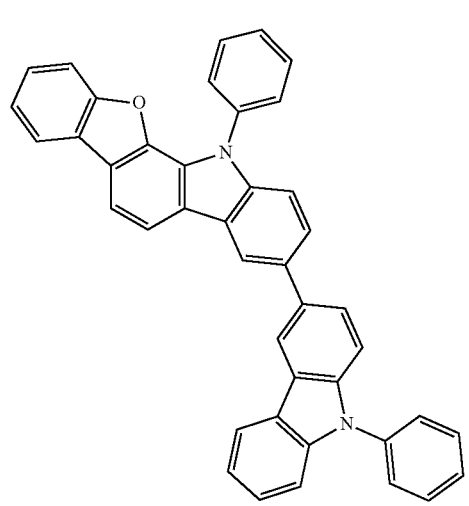
B-61
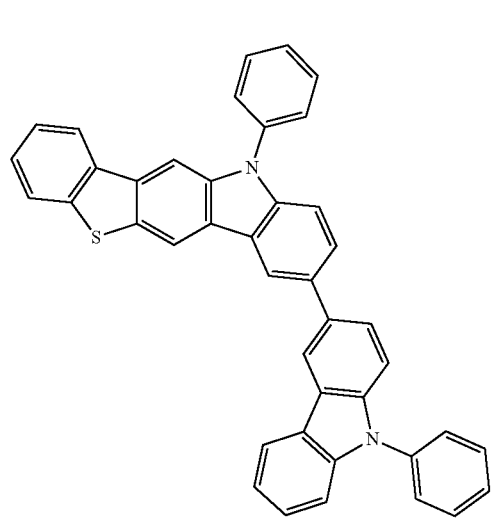

B-62
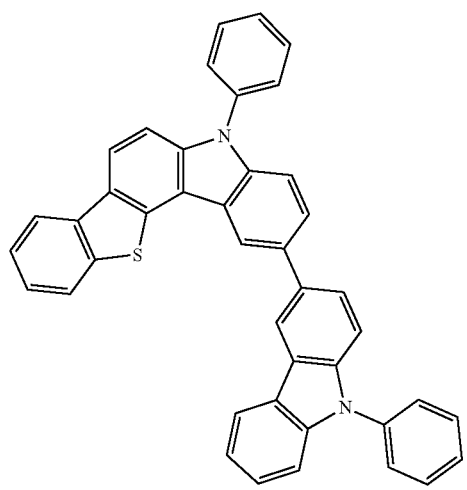
B-64
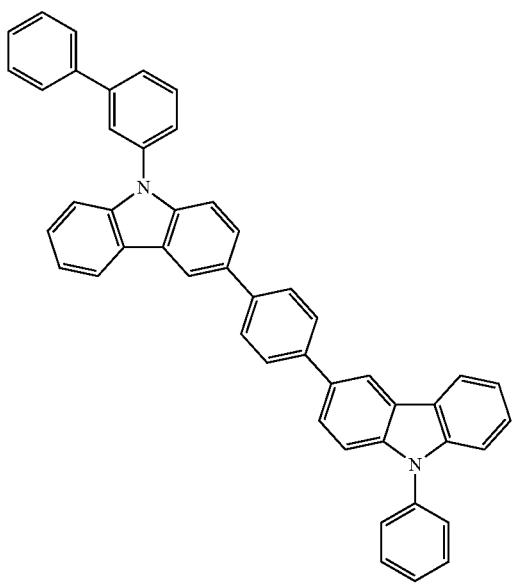
B-63
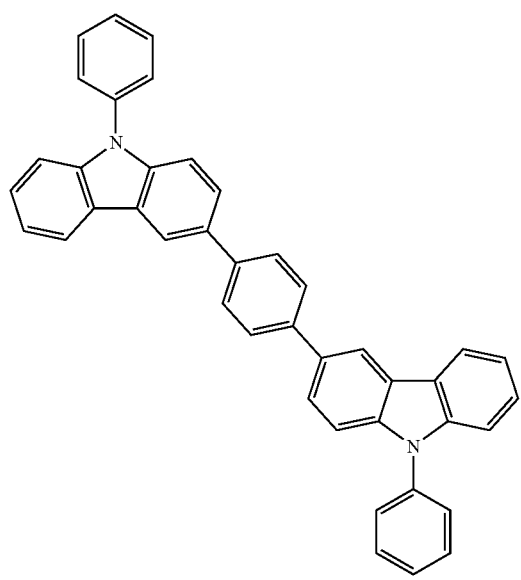
B-65
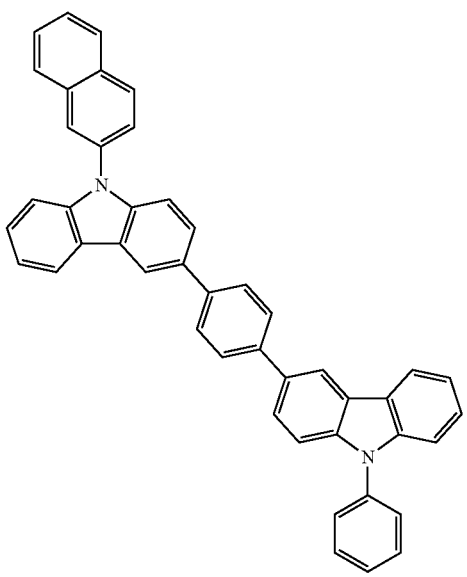

167
-continued
B-66
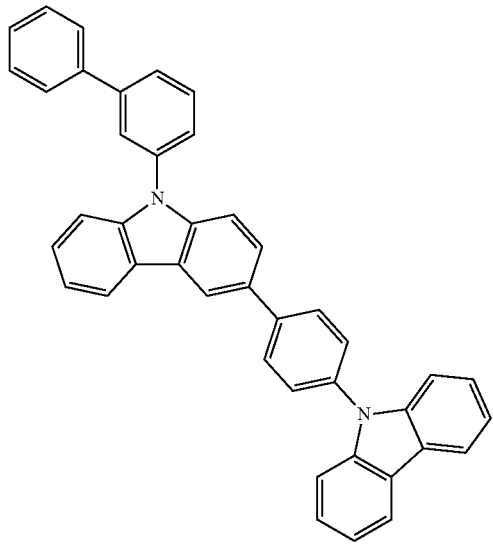
B-67
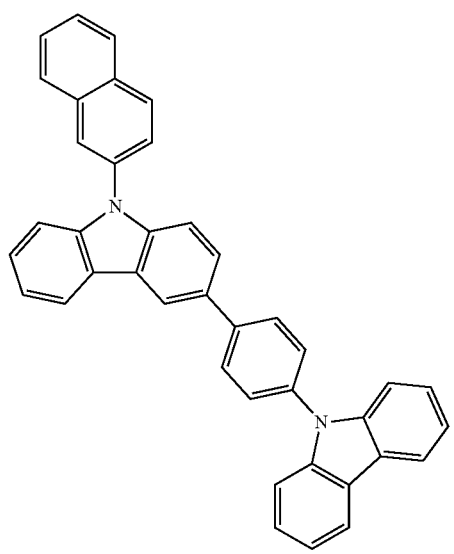
B-68
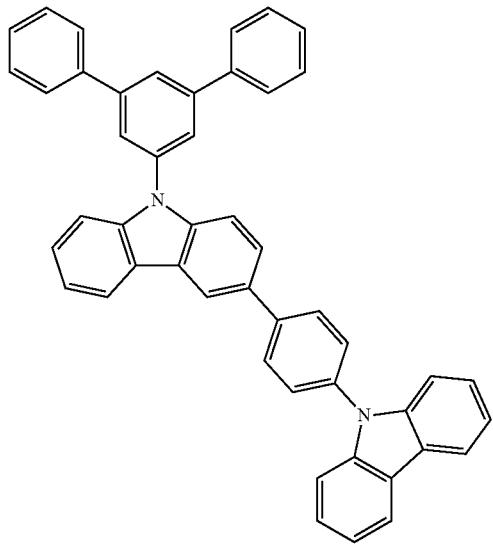
168
-continued
B-69
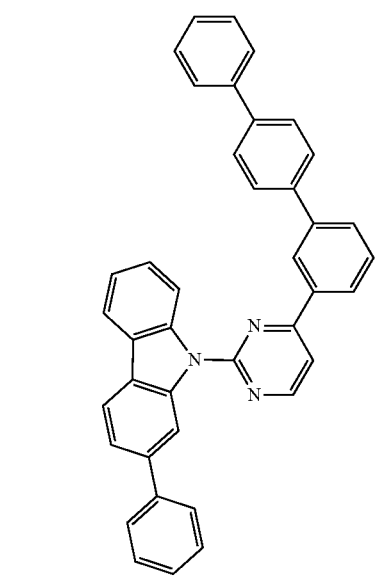
B-70
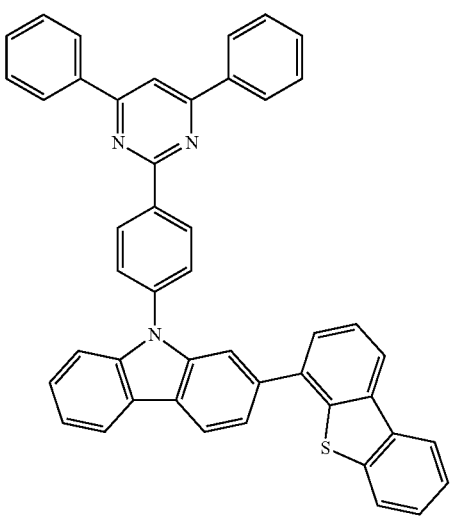
B-71
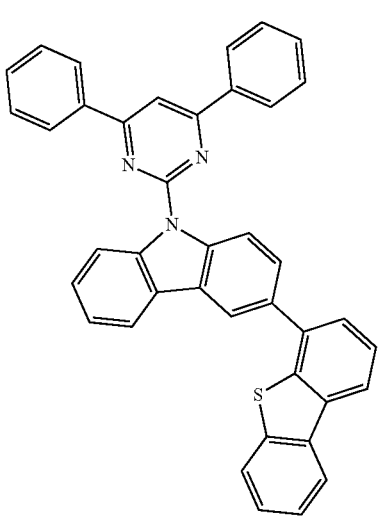

B-72
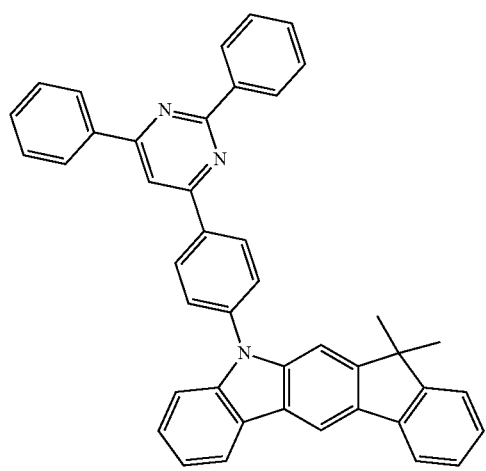
B-73
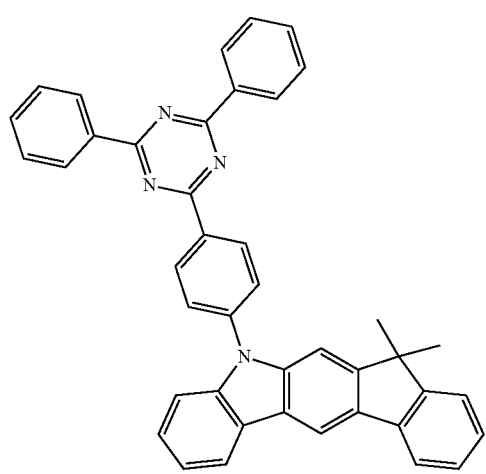
B-74
B-75
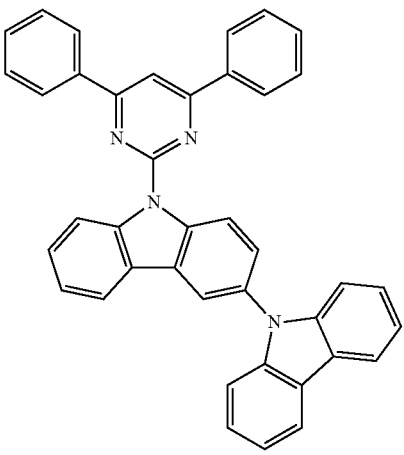
B-76
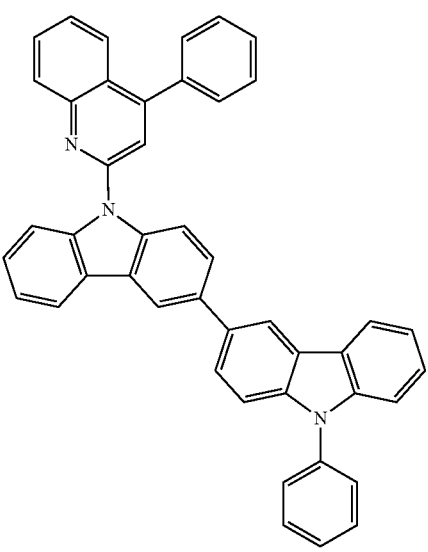
B-77
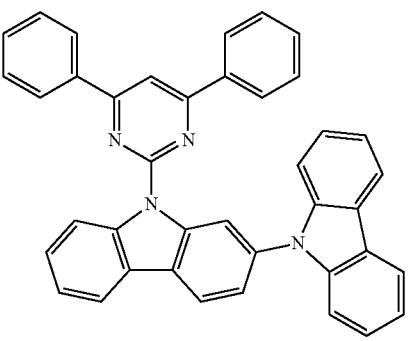

B-78
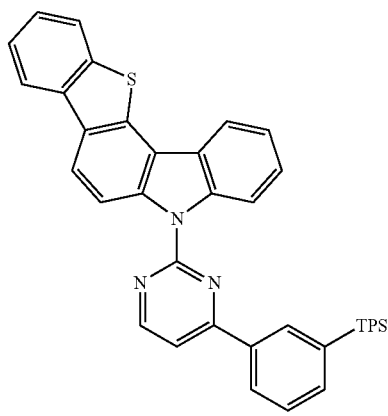
B-79
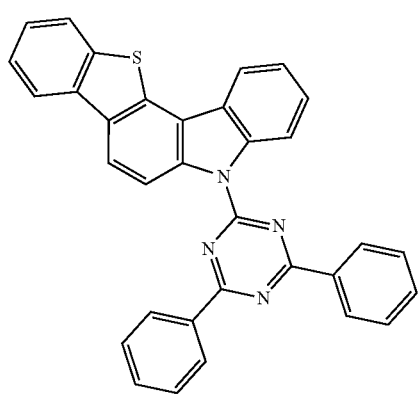
B-80
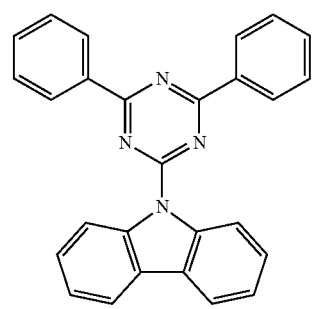
B-81
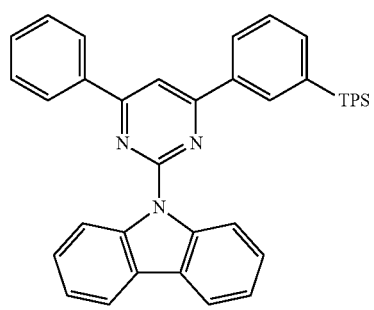
B-82
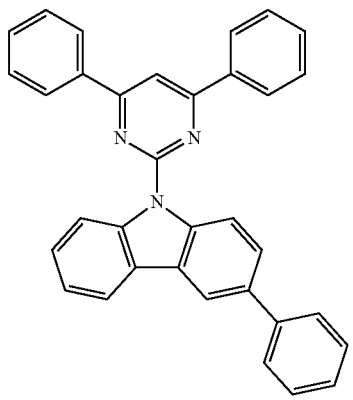
B-83
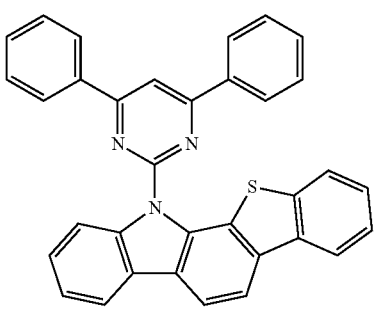
B-84
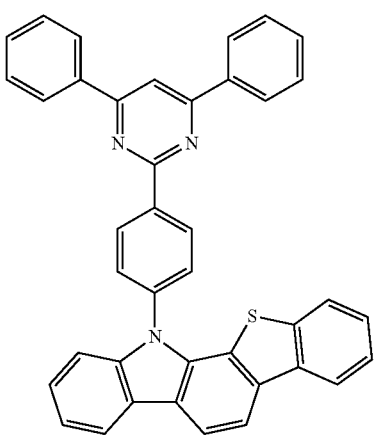
B-85
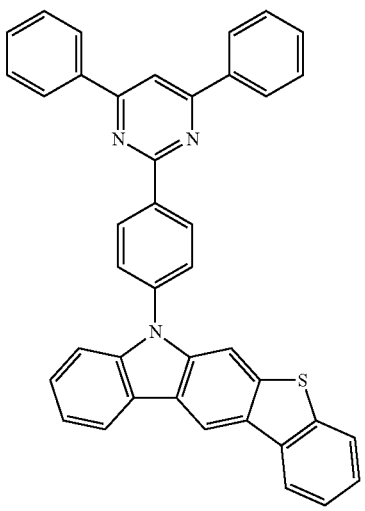

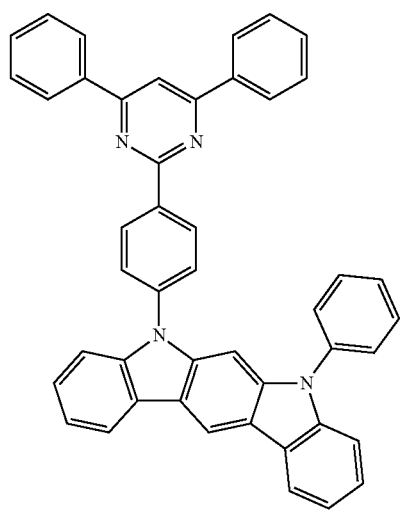
B-86
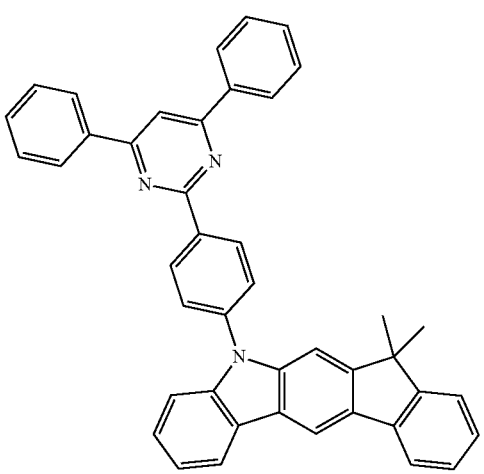
B-89
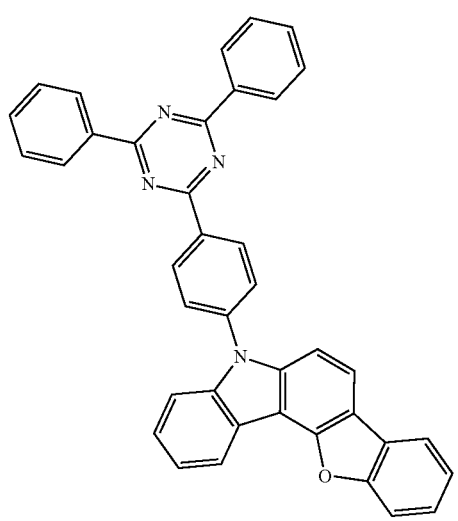
B-87
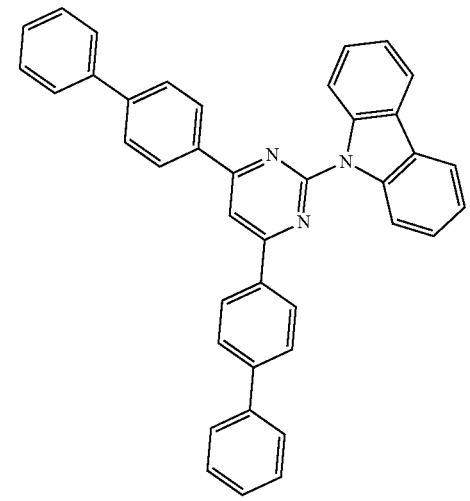
B-90
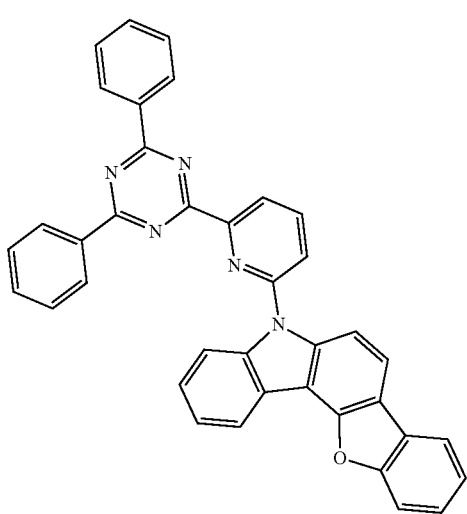
B-88
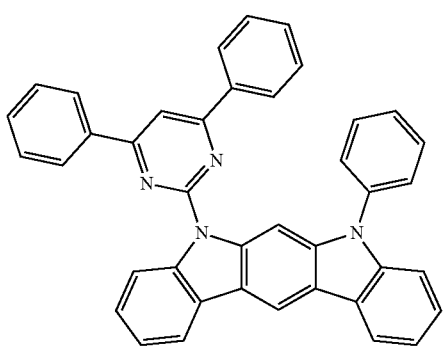
B-91

B-92
B-93
B-94
B-95
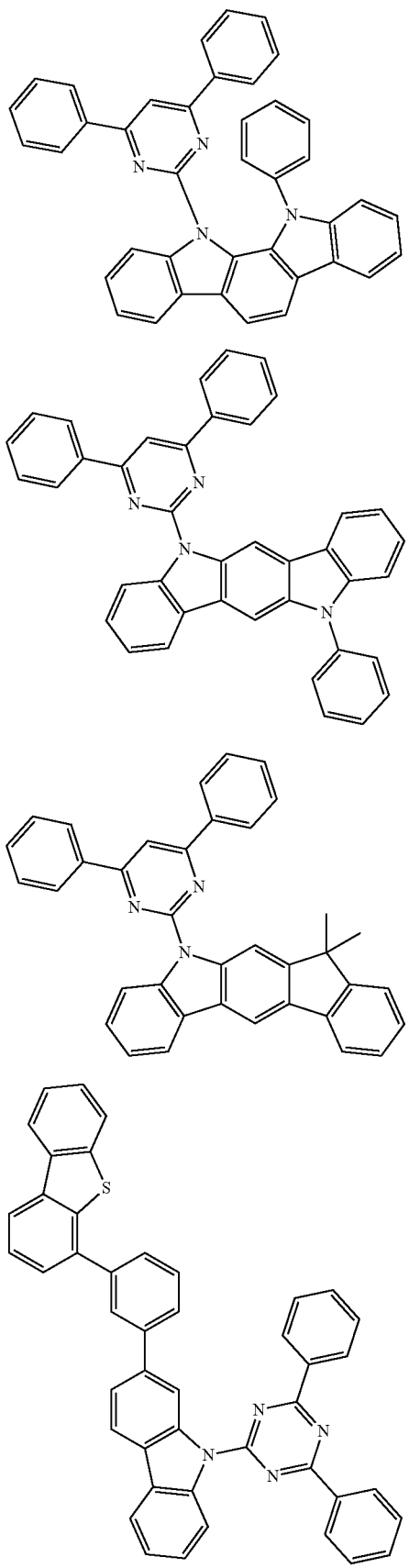
B-96
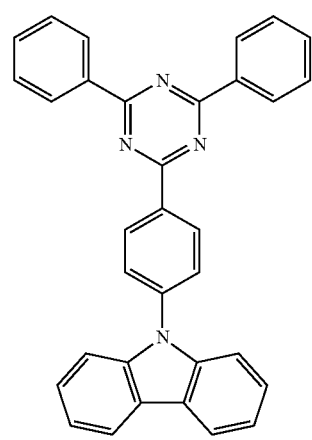
B-97
B-98
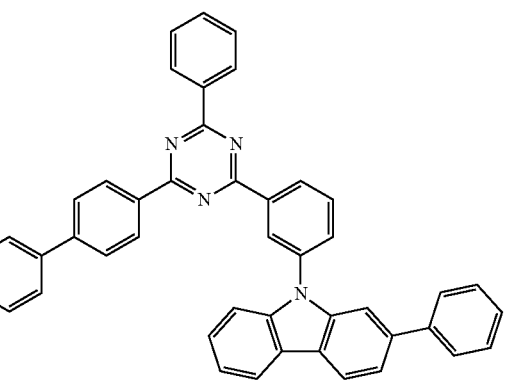

B-99
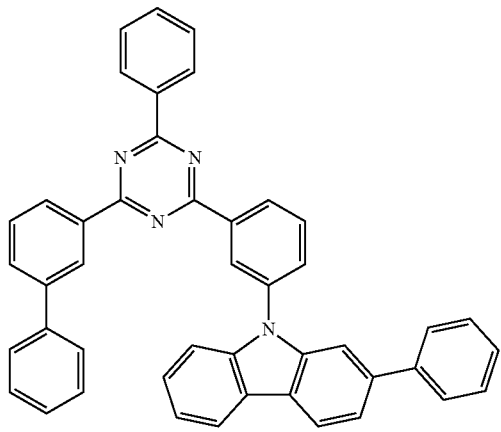
B-100
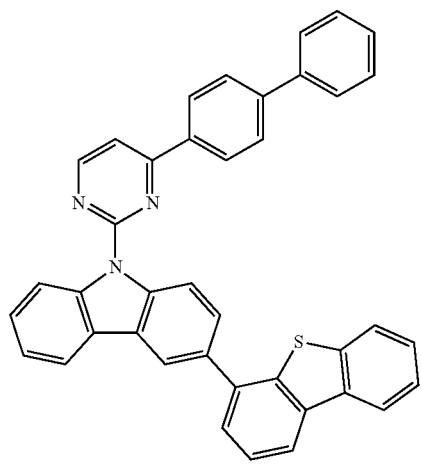
B-101
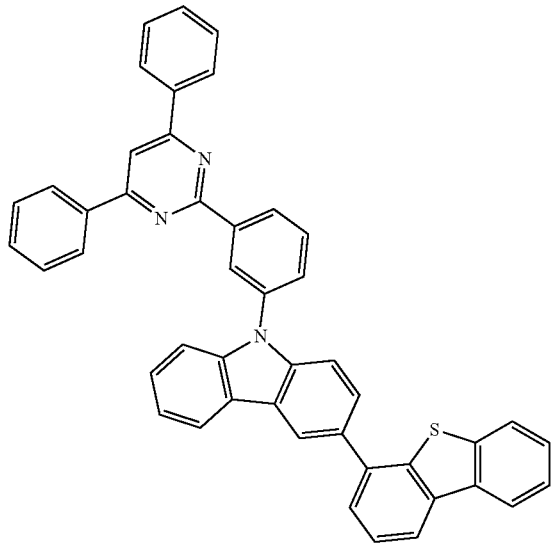
B-102
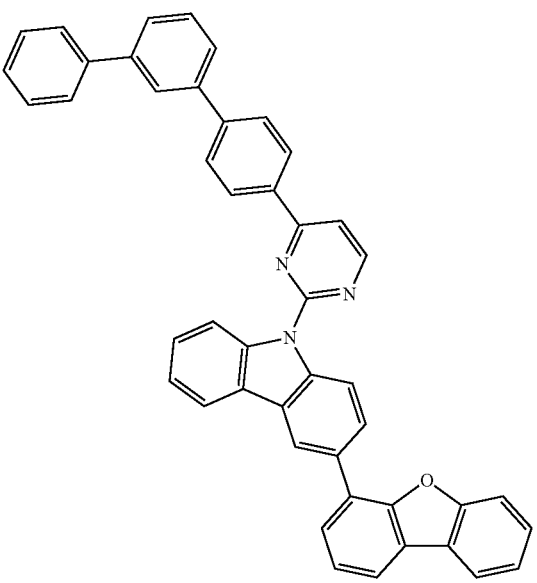
B-103
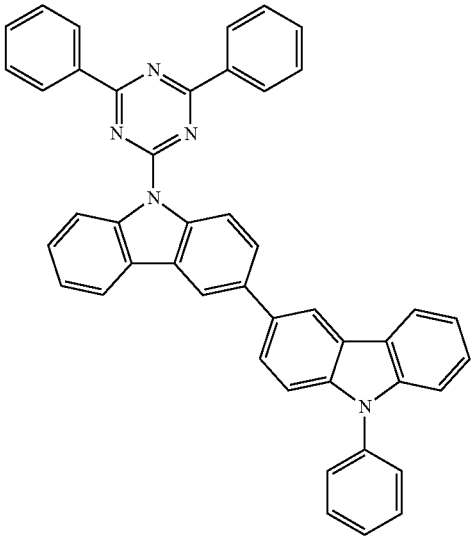

B-104
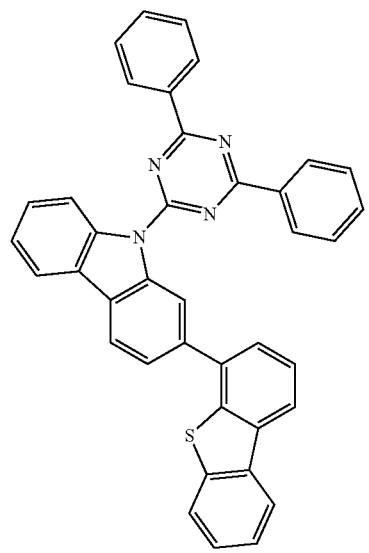
B-105
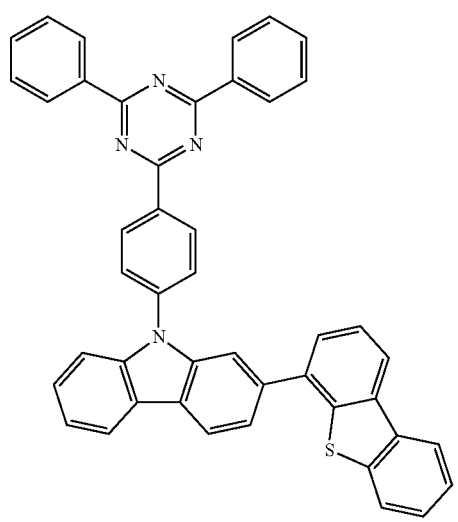
B-106
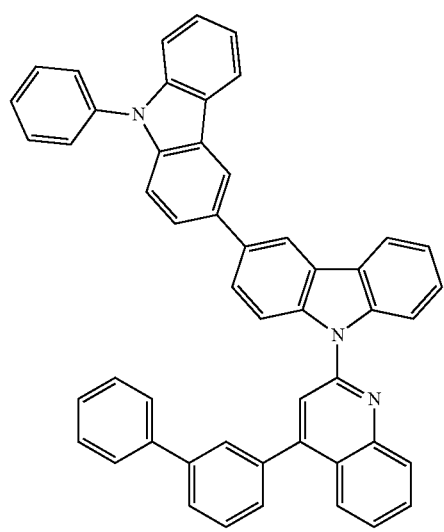
B-107
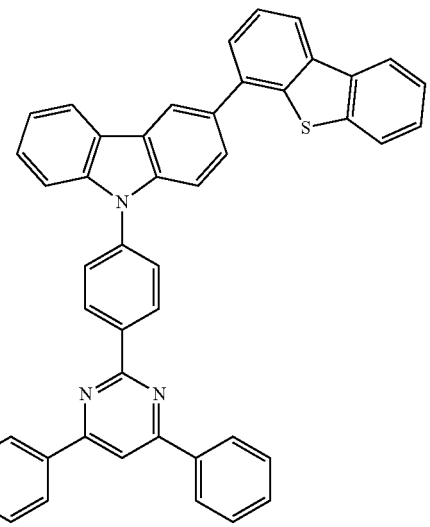
B-108
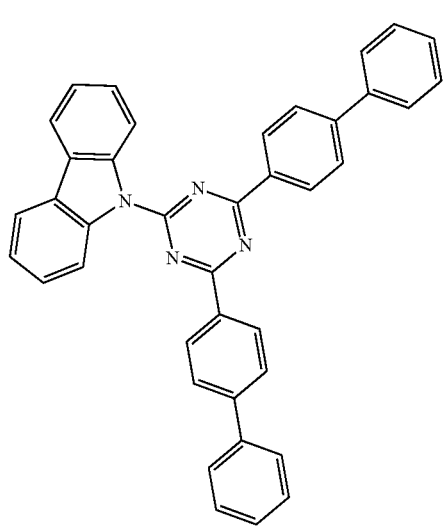
B-109
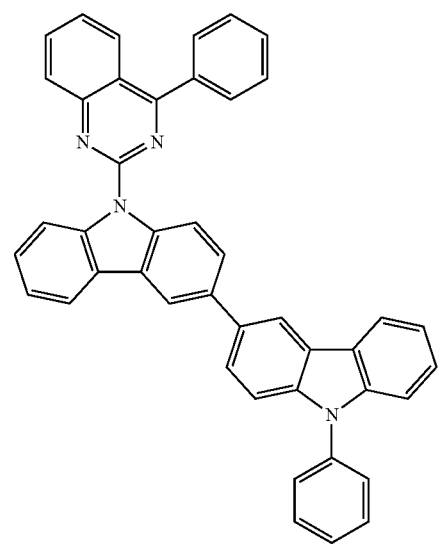

-continued
B-110
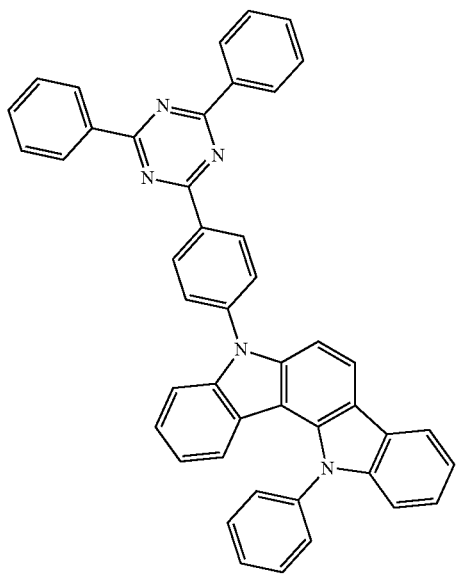
B-111
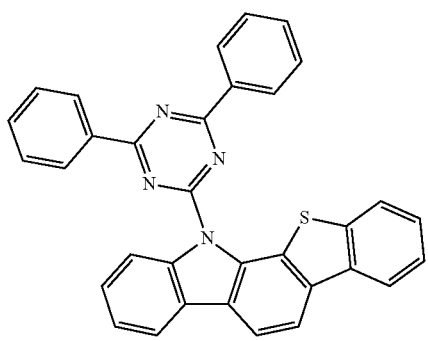
B-112
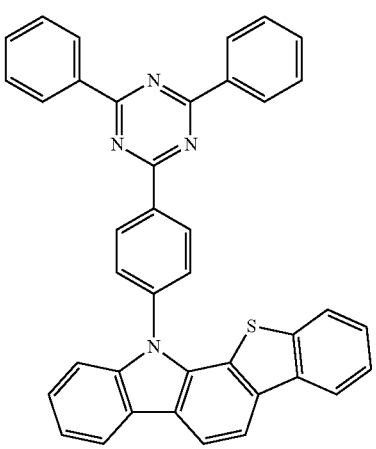
B-113
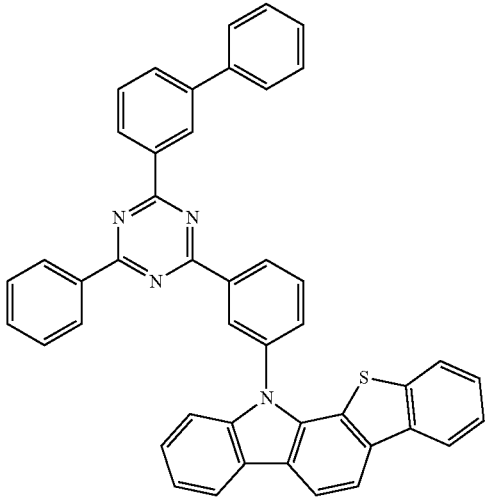
B-114
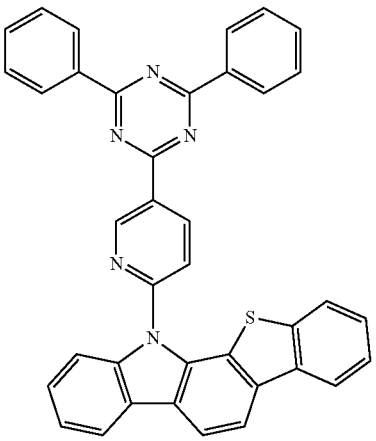
B-115
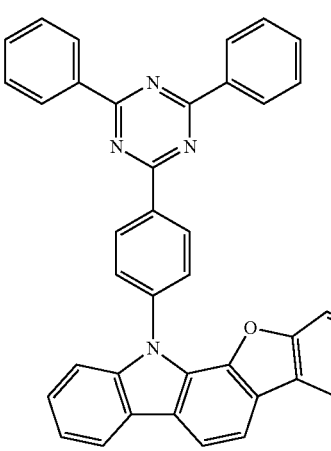

B-116
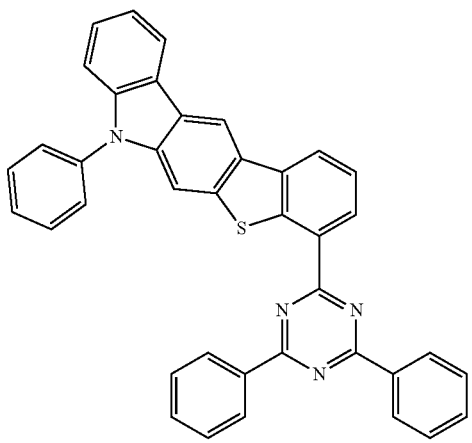
B-119
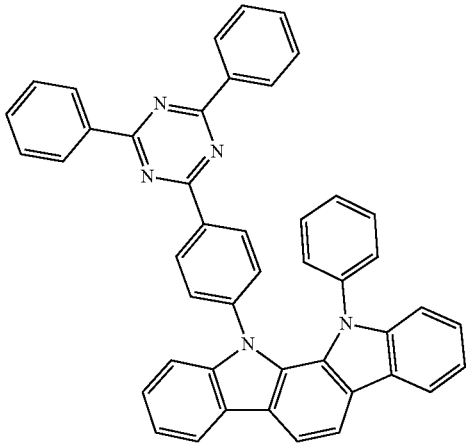
B-117
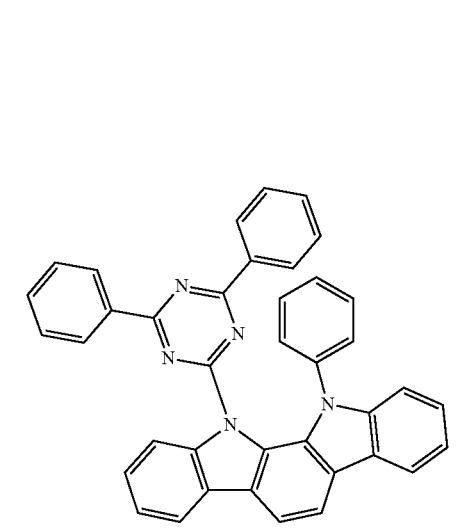
B-120
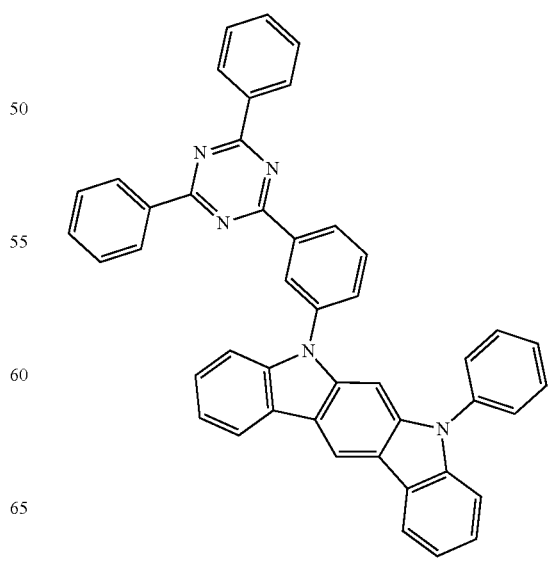
B-118
B-121
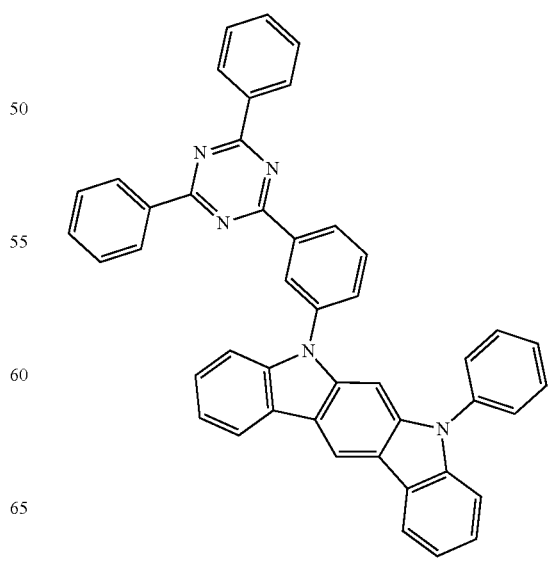

B-122
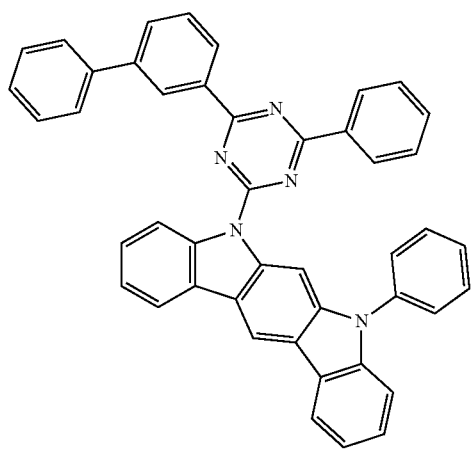
B-125
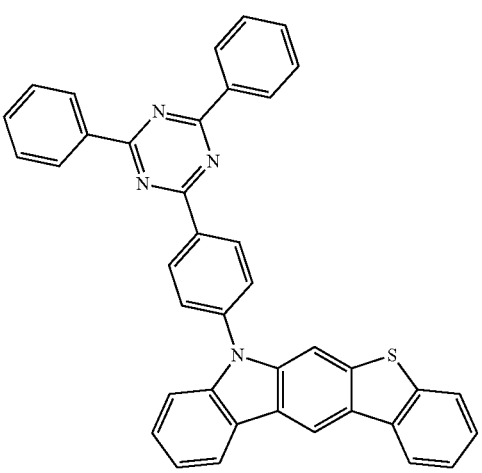
B-123
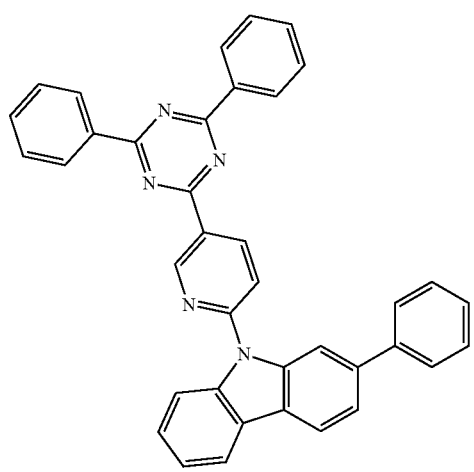
B-126
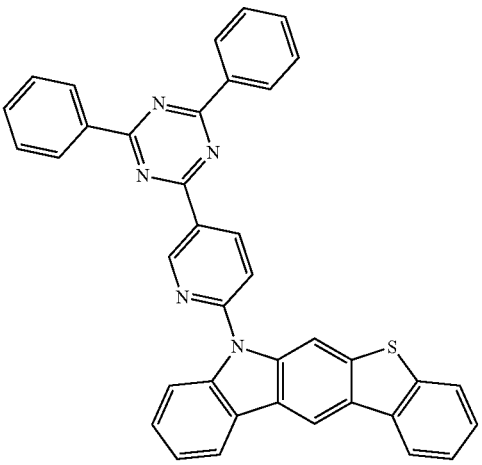
B-124
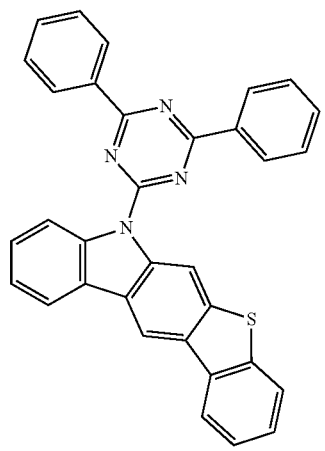
B-127
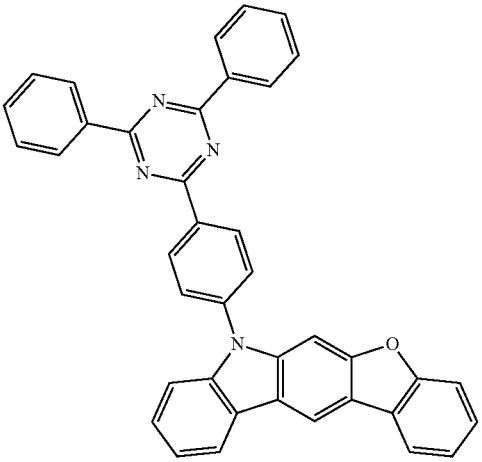

B-128
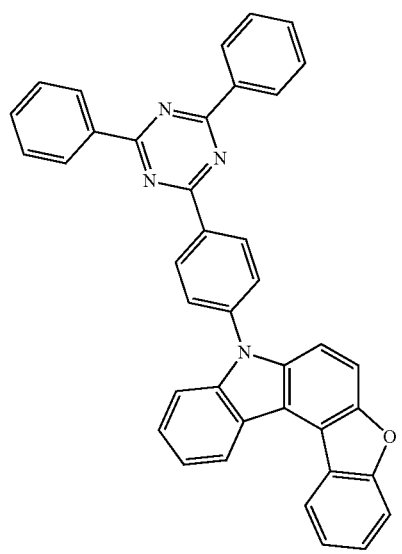
B-129
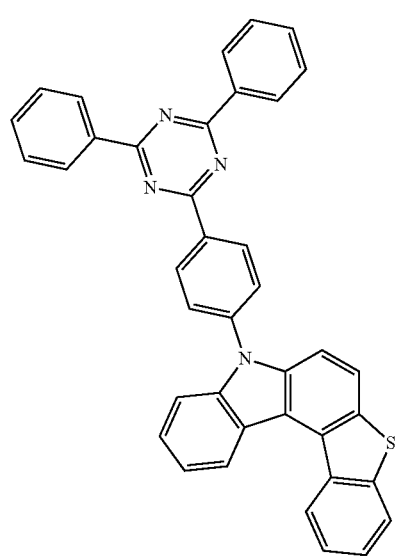
B-130
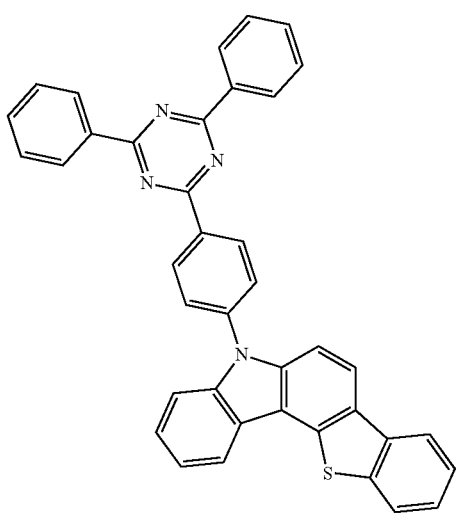
B-131
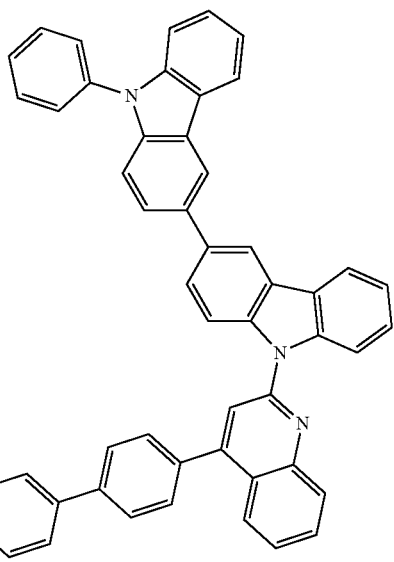
B-132
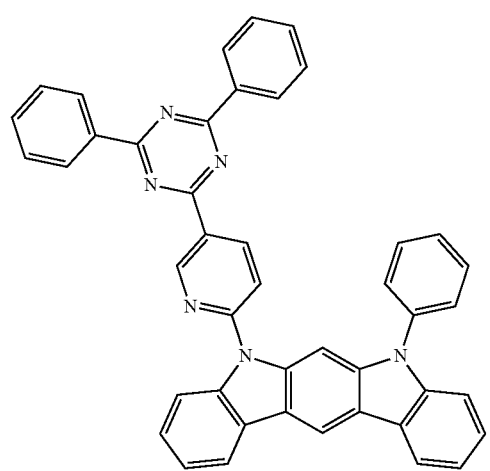
B-133
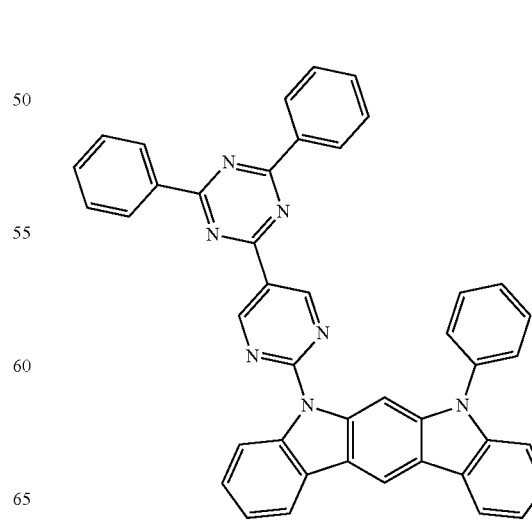

B-134
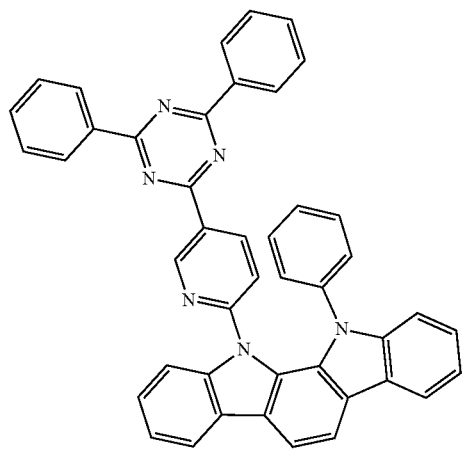
B-135
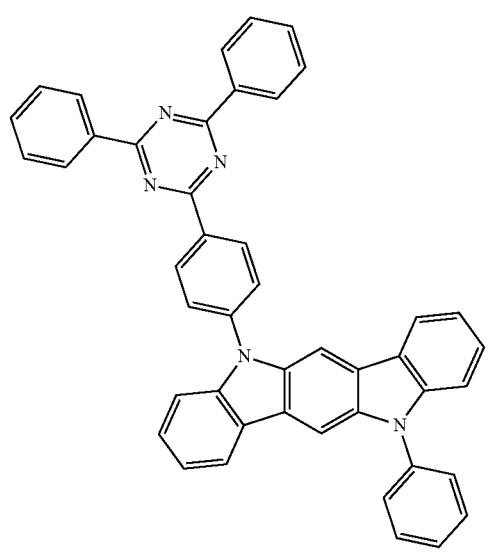
B-136
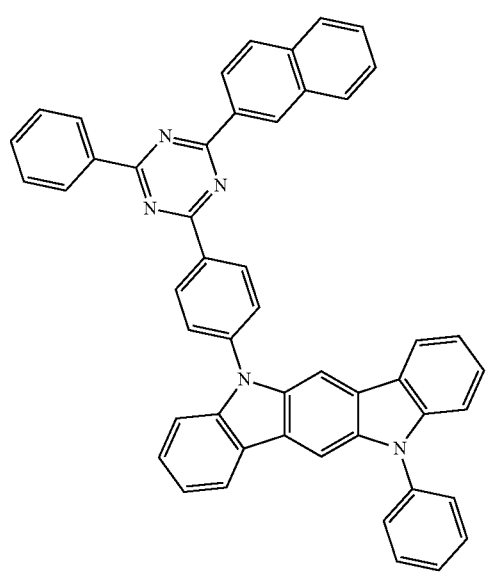
B-137
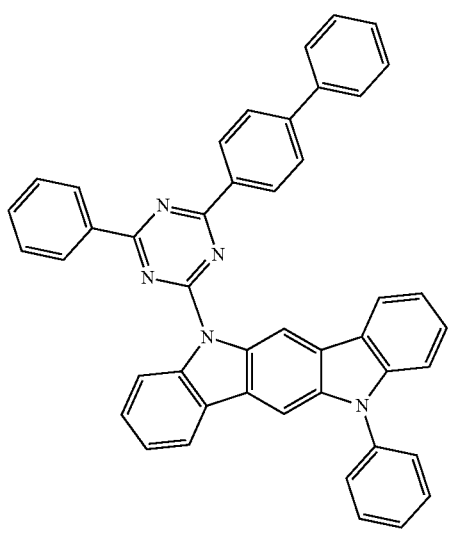
B-138
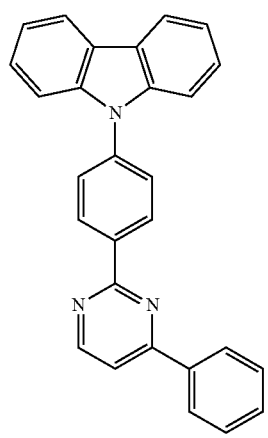
B-139
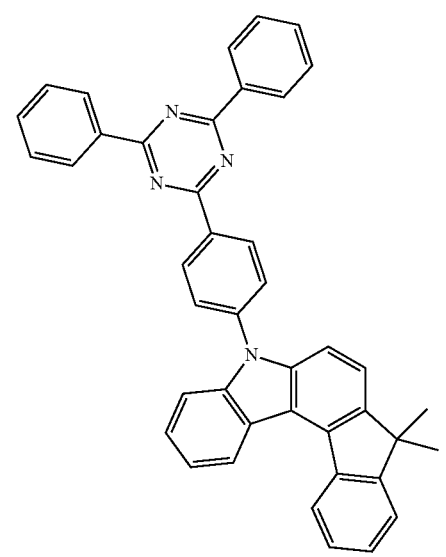

B-140
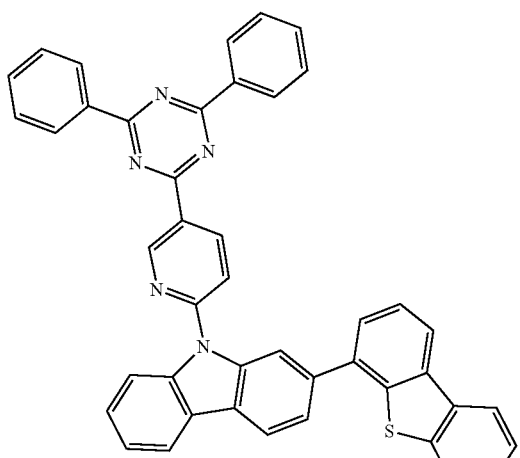
B-141
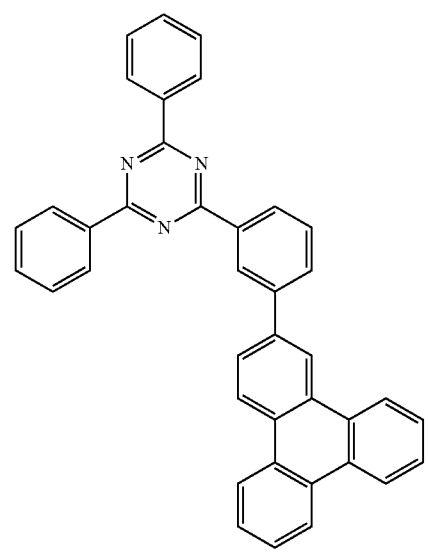
B-142
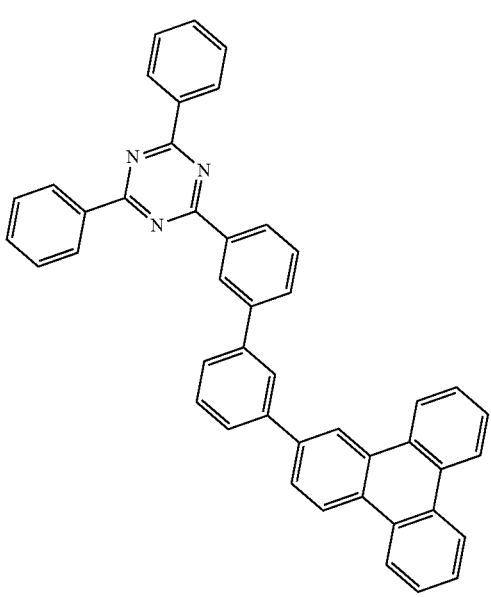
B-143
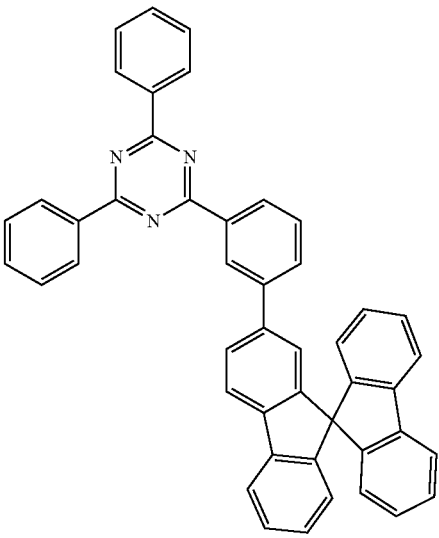
B-144
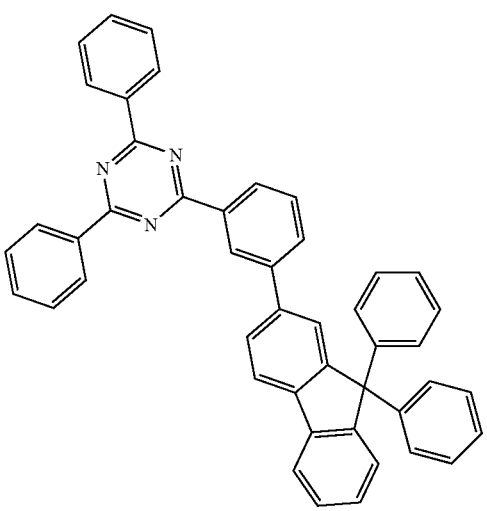
B-145
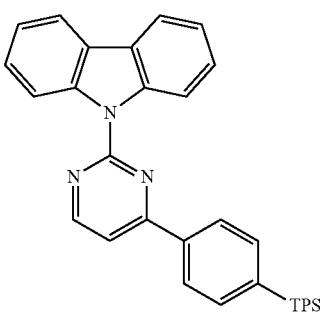

B-146
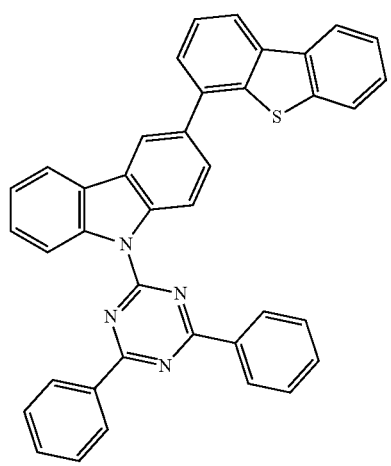
B-147
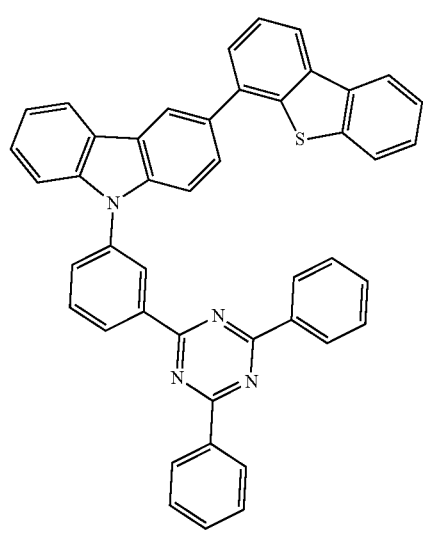
B-148
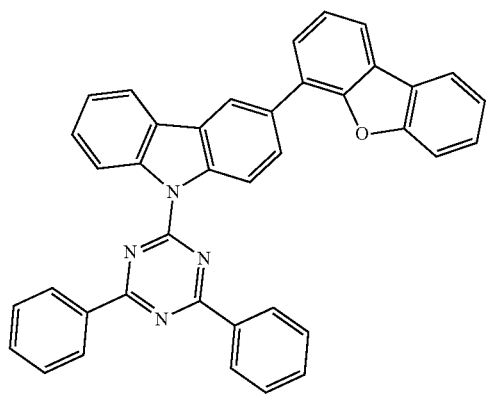
B-149
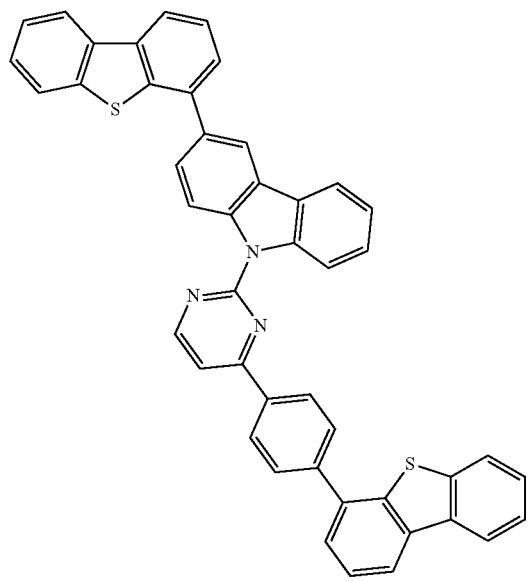
B-150
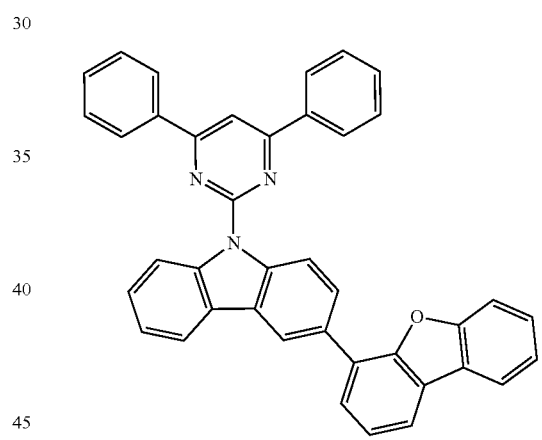
B-151
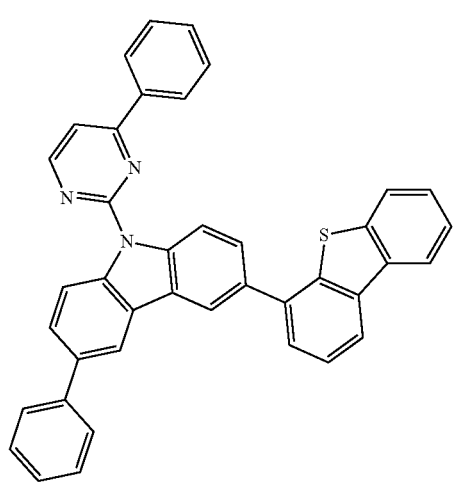

B-152
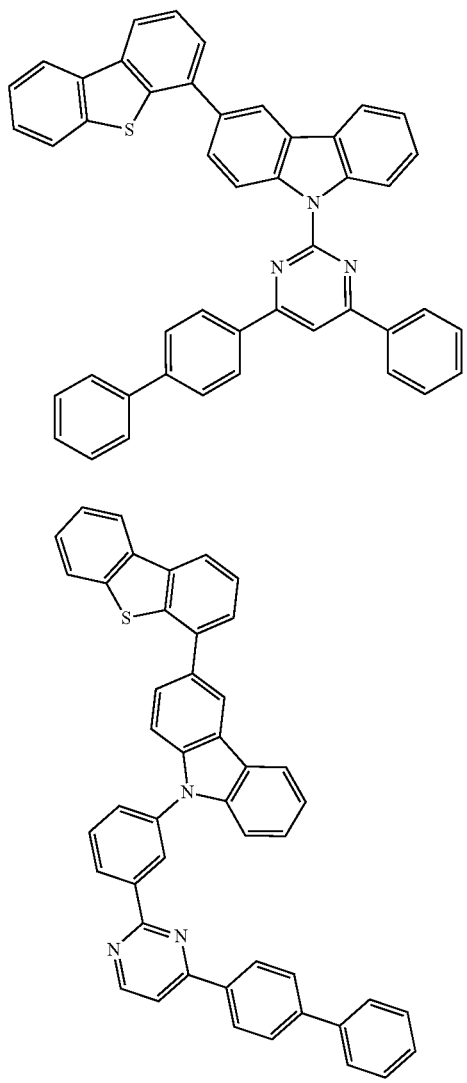
B-153
B-154
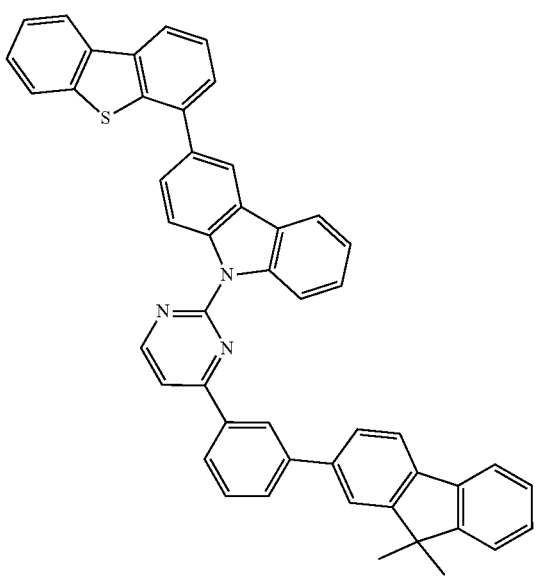
B-155
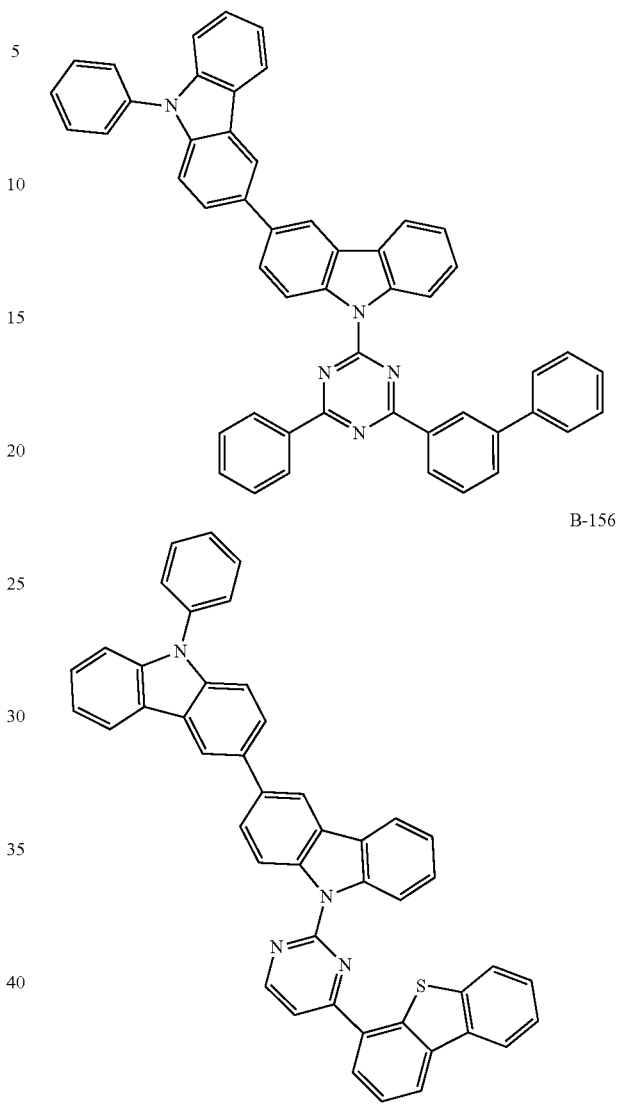
B-156
B-157
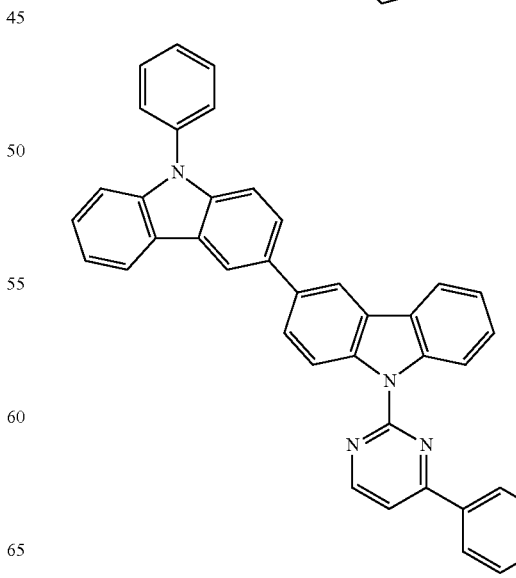

B-158
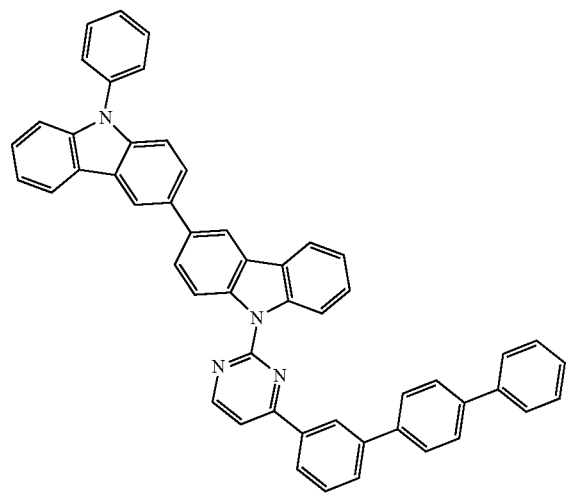
B-159
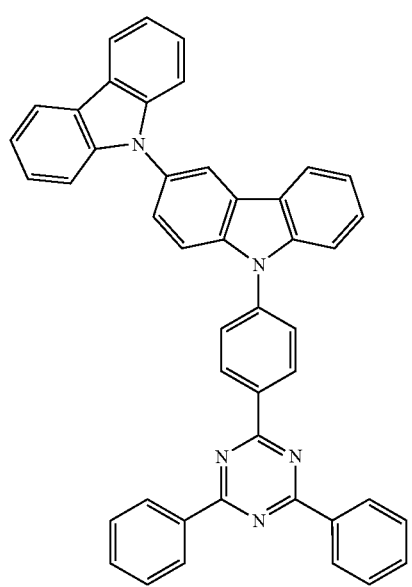
B-160
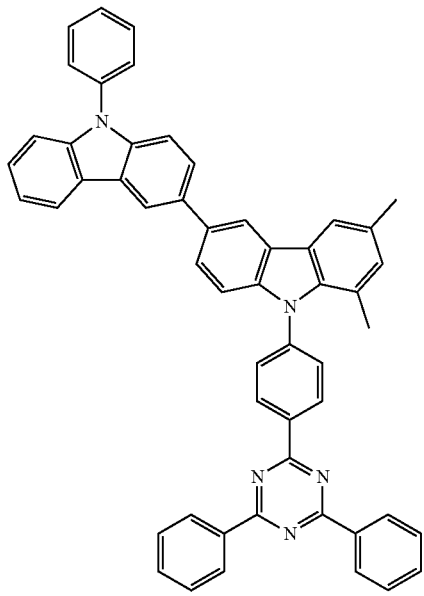
B-161
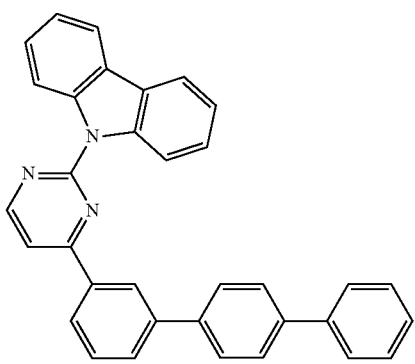
B-162
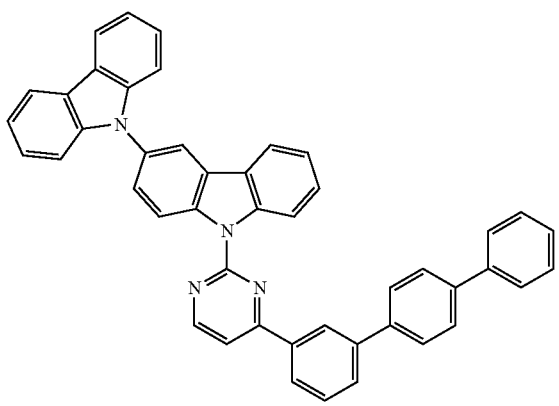

B-163
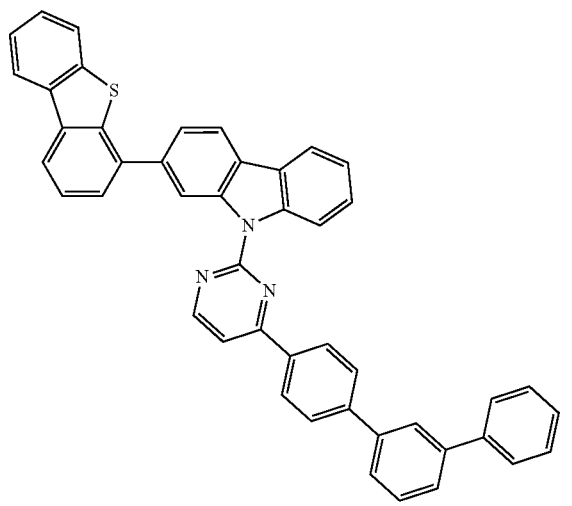
B-164
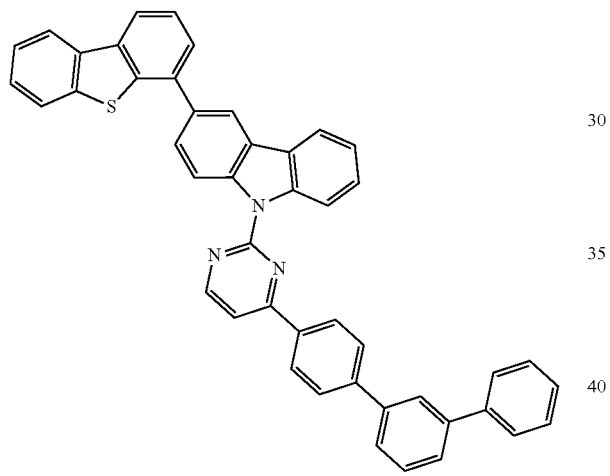
B-165
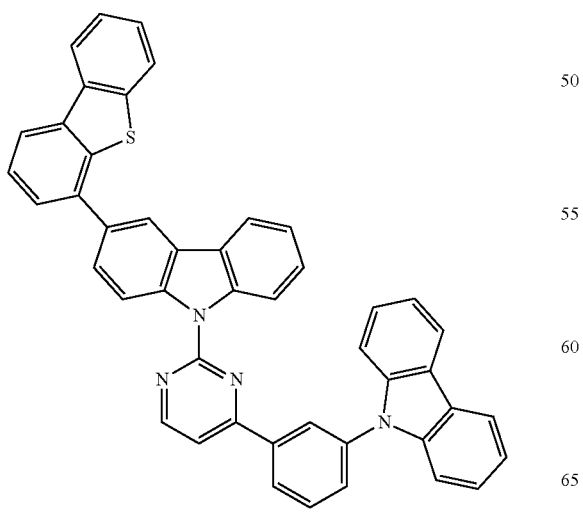
B-166
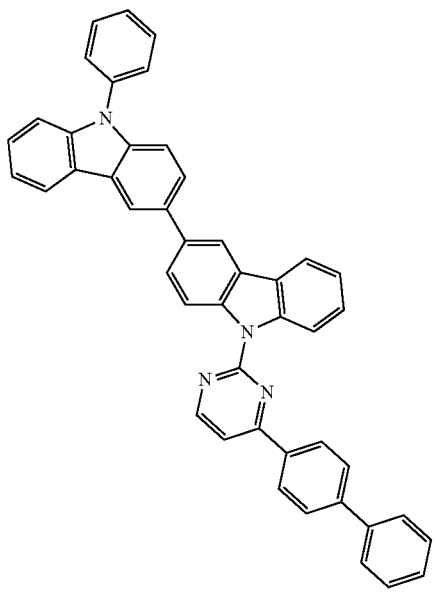
B-167
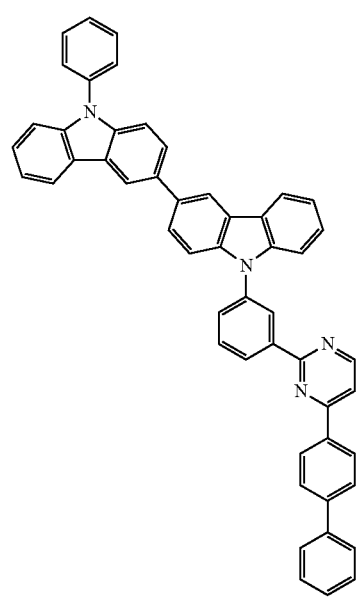

B-168
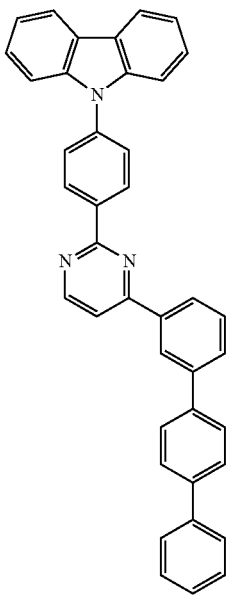
B-169
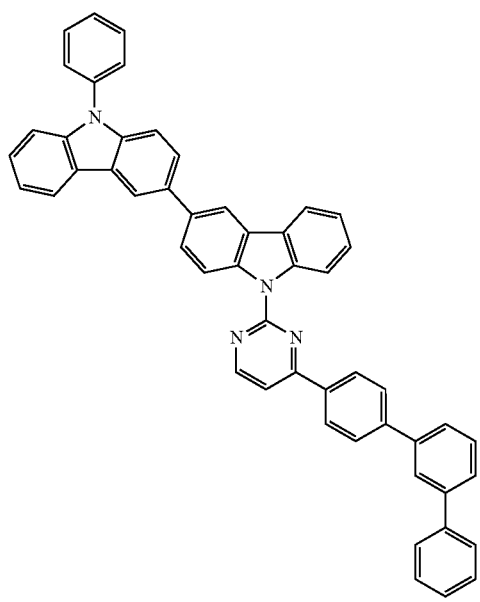
B-170
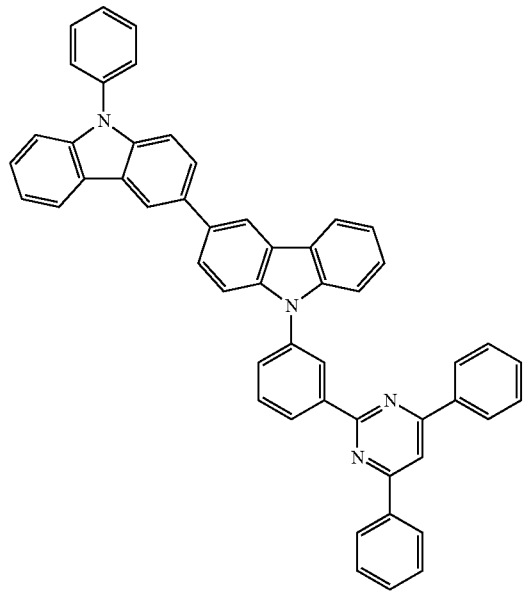
B-171
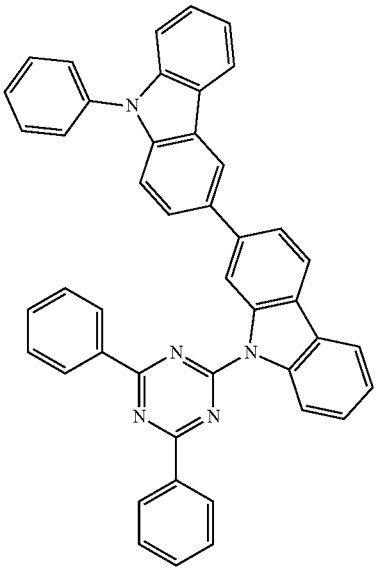

B-172
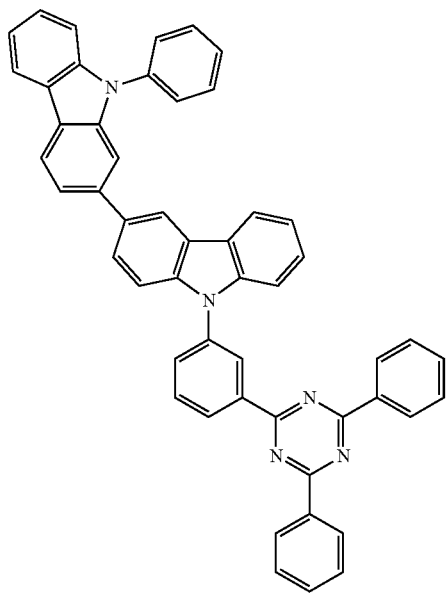
B-174
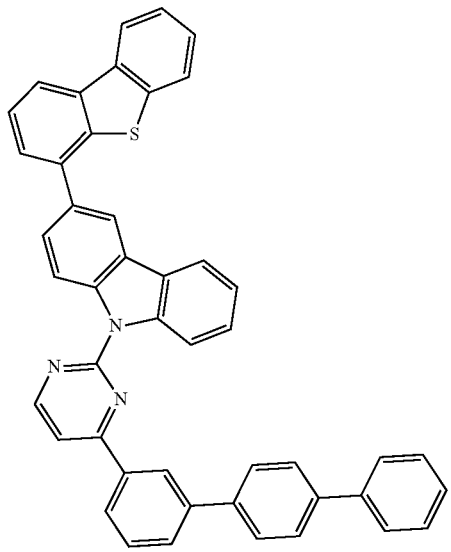
B-173
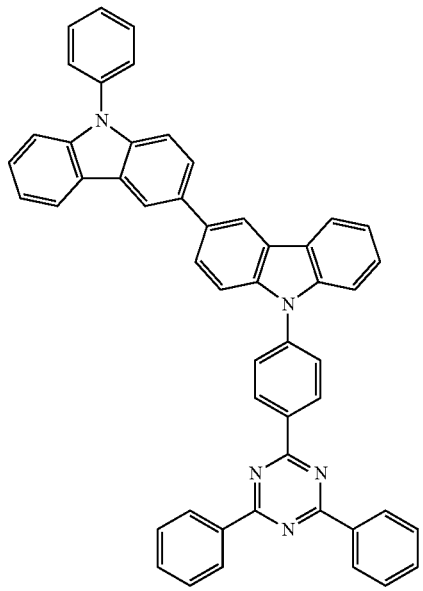
B-175
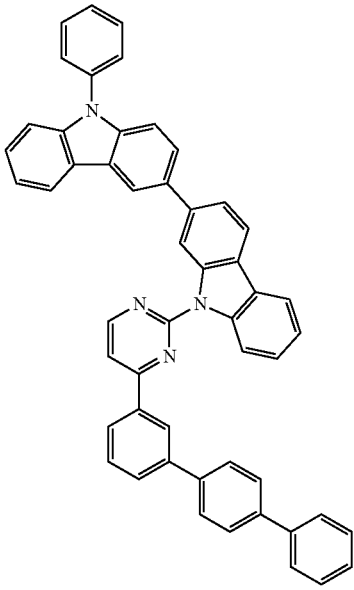

B-176
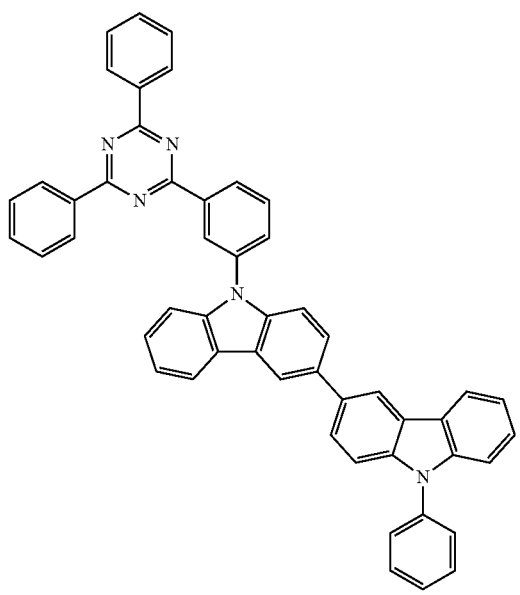
B-177
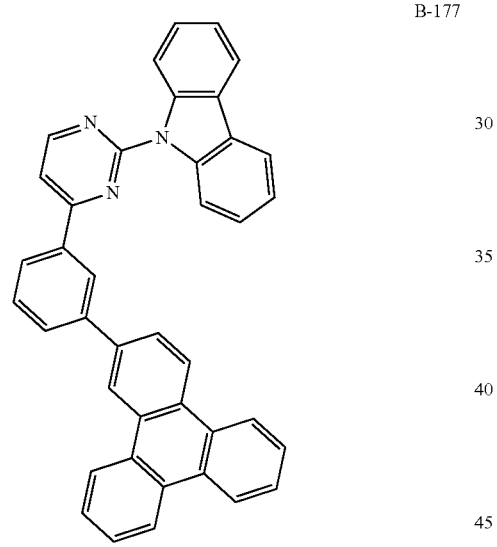
B-178
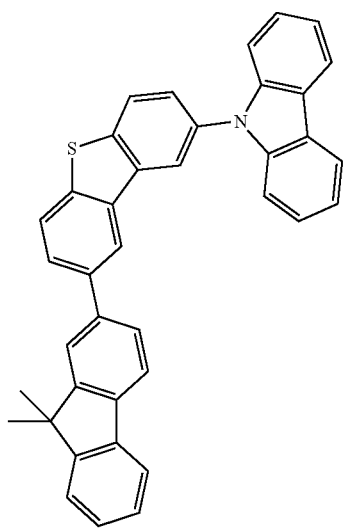
B-179
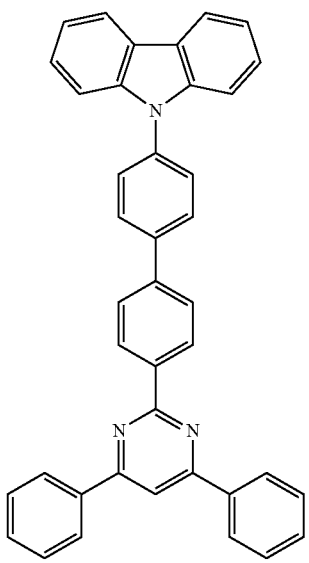
B-180
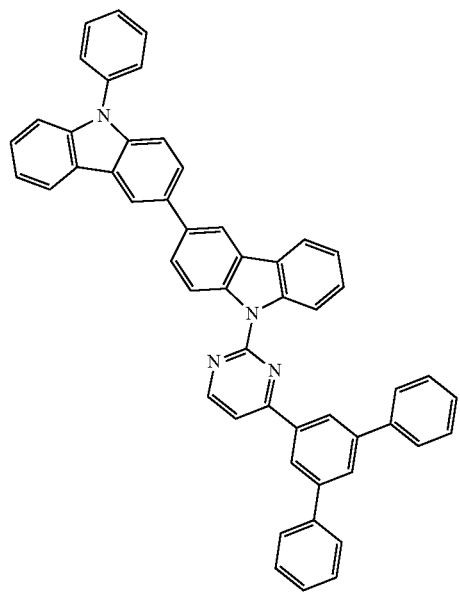

B-181
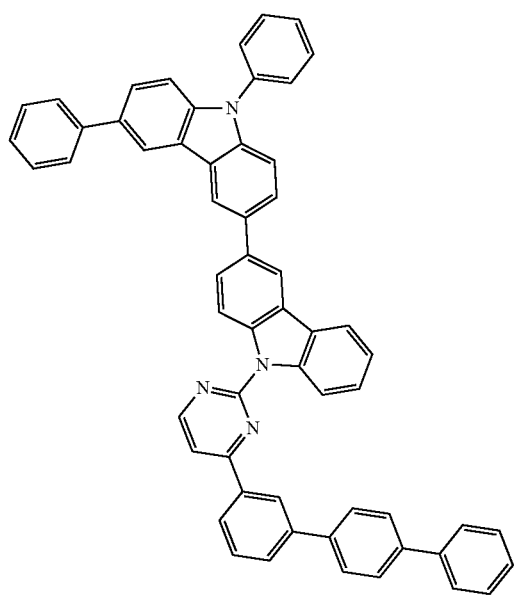
B-182
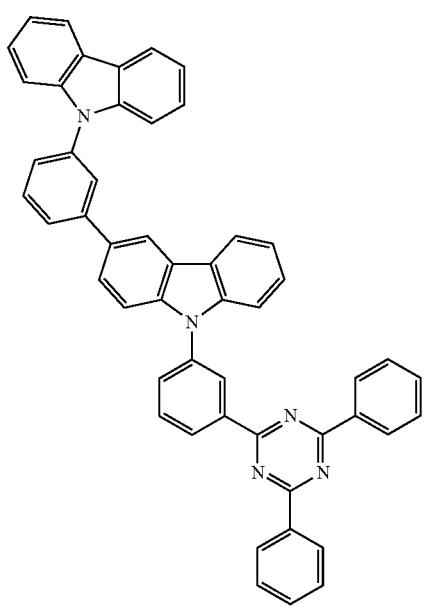
B-183
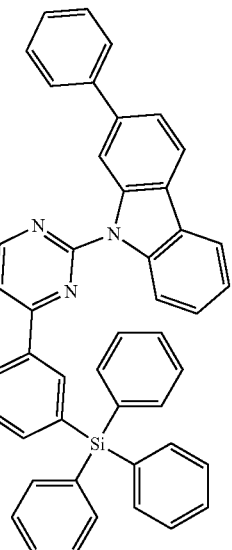
B-184
B-185
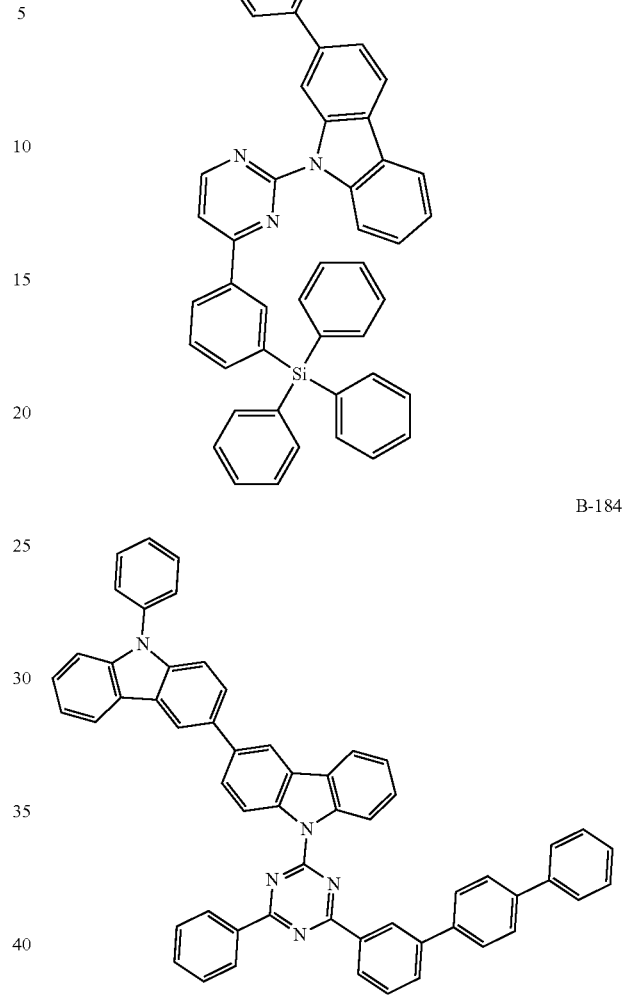

B-186
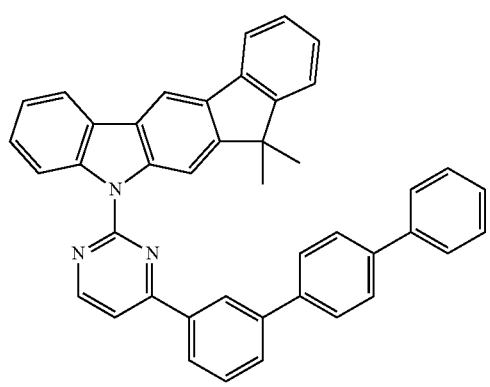
B-189
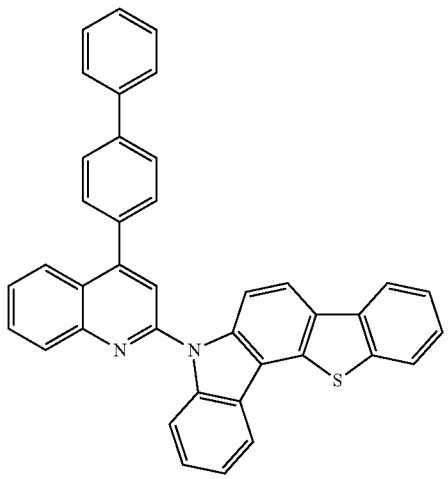
B-187
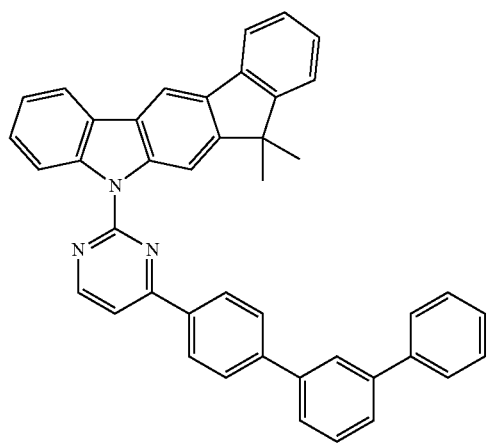
B-190
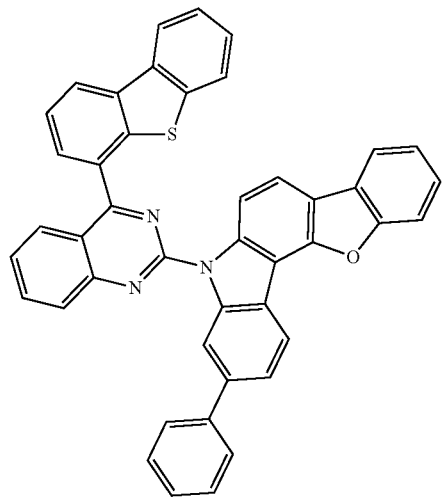
B-188
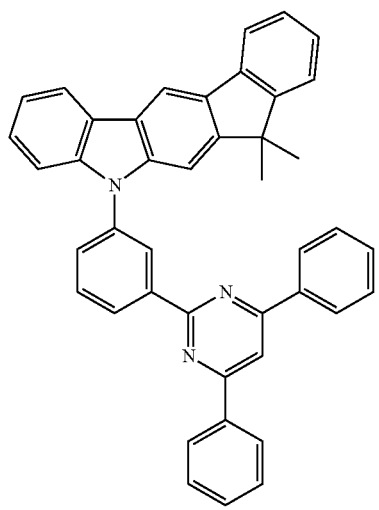
B-191
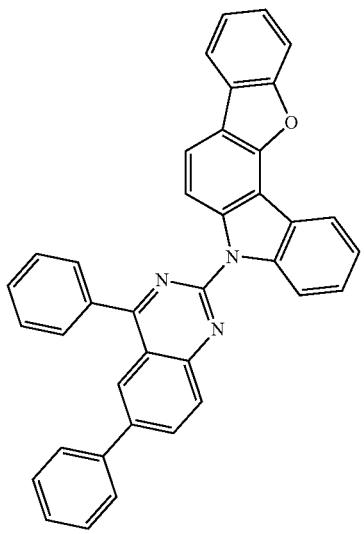

-continued

B-192

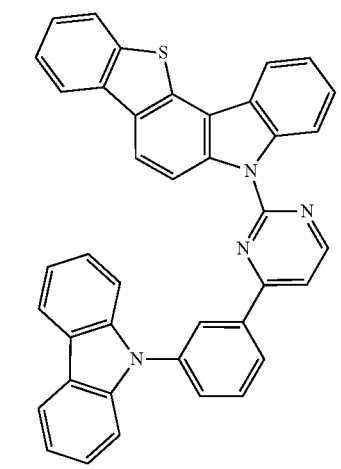

B-193

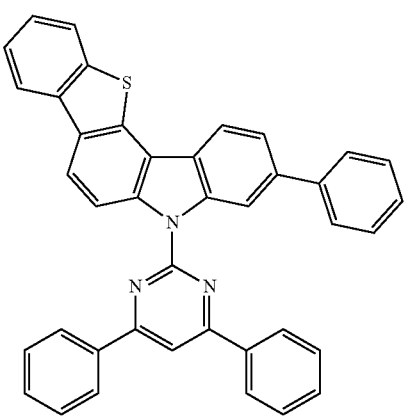

B-194

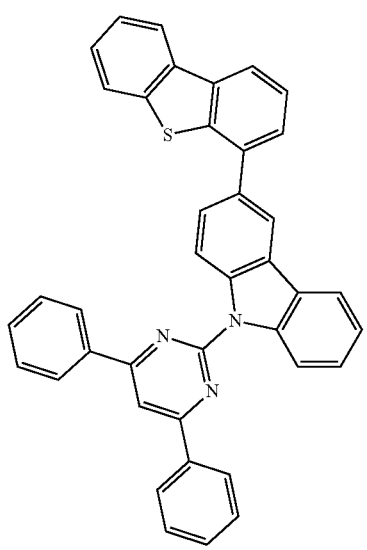

-continued

B-195

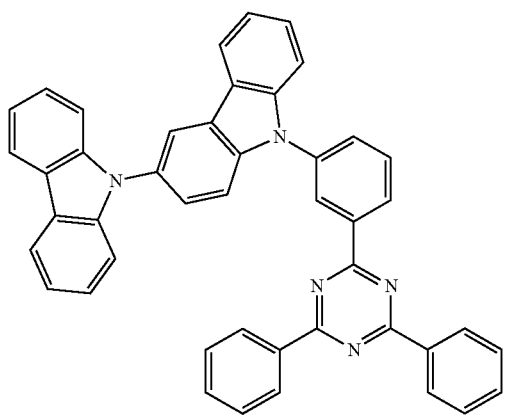

B-196

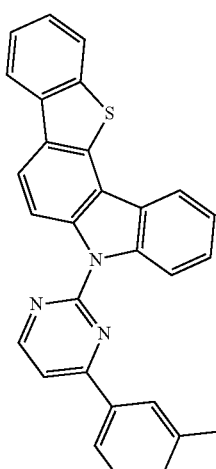

B-197

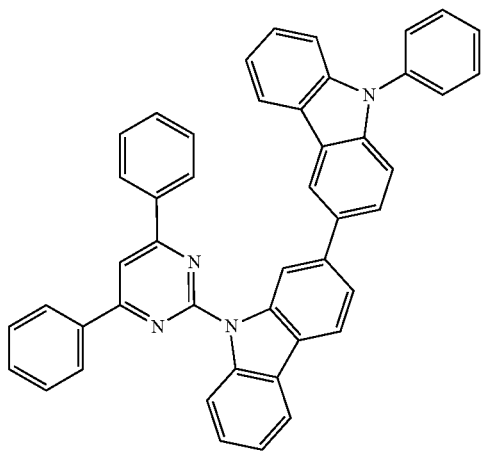

[Wherein, TPS represents a triphenylsilyl group]

The dopant comprised in the organic electroluminescent device of the present disclosure is preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise the compound represented by the following formula 101:

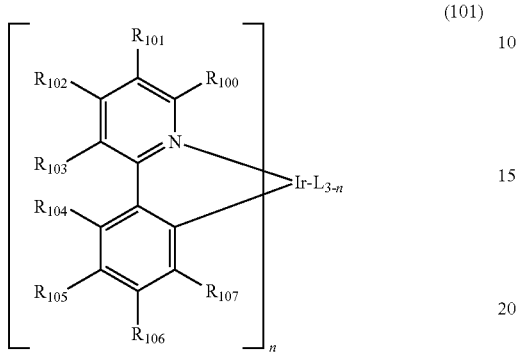

(101)

In formula 101,
wherein, L is selected from the following structure 1 or 2:

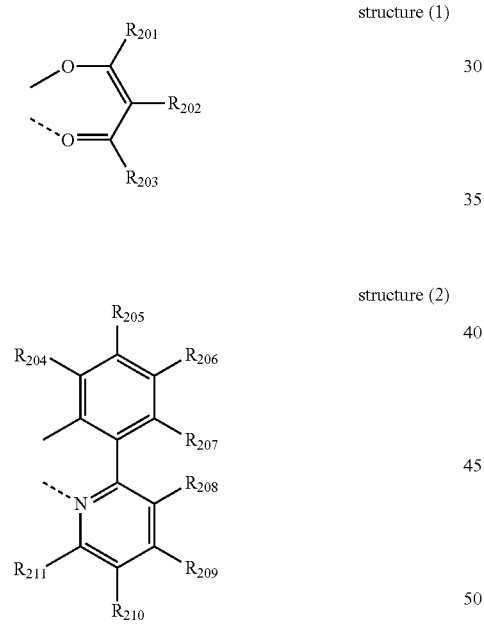

structure (1)

structure (2)

$R_{100}$ to $R_{103}$ each independently represent hydrogen, deuterium, halogen, a halogen-substituted or unsubstituted (C1-C30)alkyl, a substituted or unsubstituted (C3-C30) cycloalkyl, a substituted or unsubstituted (C6-C30)aryl, cyano, a substituted or unsubstituted (3- to 30-membered)heteroaryl, or a substituted or unsubstituted (C1-C30)alkoxy; or $R_{100}$ to $R_{103}$ may be linked to adjacent substituents to form a substituted or unsubstituted fused ring, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, halogen, a halogen-substituted or unsubstituted (C1-C30)alkyl, a substituted or unsubstituted (C3-C30) cycloalkyl, a substituted or unsubstituted (C6-C30)aryl, a substituted or unsubstituted (3- to 30-membered) heteroaryl, cyano, or a substituted or unsubstituted (C1-C30)alkoxy; or $R_{104}$ to $R_{107}$ may be linked to adjacent substituents to form a substituted or unsubstituted fused ring, e.g., a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{211}$ each independently represent hydrogen, deuterium, halogen, a halogen-substituted or unsubstituted (C1-C30)alkyl, a substituted or unsubstituted (C3-C30) cycloalkyl, or a substituted or unsubstituted (C6-C30) aryl; $R_{201}$ to $R_{211}$ may be linked to adjacent substituents to form a substituted or unsubstituted fused ring;

n represents an integer of 1 to 3.

The specific examples of the dopant compound include the following, but is not limited thereto:

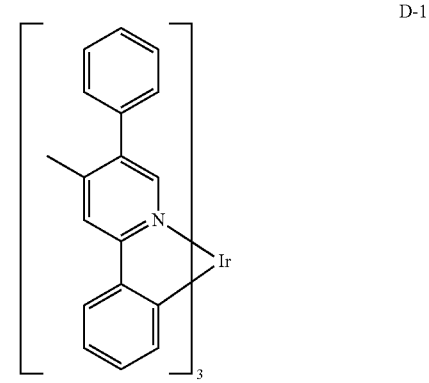

D-1

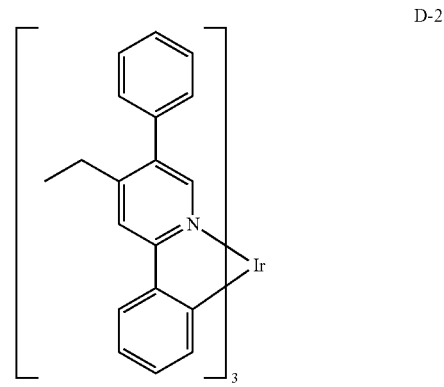

D-2

-continued
D-3
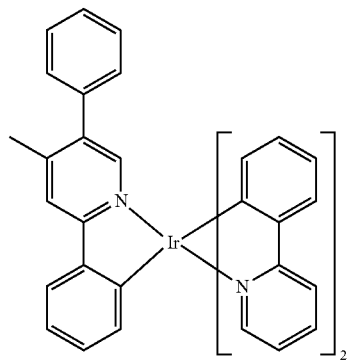
D-4
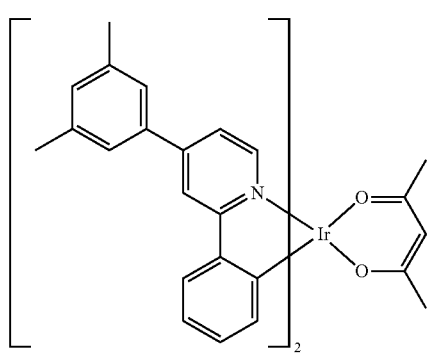
D-5
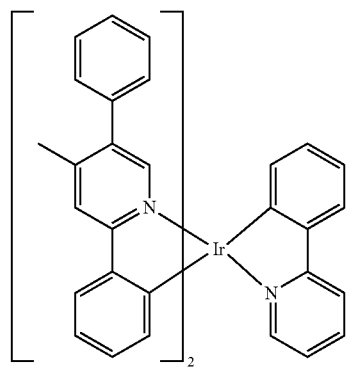
D-6
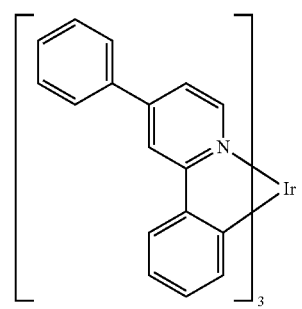
-continued
D-7
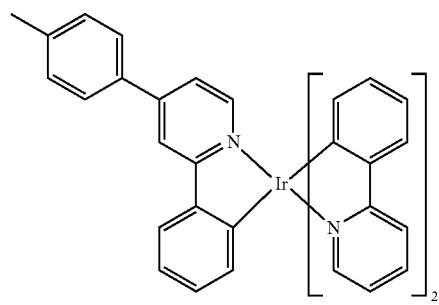
D-8
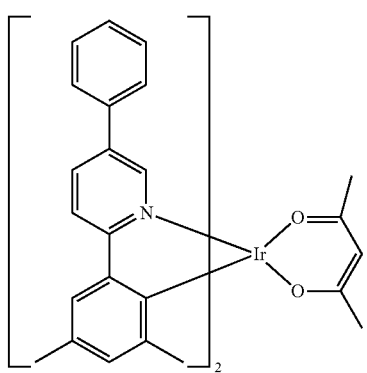
D-9
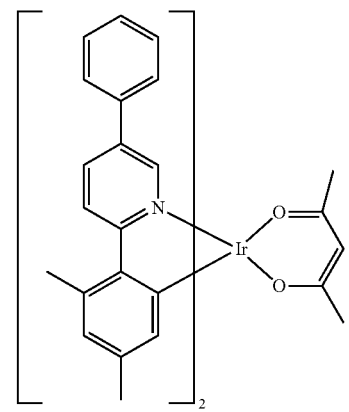
D-10

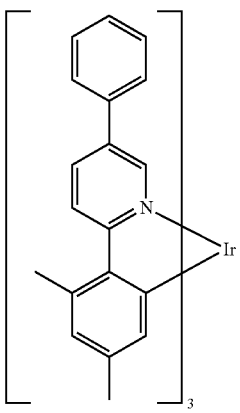
D-11
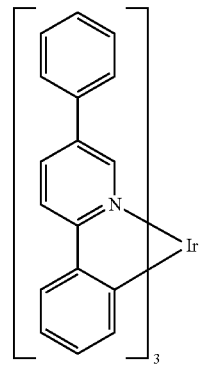
D-15
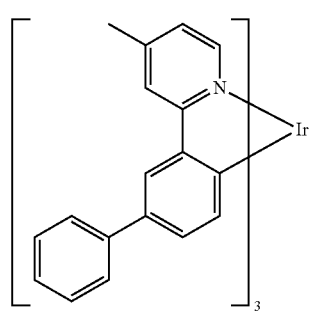
D-12
D-16
D-13
D-17
D-14
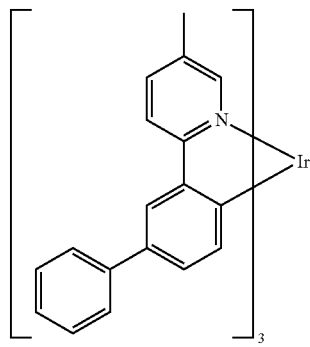
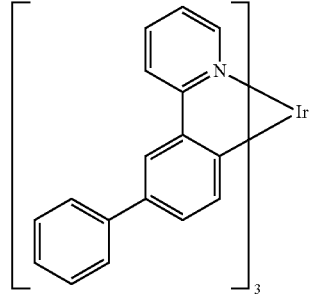
D-18

-continued
D-19
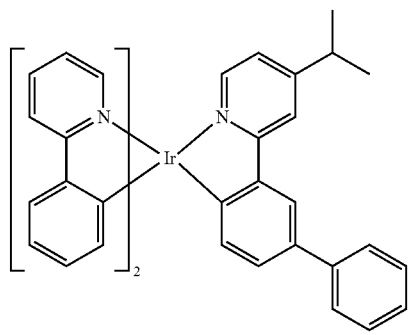
D-20
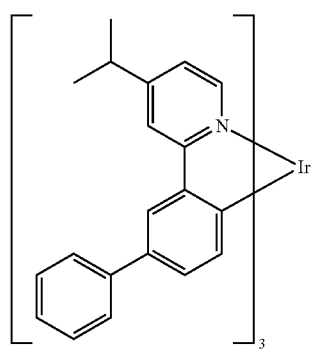
D-21
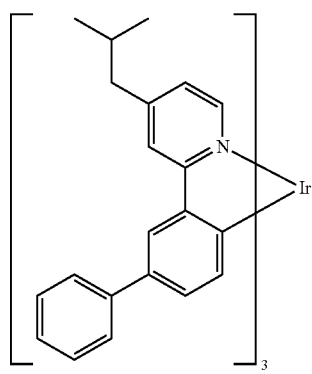
D-22
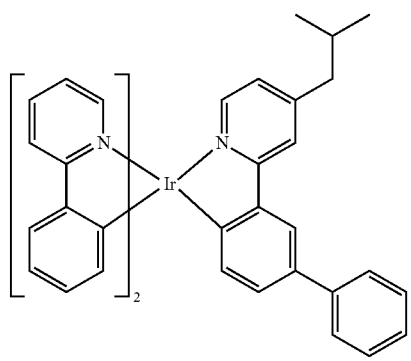
-continued
D-23
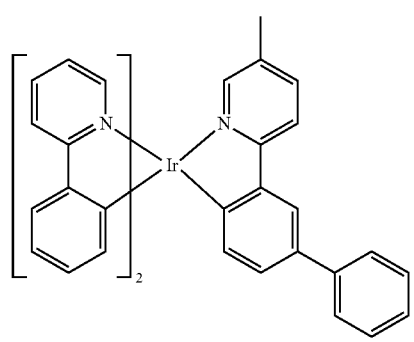
D-24
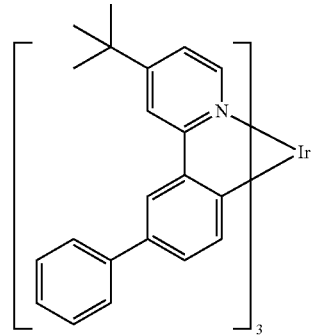
D-25
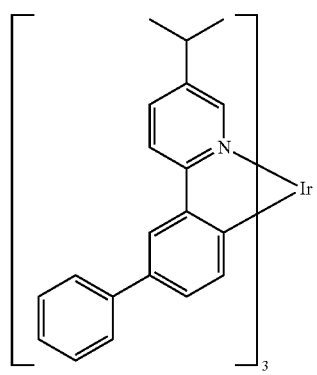
D-26
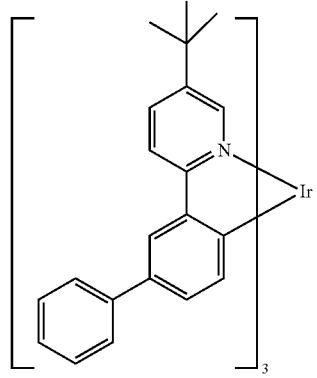

-continued
D-27
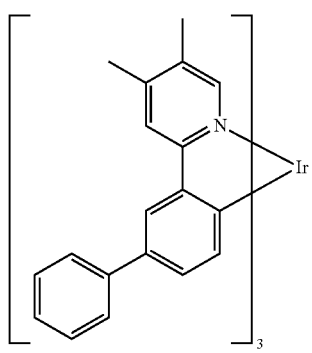
D-28
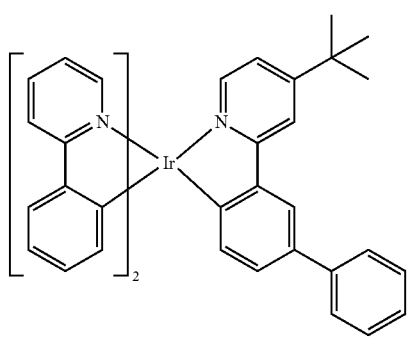
D-29
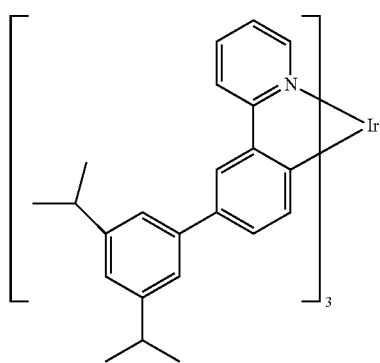
D-30
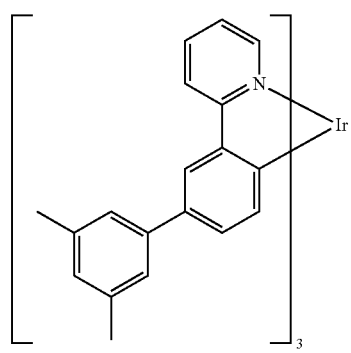
-continued
D-31
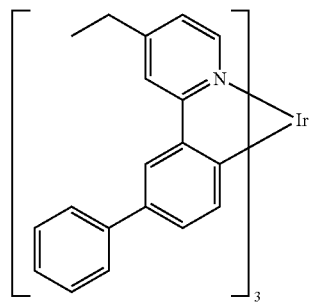
D-32
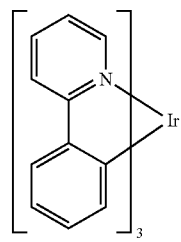
D-33
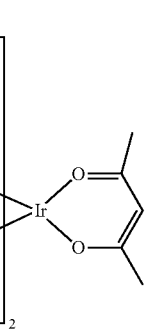
D-34
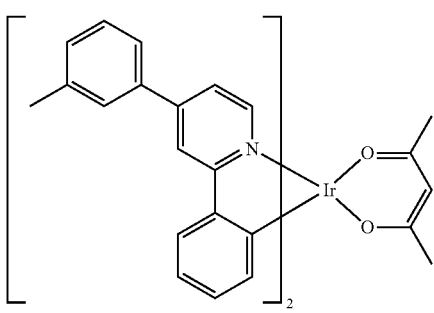
D-35
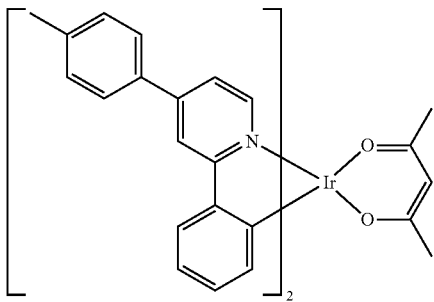

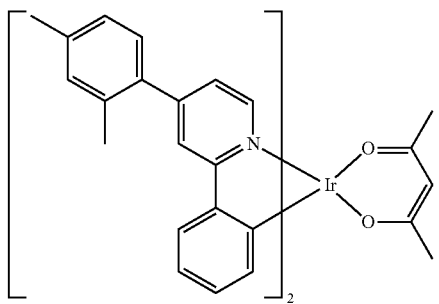
D-36
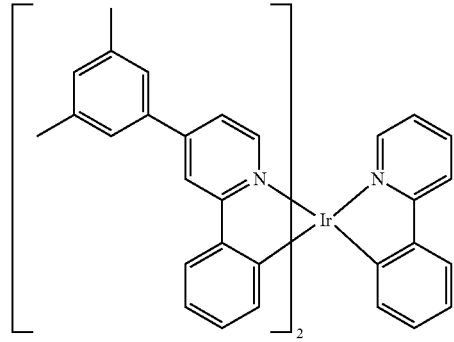
D-40
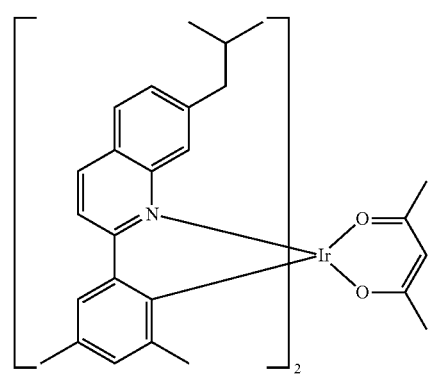
D-37
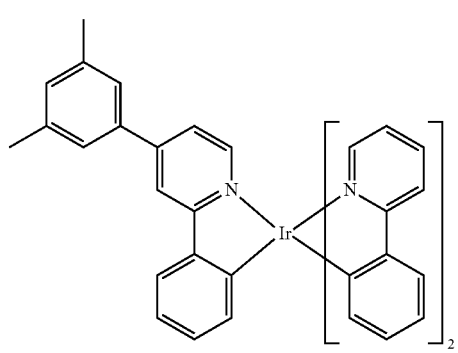
D-41
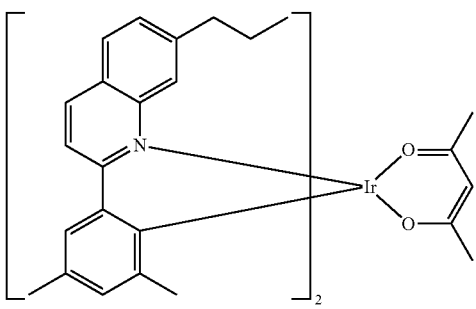
D-38
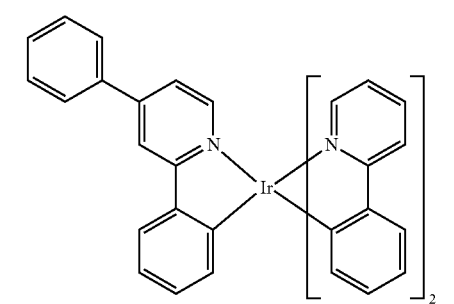
D-42
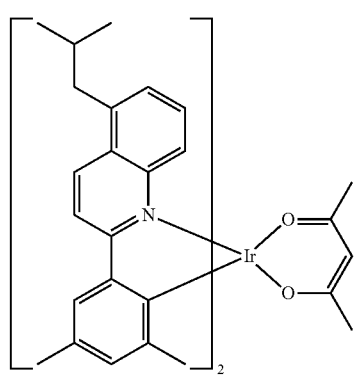
D-39
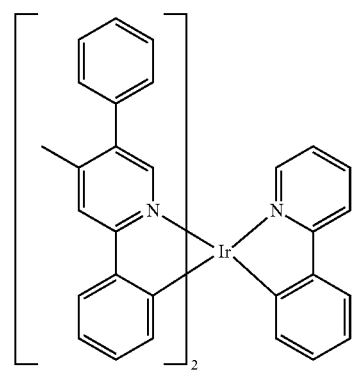
D-43

D-44
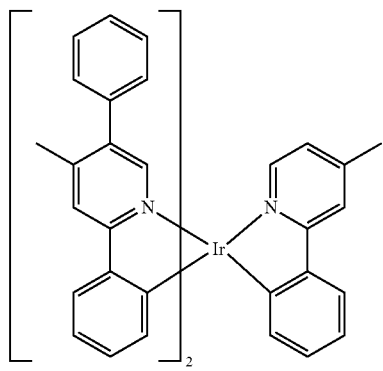
D-45
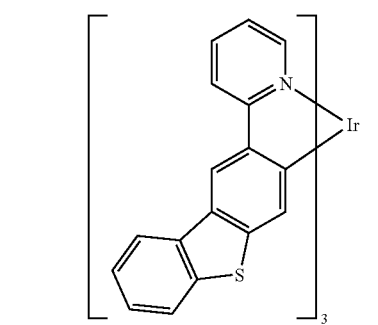
D-46
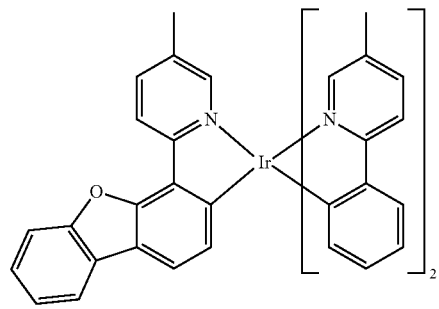
D-47
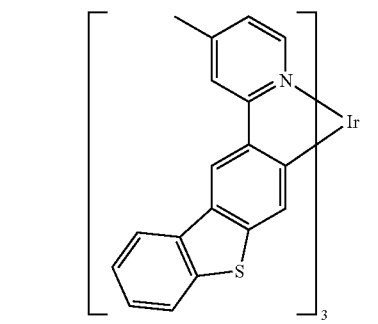
D-48
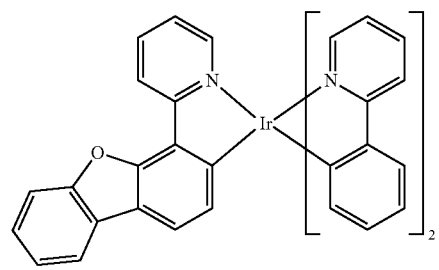
D-49
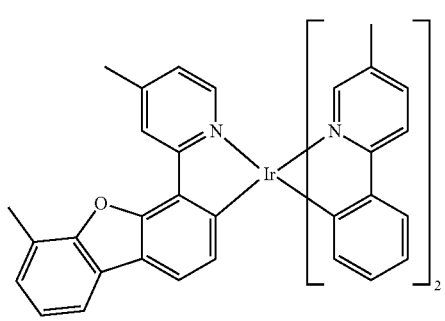
D-50
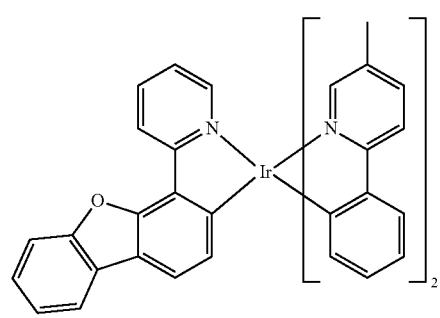
D-51
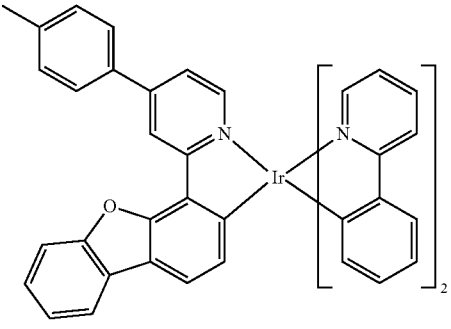
D-52
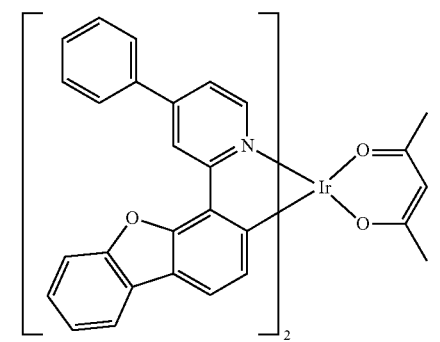
D-53
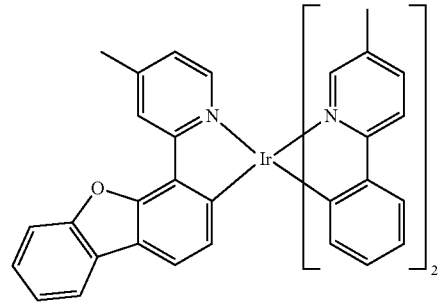

-continued
D-54
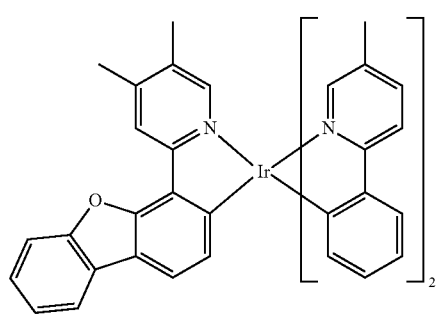
D-55
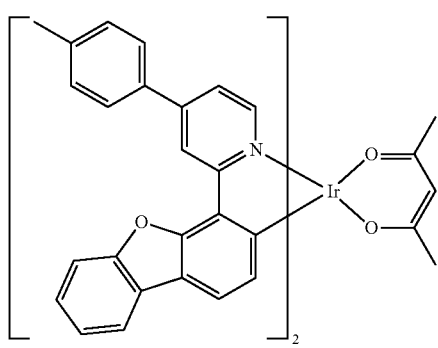
D-56
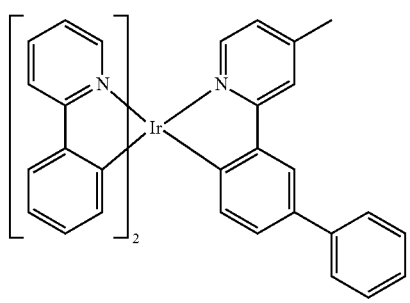
D-57
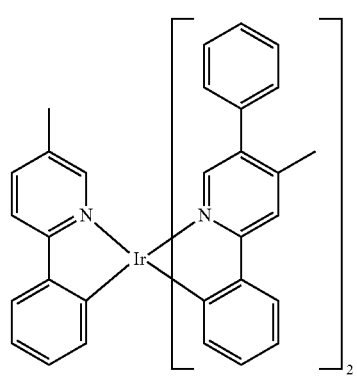
-continued
D-58
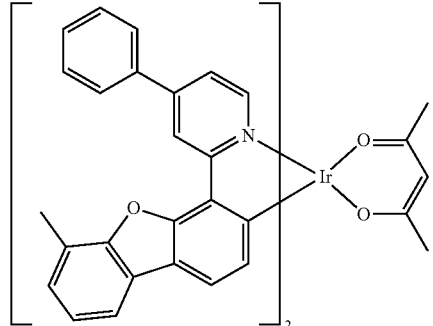
D-59
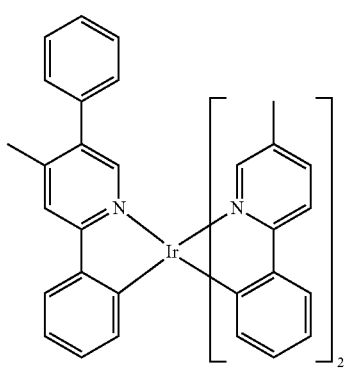
D-60
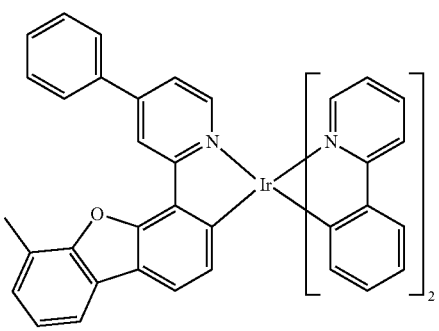
D-61
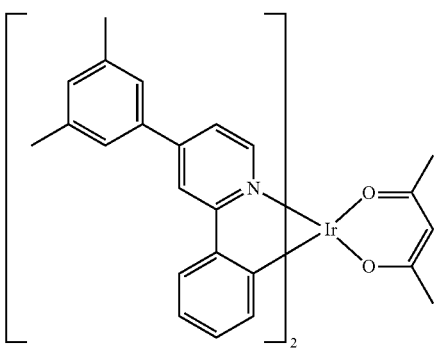

D-62
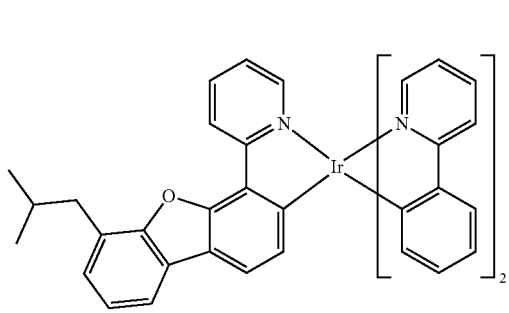
D-63
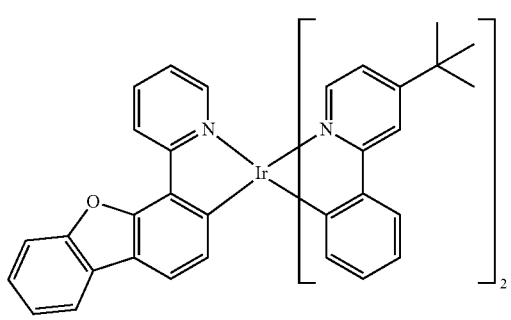
D-64
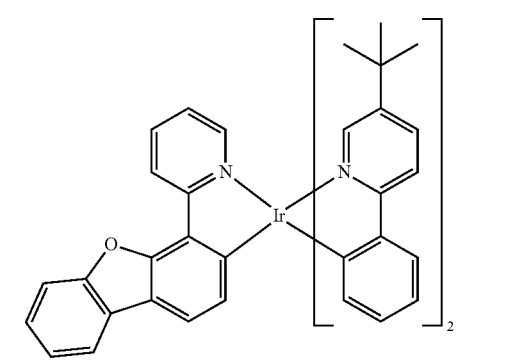
D-65
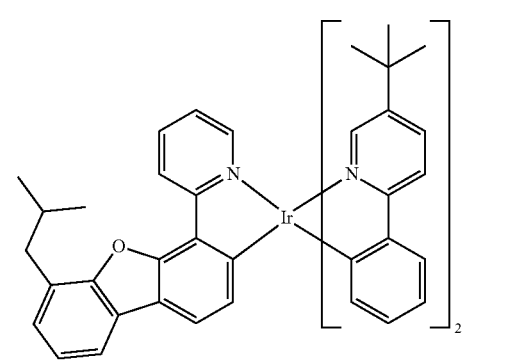
D-66
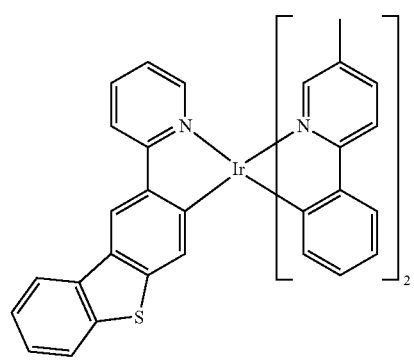
D-67
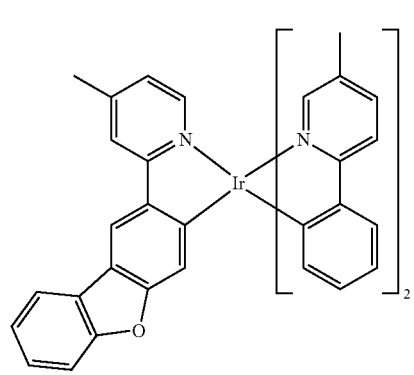
D-68
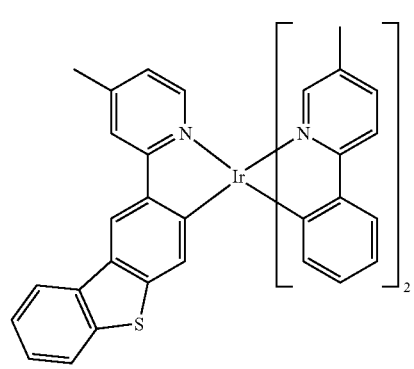
D-69
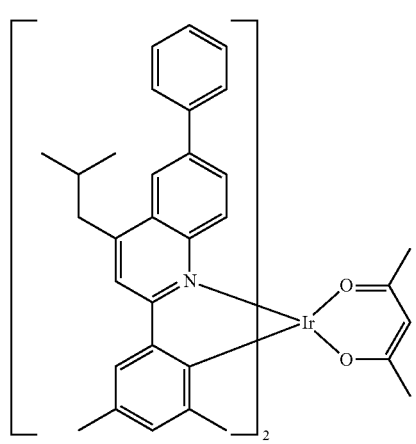

-continued
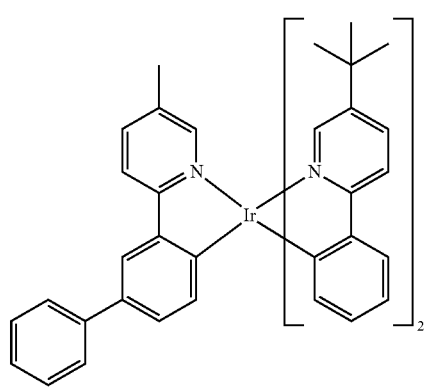
D-70
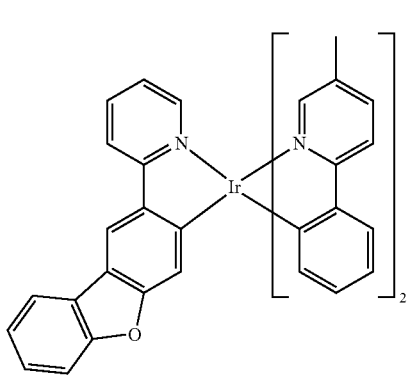
D-74
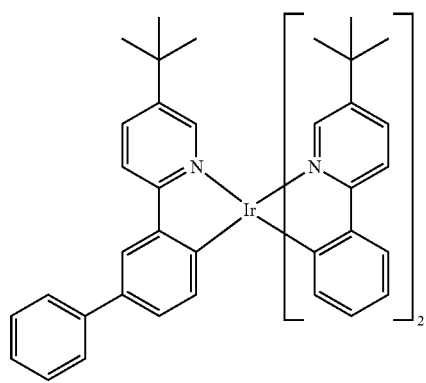
D-71
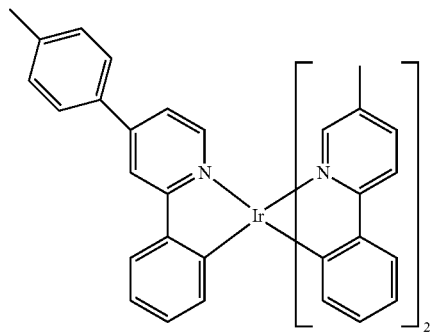
D-75
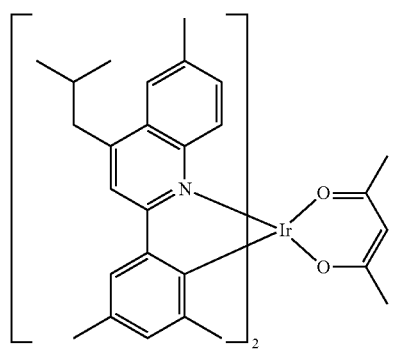
D-72
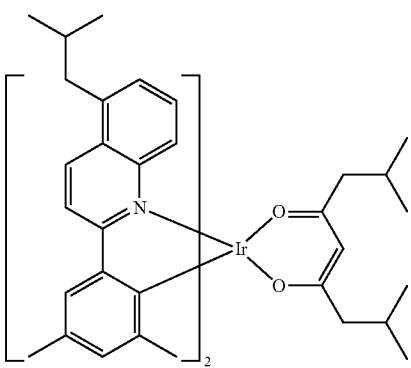
D-76
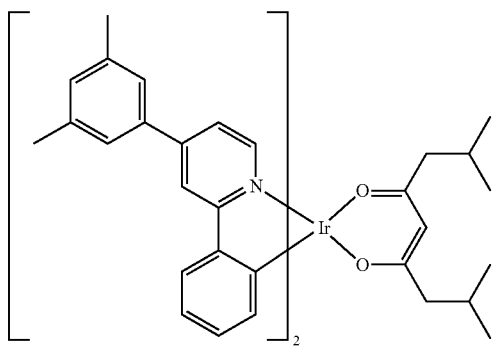
D-73
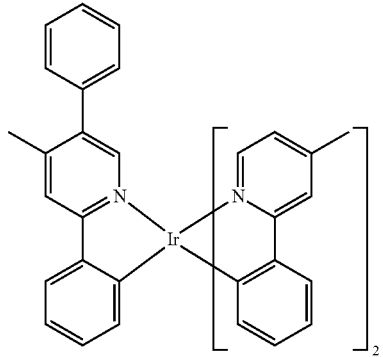
D-77

-continued
D-78
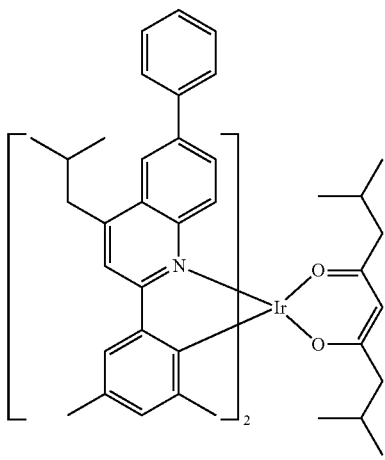
D-79
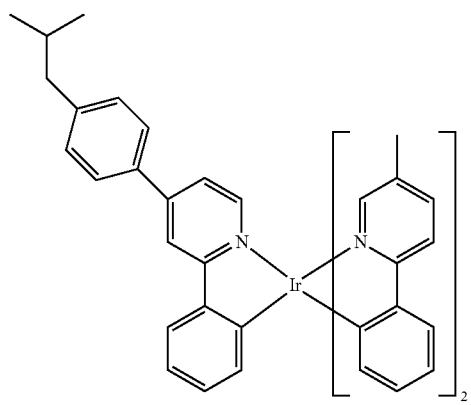
D-80
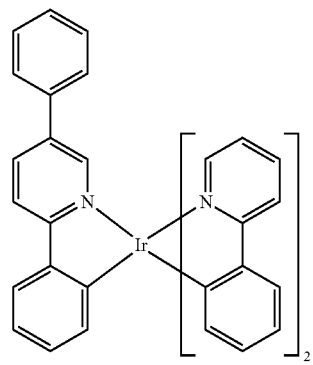
-continued
D-81
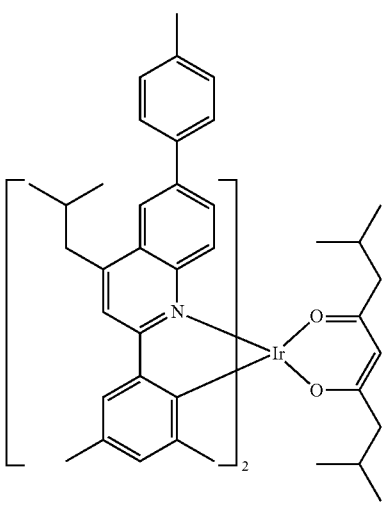
D-82
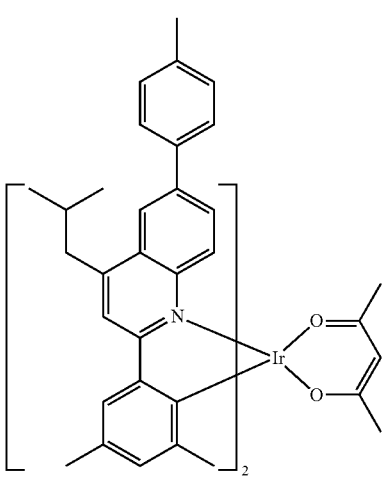
D-83
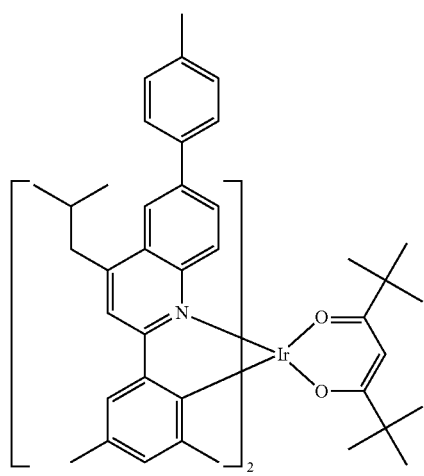

-continued
D-84
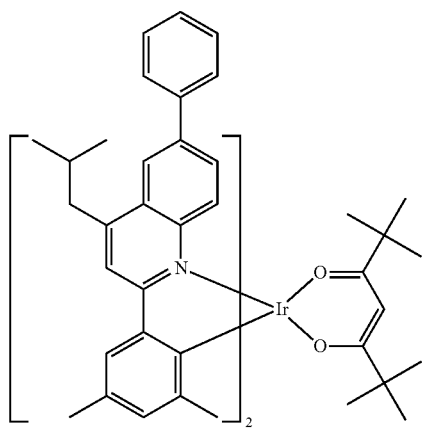
D-85
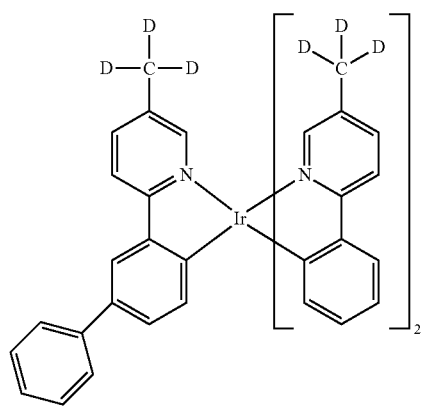
D-86
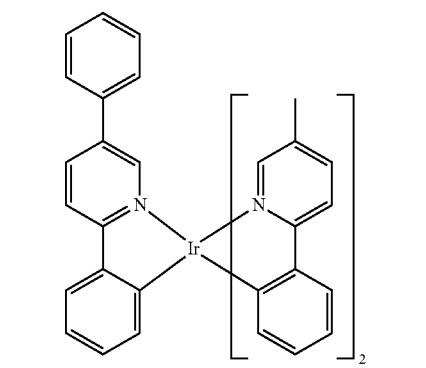
D-87
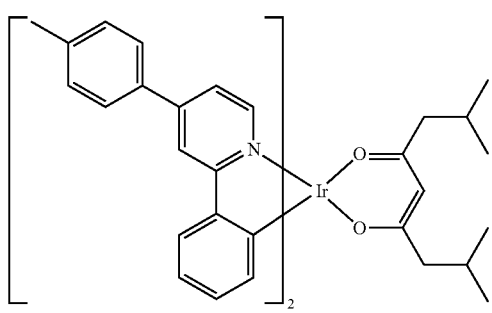
-continued
D-88
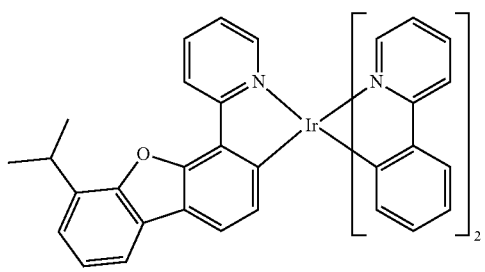
D-89
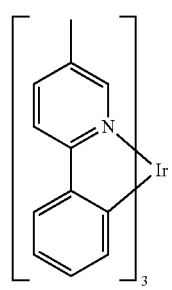
D-90
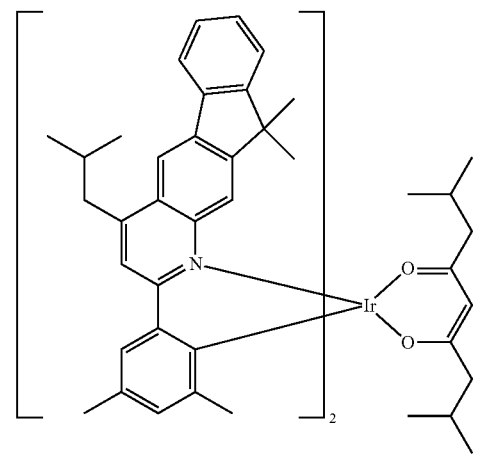
D-91
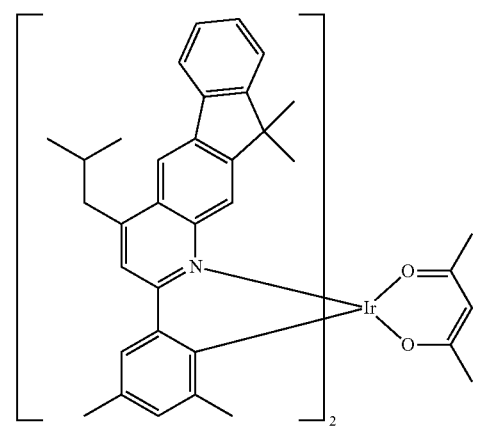

-continued
D-92
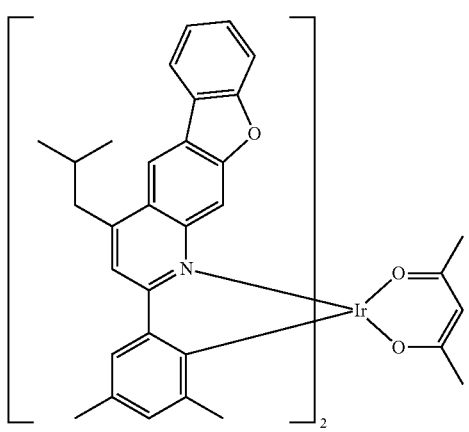
D-93
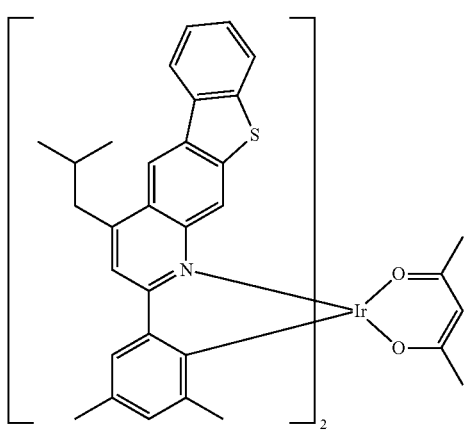
D-94
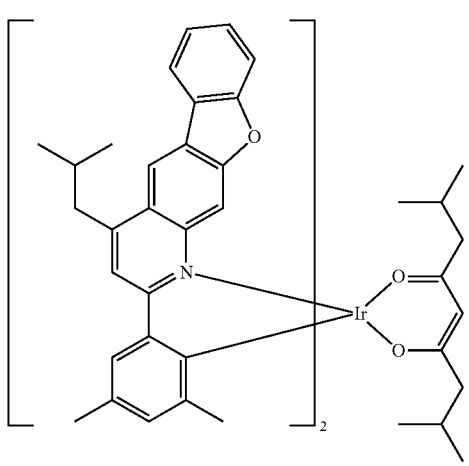
-continued
D-95
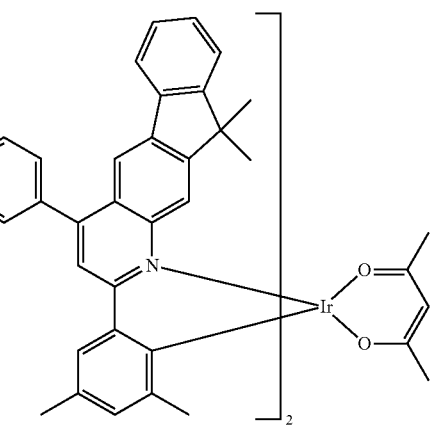
D-96
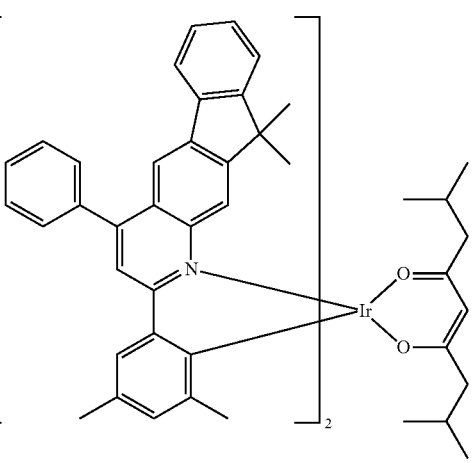
D-97
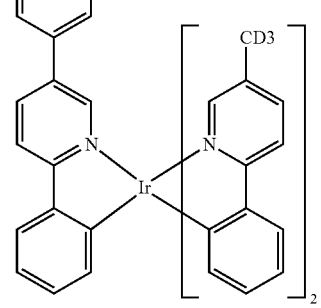
D-98
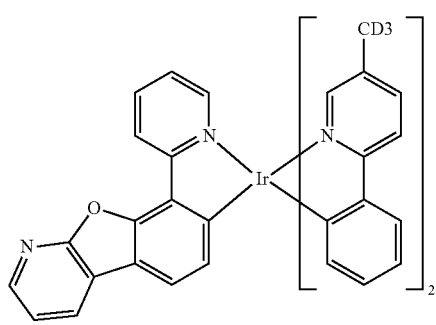

D-99
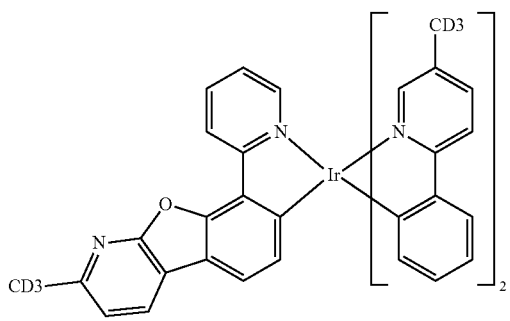
D-100
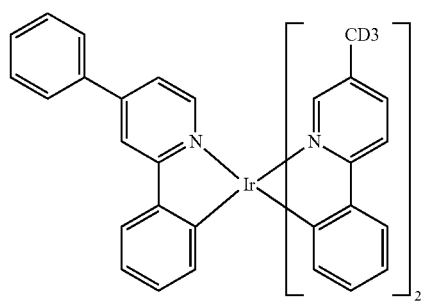
D-101
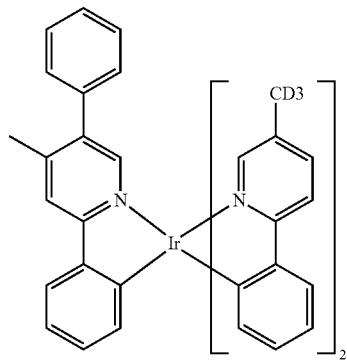
D-102
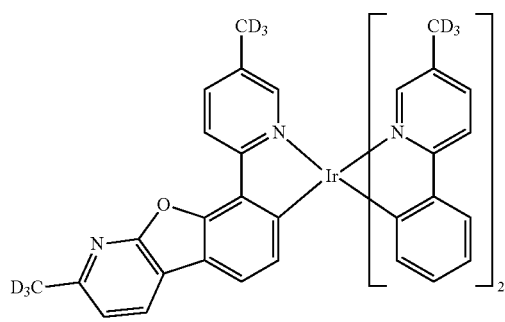
D-103
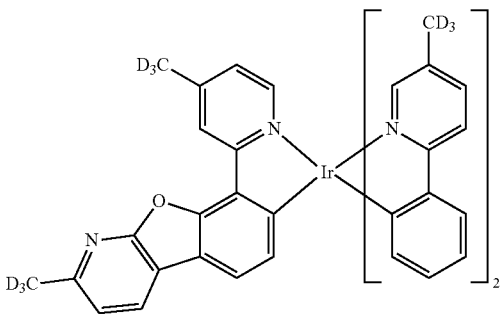
D-104
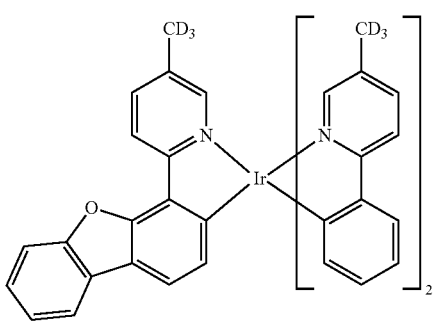
D-105
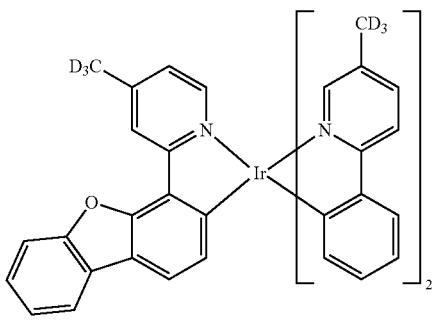
D-106
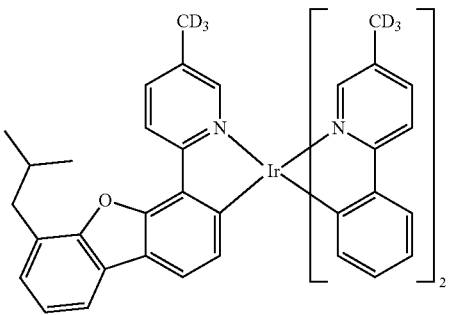
D-107
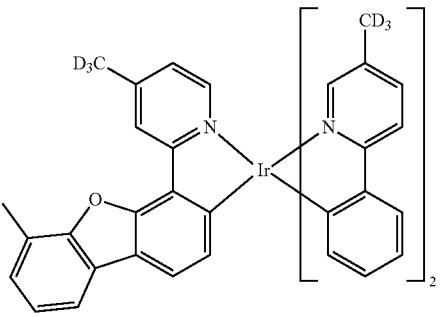

D-108

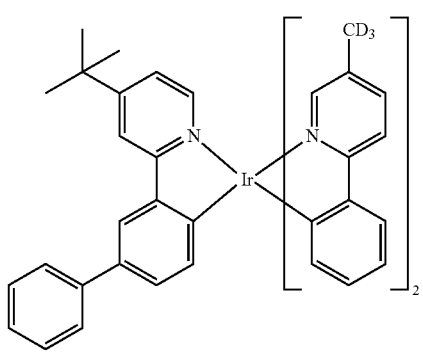

D-109

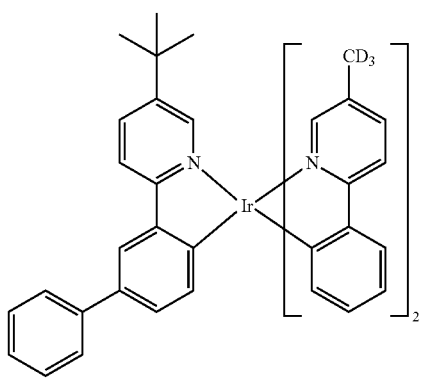

D-110

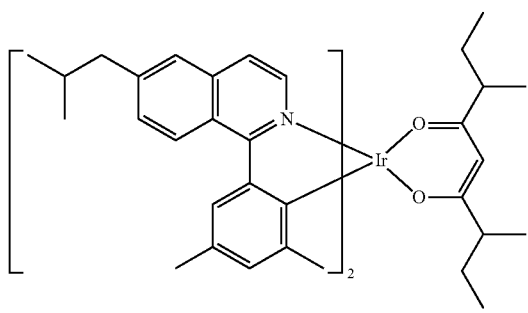

D-111

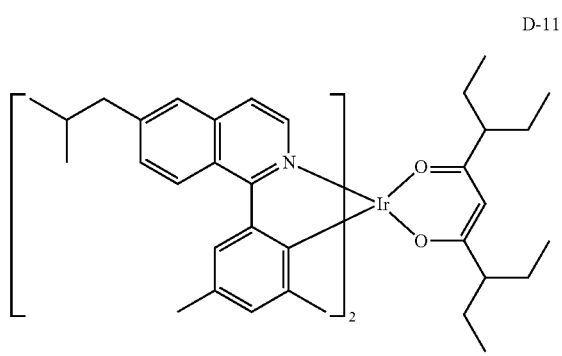

D-112

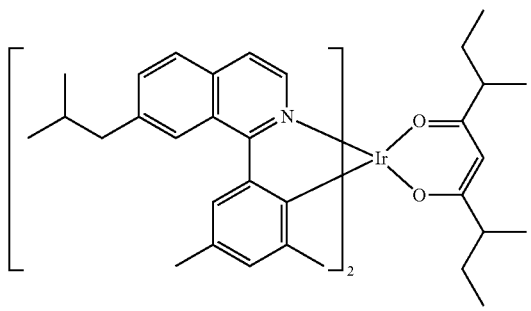

D-113

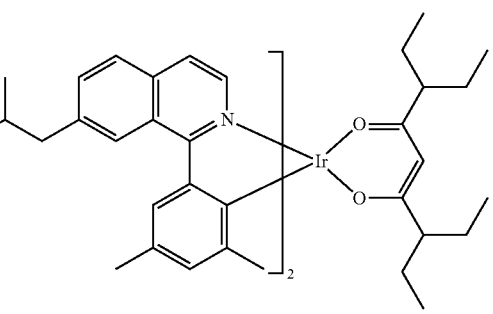

D-114

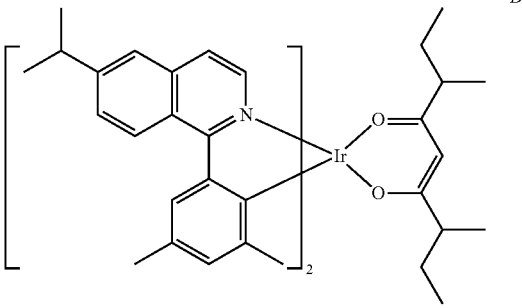

D-115

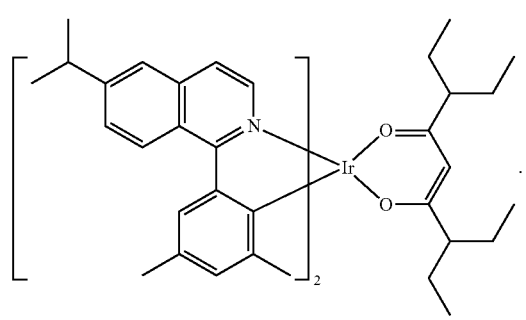

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When forming a layer by the dopant and the host compounds of the present disclosure, co-evaporation or mixture-evaporation may be used, but is not limited thereto.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

The co-deposition is a mixed deposition method in which two or more isomer materials are put into respective individual crucible sources and a current is applied to both cells simultaneously to evaporate the materials and to perform mixed deposition; and the mixed deposition is a mixed deposition method in which two or more isomer materials are mixed in one crucible source before deposition, and then a current is applied to one cell to evaporate the materials.

Also, the organic electroluminescent device of the present disclosure can be used for the manufacture of display devices such as smartphones, tablets, notebooks, PCs, TVs, or display devices for vehicles, or lighting devices such as outdoor or indoor lighting.

Hereinafter, the preparation method of a host compound according to the present disclosure, and the properties of the device comprising the same will be explained in detail with reference to the representative compounds of the present disclosure in order to understand the present disclosure in detail.

[Example 1] Preparation of Compound C-193 and stirred for 30 minutes, bis(pinacolato)diboron (167 g, 660 mmol) was added thereto, and the mixture was stirred at room temperature for 24 hours. After completion of the reaction, the organic layer was extracted with ethyl acetate, the residual moisture was then removed with magnesium sulfate and dried, and the resulting product was purified by column chromatography to obtain compound 1 (27 g, yield: 22%).

Preparation of Compound 2

Compound 1 (27 g, 100 mmol), 2-chloro-4,6-diphenyl-1,3,5-triazine (26.7 g, 100 mmol), tetrakis(triphenylphosphine)palladium(0) (Pd(PPh$_3$)$_4$) (11.5 g, 0.10 mmol), and potassium carbonate (41.4 g, 300 mmol), 150 mL of ethanol, 150 mL of water, and 300 mL of toluene were added into a flask and dissolved. The mixture was then refluxed and stirred for 3 hours at 120° C. After completion of the reaction, the organic layer was extracted with ethyl acetate, the residual moisture was then removed with magnesium sulfate and dried, and the resulting product was purified by column chromatography to obtain compound 2 (29.7 g, yield: 79%).

Preparation of Compound 3

Compound 2 (29.7 g, 79 mmol) and 400 mL of dichloromethane were added into a flask and dissolved. Next, 33

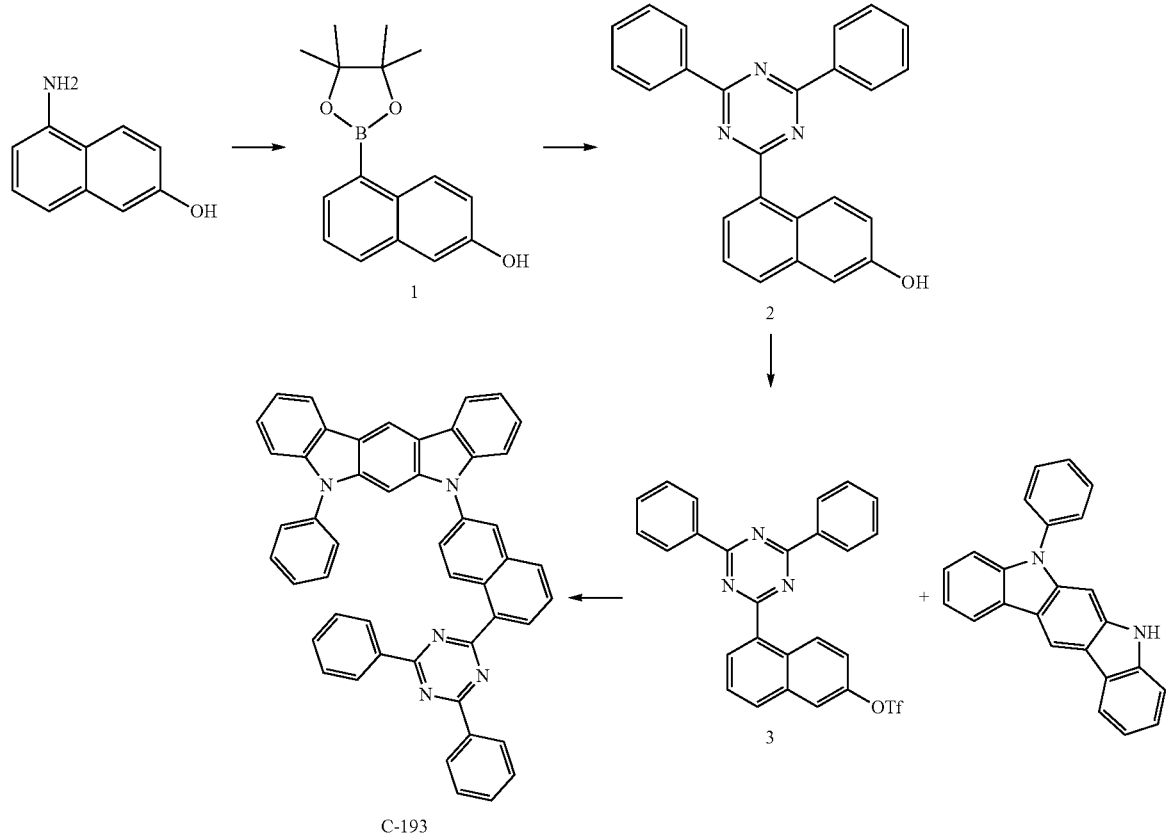 [SMILES: Nc1cccc2cc(O)ccc12 ; CC1(C)OB(c2cccc3cc(O)ccc23)OC1(C)C ; Oc1ccc2c(-c3nc(-c4ccccc4)nc(-c4ccccc4)n3)cccc2c1 ; c1ccc(-c2nc(-c3ccccc3)nc(-c3cccc4cc(-n5c6ccccc6c6cc7c8ccccc8n(-c8ccccc8)c7cc65)ccc34)n2)cc1 ; O=S(=O)(Oc1ccc2c(-c3nc(-c4ccccc4)nc(-c4ccccc4)n3)cccc2c1)C(F)(F)F ; c1ccc(-n2c3ccccc3c3cc4c(cc32)[nH]c2ccccc24)cc1]

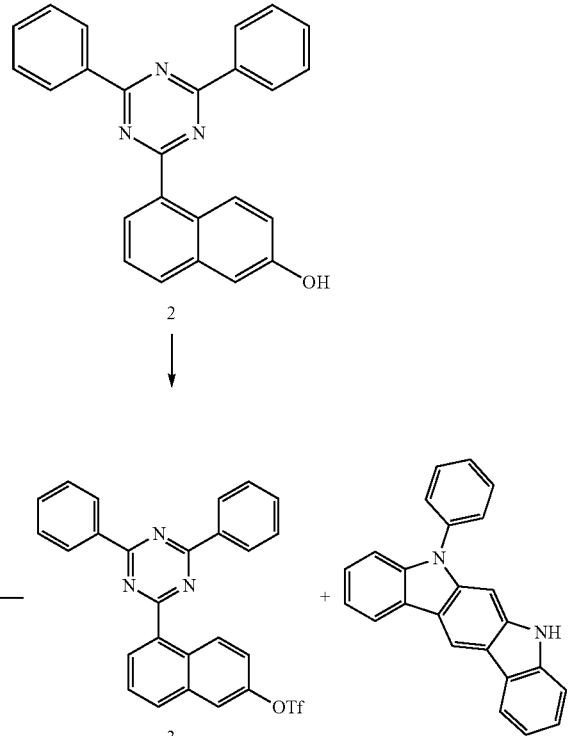

Preparation of Compound 1

5-aminonaphthalen-2-ol (70 g, 440 mmol) and 1.7 L of methanol were added into a flask and dissolved. Next, 400 mL of HCl and 640 mL of water were added thereto, and stirred for 2 minutes at room temperature. After sodium nitrite (30.34 g, 440 mmol) was added into the above flask mL of triethylamine was added thereto and stirred for 10 minutes at 0° C. 16 mL of trifluoromethanesulfonic anhydride was then slowly added into the flask and stirred for 1 hour. After completion of the reaction, the organic layer was extracted with ethyl acetate, the residual moisture was then removed with magnesium sulfate and dried, and the resulting product was purified by column chromatography to obtain compound 3 (25 g, yield: 62.7%).

Preparation of Compound C-193

Compound 3 (25 g, 49 mmol), 5-phenyl-5,7-dihydroindol[2,3-b]carbazole (14.9 g, 45 mmol), tris(dibenzylideneacetone)dipalladium(0) (1.6 g, 2 mmol), 2-dicyclohexylphosphino-2',6'-dimethoxybiphenyl (1.4 g, 4 mmol), sodium-tert-butoxide (10 g, 112 mmol), and 245 mL of o-xylene were added into a flask and refluxed for 4 hours. After completion of the reaction, the organic layer was extracted with ethyl acetate after vacuum distillation, the residual moisture was then removed with magnesium sulfate and dried, and the resulting product was purified by column chromatography to obtain compound C-193 (10 g, yield: 32%).

| Compound | MW | Tg | M.P |
|---|---|---|---|
| C-193 | 689.82 | 156° C. | 298° C. |

[Example 2] Preparation of Compound C-196

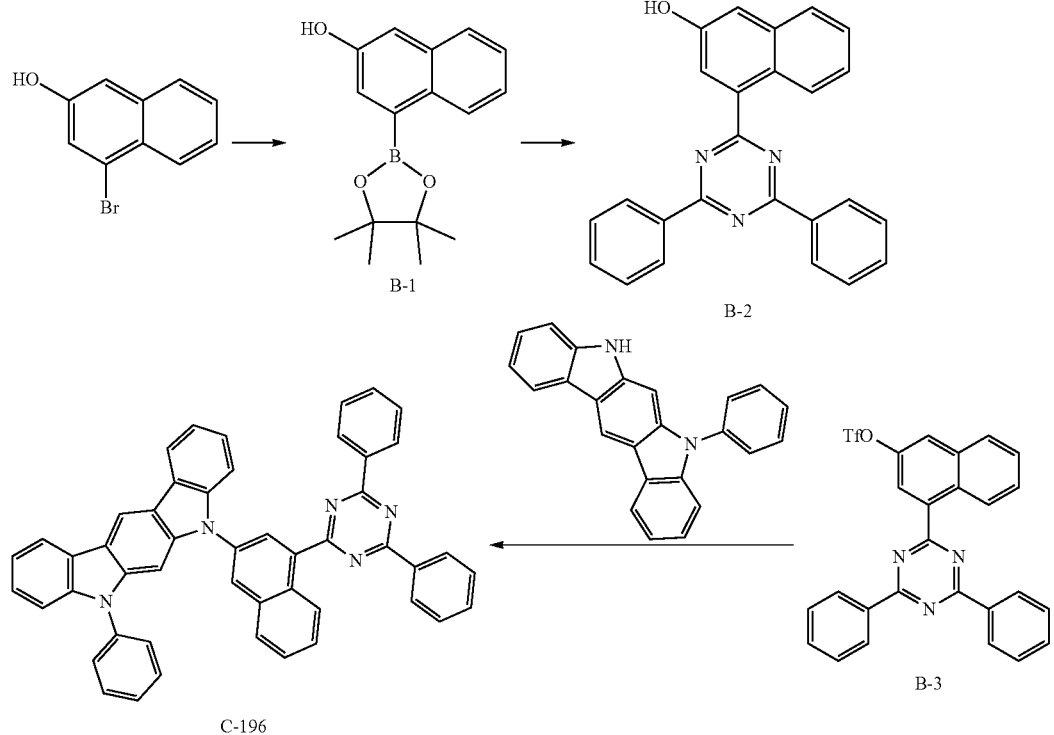

Preparation of Compound B-1

4-bromonaphthalen-2-ol (9 g, 40 mmol), bis(pinacolato)diboron (12.3 g, 48 mmol), bis(triphenylphosphine)palladium(II)dichloride (566 mg, 0.807 mmol), potassium acetate (7.9 g, 81 mmol) and 200 mL of 1,4-dioxane were added into a flask and dissolved, and then refluxed for 3 hours at 110° C. After completion of the reaction, the organic layer was extracted with ethyl acetate after vacuum distillation, the residual moisture was then removed with magnesium sulfate and dried, and the resulting product was purified by column chromatography to obtain compound B-1 (9.1 g, yield: 83%).

Preparation of Compound B-2

Compound B-1 (9.1 g, 34 mmol), 2-chloro-4,6-diphenyl-1,3,5-triazine (10.8 g, 40 mmol), tetrakis(triphenylphosphine)palladium(0) (1.9 g, 2 mmol), potassium carbonate (13.9 g, 101 mmol), 50 mL of ethanol, 50 mL of water, and 100 mL of toluene were added into a flask and dissolved, and then refluxed for 3 hours at 120° C. After completion of the reaction, the organic layer was extracted with ethyl acetate after vacuum distillation, the residual moisture was then removed with magnesium sulfate and dried, and the resulting product was purified by column chromatography to obtain compound B-2 (8 g, yield: 63%).

Preparation of Compound B-3

Compound B-2 (8.5 g, 23 mmol) and 113 mL of dichloromethane were added into a flask and dissolved. Next, 9.5 mL of triethylamine was added thereto and stirred for 10 minutes at 0° C. 7.4 mL of trifluoromethanesulfonic anhydride was then slowly added into the flask and stirred for 1 hour. After completion of the reaction, the organic layer was extracted with ethyl acetate, the residual moisture was then removed with magnesium sulfate and dried, and the resulting product was purified by column chromatography to obtain compound B-3 (5.9 g, yield: 51%).

Preparation of Compound C-196

Compound B-3 (5.9 g, 12 mmol), 5-phenyl-5,7-dihydroindol[2,3-b]carbazole (3 g, 9 mmol), tris(dibenzylideneacetone)dipalladium(0) (0.329 g, 0.361 mmol), 2-dicyclohexylphosphino-2',6'-dimethoxybiphenyl (0.297 g, 0.729 mmol), sodium-tert-butoxide (1.7 g, 112 mmol), and 361 mL of o-xylene were added into a flask and refluxed for 3 hours. After completion of the reaction, the organic layer was extracted with ethyl acetate after vacuum distillation, the residual moisture was then removed with magnesium sulfate and dried, and the resulting product was purified by column chromatography to obtain compound C-196 (1.7 g, yield: 27%).

| Compound | MW | Tg | M.P |
|---|---|---|---|
| C-196 | 689.82 | 154.6° C. | 262° C. |

[Example 3] Preparation of Compound C-9

Compound B-3 (9.6 g, 19.5 mmol), 12-phenyl-5,12-dihydroindolo[3,2-a]carbazole (6.3 g, 19.5 mmol), tris(dibenzylideneacetone)dipalladium(0) (0.7 g, 0.78 mmol), 2-dicyclohexylphosphino-2', 6'-dimethoxybiphenyl (0.6 g, 1.5 mmol), sodium-tert-butoxide (4.5 g, 48.8 mmol), and 97.5 mL of o-xylene were added into a flask and refluxed for 3 hours. After completion of the reaction, the organic layer was extracted with ethyl acetate after vacuum distillation, the residual moisture was then removed with magnesium sulfate and dried, and the resulting product was purified by column chromatography to obtain compound C-9 (1 g, yield: 7.6%).

| Compound | MW | Tg | M.P |
|---|---|---|---|
| C-9 | 689.82 | 159.68° C. | 307° C. |

Device Example 1: Producing an OLED Device Comprising a Red Light-Emitting Organic Electroluminescent Compound According to the Present Disclosure An OLED device was produced by using the organic electroluminescent compound of the present disclosure. First, a transparent electrode indium tin oxide (ITO) thin film (10 Ω/sq) on a glass substrate for an OLED device (GEOMATEC CO., LTD., Japan) was subjected to an ultrasonic washing with acetone, ethanol, and distilled water, sequentially, and then was stored in isopropanol. The ITO substrate was then mounted on a substrate holder of a vacuum vapor deposition apparatus. Compound HI-1 was introduced into a cell of the vacuum vapor deposition apparatus, and then the pressure in the chamber of the apparatus was controlled to $10^{-7}$ torr. Thereafter, an electric current was applied to the cell to evaporate the above-introduced material, thereby forming a first hole injection layer having a thickness of 80 nm on the ITO substrate. Next, compound HI-2 was introduced into another cell of the vacuum vapor deposition apparatus, and was evaporated by applying an electric current to the cell, thereby forming a second hole injection layer having a thickness of 5 nm on the first hole injection layer. Compound HT-1 was then introduced into another cell of the vacuum vapor deposition apparatus, and was evaporated by applying an electric current to the cell, thereby forming a first hole transport layer having a thickness of 10 nm on the second hole injection layer. Compound HT-2 was then introduced into another cell of the vacuum vapor deposition apparatus, and was evaporated by applying an electric current to the cell, thereby forming a second hole transport layer having a thickness of 60 nm on the first hole transport layer. After forming the hole injection layers and the hole transport layers, a light-emitting layer was formed thereon as follows: Compound C-193 was introduced into one cell of the vacuum vapor depositing apparatus as a host, and compound D-39 was introduced into another cell as a dopant. The dopant was deposited in a doping amount of 3 wt % based on the total amount of the host and dopant to form a light-emitting layer having a thickness of 40 nm on the second hole transport layer. Next, compounds ETL-1 and EIL-1 were evaporated at a 50:50 weight ratio, and were deposited to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED device was produced. Each compound was purified by vacuum sublimation under $10^{-6}$ torr and then used.

Device Example 2: Producing an OLED Device Comprising a Red Light-Emitting Organic Electroluminescent Compound According to the Present Disclosure An OLED device was produced in the same manner as in Device Example 1, except that compound C-196 was used as the host material of the light-emitting layer.

Device Example 3: Producing an OLED Device Comprising a Red Light-Emitting Organic Electroluminescent Compound According to the Present Disclosure An OLED device was produced in the same manner as in Device Example 1, except that compound C-9 was used as the host material of the light-emitting layer.

Comparative Example 1: Producing an OLED Device not Comprising a Red Light-Emitting Organic Electroluminescent Compound According to the Present Disclosure An OLED device was produced in the same manner as in Device Example 1, except that compound H-1 was used as the host material of the light-emitting layer.

Comparative Example 2: Producing an OLED Device not Comprising a Red Light-Emitting Organic Electroluminescent Compound According to the Present Disclosure An OLED device was produced in the same manner as in Device Example 1, except that compound H-2 was used as the host material of the light-emitting layer.

Comparative Example 3: Producing an OLED Device not Comprising a Red Light-Emitting Organic Electroluminescent Compound According to the Present Disclosure An OLED device was produced in the same manner as in Device Example 1, except that compound H-3 was used as the host material of the light-emitting layer.

Comparative Example 4: Producing an OLED Device not Comprising a Red Light-Emitting Organic Electroluminescent Compound According to the Present Disclosure An OLED device was produced in the same manner as in Device Example 1, except that compound H-4 was used as the host material of the light-emitting layer.

The compounds used in Device Examples 1 to 3 and Comparative Examples 1 to 4, are shown in Table 1 below.

Table 1

| Hole Injection Layer/ Hole Transport Layer | | |
|---|---|---|
| 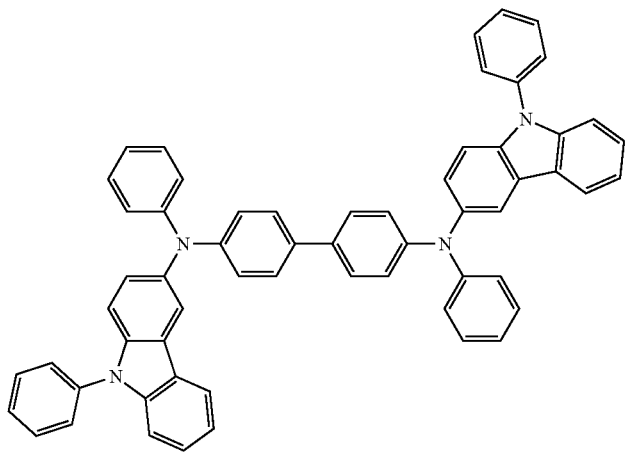<br>HI-1 | | 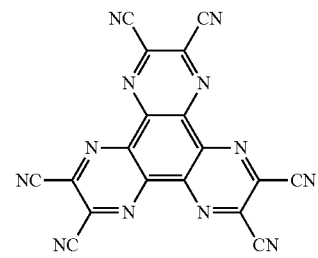<br>HI-2 |
| 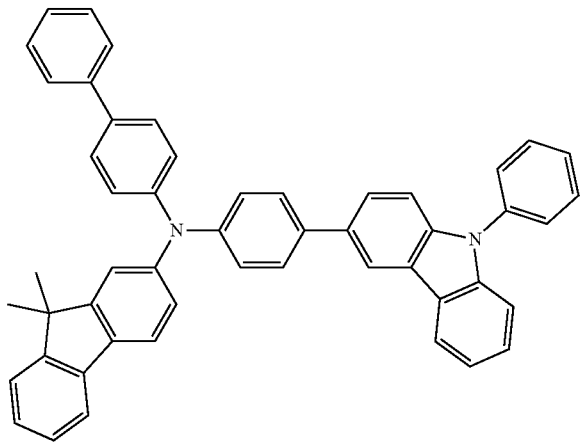<br>HT-1 | | 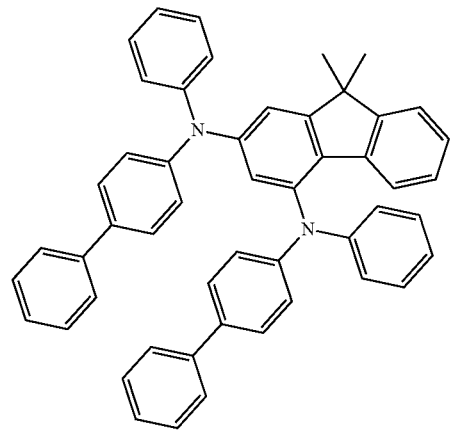<br>HT-2 |

Light Emitting Layer
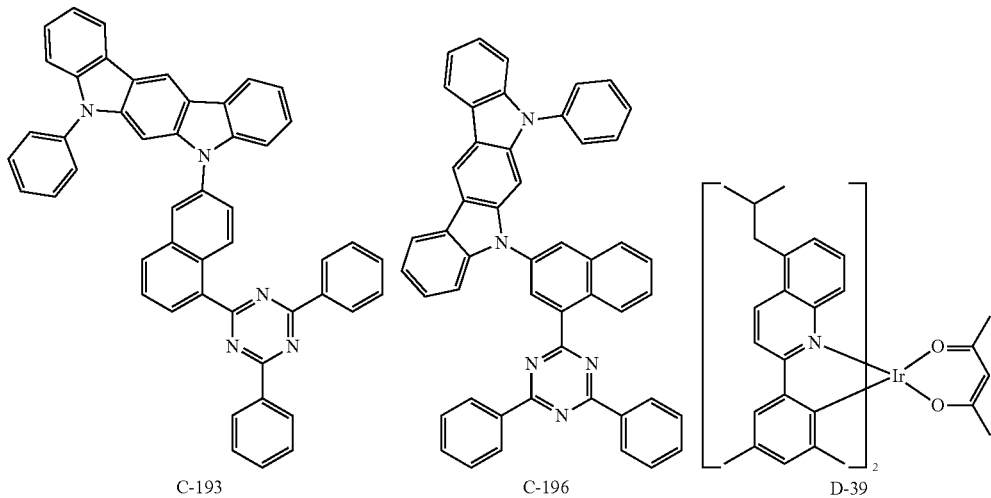
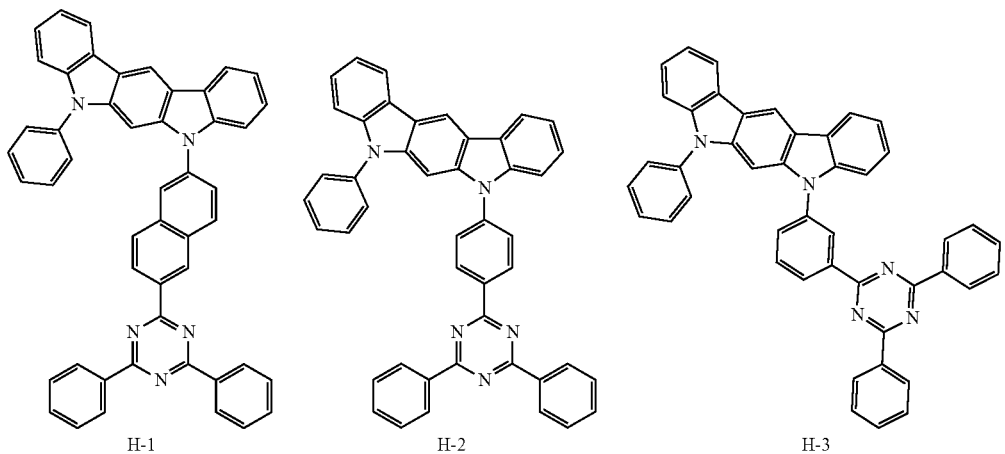
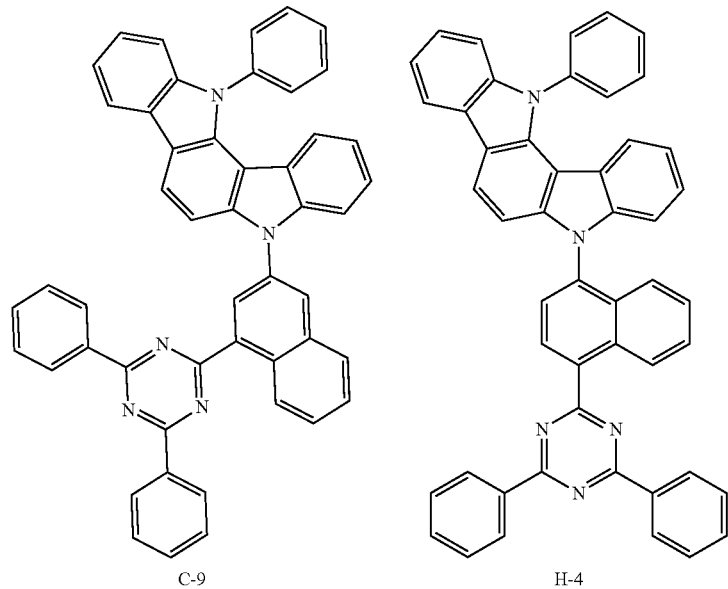

| Electron Transport Layer/ Electron Injection Layer | 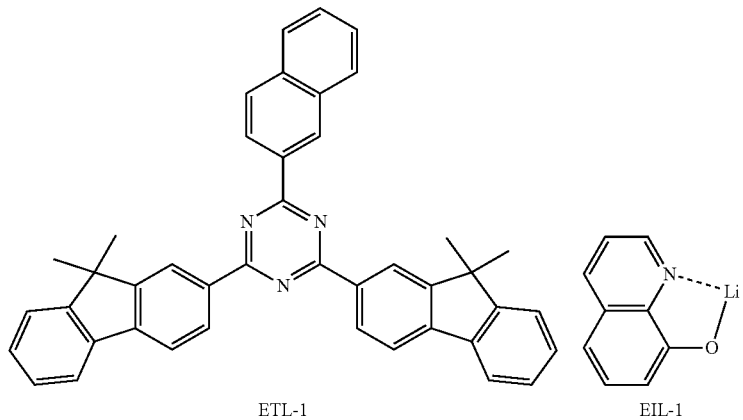 |
|---|---|
| | ETL-1      EIL-1 |

Evaluation: Lifespan Characteristics Measurement of an Organic Electroluminescent Device The driving voltage and the color of light-emission at a luminance of 1,000 nits, and the time taken for the light-emission to be reduced from 100% to 95% at a luminance of 5,000 nit (lifespan; T95) of the organic electroluminescent device produced in Device Examples 1 to 3 and Comparative Examples 1 to 4, were measured and shown in the following Table 2.

TABLE 2

|  | Driving Voltage (V) | Color of Light-Emission | Lifespan (T95, hr) |
|---|---|---|---|
| Device Example 1 | 2.9 | Red | 222.2 |
| Device Example 2 | 2.9 | Red | 531.7 |
| Device Example 3 | 3.1 | Red | 319.9 |
| Comparative Example 1 | 2.8 | Red | 124.1 |
| Comparative Example 2 | 2.8 | Red | 83.7 |
| Comparative Example 3 | 2.9 | Red | 100.9 |
| Comparative Example 4 | 2.9 | Red | 91.8 |

Referring to Table 2 above, it was confirmed that the organic electroluminescent device according to Device Examples 1 to 3 have significantly improved lifespan characteristics as compared with Comparative Examples 1 to 4. As set forth above, by asymmetrically linking an indolocarbazole to a nitrogen-containing aromatic hexagonal ring group at a naphthalene linker, the donor-acceptor electron bonding of the compound in the excited state is weakened due to the breaking of the electron conjugation, and the compound has a high HOMO energy level, resulting in that the hole current characteristic is relatively improved as compared with the Comparative Examples.

In addition, the host compounds included in the Comparative Examples have a fast electron current characteristic, but have a very slow hole current characteristic, resulting in a decrease in lifespan due to charge imbalance; however, the organic electroluminescent compound according to one embodiment includes an asymmetric linking within its structure, and thus the charge balance can be improved due to the enhancement of the hole conduction characteristic, thereby contributing to improvement of device characteristics.

In other words, the device using the organic electroluminescent compound according to the present disclosure as a host material for luminescence presents improved lifespan characteristics, and thus it can have an advantage in a device requiring long lifespan such as a flexible display, a white organic light-emitting device, a lighting, and an automobile display.

The invention claimed is:

1. An organic electroluminescent compound represented by formula 2, 3, 4, 5 or 7:

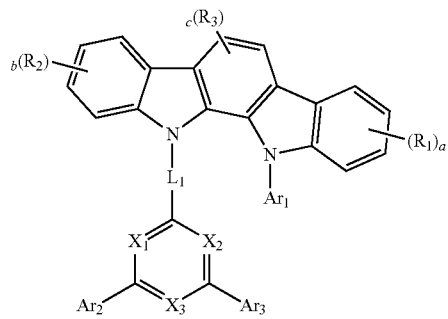

(2)

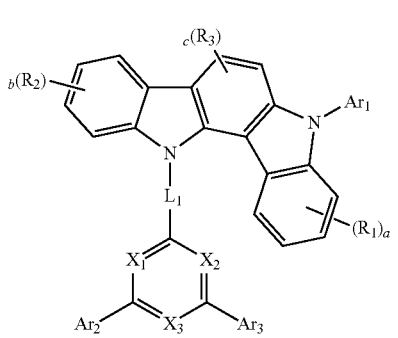

(3)

(4)

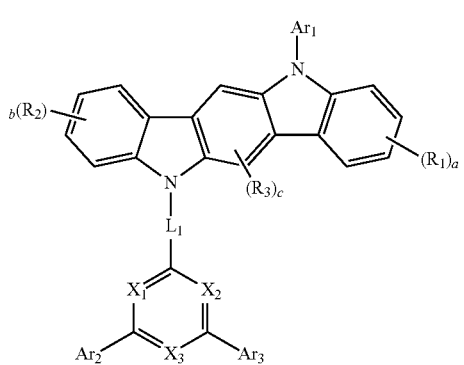

(5)

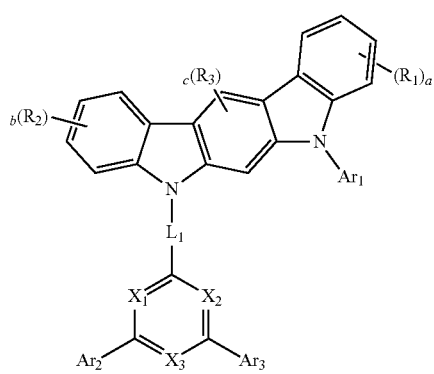

(7)

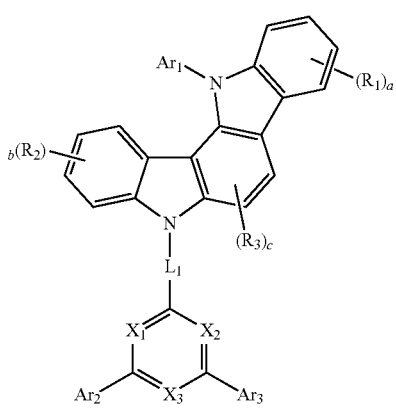

wherein, $X_1$ to $X_3$ each independently represent $CR_{12}$ or N;

at least one of $X_1$ to $X_3$ represents N;

$Ar_1$ to $Ar_3$ each independently represent a substituted or unsubstituted (C1-C30)alkyl, a substituted or unsubstituted (C6-C30)aryl, or a substituted or unsubstituted (3- to 30-membered)heteroaryl;

$R_1$ to $R_3$, and $R_{12}$ each independently represent hydrogen, deuterium, halogen, cyano, carboxyl, nitro, hydroxyl, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered) heterocycloalkyl, a substituted or unsubstituted (C6-C30)aryl, or a substituted or unsubstituted (3- to 30-membered)heteroaryl; or $R_1$ and $R_3$ may be linked to an adjacent substituent to form a substituted or unsubstituted (C3-C30) mono- or polycyclic, alicyclic or aromatic ring or a combination thereof;

a and b each independently represent an integer from 0 to 4; c represents an integer from 0 to 2; when a or b is an integer of 2 or more or c is 2, each of $R_1$, each of $R_2$, or each of $R_3$ may be the same or different;

$L_1$ is represented by the following formula R-1:

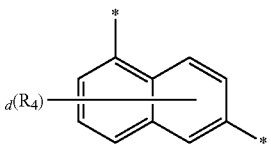

R-1 wherein, $R_4$ represents hydrogen, deuterium, halogen, cyano, carboxyl, nitro, hydroxyl, a substituted or unsubstituted (C1-C30)alkyl, a substituted or unsubstituted (C3-C30) cycloalkyl, a substituted or unsubstituted (C3-C30) cycloalkenyl, a substituted or unsubstituted (3- to 7-membered)heterocycloalkyl, a substituted or unsubstituted (C6-C30)aryl or a substituted or unsubstituted (3- to 30-membered)heteroaryl;

d represents an integer from 0 to 6, when d is an integer of 2 or more, each of $R_4$ may be the same or different;

\* represents a linkage position with an adjacent ring in formula 1.

2. The organic electroluminescent compound according to claim 1, wherein the substituents of the substituted (C1-C30)alkyl, the substituted (C3-C30)cycloalkyl, the substituted (C3-C30)cycloalkenyl, the substituted (3- to 7-b membered)heterocycloalkyl, the substituted (C6-C30)aryl, the substituted (3- to 30-membered)heteroaryl, and the substituted (C3-C30) mono- or polycyclic, alicyclic, or aromatic ring, or a combination thereof in $Ar_1$ to $Ar_3$, $R_1$ to $R_4$, and $R_{12}$, each independently, are at least one selected from the group consisting of deuterium, halogen, cyano, carboxyl, nitro, hydroxyl, (C1-C30)alkyl, halo(C1-C30)alkyl, (C2-C30)alkenyl, (C2-C30)alkynyl, (C1-C30)alkoxy, (C1-C30) alkylthio, (C3-C30)cycloalkyl, (C3-C30)cycloalkenyl, (3- to 7-membered)heterocycloalkyl, (C6-C30)aryloxy, (C6-C30) arylthio, unsubstituted (5- to 30-membered)heteroaryl, (5- to 30-membered)heteroaryl substituted with (C6-C30)aryl, unsubstituted (C6-C30)aryl, (C6-C30)aryl substituted with (5- to 30-membered)heteroaryl, tri(C1-C30)alkylsilyl, tri (C6-C30)arylsilyl, di(C1-C30)alkyl(C6-C30)arylsilyl, (C1-C30)alkyldi(C6-C30)arylsilyl, amino, mono- or di-(C1-C30)alkylamino, unsubstituted mono- or di-(C6-C30) arylamino, mono- or di-(C6-C30)arylamino substituted with (C1-C30)alkyl, (C1-C30)alkyl(C6-C30)arylamino, (C1-C30)alkylcarbonyl, (C1-C30)alkoxycarbonyl, (C6-C30)

arylcarbonyl, di(C6-C30)arylboronyl, di(C1-C30)alkylboronyl, (C1-C30)alkyl(C6-C30)arylboronyl, (C6-C30)aryl (C1-C30)alkyl, and (C1-C30)alkyl(C6-C30)aryl.

3. The organic electroluminescent compound according to claim 1, wherein at least two of $X_1$ to $X_3$ represent N;
$Ar_1$ to $Ar_3$ each independently represent a substituted or unsubstituted (C6-C25)aryl;
$R_1$ to $R_4$, and $R_{12}$ each independently represent hydrogen or deuterium.

4. The organic electroluminescent compound according to claim 1, wherein the compound represented by formula 2 to 5 or 7 is selected from the following compounds:

C-4
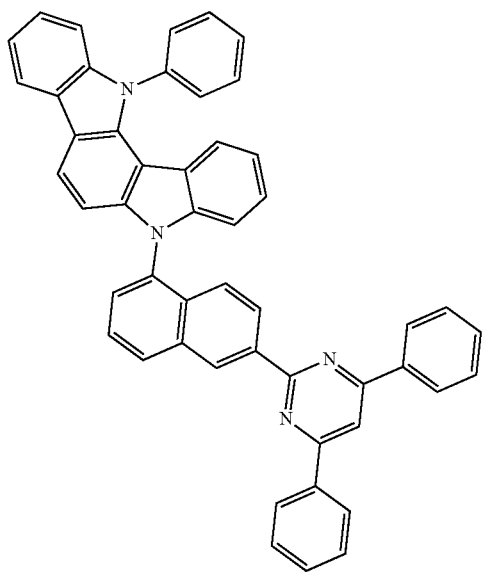

C-5
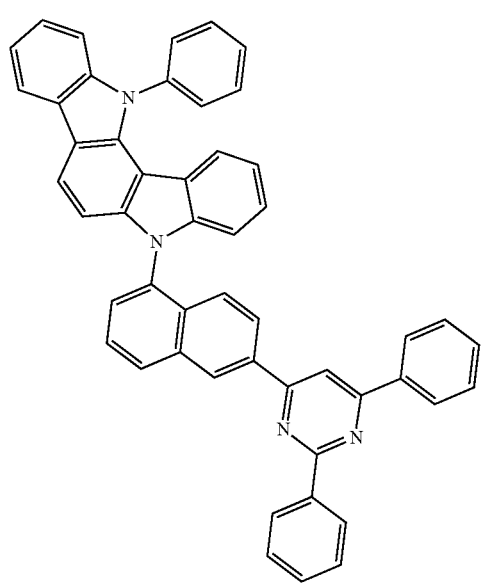

C-6
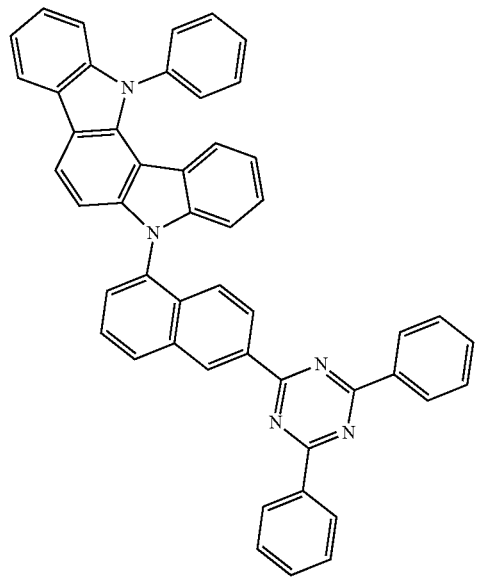

C-10
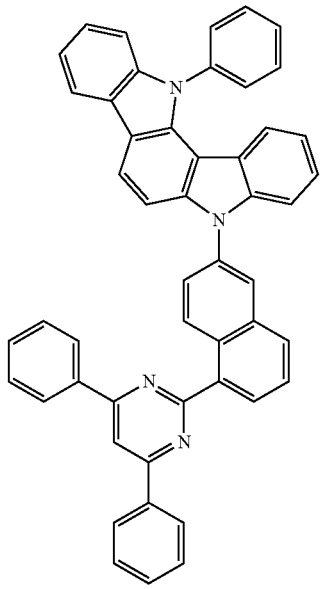

C-11
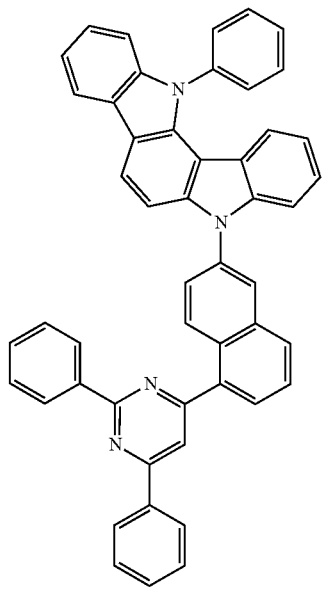
C-12
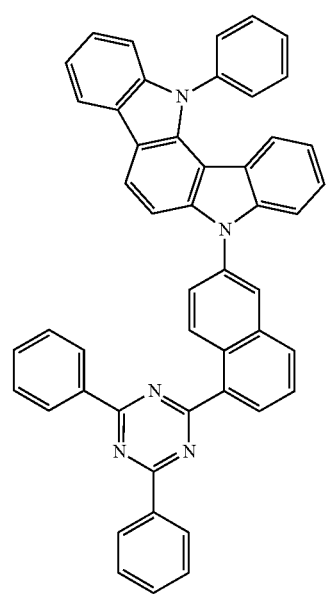
C-19
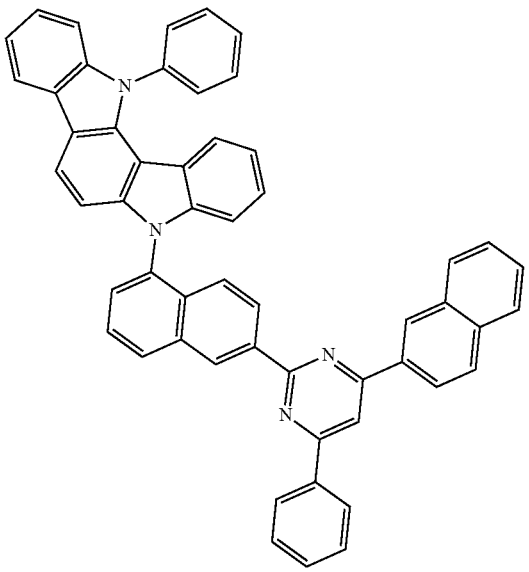
C-20
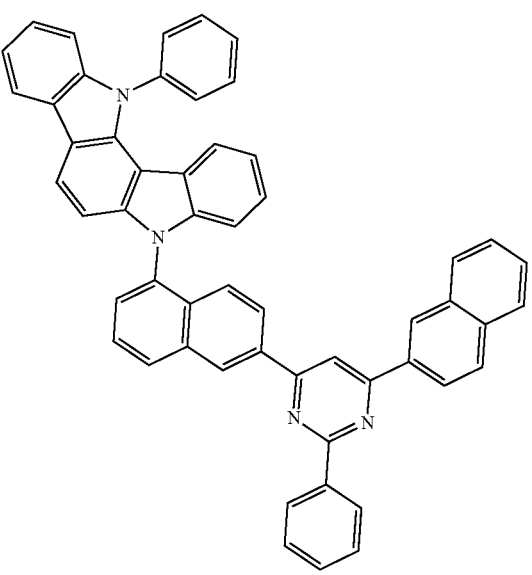

C-21
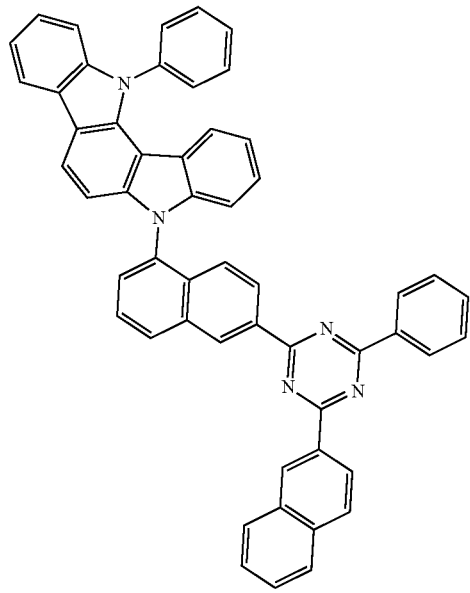
C-26
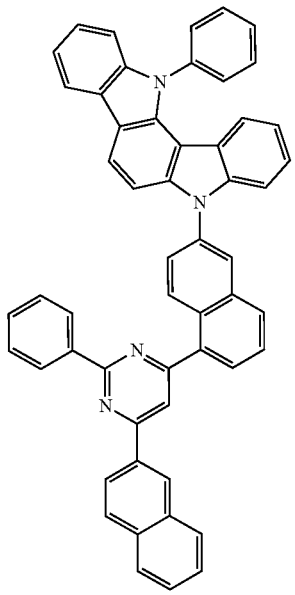
C-25
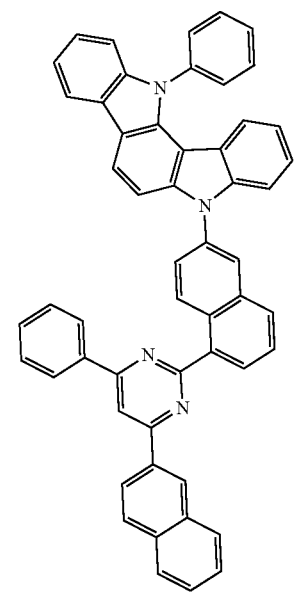
C-27
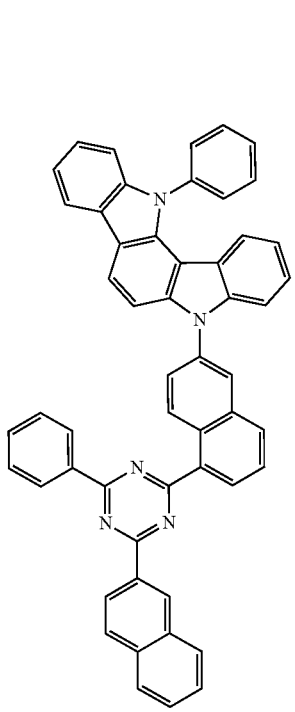

-continued
C-34
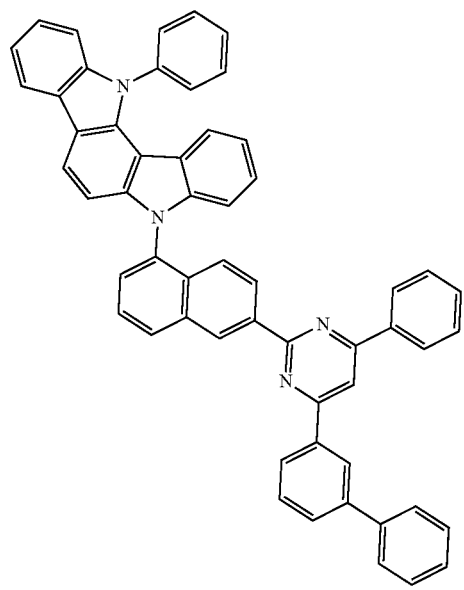
C-35
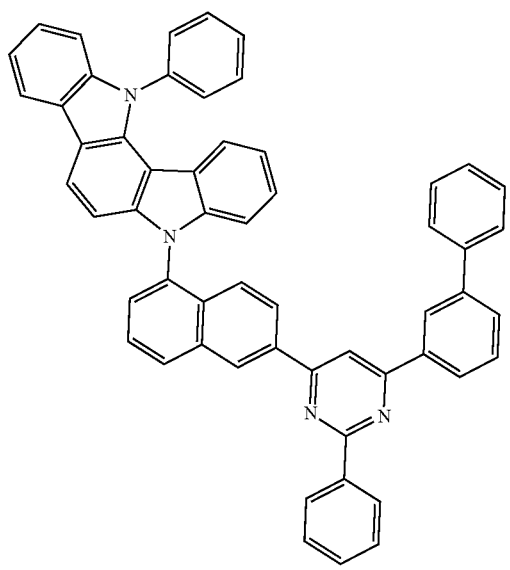
C-36
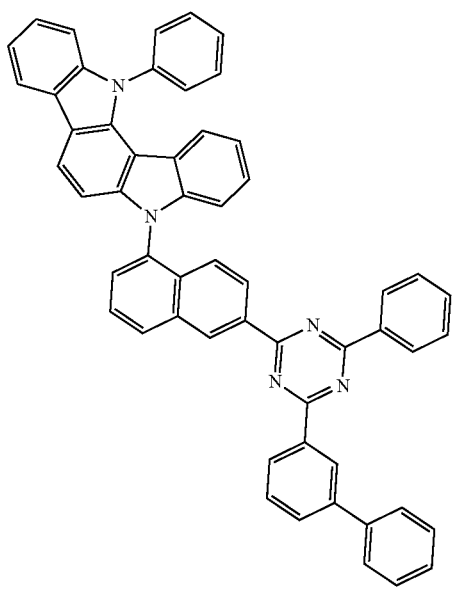
C-40
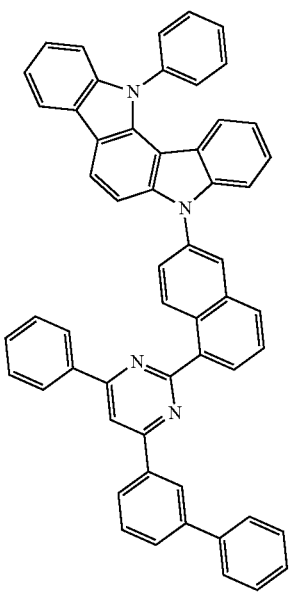

C-41
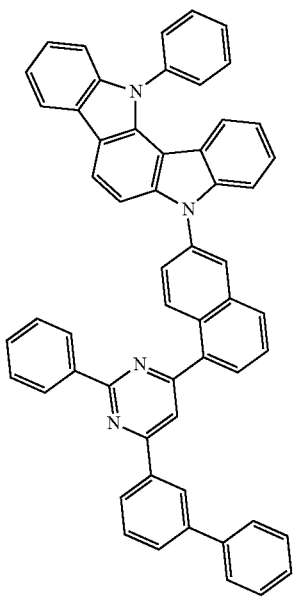
C-49
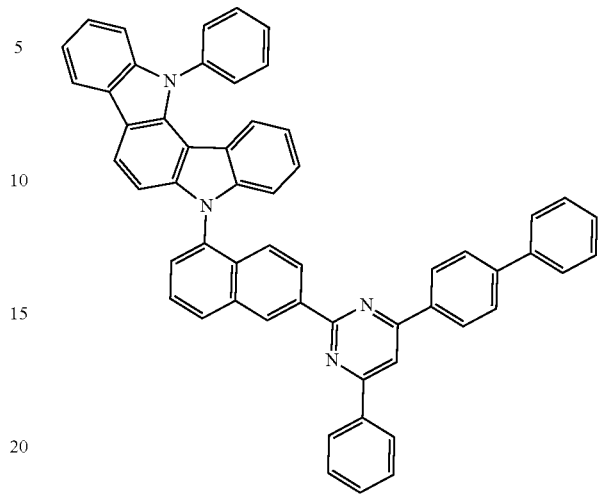
C-42
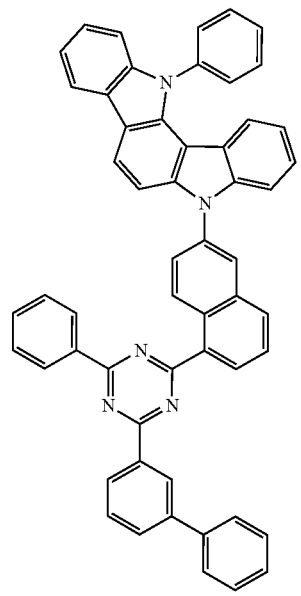
C-50
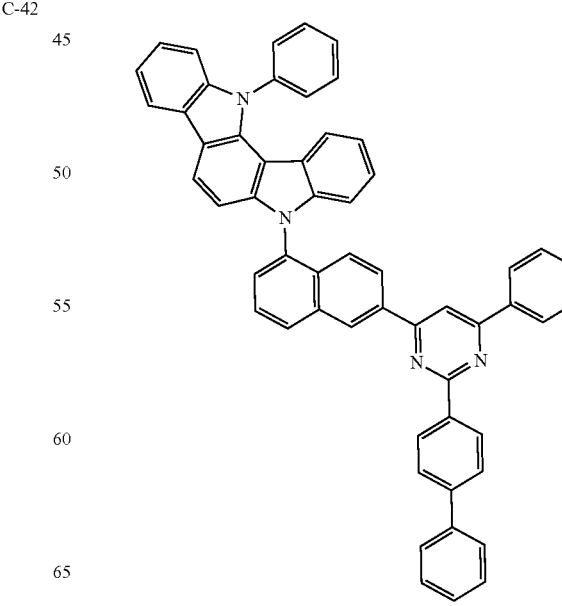

C-51
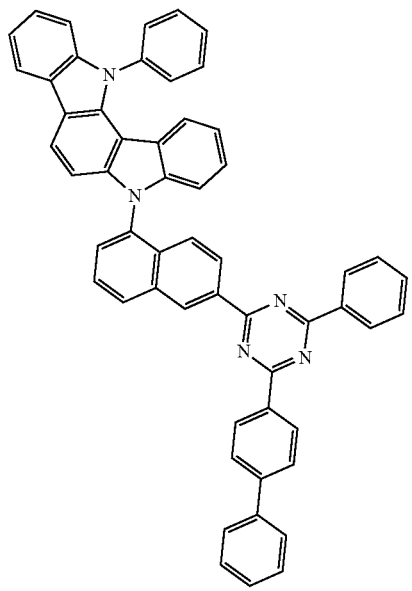
C-55
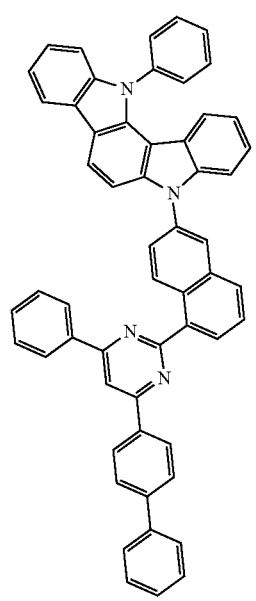
C-56
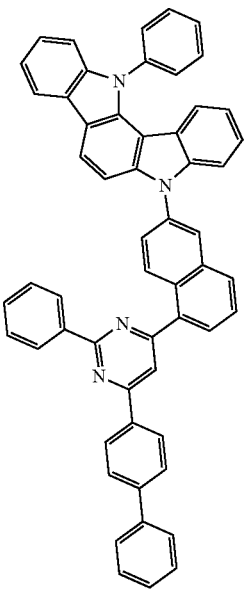
C-57
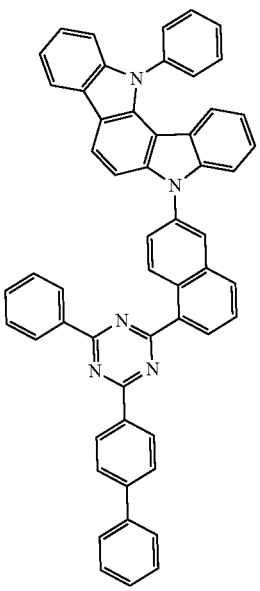

C-64
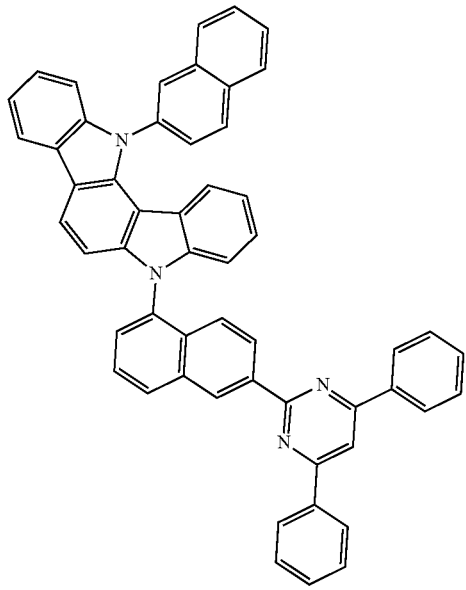
C-66
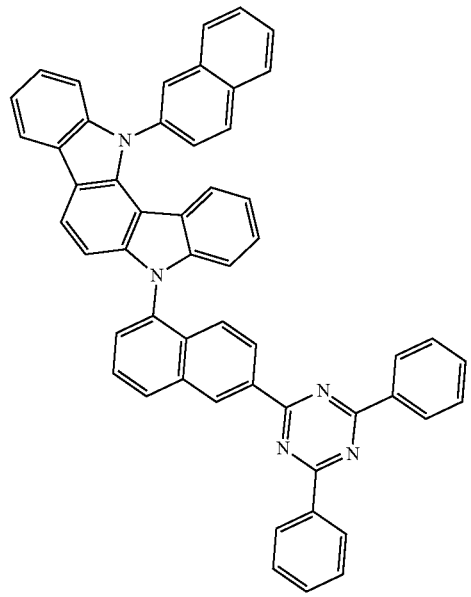
C-65
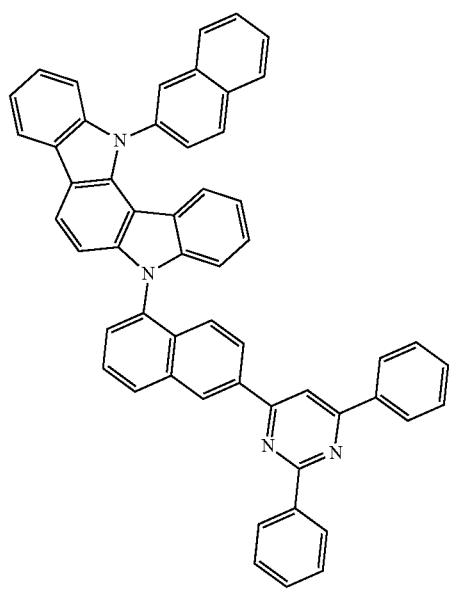
C-70
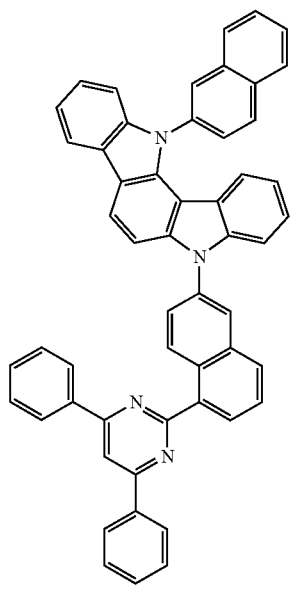

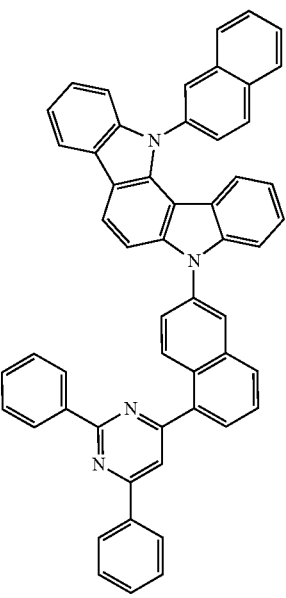
C-71
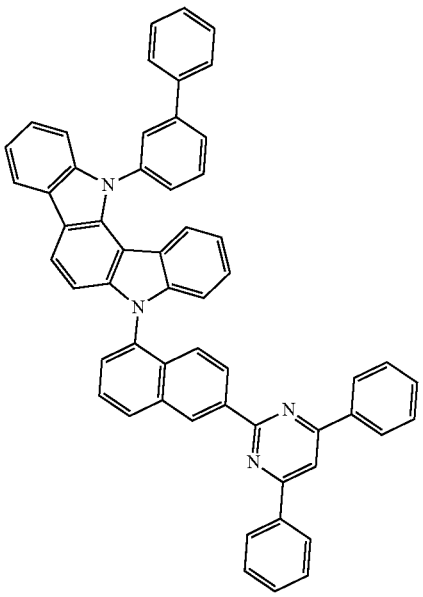
C-79
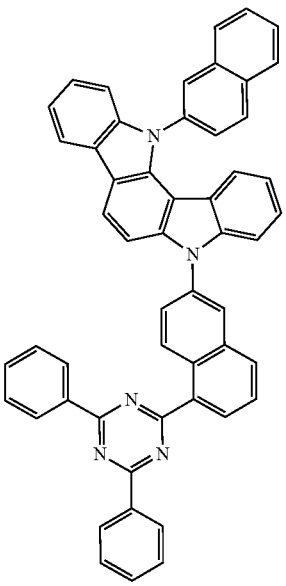
C-72
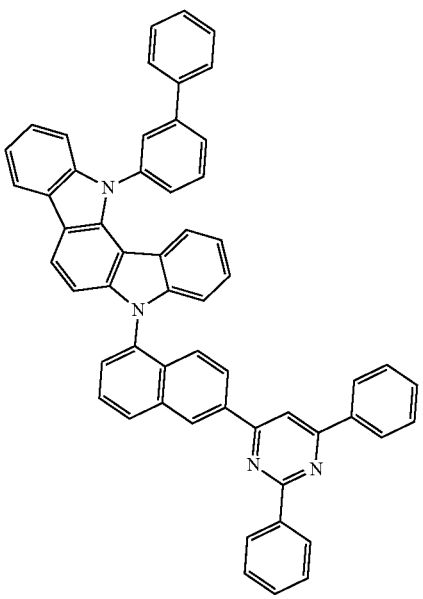
C-80

C-81
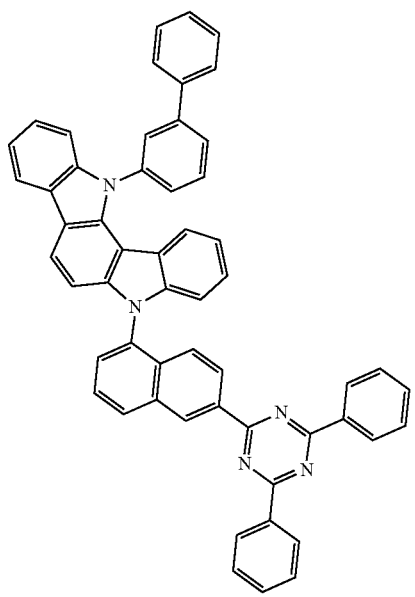
C-86
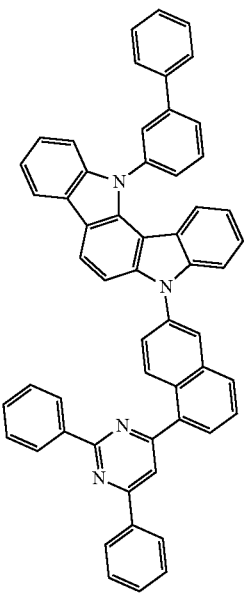
C-85
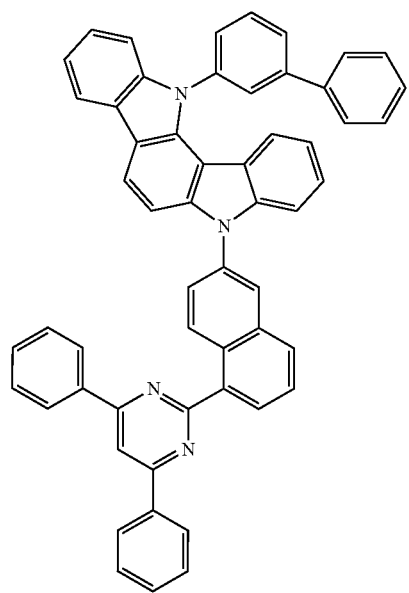
C-87
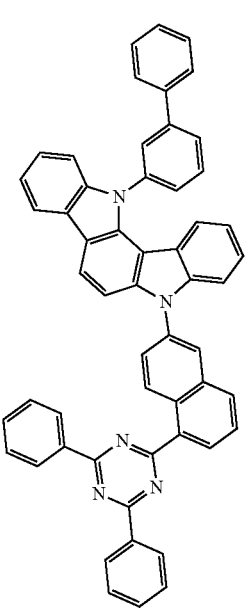

C-189
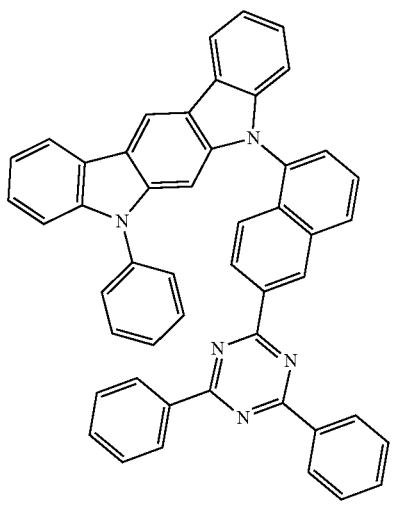
C-190
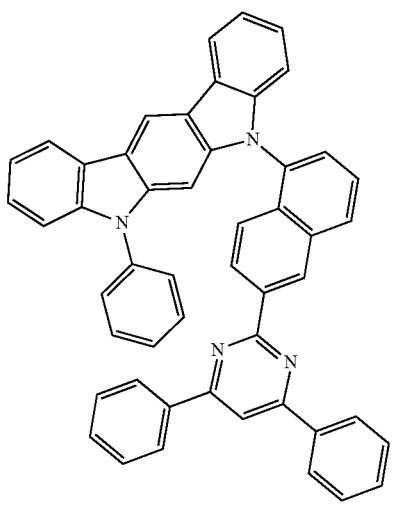
C-191
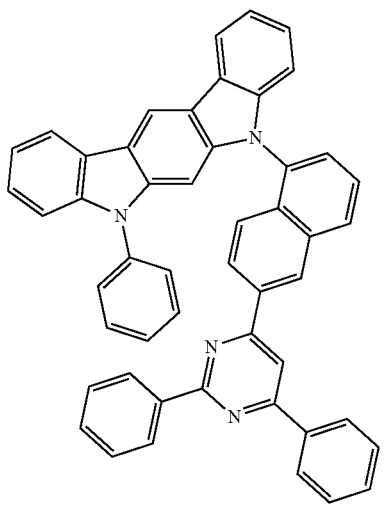
C-192
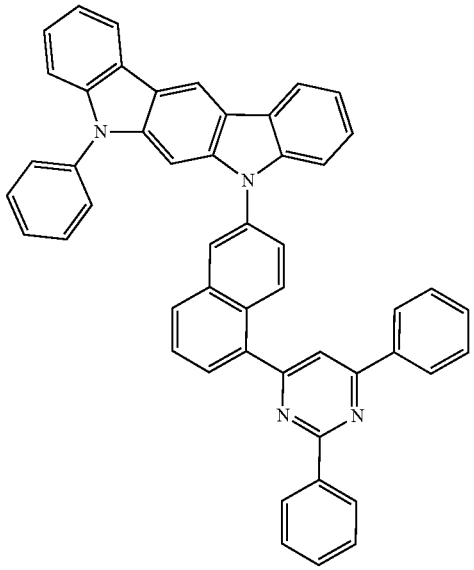
C-193
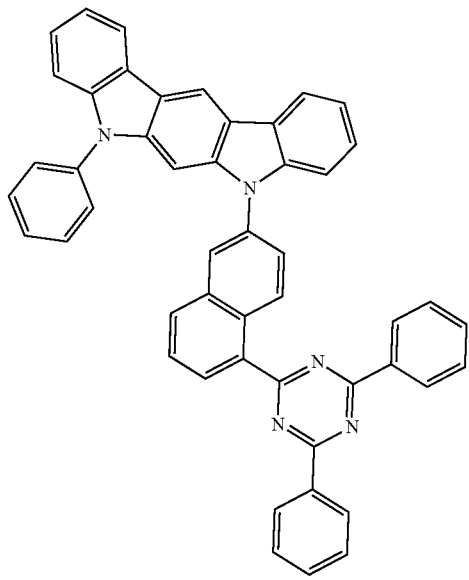

C-194
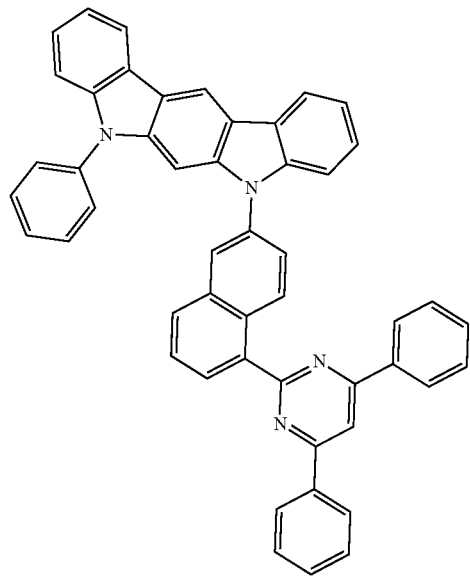
C-205
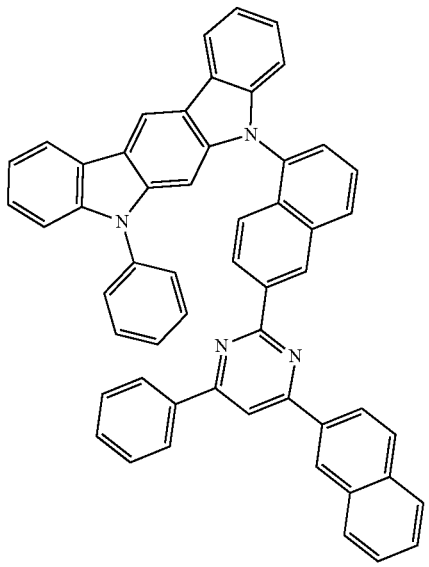
C-204
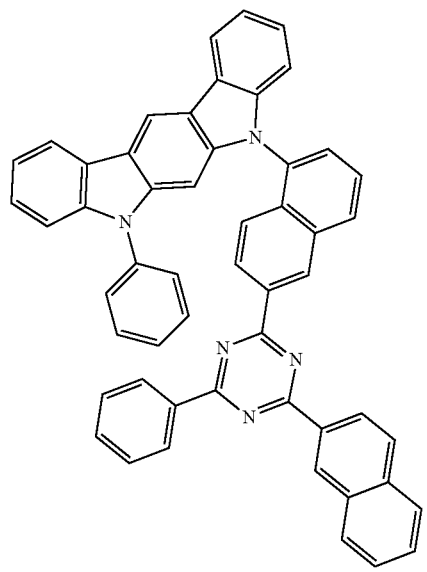
C-206
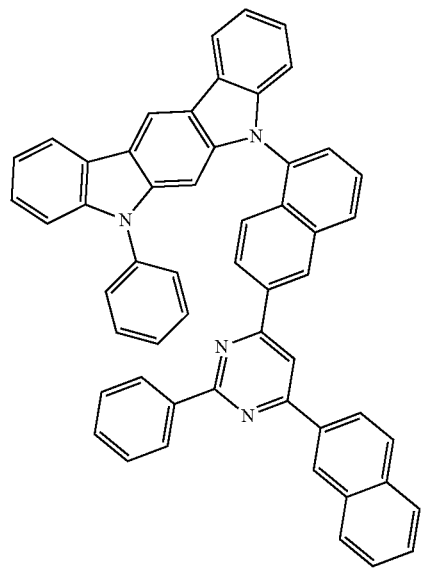

C-207
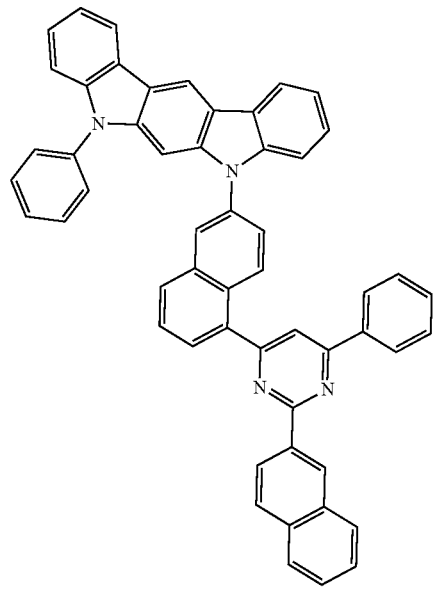
C-208
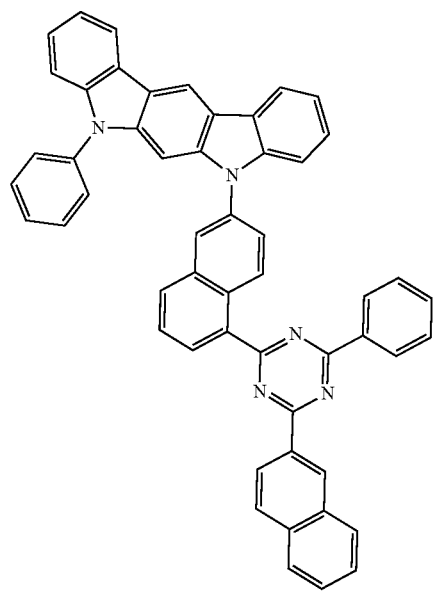
C-209
(structure)
C-219
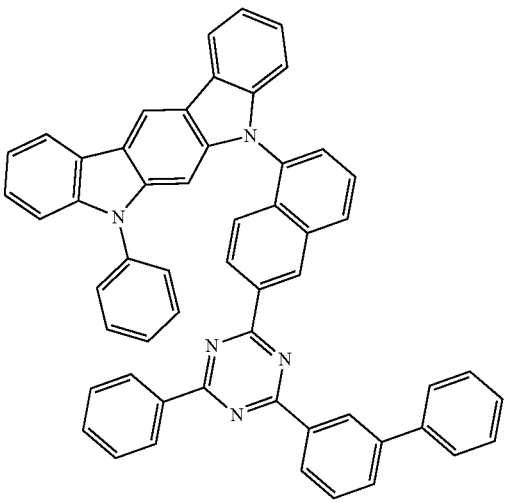

C-220
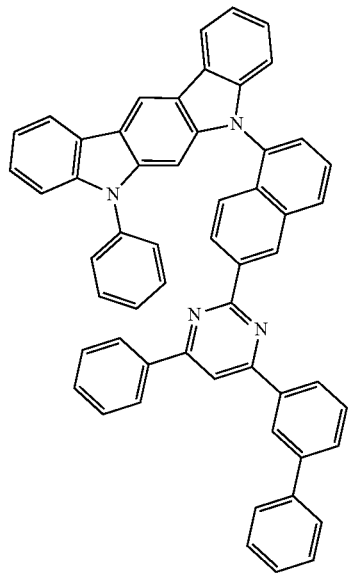
C-222
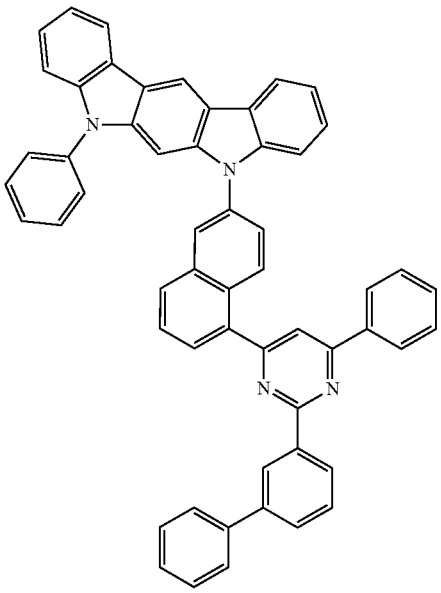
C-221
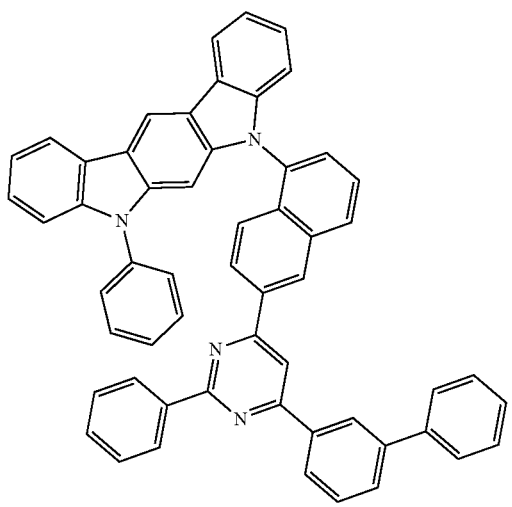
C-223
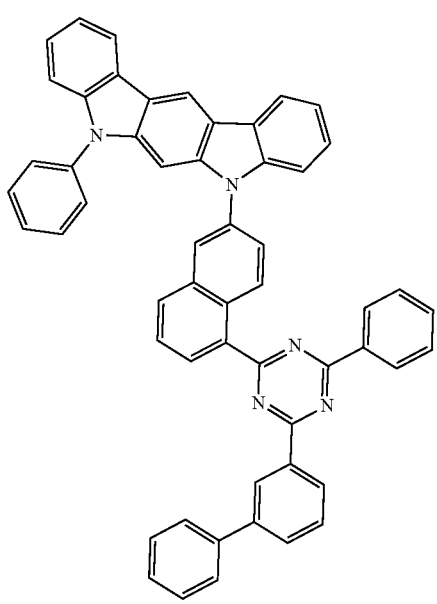

C-224
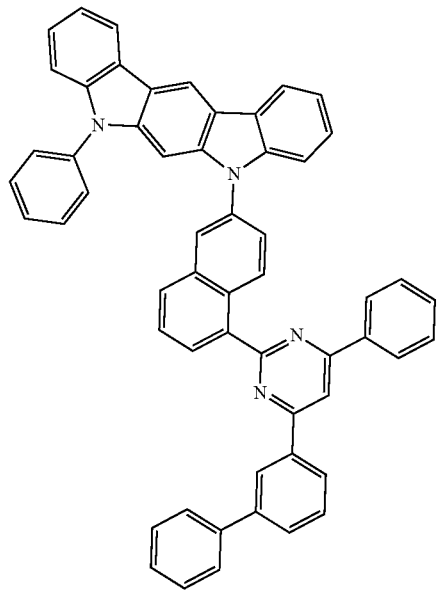
C-235
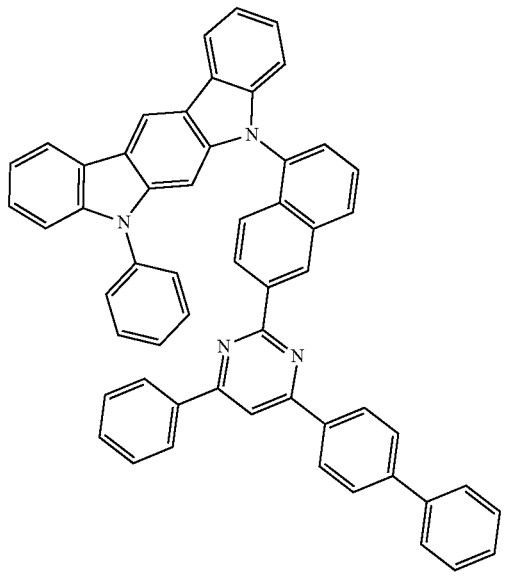
C-234
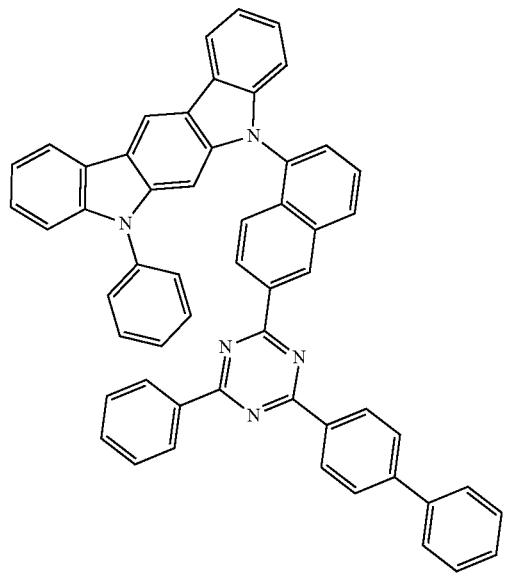
C-236
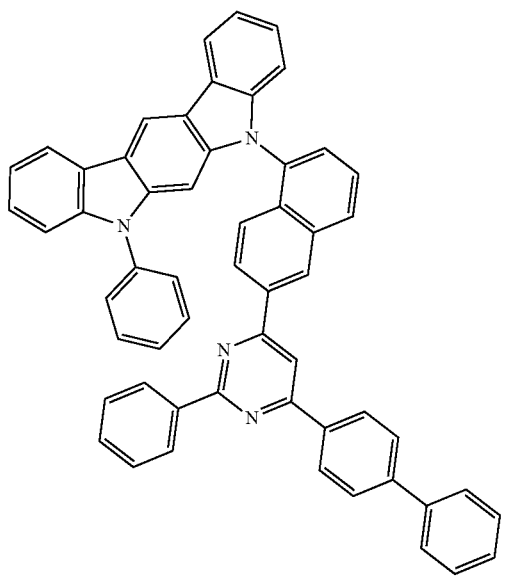

C-237
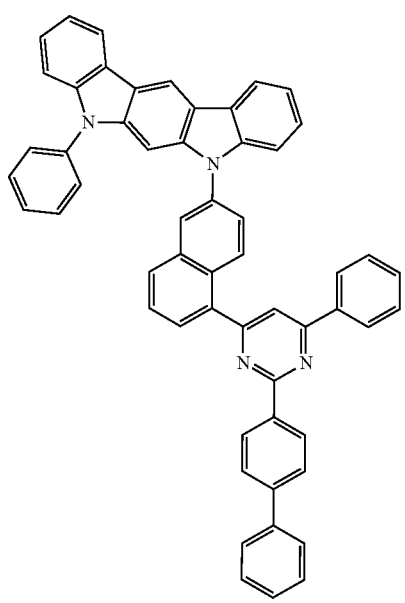
C-239
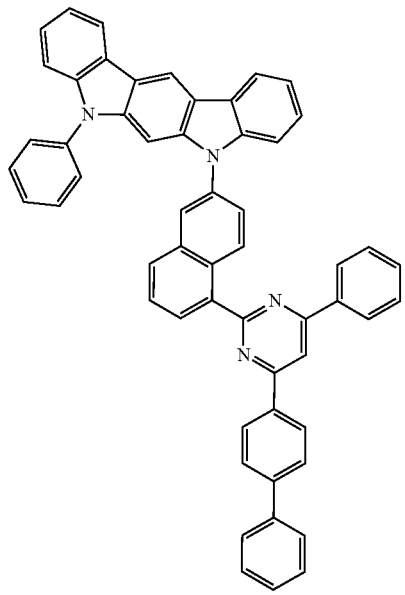
C-238
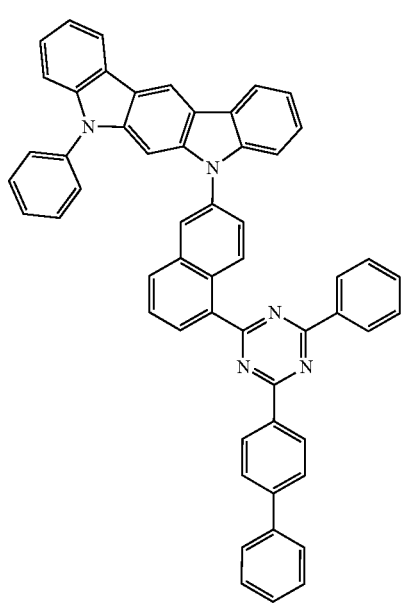
C-249
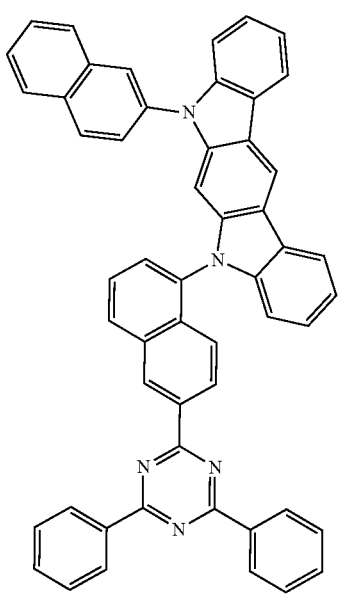

C-250
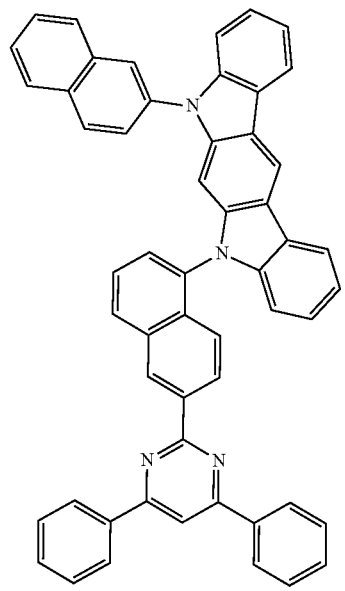
C-252
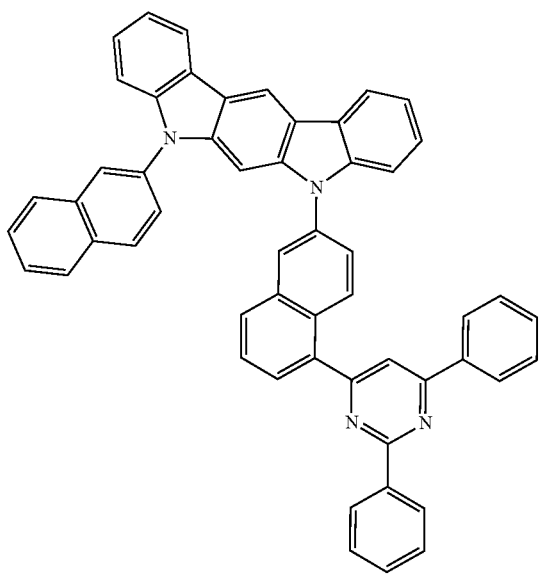
C-251
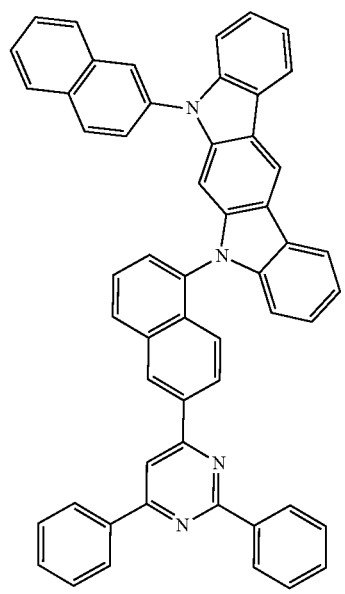
C-253
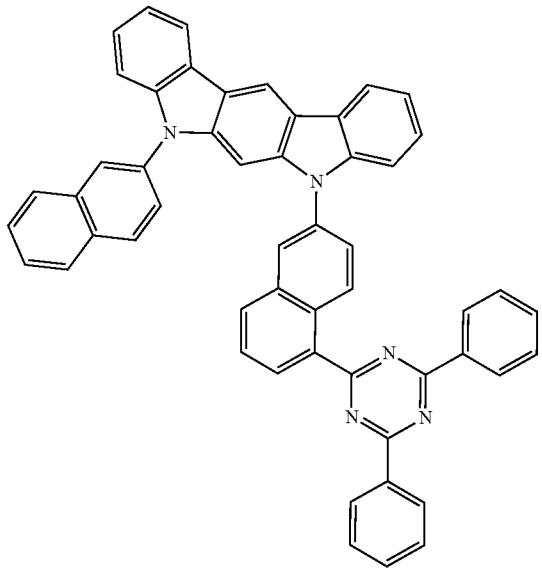

C-254
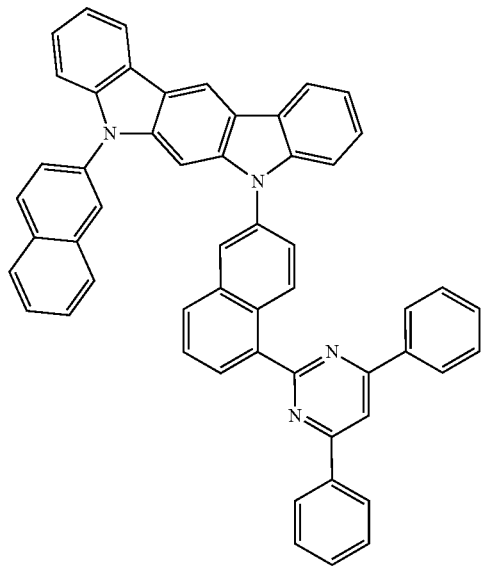
C-265
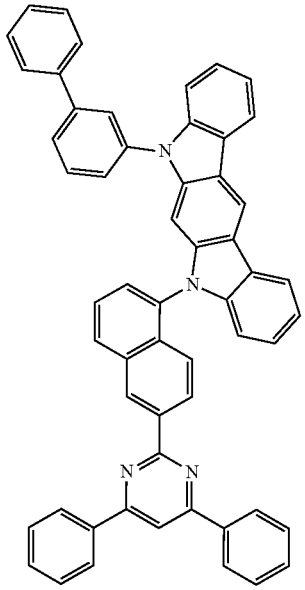
C-264
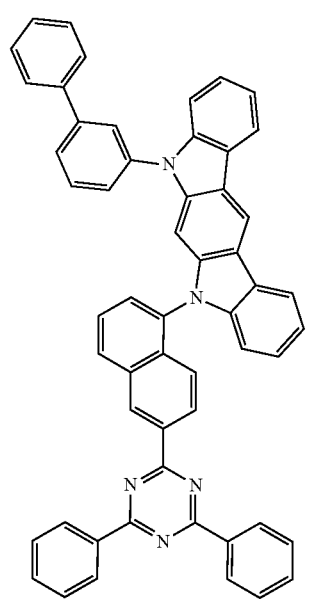
C-266

C-267
C-268
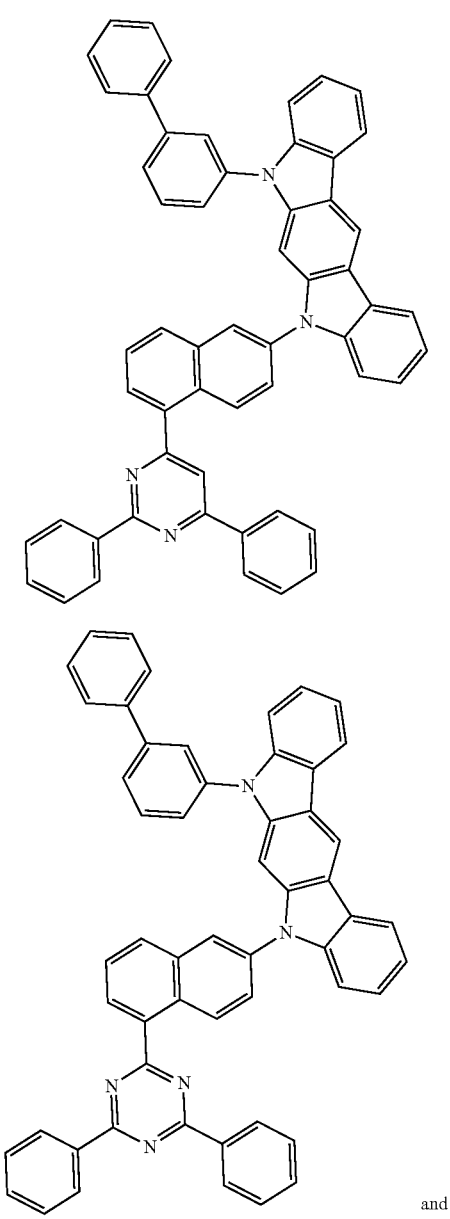
and
C-269
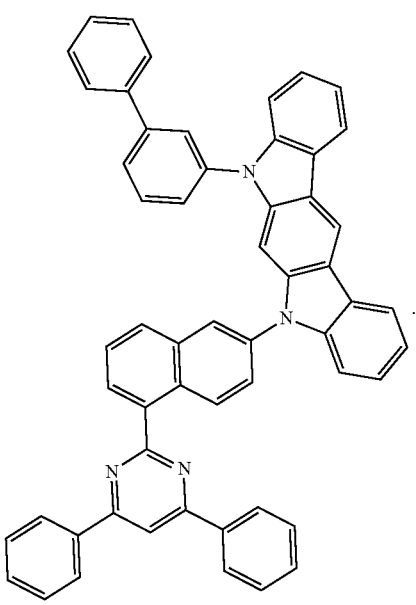
5. An organic electroluminescent material comprising the organic electroluminescent compound according to claim 1.
6. An organic electroluminescent device comprising the organic electroluminescent compound according to claim 1.
* * * * *